US010906974B2

(12) United States Patent
Iida et al.

(10) Patent No.: US 10,906,974 B2
(45) Date of Patent: ***Feb. 2, 2021

(54) ANTI-GPR20 ANTIBODY AND ANTI-GPR20 ANTIBODY-DRUG CONJUGATE

(71) Applicant: DAIICHI SANKYO COMPANY, LIMITED, Tokyo (JP)

(72) Inventors: Kenji Iida, Tokyo (JP); Takehiro Hirai, Tokyo (JP); Tomoko Terauchi, Tokyo (JP); Kensuke Nakamura, Tokyo (JP)

(73) Assignee: DAIICHI SANKYO COMPANY, LIMITED, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/990,330

(22) Filed: Aug. 11, 2020

(65) Prior Publication Data

US 2020/0362032 A1 Nov. 19, 2020

Related U.S. Application Data

(63) Continuation of application No. 16/330,085, filed as application No. PCT/JP2018/001065 on Jan. 16, 2018.

(30) Foreign Application Priority Data

Jan. 17, 2017 (JP) ................... 2017-006004

(51) Int. Cl.
*C07K 16/28* (2006.01)
*A61K 47/68* (2017.01)
(Continued)

(52) U.S. Cl.
CPC .......... *C07K 16/28* (2013.01); *A61K 31/4745* (2013.01); *A61K 39/395* (2013.01);
(Continued)

(58) Field of Classification Search
None
See application file for complete search history.

(56) References Cited

U.S. PATENT DOCUMENTS 5,480,968 A 1/1996 Kraus et al.
5,677,171 A 10/1997 Hudziak et al.
(Continued)

FOREIGN PATENT DOCUMENTS

CA 2927832 A1 11/2011
CA 2815154 A1 2/2012
(Continued)

OTHER PUBLICATIONS

Adams et al., "Humanization of a recombinant monoclonal antibody to produce a therapeutic HER dimerization inhibitor, pertuzumab," Cancer Immunol. Immunother. 55:717-727 (2006).
(Continued)

*Primary Examiner* — Karl J Puttlitz
(74) *Attorney, Agent, or Firm* — Foley & Lardner LLP

(57) ABSTRACT

It is an object of the present invention to provide an antibody specifically binding to GPR20-positive tumor cells such as GIST, a pharmaceutical product comprising the antibody and having therapeutic effects on a tumor, a method for treating a tumor using the aforementioned pharmaceutical product, and the like. It is another object of the present invention to provide an anti-GPR20 antibody having internalization activity, an antibody-drug conjugate containing the antibody, and the like.

30 Claims, 29 Drawing Sheets

Specification includes a Sequence Listing.

(51) Int. Cl.

| | |
|---|---|
| *A61K 31/4745* | (2006.01) |
| *A61K 47/64* | (2017.01) |
| *A61K 39/395* | (2006.01) |
| *A61P 35/00* | (2006.01) |
| *A61K 45/06* | (2006.01) |
| *C12N 15/09* | (2006.01) |
| *C12N 5/10* | (2006.01) |
| *A61K 39/00* | (2006.01) |

(52) U.S. Cl.
CPC .......... *A61K 39/3955* (2013.01); *A61K 45/06* (2013.01); *A61K 47/64* (2017.08); *A61K 47/6415* (2017.08); *A61K 47/6803* (2017.08); *A61K 47/6849* (2017.08); *A61P 35/00* (2018.01); *C12N 5/10* (2013.01); *C12N 15/09* (2013.01); *A61K 2039/505* (2013.01); *C07K 2317/21* (2013.01); *C07K 2317/24* (2013.01); *C07K 2317/52* (2013.01); *C07K 2317/732* (2013.01); *C07K 2317/77* (2013.01)

(56) References Cited

U.S. PATENT DOCUMENTS

| | | | |
|---|---|---|---|
| 5,821,337 | A | 10/1998 | Carter et al. |
| 5,834,476 | A | 11/1998 | Terasawa et al. |
| 5,837,673 | A | 11/1998 | Tsujihara et al. |
| 5,892,043 | A | 4/1999 | Tsujihara et al. |
| 5,968,511 | A | 10/1999 | Akita et al. |
| 6,071,719 | A | 6/2000 | Halsey et al. |
| 6,096,868 | A | 8/2000 | Halsey et al. |
| 6,214,345 | B1 | 4/2001 | Firestone et al. |
| 6,291,671 | B1 | 9/2001 | Inoue et al. |
| 6,835,807 | B1 | 12/2004 | Susaki et al. |
| 7,041,818 | B2 | 5/2006 | Susaki et al. |
| 7,585,491 | B2 | 9/2009 | Govindan |
| 7,833,979 | B2 | 11/2010 | Sullivan et al. |
| 7,837,980 | B2 | 11/2010 | Alley et al. |
| 7,999,083 | B2 | 8/2011 | Govindan et al. |
| 8,226,945 | B2 | 7/2012 | Ebens, Jr. et al. |
| 8,268,319 | B2 | 9/2012 | Govindan |
| 8,394,607 | B2 | 3/2013 | Ebens, Jr. et al. |
| 8,425,912 | B2 | 4/2013 | Govindan |
| 8,524,865 | B2 | 9/2013 | Ebens, Jr. et al. |
| 8,741,291 | B2 | 6/2014 | Bhat et al. |
| 8,907,071 | B2 | 12/2014 | Sullivan et al. |
| 8,968,741 | B2 | 3/2015 | Ebens et al. |
| 2003/0018989 | A1 | 1/2003 | Brennan et al. |
| 2003/0148931 | A1 | 8/2003 | Takahashi et al. |
| 2003/0166513 | A1 | 9/2003 | Imura et al. |
| 2004/0185053 | A1 | 9/2004 | Govindan |
| 2005/0123536 | A1 | 6/2005 | Law et al. |
| 2005/0228007 | A1 | 10/2005 | Jagtap et al. |
| 2006/0018899 | A1 | 1/2006 | Kao et al. |
| 2006/0134109 | A1 | 6/2006 | Gaitanaris et al. |
| 2006/0193865 | A1 | 8/2006 | Govindan |
| 2007/0071764 | A1 | 3/2007 | Sullivan et al. |
| 2008/0050310 | A1 | 2/2008 | Ebens, Jr. et al. |
| 2008/0131363 | A1 | 6/2008 | Govindan et al. |
| 2008/0161245 | A1 | 7/2008 | Kratz et al. |
| 2008/0260744 | A1 | 10/2008 | Gaitanaris et al. |
| 2008/0305044 | A1 | 12/2008 | McDonagh et al. |
| 2009/0178153 | A1 | 7/2009 | Gaitanaris et al. |
| 2009/0274713 | A1 | 11/2009 | Chari et al. |
| 2009/0286258 | A1 | 11/2009 | Kaur et al. |
| 2009/0291093 | A1 | 11/2009 | Govindan |
| 2010/0068181 | A1 | 3/2010 | Paliwal et al. |
| 2010/0120816 | A1 | 5/2010 | Fontana et al. |
| 2010/0303802 | A1 | 12/2010 | Zoffmann et al. |
| 2011/0045587 | A1 | 2/2011 | Sullivan et al. |
| 2011/0059076 | A1 | 3/2011 | McDonagh et al. |
| 2011/0070248 | A1 | 3/2011 | Ichikawa et al. |
| 2011/0185439 | A1 | 7/2011 | Gaitanaris et al. |
| 2011/0229406 | A1 | 9/2011 | Hettmann et al. |
| 2011/0293513 | A1 | 12/2011 | Govindan et al. |
| 2012/0121615 | A1 | 5/2012 | Flygare et al. |
| 2012/0171201 | A1 | 7/2012 | Sapra |
| 2012/0201809 | A1 | 8/2012 | Bhat et al. |
| 2013/0089872 | A1 | 4/2013 | Nakamura et al. |
| 2013/0123178 | A1 | 5/2013 | Dimarchi et al. |
| 2013/0216561 | A1 | 8/2013 | Govindan |
| 2013/0247233 | A1 | 9/2013 | Gaitanaris et al. |
| 2014/0004078 | A1 | 1/2014 | Govindan |
| 2015/0297748 | A1 | 10/2015 | Masuda et al. |
| 2015/0352224 | A1 | 12/2015 | Naito et al. |
| 2016/0219845 | A1 | 8/2016 | Gaitanaris et al. |
| 2016/0282365 | A1 | 9/2016 | Gaitanaris et al. |
| 2016/0287722 | A1 | 10/2016 | Govindan |
| 2017/0188555 | A1 | 7/2017 | Gaitanaris et al. |

FOREIGN PATENT DOCUMENTS

| | | |
|---|---|---|
| CA | 2859255 A1 | 6/2013 |
| CN | 1227499 A | 9/1999 |
| CN | 101023100 A | 8/2007 |
| CN | 101490087 A | 7/2009 |
| CN | 102481364 A | 5/2012 |
| EP | 0 495 432 A1 | 7/1992 |
| EP | 0 737 686 A1 | 10/1996 |
| EP | 0 916 348 A1 | 5/1999 |
| EP | 1 155 702 A1 | 11/2001 |
| EP | 2 594 589 A1 | 5/2013 |
| EP | 2 799 452 A1 | 11/2014 |
| EP | 2 907 824 A1 | 8/2015 |
| JP | H05-059061 A | 3/1993 |
| JP | H06-87746 A | 3/1994 |
| JP | H08-337584 A | 12/1996 |
| JP | H10-095802 A | 4/1998 |
| JP | H11-092405 A | 4/1999 |
| JP | 2002-060351 A | 2/2002 |
| JP | 2005-511627 A | 4/2005 |
| JP | 2006-511526 A | 4/2006 |
| JP | 2007-527872 A | 10/2007 |
| JP | 2008-521828 A | 6/2008 |
| JP | 2009-538629 A | 11/2009 |
| JP | 2010-513524 A | 4/2010 |
| JP | 2011-519864 A | 7/2011 |
| JP | 2011-524001 A | 8/2011 |
| JP | 2012-509259 A | 4/2012 |
| JP | 2012-100671 A | 5/2012 |
| JP | 2013-500253 A | 1/2013 |
| JP | 2013-534535 A | 9/2013 |
| JP | 2013-534906 A | 9/2013 |
| KR | 1020010052385 A | 6/2001 |
| KR | 1020110044808 A | 4/2011 |
| RU | 2450008 C2 | 7/2010 |
| TW | I232930 | 5/2005 |
| TW | 200817434 A | 4/2008 |
| WO | WO-97/46260 A1 | 12/1997 |
| WO | WO-99/46296 A1 | 9/1999 |
| WO | WO-00/25825 A1 | 5/2000 |
| WO | WO-01/00244 A2 | 1/2001 |
| WO | WO-02/00734 A1 | 1/2002 |
| WO | WO-03/013602 A1 | 2/2003 |
| WO | WO 03/015826 A1 | 2/2003 |
| WO | WO 03/043583 A2 | 5/2003 |
| WO | WO-03/074566 A2 | 9/2003 |
| WO | WO-2004/040000 A2 | 5/2004 |
| WO | WO-2005/040825 A2 | 5/2005 |
| WO | WO-2005/112919 A2 | 12/2005 |
| WO | WO 2006/065533 A2 | 6/2006 |
| WO | WO 2006/092230 A2 | 9/2006 |
| WO | WO-2007/077028 A2 | 7/2007 |
| WO | WO-2008/100624 A2 | 8/2008 |
| WO | WO-2008/144891 A1 | 12/2008 |
| WO | WO-2011/011474 A1 | 1/2011 |
| WO | WO 2011/021397 A1 | 2/2011 |
| WO | WO-2011/068845 A1 | 6/2011 |
| WO | WO-2011/145744 A1 | 11/2011 |
| WO | WO-2011/155579 A1 | 12/2011 |
| WO | WO-2012/019024 A2 | 2/2012 |
| WO | WO-2012/064733 A2 | 5/2012 |
| WO | WO-2013/068946 A2 | 5/2013 |
| WO | WO-2013/077458 A1 | 5/2013 |

(56) References Cited

FOREIGN PATENT DOCUMENTS

| WO | WO 2013/163229 A1 | 10/2013 |
|---|---|---|
| WO | WO 2013/188740 A1 | 12/2013 |
| WO | WO-2014/057687 A1 | 4/2014 |
| WO | WO-2014/061277 A1 | 4/2014 |
| WO | WO-2014/107024 A1 | 7/2014 |
| WO | WO-2015/142675 A2 | 9/2015 |

OTHER PUBLICATIONS

Alimandi et al., "Cooperative signaling of ErbB3 and ErbB2 in neoplastic transformation and human mammary carcinomas," Oncogene 10:1813-1821 (1995).
Allander et al., "Gastrointestinal Stromal Tumors with KIT Mutations Exhibit a Remarkably Homogeneous Gene Expression Profile," Cancer Research, vol. 61, pp. 8624-8628, Dec. 15, 2001.
Alley et al., "Antibody-drug conjugates: targeted drug delivery for cancer," Current Opinion in Chemical Biology 14:529-537 (2010).
Barginear et al., "Trastuzumab-DM1: A Review of the Novel Immuno-Conjugate for HER2-Overexpressing Breast Cancer," The Open Breast Cancer Journal 1:25-30 (2009).
Barok et al, Trastuzumab-DM1 is highly effective in preclinical models of HER2-positive gastric cancer, Cancer Letters, 2011, vol. 306, No. 2, pp. 172-179.
Baselga et al., "Phase II Study of Weekly Intravenous Recombinant Humanized Anti-p185HER2 Monoclonal Antibody in Patients with HER2/neu-Overexpressing Metastatic Breast Cancer," J. Clin. Oncol. 14(3):737-744 (Mar. 1996).
Basu et al., "The Epithelial/Carcinoma Antigen EGP-1 Recognized by Monoclonal Antibody RS7-3G11, is Phosphorylated on Serine 303," Int. J. Cancer 62(4):472-479 (1995).
Bauer et al., "Emerging Agents for the Treatment of Advanced, Imatinib-Resistant Gastrointestinal Stromal Tumors: Current Status and Future Directions," Drugs, vol. 75, 2015, pp. 1323-1334.
Beck, Alain, "The Next Generation of Antibody-drug Conjugates Comes of Age," Discovery Medicine 10(53):329-339 (Oct. 16, 2010).
Bouchard et al., "Antibody-drug conjugates—A new wave of cancer drugs," Bioorganic & Medicinal Chemistry Letters, vol. 24, 2014, pp. 5357-5363.
Burke P J et al. (2009), "Design, Synthesis, and Biological Evaluation of Antibody-Drug Conjugates Comprised of Potent Camptothecin Analogues", Bioconjugate Chemistry, vol. 20, No. 6, pp. 1242-1250.
Burris, III et al., "Phase II Study of the Antibody Drug Conjugate Trastuzumab-DM1 for the Treatment of Human Epidermal Growth Factor Receptor 2 (HER2)—Positive Breast Cancer After Prior HER2-Directed Therapy," J. Clin. Oncol. 29(4):398-405 (Feb. 2011).
Calabrese et al., "Assignment of TACSID1 (alias TROP1, M4S1) to human chromosome 2p21 and refinement of mapping of TACSTD2 (alias TROP2, M1S1) to human chromosome 1p32 by in situ hybridization," Cytogenet Cell Genet. 92(1-2):164-165 (2001).
Canadian Intellectual Property Office, "Interview Summary," issued in connection with Canadian Patent Application No. 2,885,800, dated Mar. 28, 2017.
Canadian Intellectual Property Office, "Office Action," issued in connection with Canadian Patent Application No. 2,939,802, dated Apr. 13, 2018.
Chi et al., ETV1 is a lineage survival factor that cooperates with KIT in gastrointestinal stromal tumours, Nature, vol. 467, Oct. 14, 2010, pp. 849-855.
Conjugation site modulates the in vivo stability and therapeutic activity of antibody-drug conjugates, Shen et al, Nature Biotechnology, 2012, vol. 30, pp. 184-189.
Corless et al., "Gastrointestinal stromal tumours: origin and molecular oncology," Nature Reviews, Cancer, vol. 11, Dec. 2011, pp. 865-878.
Coussens et al., "Tyrosine Kinase Receptor with Extensive Homology to EGF Receptor Shares Chromosomal Location with neu Oncogene," Science 230(4730):1132-1139 (Dec. 1985).
Damle, Nitin K., "Tumour-targeted chemotherapy with immunoconjugates of calicheamicin," Expert Opin. Biol. Ther. 4(9):1445-1452 (2004).
De Jager et al., "DX-8951f: Summary of Phase I Clinical Trials," Ann. N. Y. Acad. Sci. 922:260-273 (2000).
Defazio et al., "Expression of c-erbB Receptors, Heregulin and Oestrogen Receptor in Human Breast Cell Lines," Int. J. Cancer 87:487-498 (2000).
Demetri et al., "NCCN Task Force Report: Update on the Management of Patients with Gastrointestinal Stromal Tumors," Journal of the National Comprehensive Cancer Network, vol. 8, Supplement 2, Apr. 2010, pp. S-1-S-41.
Di Fiore et al., "erbB-2 Is a Potent Oncogene When Overexpressed in NIH/3T3 Cells," Science 237:178-182 (Jul. 1987).
Donaghy, Heather, "Effects of antibody, drug and linker on the preclinical and clinical toxicities of antibody-drug conjugates," mAbs, vol. 8, No. 4, 2016, pp. 659-671.
Dosio et al., "Antibody-targeted leucinostatin A", Journal of Controlled Release, No. 32, (1994), pp. 37-44.
Ducry et al., "Antibody—Drug Conjugates: Linking Cytotoxic Payloads to Monoclonal Antibodies," Bioconjugate Chem. 21:5-13 (2010).
El Sewedy et al., "Cloning of the Murine Trop2 Gene: Conservation of a PIP2-Binding Sequence in the Cytoplasmic Domain of Trop-2," Int. J. Cancer 75(2):324-330 (1998).
Esteva et al., A Phase II Study of Intravenous Exatecan Mesylate (DX-8951f) Administered Daily for 5 Days Every 3 Weeks to Patients with Metastatic Breast Carcinoma, American Cancer Society, 2003,900-907.
European Patent Office, "Communication with extended European Search Report," issued in connection with European Patent Application No. 13845596.9, dated May 6, 2016.
European Patent Office, "Communication with extended European Search Report," issued in connection with European Patent Application No. 13847461.4, dated May 13, 2016.
European Search Report issued in corresponding application No. 14874745.4 dated May 10, 2017.
Extended European Search Report issued in European Patent Application No. 15743738.5 dated Aug. 9, 2017.
Extended European Search Report issued in European Patent Application No. 15776810.2 dated Aug. 11, 2017.
Faulk et al., "Antigens of human trophoblasts: A working hypothesis for their role in normal and abnormal pregnancies," Proc. Natl. Acad. Sci. USA 75(4):1947-1951 (1978).
Fendly et al., "Characterization of Murine Monoclonal Antibodies Reactive to Either the Human Epidermal Growth Factor Receptor or HER2/neu Gene Product," Cancer Research 50:1550-1558 (1990).
Fong et al., "High expression of TROP2 correlates with poor prognosis in pancreatic cancer," Br. J. Cancer 99(8):1290-1295 (2008).
Fong et al., "TROP2: a novel prognostic marker in squamous cell carcinoma of the oral cavity," Mod. Pathol. 21(2):186-191 (2008).
Fornaro et al., "Cloning of the Gene Encoding Trop-2, a Cell-Surface Glycoprotein Expressed by Human Carcinomas," Int. J. Cancer 62(5):610-618 (1995).
Fukushige et al., "Localization of a Novel v-erbB-Related Gene, c-erbB-2, on Human Chromosome 17 and Its Amplification in a Gastric Cancer Cell Line," Mol. Cell. Biol. 6(3):955-958 (1986).
Gomez-Monterrey et al., "Design, Synthesis, and Cytotoxic Evaluation of Acyl Derivatives of 3-Aminonaphtho[2,3-b]thiophene-4,9-dione, a Quinone-Based System," Journal of Medicinal Chemistry, 2011, 54(12):4077-4091, abstract.
Graus-Porta et al., "ERbB-2, the preferred heterodimerization partner of all ErbB receptors, is a mediator of lateral signaling," EMBO J. 16(7):1647-1655 (1997).
Gravalos et al., "HER2 in gastric cancer: a new prognostic factor and a novel therapeutic target," Ann. Oncol. 19:1523-1529 (2008).
Hardwick et al., "Immunohistochemical detection of p53 and c-erbB-2 in oesophageal carcinoma; no correlation with prognosis," Eur. J. Surg. Oncol. 23:30-35 (1997).

(56) References Cited

OTHER PUBLICATIONS

Hase et al., "Characterization of an Orphan G Protein-coupled Receptor, GPR20, That Constitutively Activates Gi Proteins*," the Journal of Biological Chemistry, vol. 283, No. 19, May 9, 2008, pp. 12747-12755.

Hinrichs et al., "Antibody Drug Conjugates: Nonclinical Safety Considerations," the AAPS Journal, vol. 17, No. 5, Sep. 2015, pp. 1055-1064.

Hudis, M.D., Clifford A., "Trastuzumab—Mechanism of Action and Use in Clinical Practice," N. Engl. J. Med. 357(1):39-51 (2007).

Hudziak et al., "Increased expression of the putative growth factor receptor p185HER2 causes transformation and tumorigenesis of NIH 3T3 cells," Proc. Natl. Acad. Sci. USA 84:7159-7163 (1987).

Inoue et al., "CM-Dextran-Polyalcohol-Camptothecin Conjugate: DE-310 with A Novel Carrier System and Its Preclinical Data," Polymer Drugs in the Clinical Stage, 145-153 (2003).

Intellectual Property Office of Singapore, "Invitation to Respond to Written Opinion," issued in connection with Singaporean Patent Application No. 11201502887W, dated Apr. 22, 2016.

International Search Report for PCT/JP2014/006421 dated Mar. 17, 2015.

International Search Report issued in International Patent Application No. PCT/JP2015/000355 dated Apr. 21, 2015.

International Search Report with English language translation and Written Opinion issued in International Application No. PCT/JP2015/002020 dated Jul. 20, 2015.

International Search Report with English language translation and Written Opinion issued in International Application No. PCT/JP2017/036215 dated Nov. 21, 2017.

International Searching Authority, "International Search Report," issued in connection with International Patent Application No. PCT/JP2013/006069, dated Dec. 17, 2013.

International Searching Authority, "International Search Report," issued in connection with International Patent Application No. PCT/JP2013/006178, dated Dec. 17, 2013.

Japanese Patent Office, "Decision to Grant a Patent," in connection with Japanese Patent Application No. 2016-166850, dated Oct. 18, 2016.

Japanese Patent Office, "Decision to Grant Patent," issued in connection with Japanese Patent Application No. 2016-117096, dated Jul. 4, 2017.

Japanese Patent Office, "Notification of Reasons for Refusal," in connection with Japanese Patent Application No. 2016-540705, dated Dec. 6, 2016.

Joto et al., "DX-8951F, A Water-Soluble Camptothecin Analog, Exhibits Potent Antitumor Activity Against a Human Lung Cancer Cell Line and its SN-38-Resistant Variant," Int. J. Cancer 72:680-686 (1997).

Kamath et al., "Challenges and advances in the assessment of the disposition of antibody-drug conjugates," Biopharmaceutics & Drug Disposition, 2015, 9 pages.

Kaptain et al., "Her-2/neu and Breast Cancer," Diagn. Mol. Pathol. 10(3):139-152 (2001).

Karunagaran et al., "ErbB-2 is a common auxiliary subunit of NDF and EGF receptors: implications for breast cancer," EMBO J. 15(2):254-264 (1996).

Korkaya et al., "HER2 regulates the mammary stem/progenitor cell population driving tumorigenesis and invasion," Oncogene 27:6120-6130 (2008).

Kraus et al., "Demonstration of ligand-dependent signaling by the erbB-3 tyrosine kinase and its constitutive activation in human breast tumor cells," Proc. Natl. Acad. Sci. USA 90:2900-2904 (Apr. 1993).

Kraus et al., "Isolation and characterization of ERBB3, a third member of the ERBB/epidermal growth factor receptor family: Evidence for overexpression in a subset of human mammary tumors," Proc. Natl. Acad. Sci. USA 86:9193-9197 (Dec. 1989).

Kumazawa et al., "Antitumor activity of DX-8951f: a new camptothecin derivative," Exp. Opin. Invest. Drugs 7(4):625-632 (1998).

Kumazawa et al., "DE-310, a novel macromolecular carrier system for the camptothecin analog DX-8951f: Potent antitumor activities in various murine tumor models," Cancer Sci. 95(2):168-175 (Feb. 2004).

Kumazawa et al., "Potent and broad antitumor effects of DX-8951f, a water-soluble camptothecin derivative, against various human tumors xenografted in nude mice," Cancer Chemother. Pharmacol. 42:210-220 (1998).

Linnenbach et al., "Sequence investigation of the major gastrointestinal tumor-associated antigen gene family, GA733," Proc. Natl. Acad. Sci. 86(1):27-31 (Jan. 1989).

Lipinski et al., "Human trophoblast cell-surface antigens defined by monoclonal antibodies," Proc. Natl. Acad. Sci. 78(8):5147-5150 (Aug. 1981).

Loo et al., "Development of an Fc-Enhanced Anti-B7-H3 Monoclonal Antibody with Potent Antitumor Activity," Clinical Cancer Research, vol. 18, No. 4, Jul. 15, 2012, pp. 3834-3845.

Martin et al., "Constitutive Activity among Orphan Class-A G Protein Coupled Receptors," PLOS One, Sep. 18, 2015, pp. 1-12.

Masubuchi, N., "Pharmacokinetics of DE-310, a novel macromolecular carrier system for the camptothecin analog DX-8951f, in tumor-bearing mice," Pharmazie 59: 374-377 (2004).

McDonagh et al., "Engineered antibody-drug conjugates with defined sites and stoichiometries of drug attachment," Protein Engineering, Design & Selection, 2006, 19(7):299-307.

Methods for site-specific drug conjugation to antibodies, Behrens et al, mAbs, 2014, vol. 6, No. 1, pp. 46-53.

Mitsui et al., "A New Water-soluble Camptothecin Derivative, DX-8951f, Exhibits Potent Antitumor Activity against Human Tumors in vitro and in vivo," Jpn. J. Cancer Res. 86:776-782 (Aug. 1995).

Mühlmann et al., "TROP2 expression as prognostic marker for gastric carcinoma," J. Clin. Pathol. 62(2):152-158 (2009).

Naidu et al., "Expression of c-erbB3 protein in primary breast carcinomas," British Journal of Cancer 78(10): 1385-1390 (1998).

Nakada et al., "Novel antibody drug conjugates containing exatecan derivative-based cytotoxic payloads," Bioorganic & Medicinal Chemistry Letters, vol. 26, 2016, pp. 1542-1545.

Ning et al., "TROP2 expression and its correlation with tumor proliferation ana angiogenesis in human gliomas," Neurol. Sci. 34(10):1745-1750 (2013).

O'Dowd et al., "Cloning and chromosomal mapping of four putative novel human G-protein-coupled receptor genes," Gene. vol. 187, 1997, pp. 75-81.

Ochi, Yusuke, "A possible mechanism for the long-lasting antitumor effect of the macromolecular conjugate DE-310: mediation by cellular uptake and drug release of its active camptothecin analog DX-8951," Cancer Chemother Pharmacol (2005) 55: 323-332.

Office Action with Search Report dated Aug. 29, 2017, in RU 2015113767.

Ogitani et al., "Bystander killing effect of DS-8201a, a novel anti-human epidermal growth factor receptor 2 antibody-drug conjugate, in tumors with human epidermal growth factor receptor 2 heterogeneity," Cancer Science, vol. 107, 2016, pp. 1039-1046.

Ogitani et al., "DS-8201a, A Novel HER2-Targeting ADC with a Novel DNA Topoisomerase I Inhibitor, Demonstrates a Promising Antitumor Efficacy with Differentiation from T-DM1," Clinical Cancer Research, vol. 22, No. 20, Oct. 15, 2016, pp. 5097-5108.

Ogitani et al., "Wide application of a novel topoisomerase I inhibitor-based drug conjugation technology," Bioorganic & Medicinal Chemistry Letters, vol. 26, 2016, 5069-5072.

Oguma et al, Validation study of a method for assaying DE-310, a macromolecular carrier conjugate containing an anti-tumor camptothecin derivative, and the free drug in tumor tissue by high performance liquid chromatography/atmospheric pressure chemical ionization tandem mass spectrometry, Biomedical Chromatography, 2005, vol. 19, No. 1, pp. 19-26.

Ohmachi et al., "Clinical Significance of TROP2 Expression in Colorectal Cancer," Clin. Cancer Res. 12(10):3057-3063 (May 15, 2006).

Opposition dated May 9, 2017, against CO NC2016/0000187, with partial English translation.

(56) References Cited

OTHER PUBLICATIONS

Perez et al., "Antibody-drug conjugates: current status and future directions," Drug Discovery Today, vol. 19, No. 7, Jul. 2014, pp. 869-881.
Peters et al., "Antibody-drug conjugates as novel anti-cancer chemotherapeutics," Bioscience Reports, vol. 35, 2015, pp. 1-20.
Plowman et al., "Molecular cloning and expression of an additional epidermal growth factor receptor-related gene," Proc. Natl. Acad. Sci. USA 87:4905-4909 (Jul. 1990).
Polakis, Paul, "Antibody Drug Conjugates for Cancer Therapy," Pharmacological Reviews, vol. 68, pp. 3-19, Jan. 2016.
Ripani et al., "Human Trop-2 is a Tumor-Associated Calcium Signal Transducer," Int. J. Cancer 76(5):671-676 (1998).
Russian Office Action dated Oct. 11, 2018 in corresponding application No. 2016123597.
Scott et al., "Antibody therapy of cancer," Nature Reviews, vol. 12, Apr. 2012, pp. 278-287.
Senter et al., "The discovery and development of brentuximab vedotin for use in relapsed Hodgkin lymphoma and systemic anaplastic large cell lymphoma," Nature Biotechnology 30(7):631-637 (Jul. 2012).
Shiose et al., "Relationship between Drug Release of DE-310, Macromolecular Prodrug of DX-8951f, and Cathepsins Activity in Several Tumors," Biol. Pharm. Bull., 2007, 30(12):2365-2370.
Shiose, Yoshinobu, "Systematic Research of Peptide Spacers Controlling Drug Release from Macromolecular Prodrug System, Carboxymethyldextran Polyalcohol-Peptide-Drug Conjugates," Bioconjugate Chem. 20, 60-70 (2009).
Sliwkowski et al., "Coexpression of erbB2 and erbB3 Proteins Reconstitutes a High Affinity Receptor for Heregulin." J. Biol. Chem. 269(20):14661-14665 (1994).
Sliwkowski et al., "Nonclinical Studies Addressing the Mechanism of Action of Trastuzumab (Herceptin)," Semin. Oncol. 26(4) Suppl. 12: 60-70 (Aug. 1999).
Soepenberg et al., "Phase I and Pharmacokinetic Study of DE-310 in Patients with Advanced Solid Tumors," Clin. Cancer Res. 11:703-711 (Jan. 15, 2005).
Soepenberg, Otto, "Liquid chromatographic assays for DE-310, a novel camptothecin analog, and two major enzymatic products in human matrices," Journal of Chromatography B, 799, 15-22 (2004).
Taiwanese Office Action dated Jul. 30, 2018 in corresponding application No. 104111534.
Taiwanese Office Action dated May 15, 2017 in corresponding application No. 102136742.
Taiwanese Patent Office, "Allowance", issued in connection with Taiwanese Patent Application No. 104103127,dated Apr. 11, 2018.
Takiguchi et al., "Antitumor Effect of DX-8951, a Novel Camptothecin Analog, on Human Pancreatic Tumor Cells and Their CPT-11-resistant Variants Cultured in vitro and Xeografted in Nude Mice," Jpn. J. Cancer Res. 88:760-769 (Aug. 1997).

The Korean Intellectual Property Office, "Notice of Grounds for Rejection," issued in connection with Korean Patent Application No. 10-2016-7015961, dated May 1, 2018.
The State Intellectual Property Office of People's Republic of China, "The First Office Action," issued in connection with Chinese Patent Application No. 201380053256.2, dated Nov. 1, 2016.
Thomas M. Cardillo, "Humanized Anti-Trop-2 IgG-SN-38 Conjugate for Effective Treatment of Diverse Epithelial Cancers: Preclinical Studies in Human Cancer Xenograft Models and Monkeys," Clinical Cancer Research vol. 17, No. 10, Mar. 3, 2011, pp. 3157-3169.
Tsuchikama et al., "Antibody-drug conjugates: recent advances in conjugation and linker chemistries," Protein & Cell, Oct. 14, 2016, 14 pages.
Velez et al., "APOE*E2 allele delays age of onset in PSEN1 E280A Alzheimer's disease," Molecular Psychiatry, 2015, pp. 1-9.
Vogel et al., "Efficacy and Safety of Trastuzumab as a Single Agent in First-Line Treatment of HER2-Overexpressing Metastatic Breast Cancer," J. Clin. Oncol. 20(3):719-726 (Feb. 2002).
Wang et al., "Identification of Trop-2 as an oncogene and an attractive therapeutic target in colon cancers," Mol. Cancer Ther. 7(2):280-285 (Feb. 2008).
Wente et al., "DE-310, a macromolecular prodrug of the topoisomerase-1-inhibitor exatecan (DX-8951), in patients with operable solid tumors," Investigational New Drugs 23:339-347 (2005).
Yamaguchi, Teruhide, "Current situations and the future prospect of monoclonal antibody products," Report of the National Institute of Health, vol. 132, 2014, pp. 36-46.
Yano et al., "Comparison of HER2 gene amplification assessed by fluorescence in situ hybridization and HER2 protein expression assessed by immunohistochemistry in gastric cancer," Oncol. Rep. 15:65-71 (2006).
International Searching Authority, "International Search Report," issued in connection with International Patent Application No. PCT/JP2018/001065, dated Apr. 17, 2018.
International Searching Authority, "Written Opinion," issued in connection with International Patent Application No. PCT/JP2018/001065, dated Apr. 17, 2018.
Extended European Search Report dated Nov. 30, 2020 for corresponding European Patent Application No. 18742022.9.
Haasen Dorothea et al: "G protein-coupled receptor internalization assays in the high-content screening format", Biomembranes: Transport Theory': Cells and Model Membranes; [Methods in Enzymology, ISSN 0076-6879], Elsevier, Academic Press, NL, vol. 414, Jan. 1, 2006 (Jan. 1, 2006), pp. 121-139.
Hirata T: "Producing monoclonal antibody of extracellular domain of metabotropic glutamate receptor 1, by hybridizing spleen cell of non-human animal immunized by olfactory tract, with myeloma cell, culturing hybridoma, screening culture supernatant", WPI/THOMSON,, vol. 2004, No. 36, Apr. 22, 2004 (Apr. 22, 2004).
Momoko Hase et al: Characterization of an Orphan G Protein-coupled Receptor, GPR20, That Constitutively Activates G i Proteins:, Journal of Biological Chemistry, vol. 283, No. 19, May 9, 2008 (May 5, 2009), pp. 12747-12755.

[Figure 1]

SEQ ID NO 2: Amino acid sequence of 04-046 antibody heavy chain

MEWNWVFLFLLSVTAEVHSQVQLQQSGAELAKPGSSVKISCKASGYTFTSYYIS
WIKQTTGQGLKYIGFINPGSGHTNYNEKFKGKATLTVDKSSSTAFMQLSSLTPD
DSAIYYCARGAGGFLRIITKFDYWGQGVMVTVSSAQTTAPSVYPLAPGCGDTTSS
TVTLGCLVKGYFPEPVTVTWNSGALSSDVHTFPAVLQSGLYTLTSSVTSSTWPSQ
TVTCNVAHPASSTKVDKKVERRNGGIGHKCPTCPTCHKCPVPELLGGPSVFIFPP
KPKDILLISQNAKVTCVVVDVSEEEPDVQFSWFVNNVEVHTAQTQPREEQYNST
FRVVSALPIQHQDWMSGKEFKCKVNNKALPSPIEKTISKPKGLVRKPQVYVMGP
PTEQLTEQTVSLTCLTSGFLPNDIGVEWTSNGHIEKNYKNTEPVMDSDGSFFMY
SKLNVERSRWDSRAPFVCSVVHEGLHNHHVEKSISRPPGK

Signal sequence (1-19), heavy chain variable region (20-142), heavy chain constant region (143-475)
CDRH1 (45-54), CDRH2 (69-78), CDRH3 (118-131)

SEQ ID NO 32: Nucleotide sequence of 04-046 antibody heavy chain

ATGGAATGGAACTGGGTCTTTCTCTTCCTCCTGTCAGTAACTGCAGAGGTCCAC
TCCCAGGTCCAACTGCAGCAGTCTGGAGCTGAACTGGCAAAGCCTGGCTCTTC
AGTGAAGATTTCCTGCAAGGCTTCTGGCTACACCTTCACCAGCTACTATATAAG
CTGGATAAAGCAGACGACTGGACAGGGCCTTAAGTATATTGGATTTATTAATCC
GGGAAGTGGACATACTAACTACAATGAGAAGTTCAAGGGCAAGGCCACATTGA
CTGTAGACAAATCCTCTAGCACAGCCTTCATGCAACTCAGCAGCCTGACACCTG
ACGACTCTGCGATCTATTACTGTGCAAGAGGGGCTGGGGGTTTTCTACGGATTA
TTACTAAGTTTGATTACTGGGGCCAAGGAGTCATGGTCACAGTCTCCTCAGCCC
AAACAACAGCCCCATCTGTCTATCCACTGGCTCCTGGATGTGGTGATACAACCA
GCTCCACGGTGACTCTGGGATGCCTGGTCAAGGGCTATTTCCCTGAGCCAGTC
ACCGTGACCTGGAACTCTGGAGCCCTGTCCAGCGATGTGCACACCTTTCCAGC
TGTCCTGCAGTCTGGGCTCTACACTCTCACCAGCTCAGTGACCTCCAGCACCTG
GCCCAGCCAGACCGTCACCTGCAACGTAGCCCACCCGGCCAGCAGCACCAAGG
TGGACAAGAAAGTTGAGCGCAGAAATGGCGGCATTGGACACAAATGCCCTACA
TGCCCTACATGTCACAAATGCCCAGTTCCTGAACTCTTGGGTGGACCATCTGTC
TTCATCTTCCCGCCAAAGCCCAAGGACATCCTCTTGATCTCCCAGAACGCCAAG
GTCACGTGTGTGGTGGTGGATGTGAGCGAGGAGGAGCCGGACGTCCAGTTCA
GCTGGTTTGTGAACAACGTAGAAGTACACACAGCTCAGACACAACCCCGTGAG
GAGCAGTACAACAGCACCTTCAGAGTGGTCAGTGCCCTCCCCATCCAGCACCA
GGACTGGATGAGCGGCAAGGAGTTCAAATGCAAGGTCAACAACAAAGCCCTCC
CAAGCCCCATCGAGAAAACCATCTCAAAACCCAAAGGGCTAGTCAGAAAACCA
CAGGTATACGTCATGGGTCCACCGACAGAGCAGTTGACTGAGCAAACGGTCAG
TTTGACCTGCTTGACCTCAGGCTTCCTCCCTAACGACATCGGTGTGGAGTGGAC
CAGCAACGGGCATATAGAAAAGAACTACAAGAACACCGAGCCAGTGATGGACT
CTGACGGTTCTTTCTTCATGTACAGCAAGCTCAATGTGGAAAGGAGCAGGTGG
GATAGCAGAGCGCCCTTCGTCTGCTCCGTGGTCCACGAGGGTCTGCACAATCA
CCACGTGGAGAAGAGCATCTCCCGGCCTCCGGGTAAA

Signal sequence (1-57), heavy chain variable region (58-426), heavy chain constant region (427-1425)
CDRH1(133-162), CDRH2(205-234), CDRH3 (352-393)

[Figure 2]

SEQ ID NO 7: Amino acid sequence of 04-046 antibody light chain

METDRLLLWVLLLWVPGSTGDTVLTQSPALAVSLGQRVTISCRASKSVSTYIHWY
QQRSGQQPKLLIYSASNLESGVPSRFSGSGSGTDFTLTIDPVEPDDIANYYCQQIN
ELPYTFGAGTKLELKRADAAPTVSIFPPSTEQLATGGASVVCLMNNFYPRDISVK
WKIDGTERRDGVLDSVTDQDSKDSTYSMSSTLSLTKADYESHNLYTCEVVHKTS
SSPVVKSFNRNEC

Signal sequence (1-20), light chain variable region (21-128), light chain constant region (129-233)
CDRH1 (43-53), CDRH2 (69-75), CDRH3 (108-116)

SEQ ID NO 34: Nucleotide sequence of 04-046 antibody light chain

ATGGAGACAGACAGACTCCTGCTATGGGTGCTGCTGCTCTGGGTTCCAGGCTC
CACTGGTGACACTGTGCTGACCCAGTCTCCTGCTTTGGCTGTGTCTCTAGGGC
AGAGGGTCACCATCTCCTGTAGGGCCAGCAAAAGTGTCAGTACATATATACACT
GGTACCAACAGAGGTCGGGACAGCAACCCAAACTCCTGATCTATAGTGCATCCA
ACCTAGAATCTGGAGTCCCTTCCAGGTTCAGTGGGAGTGGGTCTGGGACAGAC
TTTACCCTCACCATAGATCCTGTGGAGCCTGATGACATAGCAAACTATTACTGTC
AGCAGATTAATGAACTTCCGTACACGTTTGGAGCTGGGACCAAGCTGGAACTG
AAACGGGCTGATGCTGCACCAACTGTATCTATCTTCCCACCATCCACGGAACAG
TTAGCAACTGGAGGTGCCTCAGTCGTGTGCCTCATGAACAACTTCTATCCCAGA
GACATCAGTGTCAAGTGGAAGATTGATGGCACTGAACGACGAGATGGTGTCCT
GGACAGTGTTACTGATCAGGACAGCAAAGACAGCACGTACAGCATGAGCAGCA
CCCTCTCGTTGACCAAGGCTGACTATGAAAGTCATAACCTCTATACCTGTGAGG
TTGTTCATAAGACATCATCCTCACCCGTCGTCAAGAGCTTCAACAGGAATGAGT
GT

Signal sequence (1-60), light chain variable region (61-384), light chain constant region (385-699)
CDRL1(127-159), CDRL2(205-225), CDRL3 (322-348)

[Figure 3]

SEQ ID NO 12: Amino acid sequence of 04-079 antibody heavy chain

MEWNWVFLFLLSVTAVVHSQVQLQQSGAELAKPGSSVKISCKASGYTFTSYYIT
WIKQTTGQGLKYIGYINPGSGHTNYNEKFKGKATLTVDKSSSTAFMQLSSLTPD
DSAVYYCARGAGGFLRIISKFDYWGQGVMVTVSSAQTTAPSVYPLAPGCGDTTSS
TVTLGCLVKGYFPEPVTVTWNSGALSSDVHTFPAVLQSGLYTLTSSVTSSTWPSQ
TVTCNVAHPASSTKVDKKVERRNGGIGHKCPTCPTCHKCPVPELLGGPSVFIFPP
KPKDILLISQNAKVTCVVVDVSEEEPDVQFSWFVNNVEVHTAQTQPREEQYNST
FRVVSALPIQHQDWMSGKEFKCKVNNKALPSPIEKTISKPKGLVRKPQVYVMGP
PTEQLTEQTVSLTCLTSGFLPNDIGVEWTSNGHIEKNYKNTEPVMDSDGSFFMY
SKLNVERSRWDSRAPFVCSVVHEGLHNHHVEKSISRPPGK

Signal sequence (1-19), heavy chain variable region (20-142), heavy chain constant region (143-475)
CDRH1 (45-54), CDRH2 (69-78), CDRH3 (118-131)

SEQ ID NO 36: Nucleotide sequence of 04-079 antibody heavy chain

ATGGAGTGGAACTGGGTCTTTCTCTTCCTCCTGTCAGTAACTGCAGTCGTCCAC
TCCCAGGTCCAGCTGCAGCAGTCTGGAGCTGAGCTGGCAAAGCCTGGCTCTTC
AGTGAAGATTTCCTGCAAGGCTTCTGGCTACACCTTCACCAGCTACTATATAAC
CTGGATAAAGCAGACGACTGGACAGGGCCTTAAGTATATTGGATATATTAATCC
GGGAAGTGGACATACTAACTACAATGAAGAAGTTCAAGGGCAAGGCCACATTGA
CTGTAGACAAATCCTCCAGCACAGCCTTCATGCAACTCAGCAGCCTGACACCTG
ACGACTCTGCGGTCTATTACTGTGCAAGAGGGGCTGGGGGTTTTCTACGGATTA
TTAGTAAGTTTGATTACTGGGGCCAAGGAGTCATGGTCACAGTCTCCTCAGCCC
AAACAACAGCCCCATCTGTCTATCCACTGGCTCCTGGATGTGGTGATACAACCA
GCTCCACGGTGACTCTGGGATGCCTGGTCAAGGGCTATTTCCCTGAGCCAGTC
ACCGTGACCTGGAACTCTGGAGCCCTGTCCAGCGATGTGCACACCTTTCCAGC
TGTCCTGCAGTCTGGGCTCTACACTCTCACCAGCTCAGTGACCTCCAGCACCTG
GCCCAGCCAGACCGTCACCTGCAACGTAGCCCACCCGGCCAGCAGCACCAAGG
TGGACAAGAAAGTTGAGCGCAGAAATGGCGGCATTGGACACAAATGCCCTACA
TGCCCTACATGTCACAAATGCCCAGTTCCTGAACTCTTGGGTGGACCATCTGTC
TTCATCTTCCCGCCAAAGCCCAAGGACATCCTCTTGATCTCCCAGAACGCCAAG
GTCACGTGTGTGGTGGTGGATGTGAGCGAGGAGGAGCCGGACGTCCAGTTCA
GCTGGTTTGTGAACAACGTAGAAGTACACACAGCTCAGACACAACCCCGTGAG
GAGCAGTACAACAGCACCTTCAGAGTGGTCAGTGCCCTCCCCATCCAGCACCA
GGACTGGATGAGCGGCAAGGAGTTCAAATGCAAGGTCAACAACAAAGCCCTCC
CAAGCCCCATCGAGAAAACCATCTCAAAACCCAAAGGGCTAGTCAGAAAACCA
CAGGTATACGTCATGGGTCCACCGACAGAGCAGTTGACTGAGCAAACGGTCAG
TTTGACCTGCTTGACCTCAGGCTTCCTCCCTAACGACATCGGTGTGGAGTGGAC
CAGCAACGGGCATATAGAAAAGAACTACAAGAACACCGAGCCAGTGATGGACT
CTGACGGTTCTTTCTTCATGTACAGCAAGCTCAATGTGGAAGGAGCAGGTGG
GATAGCAGAGCGCCCTTCGTCTGCTCCGTGGTCCACGAGGGTCTGCACAATCA
CCACGTGGAGAAGAGCATCTCCCGGCCTCCGGGTAAA

Signal sequence (1-57), heavy chain variable region (58-426), heavy chain constant region (427-1425)
CDRH1(133-162), CDRH2(205-234), CDRH3 (352-393)

[Figure 4]

SEQ ID NO 17: Amino acid sequence of 04-079 antibody light chain

METDRLLLWVLLLWVPGSTGDTVLTQSPALAVSLGQRVTISCRASKSVSTYMHW
YQQRSGQQPKLLIYSASNLESGVPSRFSGSGSGTDFTLTIDPVKADDITNYYCQQ
SNELPYTFGAGTKLELKRADAAPTVSIFPPSTEQLATGGASVVCLMNNFYPRDIS
VKWKIDGTERRDGVLDSVTDQDSKDSTYSMSSTLSLTKADYESHNLYTCEVVHK
TSSSPVVKSFNRNEC

Signal sequence (1-20), light chain variable region (21-128), light chain constant region (129-233)
CDRL1 (43-53), CDRL2 (69-75), CDRL3 (108-116)

SEQ ID NO 38: Nucleotide sequence of 04-079 antibody light chain

ATGGAGACAGACAGACTCCTGCTATGGGTGCTGCTGCTCTGGGTTCCAGGCTC
CACTGGTGACACTGTGCTGACCCAGTCTCCTGCTTTGGCTGTGTCTCTAGGGC
AGAGGGTCACCATCTCTTGTAGGGCCAGCAAAAGTGTCAGTACATATATGCACT
GGTACCAACAGAGGTCGGGACAGCAACCCAAACTCCTGATCTATAGTGCATCCA
ACCTAGAATCTGGAGTCCCTTCCAGGTTCAGTGGGAGTGGGTCTGGGACAGAC
TTTACCCTCACCATAGATCCTGTGAAGGCTGATGACATAACAAACTATTACTGTC
AGCAGAGTAATGAACTTCCGTACACGTTTGGAGCTGGGACCAAGCTGGAACTG
AAACGGGCTGATGCTGCACCAACTGTATCTATCTTCCCACCATCCACGGAACAG
TTAGCAACTGGAGGTGCCTCAGTCGTGTGCCTCATGAACAACTTCTATCCCAGA
GACATCAGTGTCAAGTGGAAGATTGATGGCACTGAACGACGAGATGGTGTCCT
GGACAGTGTTACTGATCAGGACAGCAAAGACAGCACGTACAGCATGAGCAGCA
CCCTCTCGTTGACCAAGGCTGACTATGAAAGTCATAACCTCTATACCTGTGAGG
TTGTTCATAAGACATCATCCTCACCCGTCGTCAAGAGCTTCAACAGGAATGAGT
GT

Signal sequence (1-60), light chain variable region (61-384), light chain constant region (385-699)
CDRL1(127-159), CDRL2(205-225), CDRL3 (322-348)

[Figure 5]

SEQ ID NO 22: Amino acid sequence of 04-126 antibody heavy chain

MEWNWVFLFLLSVTAEVHSQVQLRQSGAELAKPGSSVKISCKASGYTFTSYYII
WMKQTAGQGLQYVGYINPGSGHTNYNEKFKGKATLTVDKSSSTAFMQLSSLTP
DDSAVYYCARGTGGFLRIISKFDYWGQGVMVTVSSAQTTAPSVYPLAPGCGDTTS
STVTLGCLVKGYFPEPVTVTWNSGALSSDVHTFPAVLQSGLYTLTSSVTSSTWPS
QTVTCNVAHPASSTKVDKKVERRNGGIGHKCPTCPTCHKCPVPELLGGPSVFIF
PPKPKDILLISQNAKVTCVVVDVSEEEPDVQFSWFVNNVEVHTAQTQPREEQYN
STFRVVSALPIQHQDWMSGKEFKCKVNNKALPSPIEKTISKPKGLVRKPQVYVM
GPPTEQLTEQTVSLTCLTSGFLPNDIGVEWTSNGHIEKNYKNTEPVMDSDGSFF
MYSKLNVERSRWDSRAPFVCSVVHEGLHNHHVEKSISRPPGK

Signal sequence (1-19), heavy chain variable region (20-142), heavy chain constant region (143-475)
CDRH1 (45-54), CDRH2 (69-78), CDRH3 (118-131)

SEQ ID NO 40: Nucleotide sequence of 04-126 antibody heavy chain

ATGGAATGGAACTGGGTCTTTCTCTTCCTCCTGTCAGTAACTGCAGAAGTCCAC
TCCCAGGTCCAGCTGCGGCAGTCTGGAGCTGAGTTGGCTAAGCCTGGCTCTTC
AGTGAAGATTTCCTGCAAGGCTTCTGGCTACACCTTCACCAGCTACTATATAATC
TGGATGAAACAGACGGCTGGCCAGGGCCTTCAGTATGTTGGATATATTAATCCG
GGAAGTGGACATACTAACTACAATGAGAAGTTCAAGGGCAAGGCCACATTGAC
TGTAGACAAATCCTCCAGCACAGCCTTCATGCAACTCAGCAGCCTGACACCTGA
CGACTCTGCGGTCTATTACTGTGCAAGAGGGACTGGGGGTTTTCTACGGATTAT
TAGTAAGTTTGATTACTGGGGCCAAGGAGTCATGGTCACAGTCTCCTCAGCCCA
AACAACAGCCCCATCTGTCTATCCACTGGCTCCTGGATGTGGTGATACAACCAG
CTCCACGGTGACTCTGGGATGCCTGGTCAAGGGCTATTTCCCTGAGCCAGTCA
CCGTGACCTGGAACTCTGGAGCCCTGTCCAGCGATGTGCACACCTTTCCAGCT
GTCCTGCAGTCTGGGCTCTACACTCTCACCAGCTCAGTGACCTCCAGCACCTG
GCCCAGCCAGACCGTCACCTGCAACGTAGCCCACCCGGCCAGCAGCACCAAGG
TGGACAAGAAAGTTGAGCGCAGAAATGGCGGCATTGGACACAAATGCCCTACA
TGCCCTACATGTCACAAATGCCCAGTTCCTGAACTCTTGGGTGGACCATCTGTC
TTCATCTTCCCGCCAAAGCCCAAGGACATCCTCTTGATCTCCCAGAACGCCAAG
GTCACGTGTGTGGTGGTGGATGTGAGCGAGGAGGAGCCGGACGTCCAGTTCA
GCTGGTTTGTGAACAACGTAGAAGTACACACAGCTCAGACACAACCCCGTGAG
GAGCAGTACAACAGCACCTTCAGAGTGGTCAGTGCCCTCCCCATCCAGCACCA
GGACTGGATGAGCGGCAAGGAGTTCAAATGCAAGGTCAACAACAAAGCCCTCC
CAAGCCCCATCGAGAAAACCATCTCAAAACCCAAAGGGCTAGTCAGAAAACCA
CAGGTATACGTCATGGGTCCACCGACAGAGCAGTTGACTGAGCAAACGGTCAG
TTTGACCTGCTTGACCTCAGGCTTCCTCCCTAACGACATCGGTGTGGAGTGGAC
CAGCAACGGGCATATAGAAAAGAACTACAAGAACACCGAGCCAGTGATGGACT
CTGACGGTTCTTTCTTCATGTACAGCAAGCTCAATGTGGAAAGGAGCAGGTGG
GATAGCAGAGCGCCCTTCGTCTGCTCCGTGGTCCACGAGGGTCTGCACAATCA
CCACGTGGAGAAGAGCATCTCCCGGCCTCCGGGTAAA

Signal sequence (1-57), heavy chain variable region (58-426), heavy chain constant region (427-1425)
CDRH1(133-162), CDRH2(205-234), CDRH3 (352-393)

[Figure 6]

SEQ ID NO 27: Amino acid sequence of 04-126 antibody light chain

METDRLLLWVLLLWVPGSTGDTVLTQSPALAVSLGQRVTISCRASKSVSTYMHW
YQQRSGQQPKLLIYSASTLESGVPSRFSGSGSGTDFTLTIDPVEADDIANYYCQQS
NELPYTFGAGTKLELKRADAAPTVSIFPPSTEQLATGGASVVCLMNNFYPRDISV
KWKIDGTERRDGVLDSVTDQDSKDSTYSMSSTLSLTKADYESHNLYTCEVVHKT
SSSPVVKSFNRNEC

Signal sequence (1-20), light chain variable region (21-128), light chain constant region (129-233)
CDRL1 (43-53), CDRL2 (69-75), CDRL3 (108-116)

SEQ ID NO 42: Nucleotide sequence of 04-126 antibody light chain

ATGGAGACAGACAGACTCCTGCTATGGGTGCTGCTGCTCTGGGTTCCAGGCTC
CACTGGTGACACTGTGCTGACCCAGTCTCCTGCTTTGGCTGTGTCTCTAGGGC
AGAGGGTCACCATCTCTTGTAGGGCCAGCAAAAGTGTCAGTACATATATGCACT
GGTACCAACAGAGGTCGGGACAGCAACCCAAACTCCTGATCTATAGTGCTTCCA
CCCTAGAATCTGGAGTCCCTTCCAGGTTCAGTGGGAGTGGGTCTGGGACAGAC
TTTACCCTCACCATAGATCCTGTGGAGGCTGATGACATAGCAAACTATTACTGTC
AGCAGAGTAATGAACTTCCGTACACGTTTGGAGCTGGGACCAAGCTGGAACTG
AAACGGGCTGATGCTGCACCAACTGTATCTATCTTCCCACCATCCACGGAACAG
TTAGCAACTGGAGGTGCCTCAGTCGTGTGCCTCATGAACAACTTCTATCCCAGA
GACATCAGTGTCAAGTGGAAGATTGATGGCACTGAACGACGAGATGGTGTCCT
GGACAGTGTTACTGATCAGGACAGCAAAGACAGCACGTACAGCATGAGCAGCA
CCCTCTCGTTGACCAAGGCTGACTATGAAAGTCATAACCTCTATACCTGTGAGG
TTGTTCATAAGACATCATCCTCACCCGTCGTCAAGAGCTTCAACAGGAATGAGT
GT

Signal sequence (1-60), light chain variable region (61-384), light chain constant region (385-699)
CDRL1(127-159), CDRL2(205-225), CDRL3 (322-348)

[Figure 7]

SEQ ID NO 44: Amino acid sequence of 04-046Ch antibody heavy chain

MKHLWFFLLLVAAPRWVLSQVQLQQSGAELAKPGSSVKISCKASGYTFTSYY
ISWIKQTTGQGLKYIGFINPGSGHTNYNEKFKGKATLTVDKSSSTAFMQLSS
LTPDDSAIYYCARGAGGFLRIITKFDYWGQGVMVTVSSASTKGPSVFPLAPSS
KSTSGGTAALGCLVKDYFPEPVTVSWNSGALTSGVHTFPAVLQSSGLYSLSSV
VTVPSSSLGTQTYICNVNHKPSNTKVDKRVEPKSCDKTHTCPPCPAPELLGG
PSVFLFPPKPKDTLMISRTPEVTCVVVDVSHEDPEVKFNWYVDGVEVHNAK
TKPREEQYNSTYRVVSVLTVLHQDWLNGKEYKCKVSNKALPAPIEKTISKAK
GQPREPQVYTLPPSREEMTKNQVSLTCLVKGFYPSDIAVEWESNGQPENNY
KTTPPVLDSDGSFFLYSKLTVDKSRWQQGNVFSCSVMHEALHNHYTQKSLS
LSPGK

Signal sequence (1-19), heavy chain variable region (20-142), heavy chain constant region (143-472)

SEQ ID NO 46: Nucleotide sequence of 04-046Ch antibody heavy chain

ATGAAACACCTGTGGTTCTTCCTCCTGCTGGTGGCAGCTCCCAGATGGGTG
CTGAGCCAGGTGCAGCTGCAGCAGTCTGGCGCCGAACTGGCCAAGCCTGG
CAGCAGCGTGAAGATCAGCTGCAAGGCCAGCGGCTACACCTTCACCAGCTA
CTACATCAGCTGGATCAAGCAGACCACCGGCCAGGGCCTGAAGTACATCGG
CTTCATCAACCCCGGCAGCGGCCACACCAACTACAACGAGAAGTTCAAGGG
CAAGGCCACCCTGACCGTGGACAAGAGCAGCAGCACCGCCTTCATGCAGC
TGTCCAGCCTGACCCCCGACGACAGCGCCATCTACTACTGTGCTAGAGGCG
CTGGCGGCTTCCTGCGGATCATCACCAAGTTCGACTACTGGGGCCAGGGCG
TGATGGTCACCGTCAGCTCAGCCTCCACCAAGGGCCCAAGCGTCTTCCCCC
TGGCACCCTCCTCCAAGAGCACCTCTGGCGGCACAGCCGCCCTGGGCTGC
CTGGTCAAGGACTACTTCCCCGAACCCGTGACCGTGAGCTGGAACTCAGGC
GCCCTGACCAGCGGCGTGCACACCTTCCCCGCTGTCCTGCAGTCCTCAGGA
CTCTACTCCCTCAGCAGCGTGGTGACCGTGCCCTCCAGCAGCTTGGGCACC
CAGACCTACATCTGCAACGTGAATCACAAGCCCAGCAACACCAAGGTGGAC
AAGAGAGTTGAGCCCAAATCTTGTGACAAAACTCACACATGCCCACCCTGC
CCAGCACCTGAACTCCTGGGGGGACCCTCAGTCTTCCTCTTCCCCCCAAAA
CCCAAGGACACCCTCATGATCTCCCGGACCCCTGAGGTCACATGCGTGGTG
GTGGACGTGAGCCACGAAGACCCTGAGGTCAAGTTCAACTGGTACGTGGA
CGGCGTGGAGGTGCATAATGCCAAGACAAAGCCCCGGGAGGAGCAGTACA
ACAGCACGTACCGGGTGGTCAGCGTCCTCACCGTCCTGCACCAGGACTGG
CTGAATGGCAAGGAGTACAAGTGCAAGGTCTCCAACAAAGCCCTCCCAGCC
CCCATCGAGAAAACCATCTCCAAAGCCAAAGGCCAGCCCGGGAACCACA
GGTGTACACCCTGCCCCCATCCCGGGAGGAGATGACCAAGAACCAGGTCA
GCCTGACCTGCCTGGTCAAAGGCTTCTATCCCAGCGACATCGCCGTGGAGT
GGGAGAGCAATGGCCAGCCCGAGAACAACTACAAGACCACCCCTCCCGTG
CTGGACTCCGACGGCTCCTTCTTCCTCTACAGCAAGCTCACCGTGGACAAG
AGCAGGTGGCAGCAGGGCAACGTCTTCTCATGCTCCGTGATGCATGAGGCT
CTGCACAACCACTACACCCAGAAGAGCCTCTCCCTGTCTCCGGCAAA

Signal sequence (1-57), heavy chain variable region (58-426), heavy chain constant region (427-1416)

[Figure 8]

SEQ ID NO 45: Amino acid sequence of 04-046Ch antibody light chain

MVLQTQVFISLLLWISGAYGDTVLTQSPALAVSLGQRVTISCRASKSVS
TYIHWYQQRSGQQPKLLIYSASNLESGVPSRFSGSGSGTDFTLTIDPV
EPDDIANYYCQQINELPYTFGAGTKLELKRAVAAPSVFIFPPSDEQLKS
GTASVVCLLNNFYPREAKVQWKVDNALQSGNSQESVTEQDSKDSTY
SLSSTLTLSKADYEKHKVYACEVTHQGLSSPVTKSFNRGEC

Signal sequence (1-20), light chain variable region (21-128), light chain constant region (129-233)

SEQ ID NO 47: Nucleotide sequence of 04-046Ch antibody light chain

ATGGTGCTGCAGACCCAGGTGTTCATCTCCCTGCTGCTGTGGATCTC
CGGCGCGTACGGCGATACCGTGCTGACACAGTCTCCAGCCCTGGCC
GTGTCCCTGGGCCAGAGAGTGACCATCAGCTGCAGAGCCAGCAAGA
GCGTGTCCACCTACATCCACTGGTATCAGCAGCGGAGCGGCCAGCA
GCCCAAGCTGCTGATCTACAGCGCCAGCAACCTGGAAAGCGGCGTG
CCCAGCAGATTTTCCGGCAGCGGCTCTGGCACCGACTTCACCCTGAC
CATCGACCCCGTGGAACCCGACGATATCGCCAACTACTACTGCCAGC
AGATCAACGAGCTGCCCTACACCTTCGGAGCCGGCACCAAGCTGGA
ACTGAAGAGAGCCGTGGCCGCCCCTCCGTGTTCATCTTCCCCCCT
CCGACGAGCAGCTGAAGTCCGGCACCGCCTCCGTGGTGTGCCTGCT
GAATAACTTCTACCCCAGAGAGGCCAAGGTGCAGTGGAAGGTGGAC
AACGCCCTGCAGTCCGGGAACTCCCAGGAGAGCGTGACCGAGCAGG
ACAGCAAGGACAGCACCTACAGCCTGAGCAGCACCCTGACCCTGAG
CAAAGCCGACTACGAGAAGCACAAGGTGTACGCCTGCGAGGTGACC
CACCAGGGCCTGAGCTCCCCCGTCACCAAGAGCTTCAACAGGGGGG
AGTGT

Signal sequence (1-60), light chain variable region (61-384), light chain constant region (385-699)

[Figure 9]

SEQ ID NO 48: Amino acid sequence of humanized h046-H4b

MKHLWFFLLLVAAPRWVLSQVQLVQSGAEVKKPGASVKVSCKASGY
TFTSYYISWIRQAPGQGLKYMGFINPGSGHTNYNEKFKGRVTITADKS
SSTATMELSSLRSEDTAVYYCARGAGGFLRIITKFDYWGQGTLVTVSS
ASTKGPSVFPLAPSSKSTSGGTAALGCLVKDYFPEPVTVSWNSGALTS
GVHTFPAVLQSSGLYSLSSVVTVPSSSLGTQTYICNVNHKPSNTKVDK
RVEPKSCDKTHTCPPCPAPELLGGPSVFLFPPKPKDTLMISRTPEVTC
VVVDVSHEDPEVKFNWYVDGVEVHNAKTKPREEQYNSTYRVVSVLT
VLHQDWLNGKEYKCKVSNKALPAPIEKTISKAKGQPREPQVYTLPPS
REEMTKNQVSLTCLVKGFYPSDIAVEWESNGQPENNYKTTPPVLDSD
GSFFLYSKLTVDKSRWQQGNVFSCSVMHEALHNHYTQKSLSLSPGK

Signal sequence (1-19), heavy chain variable region (20-142), heavy chain constant region (143-472)

[Figure 10]

SEQ ID NO 50: Amino acid sequence of humanized h046-H4e

MKHLWFFLLLVAAPRWVLSEVQLVQSGAEVKKPGASVKVSCKASGY
TFTSYYISWIRQAPGQGLKYMGFINPGSGHTNYNEKFKGRVTITADKS
SSTATMELSSLRSEDTAVYYCARGAGGFLRIITKFDYWGQGTLVTVSS
ASTKGPSVFPLAPSSKSTSGGTAALGCLVKDYFPEPVTVSWNSGALTS
GVHTFPAVLQSSGLYSLSSVVTVPSSSLGTQTYICNVNHKPSNTKVDK
RVEPKSCDKTHTCPPCPAPELLGGPSVFLFPPKPKDTLMISRTPEVTC
VVVDVSHEDPEVKFNWYVDGVEVHNAKTKPREEQYNSTYRVVSVLT
VLHQDWLNGKEYKCKVSNKALPAPIEKTISKAKGQPREPQVYTLPPS
REEMTKNQVSLTCLVKGFYPSDIAVEWESNGQPENNYKTTPPVLDSD
GSFFLYSKLTVDKSRWQQGNVFSCSVMHEALHNHYTQKSLSLSPGK

Signal sequence (1-19), heavy chain variable region (20-142), heavy chain constant region (143-472)

[Figure 11]

SEQ ID NO 52: Amino acid sequence of humanized h046-H5b

MKHLWFFLLLVAAPRWVLSQVQLVQSGAEVKKPGASVKVSCKASGYTFTS
YYISWIRQAPGQGLKYMGFINPGSGHTNYNEKFKGRVTITADKSSSTANME
LSSLRSEDTAVYYCARGAGGFLRIITKFDYWGQGTLVTVSSASTKGPSVFP
LAPSSKSTSGGTAALGCLVKDYFPEPVTVSWNSGALTSGVHTFPAVLQSS
GLYSLSSVVTVPSSSLGTQTYICNVNHKPSNTKVDKRVEPKSCDKTHTCPP
CPAPELLGGPSVFLFPPKPKDTLMISRTPEVTCVVVDVSHEDPEVKFNWYV
DGVEVHNAKTKPREEQYNSTYRVVSVLTVLHQDWLNGKEYKCKVSNKAL
PAPIEKTISKAKGQPREPQVYTLPPSREEMTKNQVSLTCLVKGFYPSDIAVE
WESNGQPENNYKTTPPVLDSDGSFFLYSKLTVDKSRWQQGNVFSCSVMH
EALHNHYTQKSLSLSPGK

Signal sequence (1-19), heavy chain variable region (20-142), heavy chain constant region (143-472)

[Figure 12]

SEQ ID NO 54: Amino acid sequence of humanized h046-H8

MKHLWFFLLLVAAPRWVLSQVQLQQSGAELAKPGSSVKISCKASGYT
FTSYYISWIKQTTGQGLKYIGFINPGSGHTNYNEKFKGKATLTVDKSS
STANMQLSSLTPDDSAIYYCARGAGGFLRIITKFDYWGQGVMVTVSSA
STKGPSVFPLAPSSKSTSGGTAALGCLVKDYFPEPVTVSWNSGALTSG
VHTFPAVLQSSGLYSLSSVVTVPSSSLGTQTYICNVNHKPSNTKVDKR
VEPKSCDKTHTCPPCPAPELLGGPSVFLFPPKPKDTLMISRTPEVTCV
VVDVSHEDPEVKFNWYVDGVEVHNAKTKPREEQYNSTYRVVSVLTV
LHQDWLNGKEYKCKVSNKALPAPIEKTISKAKGQPREPQVYTLPPSR
EEMTKNQVSLTCLVKGFYPSDIAVEWESNGQPENNYKTTPPVLDSD
GSFFLYSKLTVDKSRWQQGNVFSCSVMHEALHNHYTQKSLSLSPGK

Signal sequence (1-19), heavy chain variable region (20-142), heavy chain constant region (143-472)

[Figure 13]

SEQ ID NO 56: Amino acid sequence of humanized h046-H10

MKHLWFFLLLVAAPRWVLSQVQLQQSGAELAKPGSSVKVSCKASGY
TFTSYYISWIKQTTGQGLKYIGFINPGSGHTNYNEKFKGKATLTVDKS
SSTANMQLSSLTPDDSAIYYCARGAGGFLRIITKFDYWGQGVMVTVSS
ASTKGPSVFPLAPSSKSTSGGTAALGCLVKDYFPEPVTVSWNSGALTS
GVHTFPAVLQSSGLYSLSSVVTVPSSSLGTQTYICNVNHKPSNTKVDK
RVEPKSCDKTHTCPPCPAPELLGGPSVFLFPPKPKDTLMISRTPEVTC
VVVDVSHEDPEVKFNWYVDGVEVHNAKTKPREEQYNSTYRVVSVLT
VLHQDWLNGKEYKCKVSNKALPAPIEKTISKAKGQPREPQVYTLPPS
REEMTKNQVSLTCLVKGFYPSDIAVEWESNGQPENNYKTTPPVLDSD
GSFFLYSKLTVDKSRWQQGNVFSCSVMHEALHNHYTQKSLSLSPGK

Signal sequence (1-19), heavy chain variable region (20-142), heavy chain constant region (143-472)

[Figure 14]

SEQ ID NO 58: Amino acid sequence of humanized h046-L1

MVLQTQVFISLLLWISGAYGDIQMTQSPSSLSASVGDRVTITCRASKSV
STYIHWYQQKPGKAPKLLIYSASNLESGVPSRFSGSGSGTDFTLTISSL
QPEDFATYYCQQINELPYTFGQGTKVEIKRTVAAPSVFIFPPSDEQLK
SGTASVVCLLNNFYPREAKVQWKVDNALQSGNSQESVTEQDSKDST
YSLSSTLTLSKADYEKHKVYACEVTHQGLSSPVTKSFNRGEC

Signal sequence (1-20), light chain variable region (21-129), light chain constant region (130-234)

[Figure 15]

SEQ ID NO 60: Amino acid sequence of humanized h046-L2

MVLQTQVFISLLLWISGAYGDIQMTQSPSSLSASVGDRVTITCRASKSV
STYIHWYQQKPGKQPKLLIYSASNLESGVPSRFSGSGSGTDFTLTISSL
QPEDFATYYCQQINELPYTFGQGTKVEIKRTVAAPSVFIFPPSDEQLK
SGTASVVCLLNNFYPREAKVQWKVDNALQSGNSQESVTEQDSKDST
YSLSSTLTLSKADYEKHKVYACEVTHQGLSSPVTKSFNRGEC

Signal sequence (1-20), light chain variable region (21-129), light chain constant region (130-234)

[Figure 16]

SEQ ID NO 62: Amino acid sequence of humanized h046-L6

MVLQTQVFISLLLWISGAYGDTQLTQSPSSLSASVGDRVTITCRASKSV
STYIHWYQQKPGKQPKLLIYSASDRESGVPSRFSGSGSGTDFTLTISSL
QPEDFANYYCQQINELPYTFGQGTKVEIKRTVAAPSVFIFPPSDEQLK
SGTASVVCLLNNFYPREAKVQWKVDNALQSGNSQESVTEQDSKDST
YSLSSTLTLSKADYEKHKVYACEVTHQGLSSPVTKSFNRGEC

Signal sequence (1-20), light chain variable region (21-129), light chain constant region (130-234)

[Figure 17]

SEQ ID NO 64: Amino acid sequence of humanized h046-L7

MVLQTQVFISLLLWISGAYGDTQLTQSPSSLSASVGDRVTITCRASKSV
STYIHWYQQKPGKQPKLLIYSAGNLESGVPSRFSGSGSGTDFTLTISSL
QPEDFANYYCQQINELPYTFGQGTKVEIKRTVAAPSVFIFPPSDEQLK
SGTASVVCLLNNFYPREAKVQWKVDNALQSGNSQESVTEQDSKDST
YSLSSTLTLSKADYEKHKVYACEVTHQGLSSPVTKSFNRGEC

Signal sequence (1-20), light chain variable region (21-129), light chain constant region (130-234)

[Figure 18]

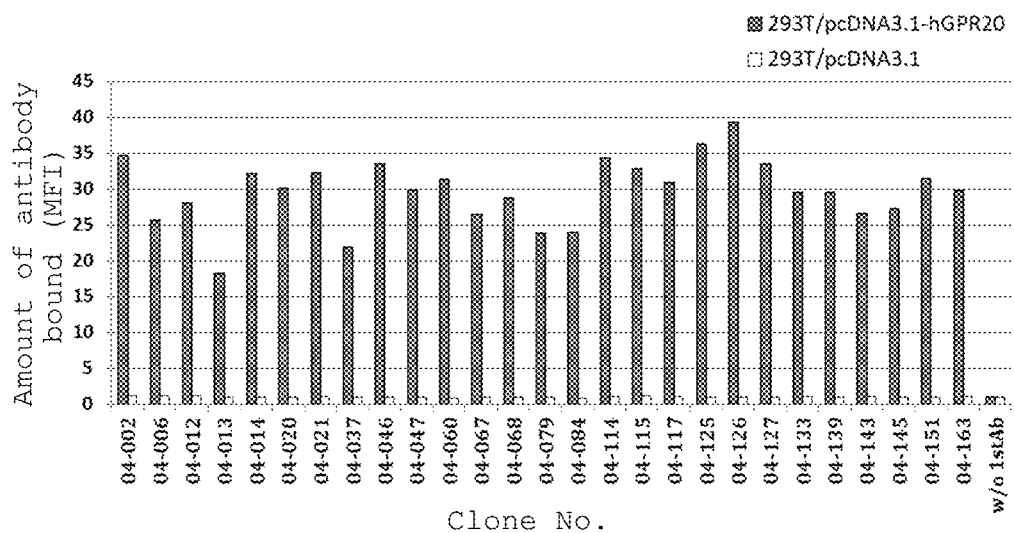

[Figure 19-1]
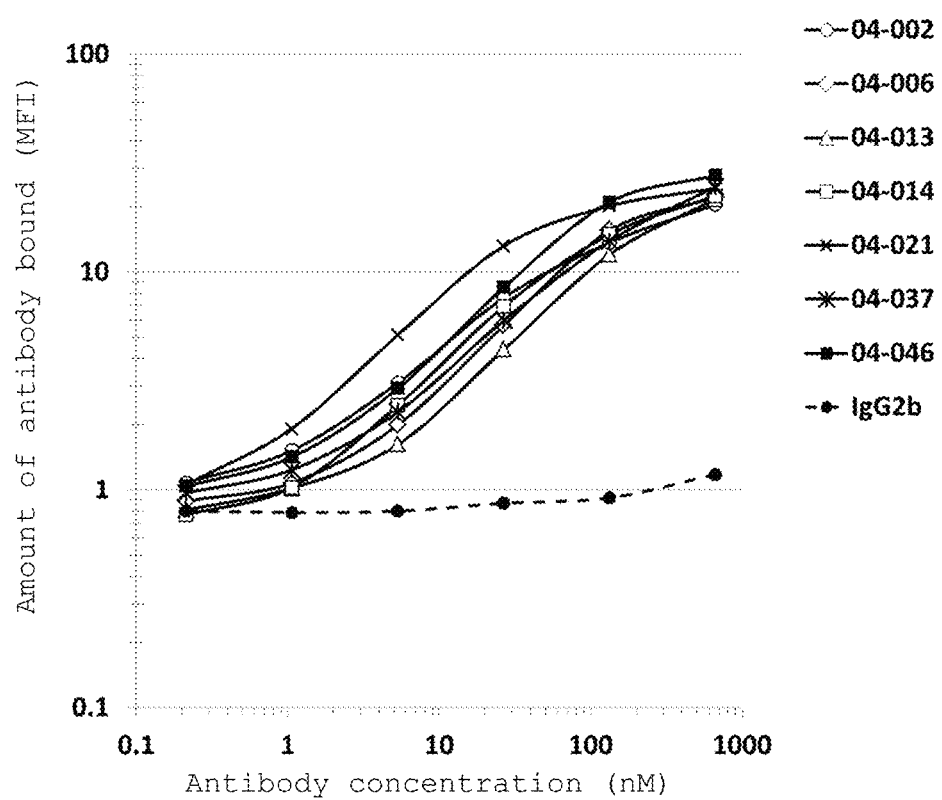

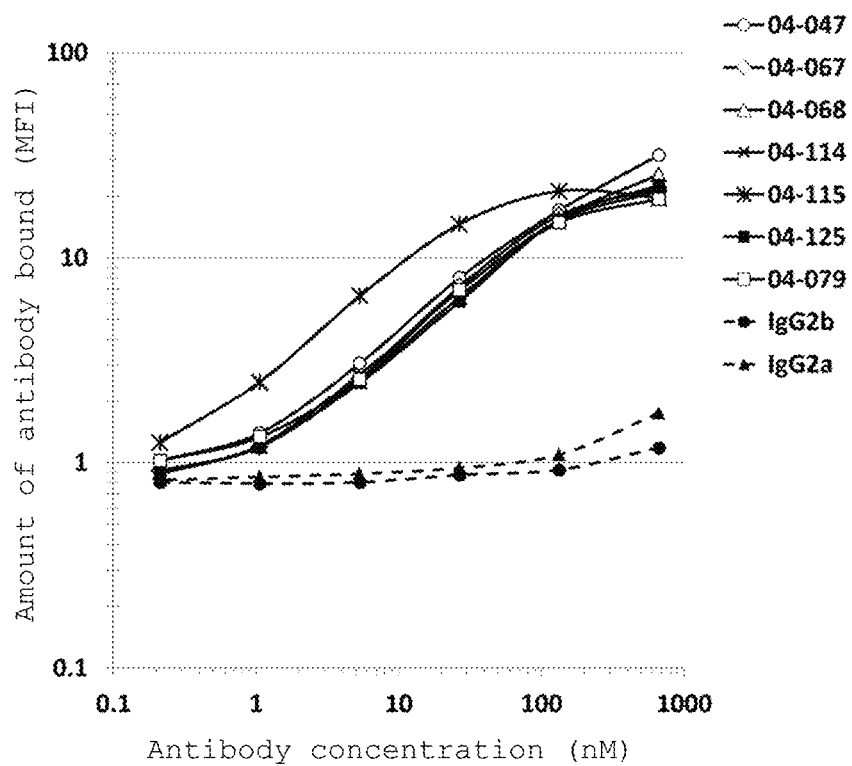
[Figure 19-2]

[Figure 19-3]
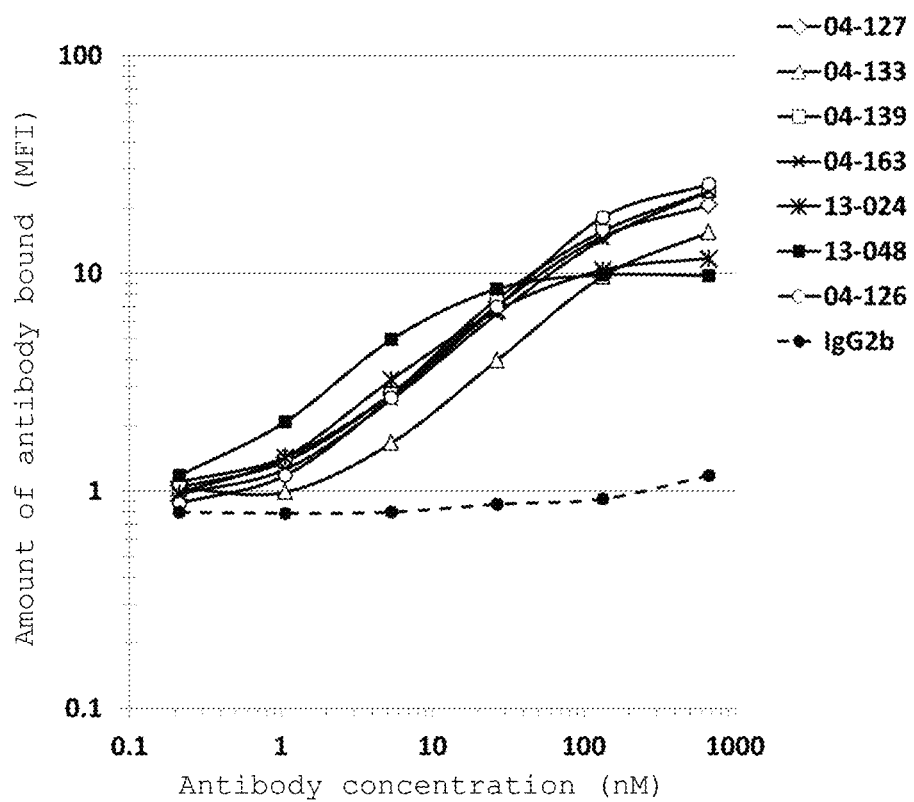

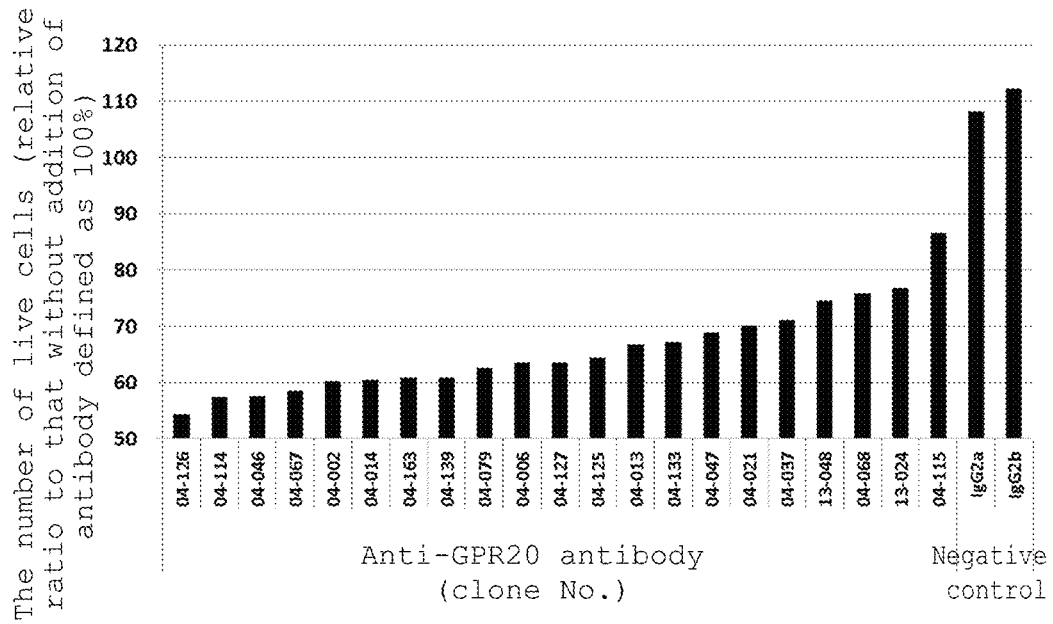
[Figure 20]

[Figure 21]

```
                            EC1 (1-48)
                    ←──────────────────────────→
Human GPR20   1:MPSVSPAGESAGAVENATAVTTVRTNASGLEVPLFHLPARLDEELBGTFP  50
Mouse GPR20   1:MPSALSMPPWDAALENTTA---AAWTNGSVPEMPLFHHPARLDEELQATFP  48

Human GPR20  51:GLWLALMAVHGAIPLAGLVLNGLALYVFCCRTRAKTPSVIYTINLVVTDL 100
Mouse GPR20  49:SLWCALMVVRGTIPLAGLVLNGLALYVFCCRTRAKTPSVTYTINLVVTDL  98

EC2 (108-125)
                    ←──────────────→
Human GPR20 101:LVGLSLPTRFAVYYGARGCLRCAFPHVLGYFLNMHCSILFLTICVDRYL 150
Mouse GPR20  99:LVGLSLPTRFAVFYGARGCLRCAFPHVLGYFLNMHCSILFLTICVDRYL 148

EC3 (190-196)
                                              ←────→
Human GPR20 151:AIVPRESRRCRQPACAKAVCAFVWLAAGAVTLSVLGV-TSSRPCCRVFA 199
Mouse GPR20 149:AIVQRESRPWRQPACAKAVCIFVWLAAGVVTLSVLGVKSG-RSCCRVFA 198

Human GPR20 200:LTVLRFLLPLLVISVFTSRIMCALSRPGLLHQSRQRRVRAMQLLLTVLII 249
Mouse GPR20 199:LTVLRFLLPLLVISVFTSRIMCALSRPGLLRQSRQRRVRAMQLLLTVLVI 248

EC4 (260-275)
                    ←────────────→
Human GPR20 250:FLVCFTPFHARQVAVALWFDMFRHTSLVVYHVAVTLSSLNSCMDPIVYCF 299
Mouse GPR20 249:FLVCFTPFHARQVAVALWFNVFKHTSLVAYHVAVTLSSLNSCMDPIVYCF 298

Human GPR20 298:VTSGFQATVRGLFGQHSE--REFSSGIVVSMHRSSKGSGRHILSAGPHAL 346
Mouse GPR20 297:ITSGFQATVRGLFYQPGEEPKESSMDVVSMHKSTKASAPIHILSIGSHTL 346

Human GPR20 349:TQALANGFEA 358
Mouse GPR20 349:TQPLTNGFEF 358
```

[Figure 22-a]
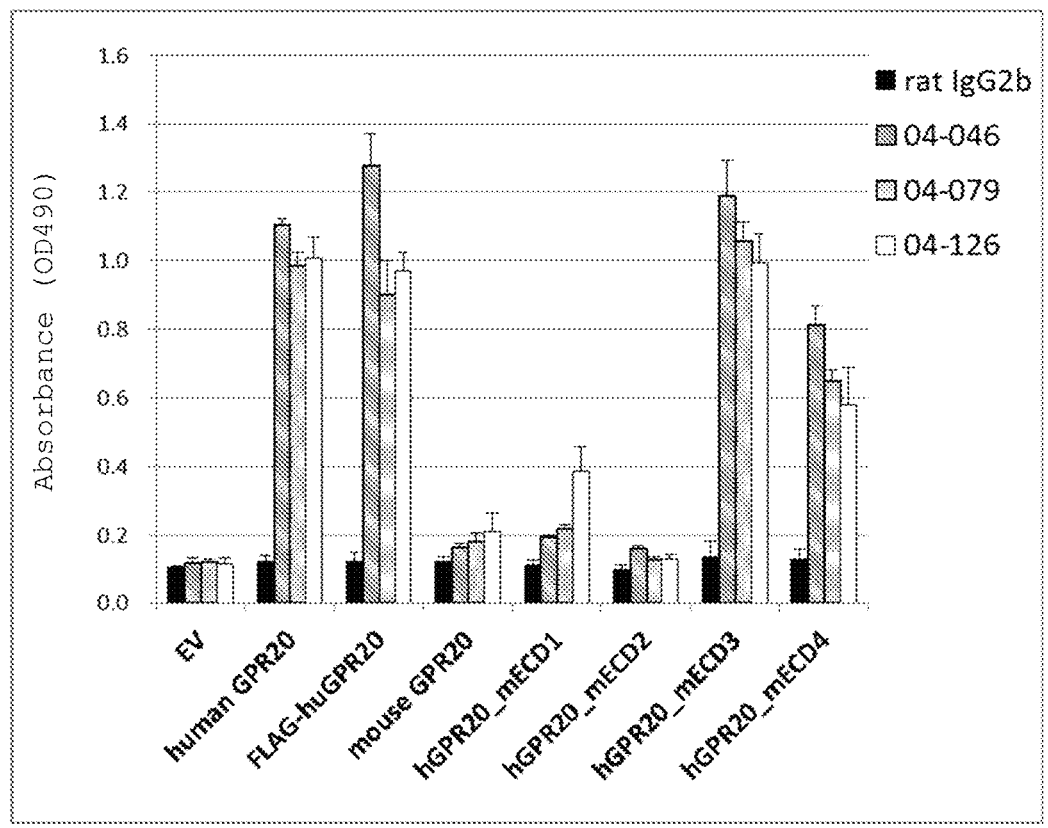

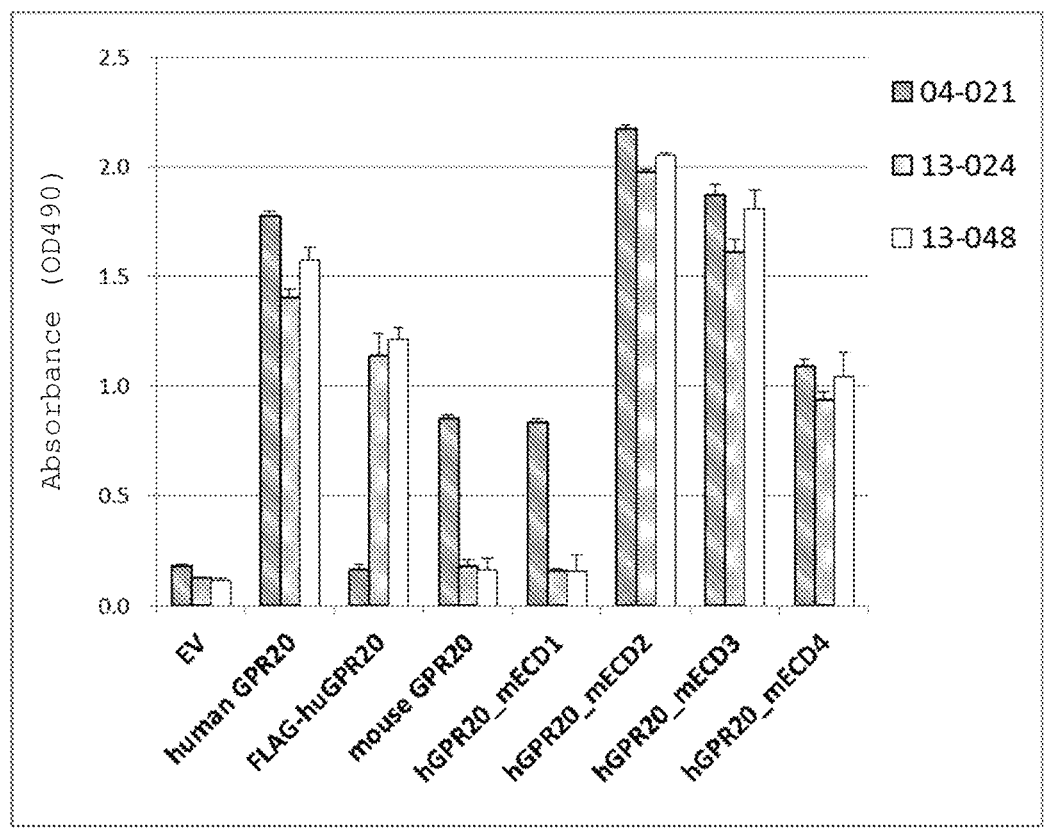
[Figure 22-b]

[Figure 23-a]
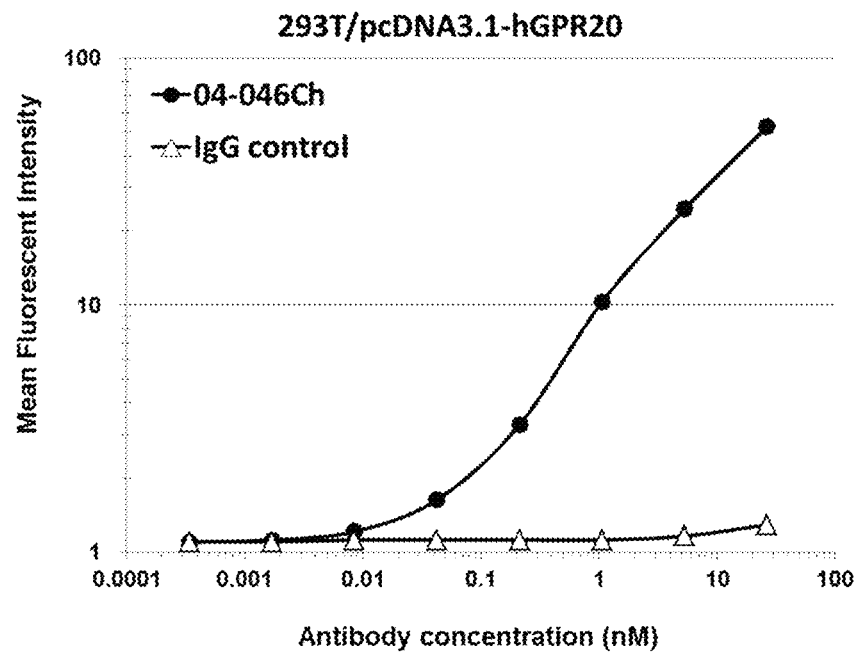
[Figure 23-b]
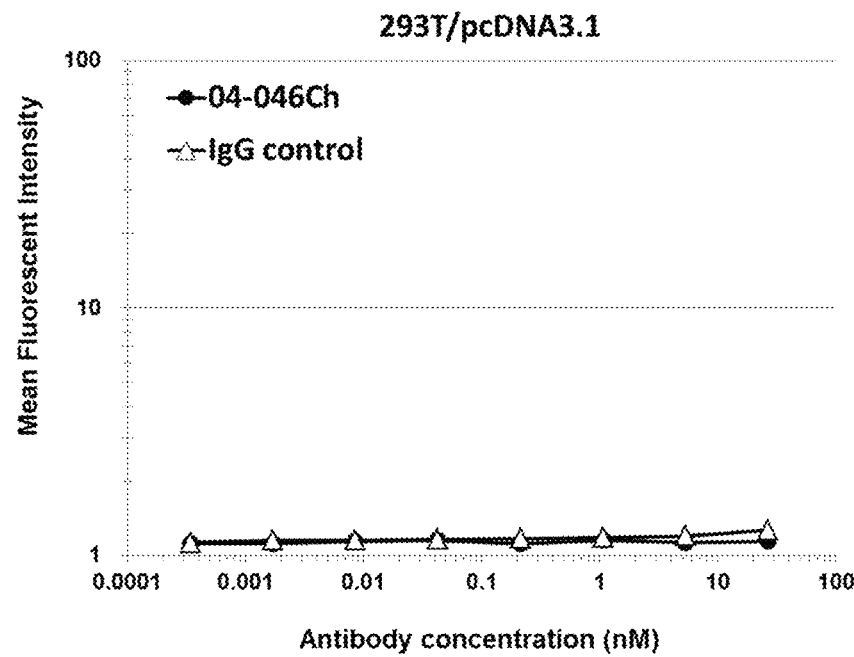

[Figure 24]
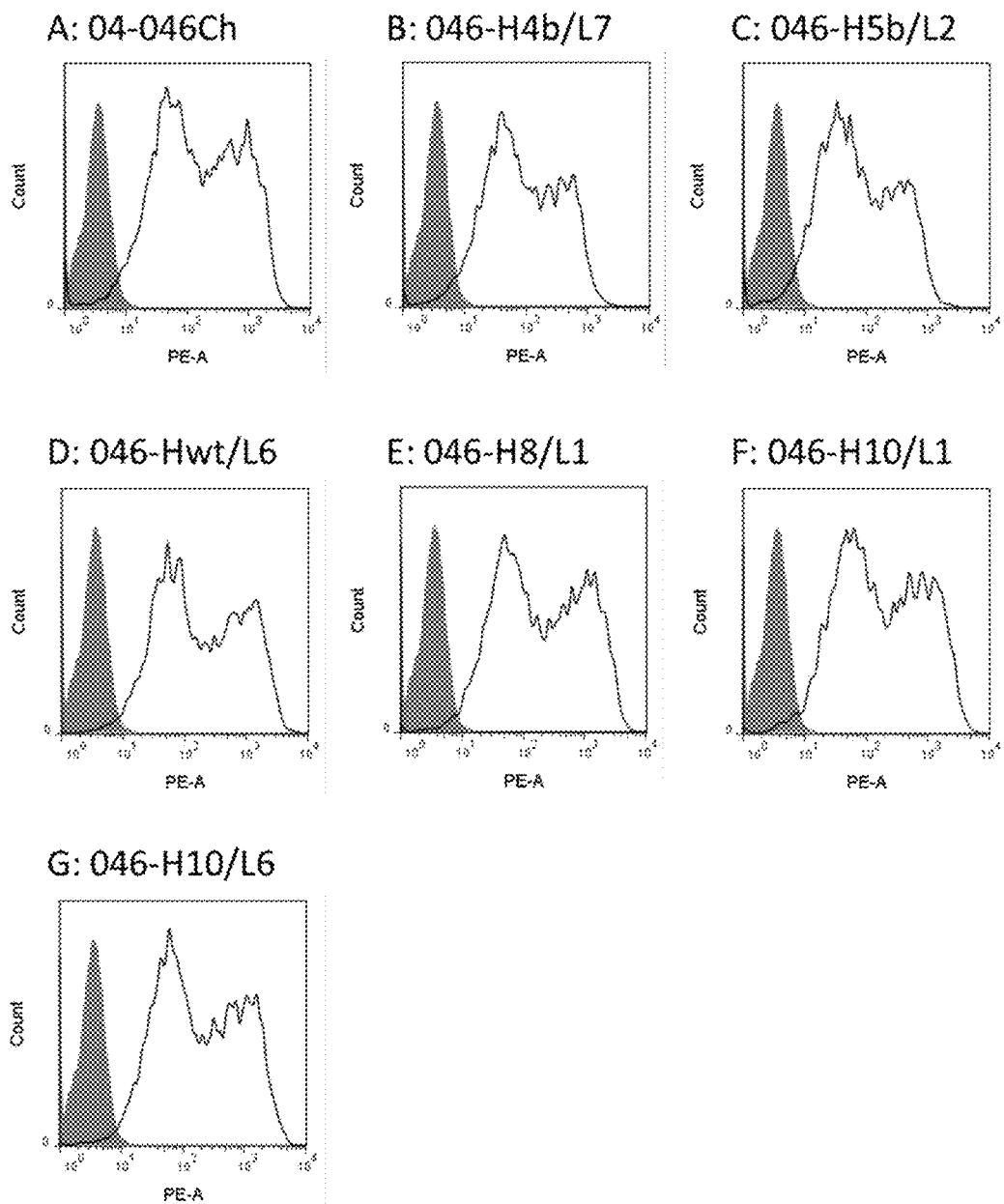

[Figure 25]
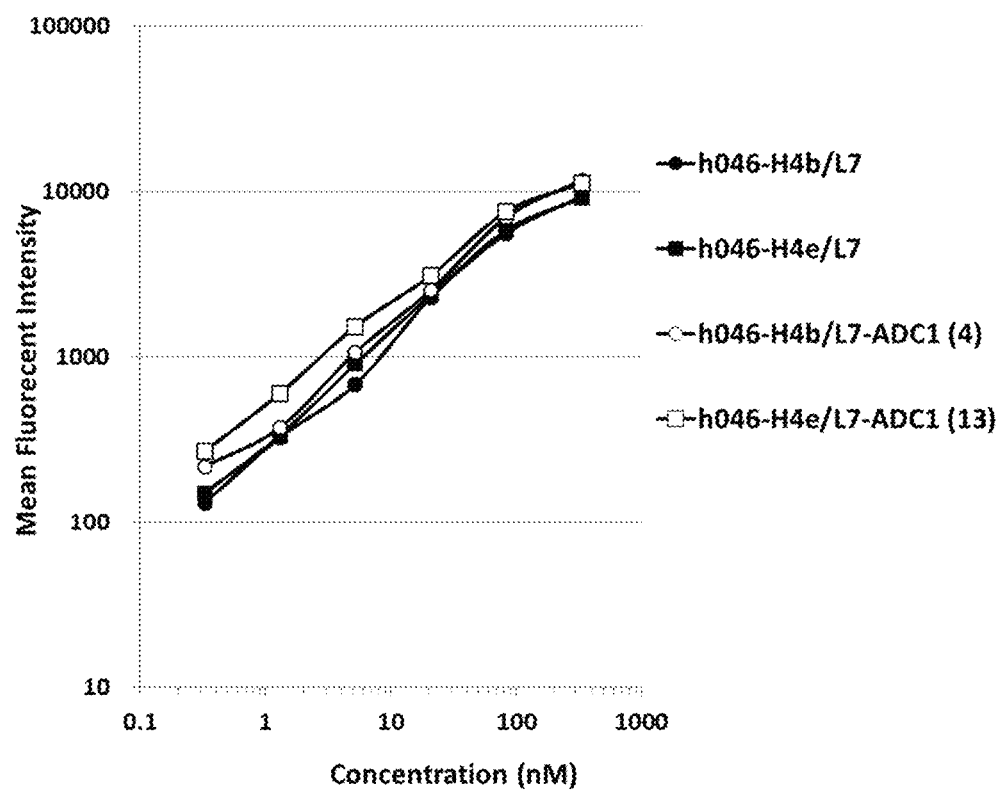

[Figure 26]
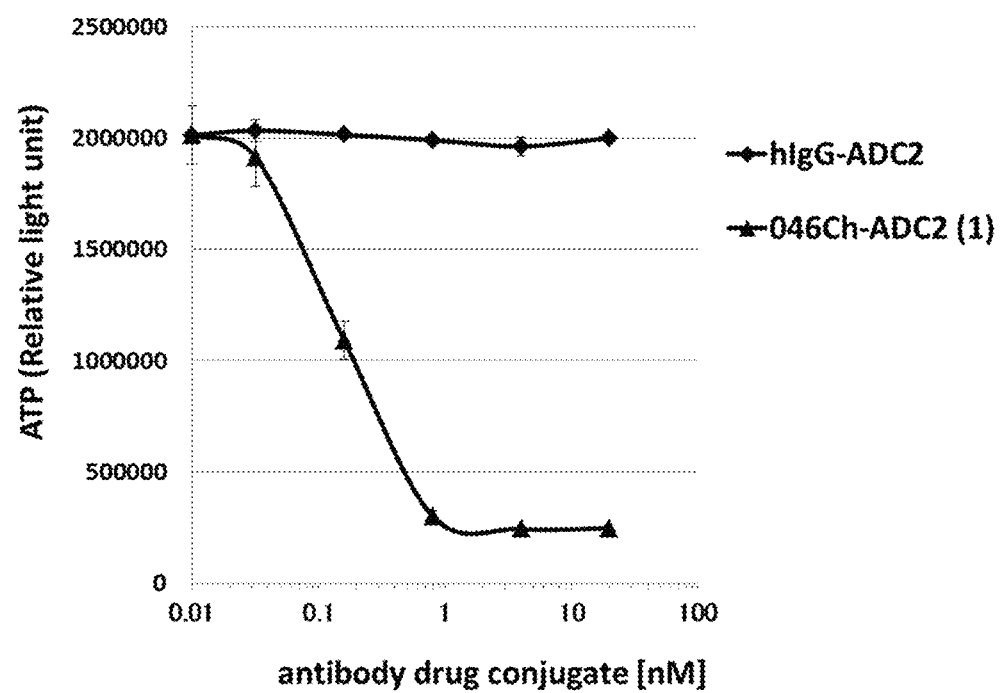

[Figure 27]
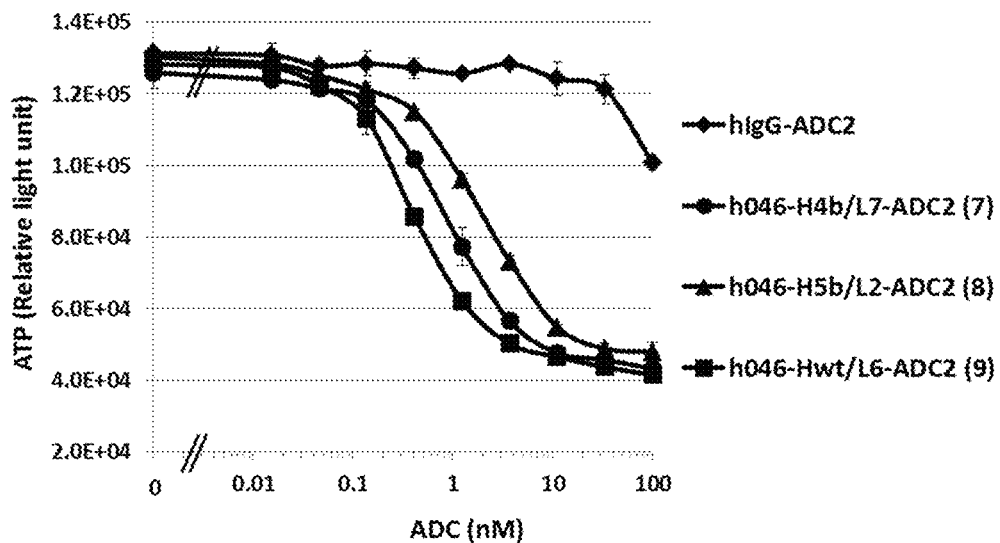
[Figure 28]
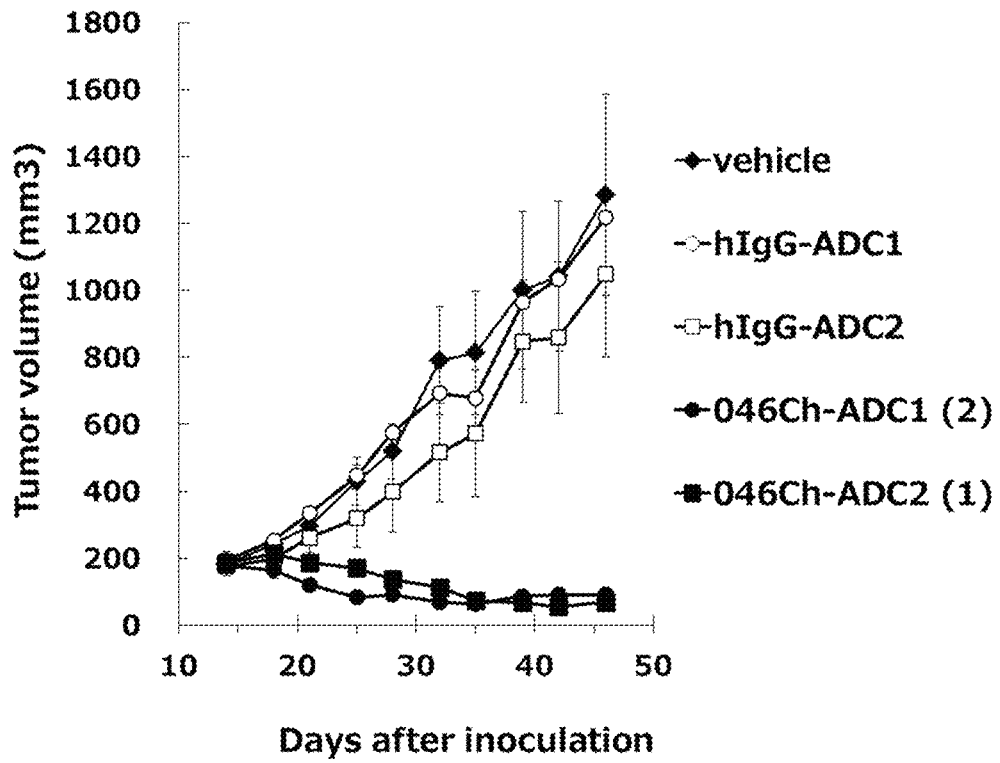

[Figure 29]
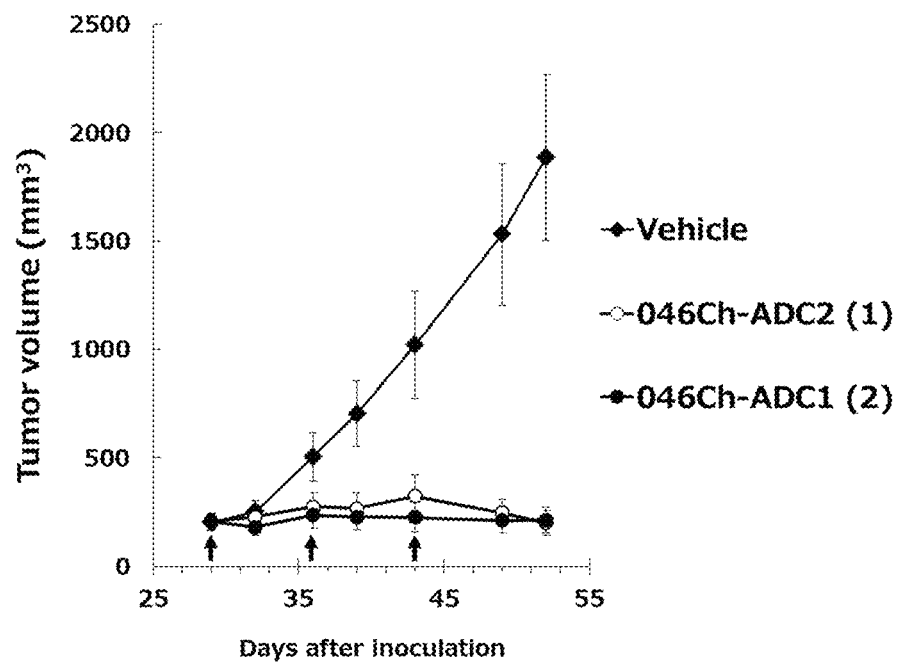
[Figure 30]
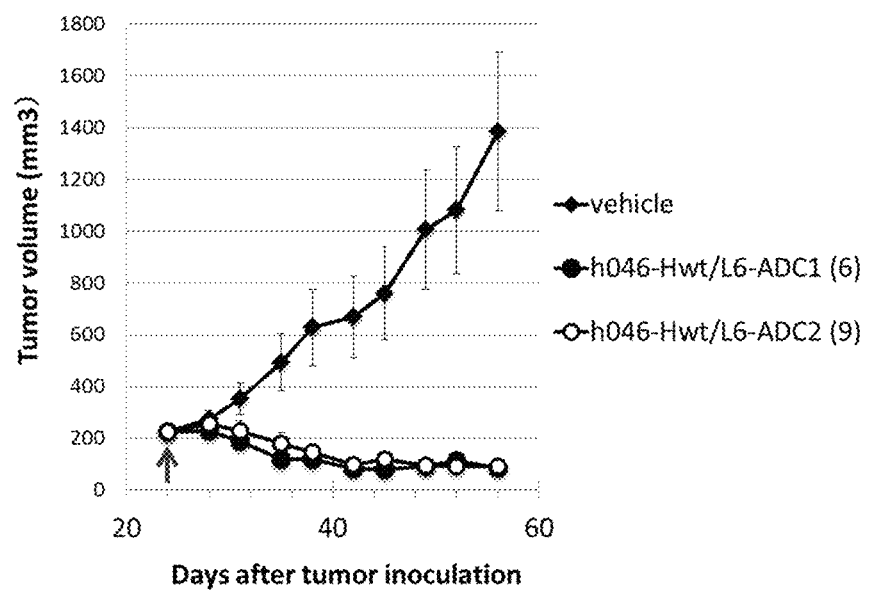

[Figure 31]
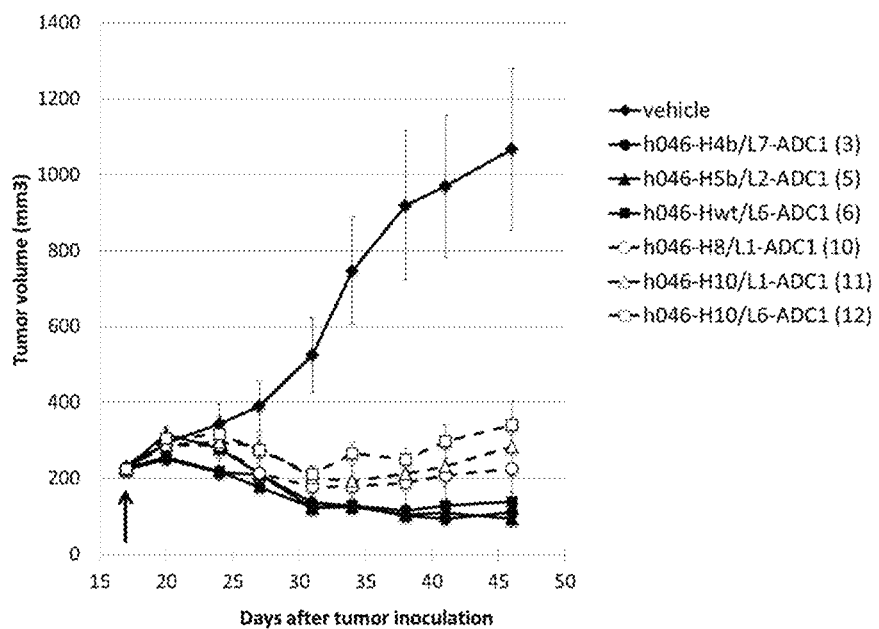
[Figure 32]
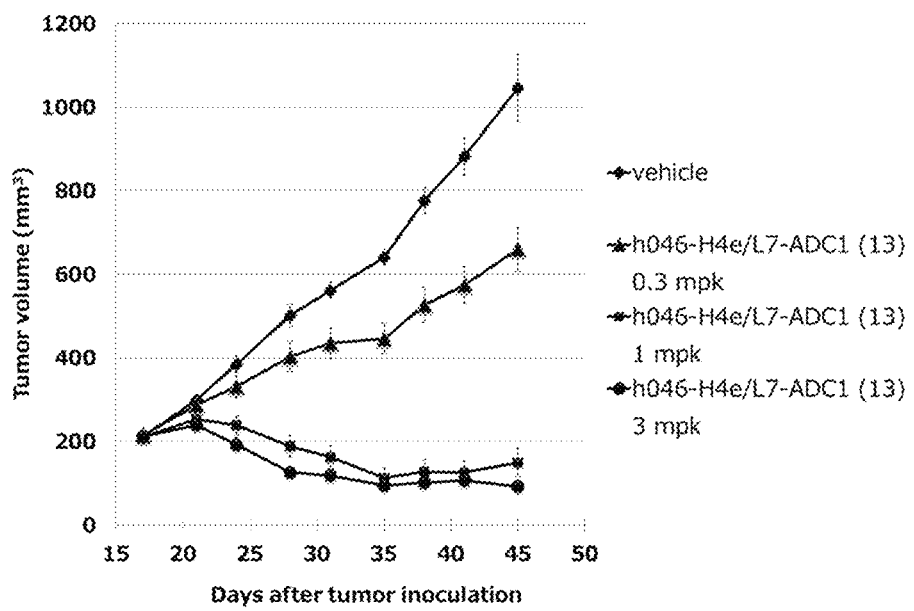

[Figure 33]
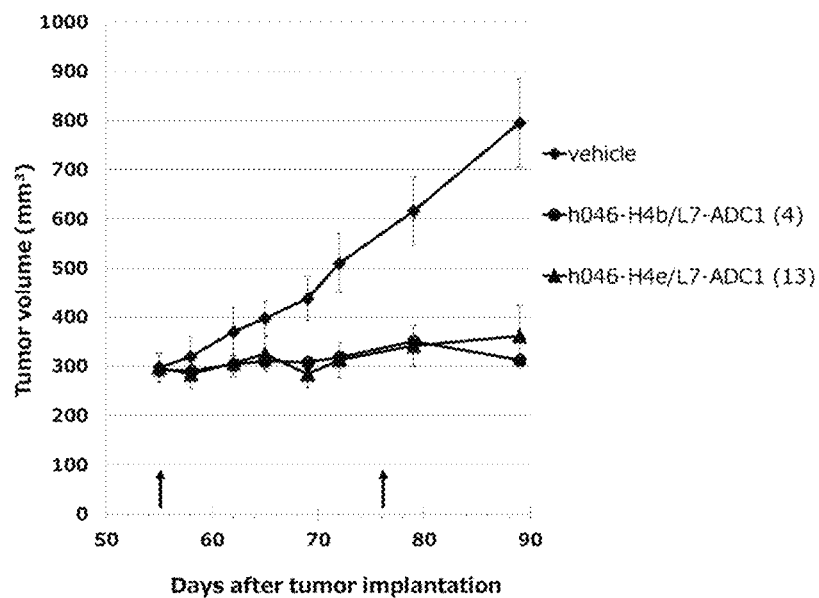
[Figure 34]
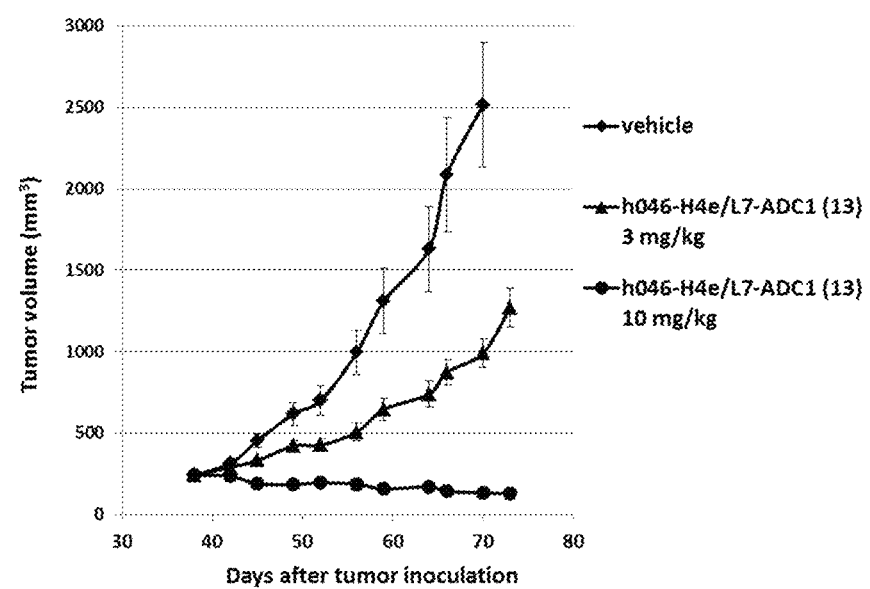

[Figure 35]
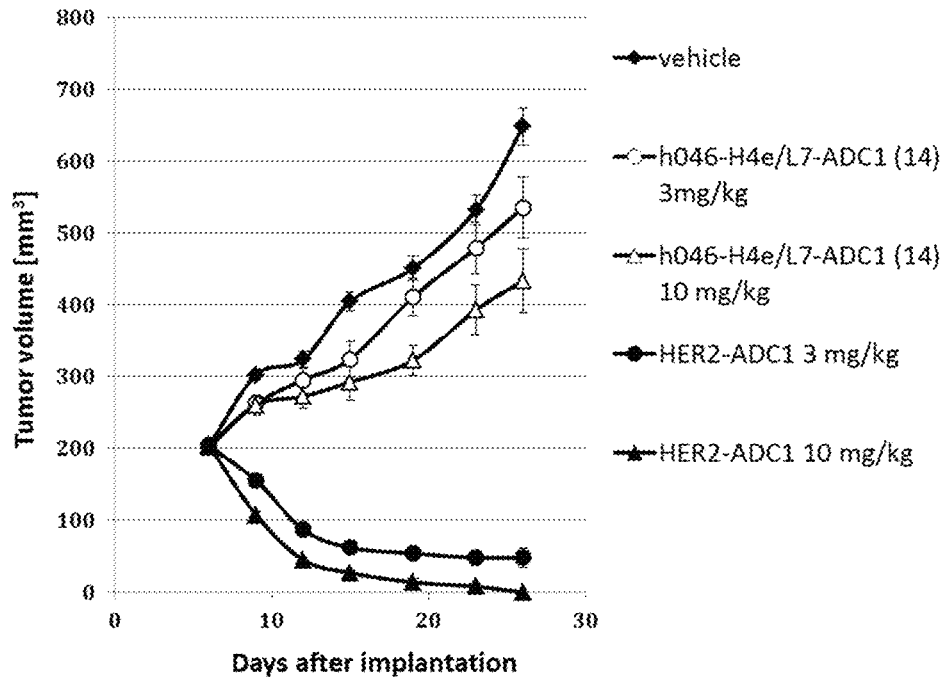
[Figure 36]
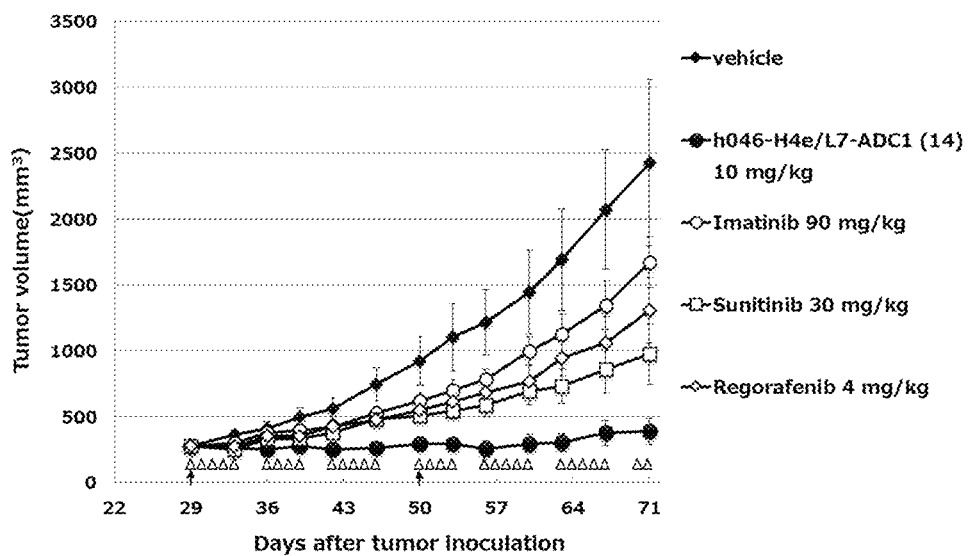

[Figure 37]
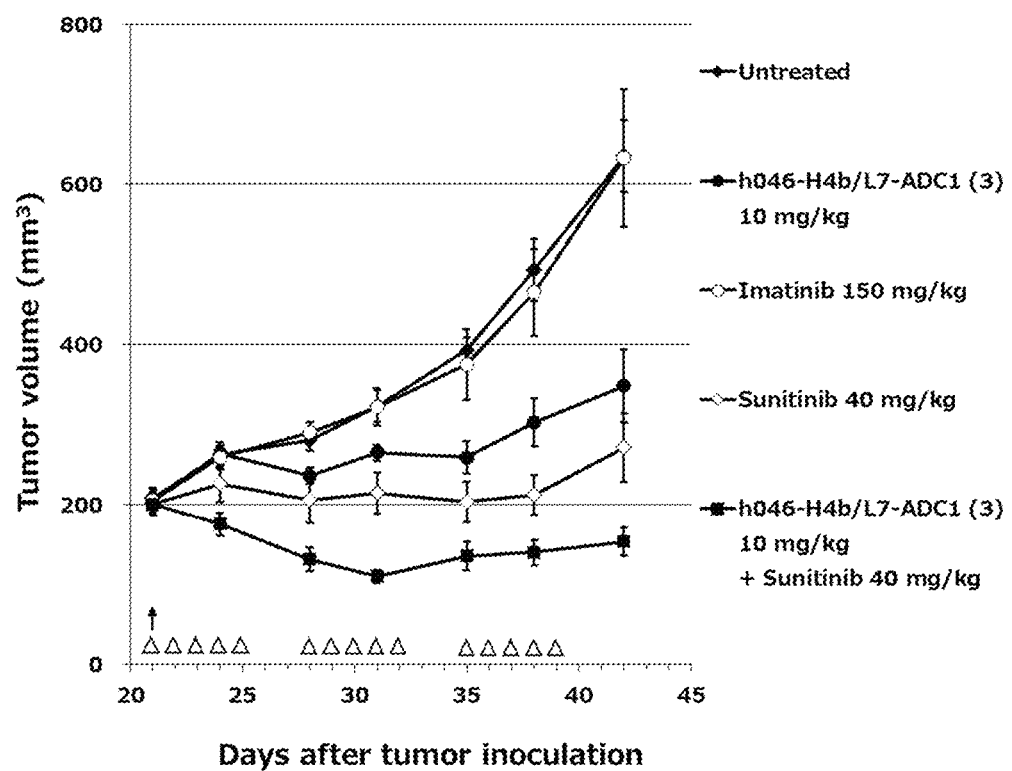

SEQUENCE LISTING

```
<160> NUMBER OF SEQ ID NOS: 113

<210> SEQ ID NO 1
<211> LENGTH: 358
<212> TYPE: PRT
<213> ORGANISM: Homo sapiens

<400> SEQUENCE: 1
```

Met Pro Ser Val Ser Pro Ala Gly Pro Ser Ala Gly Ala Val Pro Asn
1               5                   10                  15

Ala Thr Ala Val Thr Thr Val Arg Thr Asn Ala Ser Gly Leu Glu Val
                20                  25                  30

Pro Leu Phe His Leu Phe Ala Arg Leu Asp Glu Glu Leu His Gly Thr
            35                  40                  45

Phe Pro Gly Leu Trp Leu Ala Leu Met Ala Val His Gly Ala Ile Phe
        50                  55                  60

Leu Ala Gly Leu Val Leu Asn Gly Leu Ala Leu Tyr Val Phe Cys Cys
65                  70                  75                  80

Arg Thr Arg Ala Lys Thr Pro Ser Val Ile Tyr Thr Ile Asn Leu Val
                85                  90                  95

Val Thr Asp Leu Leu Val Gly Leu Ser Leu Pro Thr Arg Phe Ala Val
                100                 105                 110

Tyr Tyr Gly Ala Arg Gly Cys Leu Arg Cys Ala Phe Pro His Val Leu
            115                 120                 125

Gly Tyr Phe Leu Asn Met His Cys Ser Ile Leu Phe Leu Thr Cys Ile
        130                 135                 140

Cys Val Asp Arg Tyr Leu Ala Ile Val Arg Pro Glu Gly Ser Arg Arg
145                 150                 155                 160

Cys Arg Gln Pro Ala Cys Ala Arg Ala Val Cys Ala Phe Val Trp Leu
                165                 170                 175

Ala Ala Gly Ala Val Thr Leu Ser Val Leu Gly Val Thr Gly Ser Arg
                180                 185                 190

Pro Cys Cys Arg Val Phe Ala Leu Thr Val Leu Glu Phe Leu Leu Pro

```
                195                 200                 205
Leu Leu Val Ile Ser Val Phe Thr Gly Arg Ile Met Cys Ala Leu Ser
    210                 215                 220

Arg Pro Gly Leu Leu His Gln Gly Arg Gln Arg Val Arg Ala Met
225                 230                 235                 240

Gln Leu Leu Leu Thr Val Leu Ile Ile Phe Leu Val Cys Phe Thr Pro
                245                 250                 255

Phe His Ala Arg Gln Val Ala Val Ala Leu Trp Pro Asp Met Pro His
            260                 265                 270

His Thr Ser Leu Val Val Tyr His Val Ala Val Thr Leu Ser Ser Leu
        275                 280                 285

Asn Ser Cys Met Asp Pro Ile Val Tyr Cys Phe Val Thr Ser Gly Phe
    290                 295                 300

Gln Ala Thr Val Arg Gly Leu Phe Gly Gln His Gly Glu Arg Glu Pro
305                 310                 315                 320

Ser Ser Gly Asp Val Val Ser Met His Arg Ser Ser Lys Gly Ser Gly
                325                 330                 335

Arg His His Ile Leu Ser Ala Gly Pro His Ala Leu Thr Gln Ala Leu
            340                 345                 350

Ala Asn Gly Pro Glu Ala
        355

<210> SEQ ID NO 2
<211> LENGTH: 475
<212> TYPE: PRT
<213> ORGANISM: Rattus norvegicus
<220> FEATURE:
<221> NAME/KEY: SIGNAL
<222> LOCATION: (1)..(19)

<400> SEQUENCE: 2

Met Glu Trp Asn Trp Val Phe Leu Phe Leu Leu Ser Val Thr Ala Glu
1               5                   10                  15

Val His Ser Gln Val Gln Leu Gln Gln Ser Gly Ala Glu Leu Ala Lys
            20                  25                  30

Pro Gly Ser Ser Val Lys Ile Ser Cys Lys Ala Ser Gly Tyr Thr Phe
        35                  40                  45

Thr Ser Tyr Tyr Ile Ser Trp Ile Lys Gln Thr Thr Gly Gln Gly Leu
    50                  55                  60

Lys Tyr Ile Gly Phe Ile Asn Pro Gly Ser Gly His Thr Asn Tyr Asn
65                  70                  75                  80

Glu Lys Phe Lys Gly Lys Ala Thr Leu Thr Val Asp Lys Ser Ser Ser
                85                  90                  95

Thr Ala Phe Met Gln Leu Ser Ser Leu Thr Pro Asp Asp Ser Ala Ile
            100                 105                 110

Tyr Tyr Cys Ala Arg Gly Ala Gly Gly Phe Leu Arg Ile Ile Thr Lys
        115                 120                 125

Phe Asp Tyr Trp Gly Gln Gly Val Met Val Thr Val Ser Ser Ala Gln
    130                 135                 140

Thr Thr Ala Pro Ser Val Tyr Pro Leu Ala Pro Gly Cys Gly Asp Thr
145                 150                 155                 160

Thr Ser Ser Thr Val Thr Leu Gly Cys Leu Val Lys Gly Tyr Phe Pro
                165                 170                 175

Glu Pro Val Thr Val Thr Trp Asn Ser Gly Ala Leu Ser Ser Asp Val
            180                 185                 190
```

His Thr Phe Pro Ala Val Leu Gln Ser Gly Leu Tyr Thr Leu Thr Ser
            195                 200                 205

Ser Val Thr Ser Ser Thr Trp Pro Ser Gln Thr Val Thr Cys Asn Val
210                 215                 220

Ala His Pro Ala Ser Ser Thr Lys Val Asp Lys Lys Val Glu Arg Arg
225                 230                 235                 240

Asn Gly Gly Ile Gly His Lys Cys Pro Thr Cys Pro Thr Cys His Lys
                245                 250                 255

Cys Pro Val Pro Glu Leu Leu Gly Gly Pro Ser Val Phe Ile Phe Pro
                260                 265                 270

Pro Lys Pro Lys Asp Ile Leu Leu Ile Ser Gln Asn Ala Lys Val Thr
            275                 280                 285

Cys Val Val Val Asp Val Ser Glu Glu Glu Pro Asp Val Gln Phe Ser
            290                 295                 300

Trp Phe Val Asn Asn Val Glu Val His Thr Ala Gln Thr Gln Pro Arg
305                 310                 315                 320

Glu Glu Gln Tyr Asn Ser Thr Phe Arg Val Val Ser Ala Leu Pro Ile
                325                 330                 335

Gln His Gln Asp Trp Met Ser Gly Lys Glu Phe Lys Cys Lys Val Asn
            340                 345                 350

Asn Lys Ala Leu Pro Ser Pro Ile Glu Lys Thr Ile Ser Lys Pro Lys
        355                 360                 365

Gly Leu Val Arg Lys Pro Gln Val Tyr Val Met Gly Pro Pro Thr Glu
    370                 375                 380

Gln Leu Thr Glu Gln Thr Val Ser Leu Thr Cys Leu Thr Ser Gly Phe
385                 390                 395                 400

Leu Pro Asn Asp Ile Gly Val Glu Trp Thr Ser Asn Gly His Ile Glu
                405                 410                 415

Lys Asn Tyr Lys Asn Thr Glu Pro Val Met Asp Ser Asp Gly Ser Phe
                420                 425                 430

Phe Met Tyr Ser Lys Leu Asn Val Glu Arg Ser Arg Trp Asp Ser Arg
            435                 440                 445

Ala Pro Phe Val Cys Ser Val Val His Glu Gly Leu His Asn His His
        450                 455                 460

Val Glu Lys Ser Ile Ser Arg Pro Pro Gly Lys
465                 470                 475

<210> SEQ ID NO 3
<211> LENGTH: 123
<212> TYPE: PRT
<213> ORGANISM: Rattus norvegicus

<400> SEQUENCE: 3

Gln Val Gln Leu Gln Gln Ser Gly Ala Glu Leu Ala Lys Pro Gly Ser
1               5                   10                  15

Ser Val Lys Ile Ser Cys Lys Ala Ser Gly Tyr Thr Phe Thr Ser Tyr
            20                  25                  30

Tyr Ile Ser Trp Ile Lys Gln Thr Thr Gly Gln Gly Leu Lys Tyr Ile
        35                  40                  45

Gly Phe Ile Asn Pro Gly Ser Gly His Thr Asn Tyr Asn Glu Lys Phe
    50                  55                  60

Lys Gly Lys Ala Thr Leu Thr Val Asp Lys Ser Ser Ser Thr Ala Phe
65                  70                  75                  80

Met Gln Leu Ser Ser Leu Thr Pro Asp Asp Ser Ala Ile Tyr Tyr Cys
                85                  90                  95

-continued

Ala Arg Gly Ala Gly Gly Phe Leu Arg Ile Ile Thr Lys Phe Asp Tyr
            100                 105                 110

Trp Gly Gln Gly Val Met Val Thr Val Ser Ser
        115                 120

<210> SEQ ID NO 4
<211> LENGTH: 10
<212> TYPE: PRT
<213> ORGANISM: Rattus norvegicus

<400> SEQUENCE: 4

Gly Tyr Thr Phe Thr Ser Tyr Tyr Ile Ser
1               5                   10

<210> SEQ ID NO 5
<211> LENGTH: 10
<212> TYPE: PRT
<213> ORGANISM: Rattus norvegicus

<400> SEQUENCE: 5

Phe Ile Asn Pro Gly Ser Gly His Thr Asn
1               5                   10

<210> SEQ ID NO 6
<211> LENGTH: 14
<212> TYPE: PRT
<213> ORGANISM: Rattus norvegicus

<400> SEQUENCE: 6

Gly Ala Gly Gly Phe Leu Arg Ile Ile Thr Lys Phe Asp Tyr
1               5                   10

<210> SEQ ID NO 7
<211> LENGTH: 233
<212> TYPE: PRT
<213> ORGANISM: Rattus norvegicus
<220> FEATURE:
<221> NAME/KEY: SIGNAL
<222> LOCATION: (1)..(20)

<400> SEQUENCE: 7

Met Glu Thr Asp Arg Leu Leu Leu Trp Val Leu Leu Leu Trp Val Pro
1               5                   10                  15

Gly Ser Thr Gly Asp Thr Val Leu Thr Gln Ser Pro Ala Leu Ala Val
            20                  25                  30

Ser Leu Gly Gln Arg Val Thr Ile Ser Cys Arg Ala Ser Lys Ser Val
        35                  40                  45

Ser Thr Tyr Ile His Trp Tyr Gln Gln Arg Ser Gly Gln Gln Pro Lys
    50                  55                  60

Leu Leu Ile Tyr Ser Ala Ser Asn Leu Glu Ser Gly Val Pro Ser Arg
65                  70                  75                  80

Phe Ser Gly Ser Gly Ser Gly Thr Asp Phe Thr Leu Thr Ile Asp Pro
                85                  90                  95

Val Glu Pro Asp Asp Ile Ala Asn Tyr Tyr Cys Gln Gln Ile Asn Glu
            100                 105                 110

Leu Pro Tyr Thr Phe Gly Ala Gly Thr Lys Leu Glu Leu Lys Arg Ala
        115                 120                 125

Asp Ala Ala Pro Thr Val Ser Ile Phe Pro Pro Ser Thr Glu Gln Leu
    130                 135                 140

Ala Thr Gly Gly Ala Ser Val Val Cys Leu Met Asn Asn Phe Tyr Pro

```
            145                 150                 155                 160
Arg Asp Ile Ser Val Lys Trp Lys Ile Asp Gly Thr Glu Arg Arg Asp
                    165                 170                 175

Gly Val Leu Asp Ser Val Thr Asp Gln Asp Ser Lys Asp Ser Thr Tyr
                180                 185                 190

Ser Met Ser Ser Thr Leu Ser Leu Thr Lys Ala Asp Tyr Glu Ser His
            195                 200                 205

Asn Leu Tyr Thr Cys Glu Val His Lys Thr Ser Ser Ser Pro Val
        210                 215                 220

Val Lys Ser Phe Asn Arg Asn Glu Cys
225                 230

<210> SEQ ID NO 8
<211> LENGTH: 108
<212> TYPE: PRT
<213> ORGANISM: Rattus norvegicus

<400> SEQUENCE: 8

Asp Thr Val Leu Thr Gln Ser Pro Ala Leu Ala Val Ser Leu Gly Gln
1               5                   10                  15

Arg Val Thr Ile Ser Cys Arg Ala Ser Lys Ser Val Ser Thr Tyr Ile
                20                  25                  30

His Trp Tyr Gln Gln Arg Ser Gly Gln Pro Lys Leu Leu Ile Tyr
            35                  40                  45

Ser Ala Ser Asn Leu Glu Ser Gly Val Pro Ser Arg Phe Ser Gly Ser
        50                  55                  60

Gly Ser Gly Thr Asp Phe Thr Leu Thr Ile Asp Pro Val Glu Pro Asp
65                  70                  75                  80

Asp Ile Ala Asn Tyr Tyr Cys Gln Gln Ile Asn Glu Leu Pro Tyr Thr
                85                  90                  95

Phe Gly Ala Gly Thr Lys Leu Glu Leu Lys Arg Ala
                100                 105

<210> SEQ ID NO 9
<211> LENGTH: 11
<212> TYPE: PRT
<213> ORGANISM: Rattus norvegicus

<400> SEQUENCE: 9

Arg Ala Ser Lys Ser Val Ser Thr Tyr Ile His
1               5                   10

<210> SEQ ID NO 10
<211> LENGTH: 7
<212> TYPE: PRT
<213> ORGANISM: Rattus norvegicus

<400> SEQUENCE: 10

Ser Ala Ser Asn Leu Glu Ser
1               5

<210> SEQ ID NO 11
<211> LENGTH: 9
<212> TYPE: PRT
<213> ORGANISM: Rattus norvegicus

<400> SEQUENCE: 11

Gln Gln Ile Asn Glu Leu Pro Tyr Thr
1               5
```

```
<210> SEQ ID NO 12
<211> LENGTH: 475
<212> TYPE: PRT
<213> ORGANISM: Rattus norvegicus
<220> FEATURE:
<221> NAME/KEY: SIGNAL
<222> LOCATION: (1)..(19)

<400> SEQUENCE: 12

Met Glu Trp Asn Trp Val Phe Leu Phe Leu Leu Ser Val Thr Ala Val
1               5                   10                  15

Val His Ser Gln Val Gln Leu Gln Gln Ser Gly Ala Glu Leu Ala Lys
            20                  25                  30

Pro Gly Ser Ser Val Lys Ile Ser Cys Lys Ala Ser Gly Tyr Thr Phe
        35                  40                  45

Thr Ser Tyr Tyr Ile Thr Trp Ile Lys Gln Thr Thr Gly Gln Gly Leu
    50                  55                  60

Lys Tyr Ile Gly Tyr Ile Asn Pro Gly Ser Gly His Thr Asn Tyr Asn
65                  70                  75                  80

Glu Lys Phe Lys Gly Lys Ala Thr Leu Thr Val Asp Lys Ser Ser Ser
                85                  90                  95

Thr Ala Phe Met Gln Leu Ser Ser Leu Thr Pro Asp Asp Ser Ala Val
            100                 105                 110

Tyr Tyr Cys Ala Arg Gly Ala Gly Phe Leu Arg Ile Ile Ser Lys
        115                 120                 125

Phe Asp Tyr Trp Gly Gln Gly Val Met Val Thr Val Ser Ser Ala Gln
130                 135                 140

Thr Thr Ala Pro Ser Val Tyr Pro Leu Ala Pro Gly Cys Gly Asp Thr
145                 150                 155                 160

Thr Ser Ser Thr Val Thr Leu Gly Cys Leu Val Lys Gly Tyr Phe Pro
                165                 170                 175

Glu Pro Val Thr Val Thr Trp Asn Ser Gly Ala Leu Ser Ser Asp Val
            180                 185                 190

His Thr Phe Pro Ala Val Leu Gln Ser Gly Leu Tyr Thr Leu Thr Ser
        195                 200                 205

Ser Val Thr Ser Ser Thr Trp Pro Ser Gln Thr Val Thr Cys Asn Val
    210                 215                 220

Ala His Pro Ala Ser Ser Thr Lys Val Asp Lys Lys Val Glu Arg Arg
225                 230                 235                 240

Asn Gly Gly Ile Gly His Lys Cys Pro Thr Cys Pro Thr Cys His Lys
                245                 250                 255

Cys Pro Val Pro Glu Leu Leu Gly Gly Pro Ser Val Phe Ile Phe Pro
            260                 265                 270

Pro Lys Pro Lys Asp Ile Leu Leu Ile Ser Gln Asn Ala Lys Val Thr
        275                 280                 285

Cys Val Val Val Asp Val Ser Glu Glu Glu Pro Asp Val Gln Phe Ser
    290                 295                 300

Trp Phe Val Asn Asn Val Glu Val His Thr Ala Gln Thr Gln Pro Arg
305                 310                 315                 320

Glu Glu Gln Tyr Asn Ser Thr Phe Arg Val Val Ser Ala Leu Pro Ile
                325                 330                 335

Gln His Gln Asp Trp Met Ser Gly Lys Glu Phe Lys Cys Lys Val Asn
            340                 345                 350

Asn Lys Ala Leu Pro Ser Pro Ile Glu Lys Thr Ile Ser Lys Pro Lys
        355                 360                 365
```

Gly Leu Val Arg Lys Pro Gln Val Tyr Val Met Gly Pro Pro Thr Glu
        370                 375                 380

Gln Leu Thr Glu Gln Thr Val Ser Leu Thr Cys Leu Thr Ser Gly Phe
385                 390                 395                 400

Leu Pro Asn Asp Ile Gly Val Glu Trp Thr Ser Asn Gly His Ile Glu
                405                 410                 415

Lys Asn Tyr Lys Asn Thr Glu Pro Val Met Asp Ser Asp Gly Ser Phe
            420                 425                 430

Phe Met Tyr Ser Lys Leu Asn Val Glu Arg Ser Arg Trp Asp Ser Arg
        435                 440                 445

Ala Pro Phe Val Cys Ser Val Val His Glu Gly Leu His Asn His His
    450                 455                 460

Val Glu Lys Ser Ile Ser Arg Pro Pro Gly Lys
465                 470                 475

<210> SEQ ID NO 13
<211> LENGTH: 123
<212> TYPE: PRT
<213> ORGANISM: Rattus norvegicus

<400> SEQUENCE: 13

Gln Val Gln Leu Gln Gln Ser Gly Ala Glu Leu Ala Lys Pro Gly Ser
1               5                   10                  15

Ser Val Lys Ile Ser Cys Lys Ala Ser Gly Tyr Thr Phe Thr Ser Tyr
            20                  25                  30

Tyr Ile Thr Trp Ile Lys Gln Thr Thr Gly Gln Gly Leu Lys Tyr Ile
        35                  40                  45

Gly Tyr Ile Asn Pro Gly Ser Gly His Thr Asn Tyr Asn Glu Lys Phe
    50                  55                  60

Lys Gly Lys Ala Thr Leu Thr Val Asp Lys Ser Ser Ser Thr Ala Phe
65                  70                  75                  80

Met Gln Leu Ser Ser Leu Thr Pro Asp Asp Ser Ala Val Tyr Tyr Cys
                85                  90                  95

Ala Arg Gly Ala Gly Gly Phe Leu Arg Ile Ile Ser Lys Phe Asp Tyr
            100                 105                 110

Trp Gly Gln Gly Val Met Val Thr Val Ser Ser
        115                 120

<210> SEQ ID NO 14
<211> LENGTH: 10
<212> TYPE: PRT
<213> ORGANISM: Rattus norvegicus

<400> SEQUENCE: 14

Gly Tyr Thr Phe Thr Ser Tyr Tyr Ile Thr
1               5                   10

<210> SEQ ID NO 15
<211> LENGTH: 10
<212> TYPE: PRT
<213> ORGANISM: Rattus norvegicus

<400> SEQUENCE: 15

Tyr Ile Asn Pro Gly Ser Gly His Thr Asn
1               5                   10

<210> SEQ ID NO 16
<211> LENGTH: 14

```
<212> TYPE: PRT
<213> ORGANISM: Rattus norvegicus

<400> SEQUENCE: 16

Gly Ala Gly Gly Phe Leu Arg Ile Ile Ser Lys Phe Asp Tyr
1               5                   10

<210> SEQ ID NO 17
<211> LENGTH: 233
<212> TYPE: PRT
<213> ORGANISM: Rattus norvegicus
<220> FEATURE:
<221> NAME/KEY: SIGNAL
<222> LOCATION: (1)..(20)

<400> SEQUENCE: 17

Met Glu Thr Asp Arg Leu Leu Leu Trp Val Leu Leu Leu Trp Val Pro
1               5                   10                  15

Gly Ser Thr Gly Asp Thr Val Leu Thr Gln Ser Pro Ala Leu Ala Val
                20                  25                  30

Ser Leu Gly Gln Arg Val Thr Ile Ser Cys Arg Ala Ser Lys Ser Val
            35                  40                  45

Ser Thr Tyr Met His Trp Tyr Gln Gln Arg Ser Gly Gln Gln Pro Lys
        50                  55                  60

Leu Leu Ile Tyr Ser Ala Ser Asn Leu Glu Ser Gly Val Pro Ser Arg
65                  70                  75                  80

Phe Ser Gly Ser Gly Ser Gly Thr Asp Phe Thr Leu Thr Ile Asp Pro
                85                  90                  95

Val Lys Ala Asp Asp Ile Thr Asn Tyr Tyr Cys Gln Gln Ser Asn Glu
            100                 105                 110

Leu Pro Tyr Thr Phe Gly Ala Gly Thr Lys Leu Glu Leu Lys Arg Ala
        115                 120                 125

Asp Ala Ala Pro Thr Val Ser Ile Phe Pro Pro Ser Thr Glu Gln Leu
    130                 135                 140

Ala Thr Gly Gly Ala Ser Val Val Cys Leu Met Asn Asn Phe Tyr Pro
145                 150                 155                 160

Arg Asp Ile Ser Val Lys Trp Lys Ile Asp Gly Thr Glu Arg Arg Asp
                165                 170                 175

Gly Val Leu Asp Ser Val Thr Asp Gln Asp Ser Lys Asp Ser Thr Tyr
            180                 185                 190

Ser Met Ser Ser Thr Leu Ser Leu Thr Lys Ala Asp Tyr Glu Ser His
        195                 200                 205

Asn Leu Tyr Thr Cys Glu Val Val His Lys Thr Ser Ser Ser Pro Val
    210                 215                 220

Val Lys Ser Phe Asn Arg Asn Glu Cys
225                 230

<210> SEQ ID NO 18
<211> LENGTH: 108
<212> TYPE: PRT
<213> ORGANISM: Rattus norvegicus

<400> SEQUENCE: 18

Asp Thr Val Leu Thr Gln Ser Pro Ala Leu Ala Val Ser Leu Gly Gln
1               5                   10                  15

Arg Val Thr Ile Ser Cys Arg Ala Ser Lys Ser Val Ser Thr Tyr Met
                20                  25                  30

His Trp Tyr Gln Gln Arg Ser Gly Gln Gln Pro Lys Leu Leu Ile Tyr
```

```
                35                  40                  45
Ser Ala Ser Asn Leu Glu Ser Gly Val Pro Ser Arg Phe Ser Gly Ser
 50                  55                  60
Gly Ser Gly Thr Asp Phe Thr Leu Thr Ile Asp Pro Val Lys Ala Asp
 65                  70                  75                  80
Asp Ile Thr Asn Tyr Tyr Cys Gln Gln Ser Asn Glu Leu Pro Tyr Thr
                 85                  90                  95
Phe Gly Ala Gly Thr Lys Leu Glu Leu Lys Arg Ala
            100                 105
```

<210> SEQ ID NO 19
<211> LENGTH: 11
<212> TYPE: PRT
<213> ORGANISM: Rattus norvegicus

<400> SEQUENCE: 19

```
Arg Ala Ser Lys Ser Val Ser Thr Tyr Met His
 1               5                  10
```

<210> SEQ ID NO 20
<211> LENGTH: 7
<212> TYPE: PRT
<213> ORGANISM: Rattus norvegicus

<400> SEQUENCE: 20

```
Ser Ala Ser Asn Leu Glu Ser
 1               5
```

<210> SEQ ID NO 21
<211> LENGTH: 9
<212> TYPE: PRT
<213> ORGANISM: Rattus norvegicus

<400> SEQUENCE: 21

```
Gln Gln Ser Asn Glu Leu Pro Tyr Thr
 1               5
```

<210> SEQ ID NO 22
<211> LENGTH: 475
<212> TYPE: PRT
<213> ORGANISM: Rattus norvegicus
<220> FEATURE:
<221> NAME/KEY: SIGNAL
<222> LOCATION: (1)..(19)

<400> SEQUENCE: 22

```
Met Glu Trp Asn Trp Val Phe Leu Phe Leu Leu Ser Val Thr Ala Glu
 1               5                  10                  15
Val His Ser Gln Val Gln Leu Arg Gln Ser Gly Ala Glu Leu Ala Lys
                20                  25                  30
Pro Gly Ser Ser Val Lys Ile Ser Cys Lys Ala Ser Gly Tyr Thr Phe
            35                  40                  45
Thr Ser Tyr Tyr Ile Ile Trp Met Lys Gln Thr Ala Gly Gln Gly Leu
 50                  55                  60
Gln Tyr Val Gly Tyr Ile Asn Pro Gly Ser Gly His Thr Asn Tyr Asn
 65                  70                  75                  80
Glu Lys Phe Lys Gly Lys Ala Thr Leu Thr Val Asp Lys Ser Ser Ser
                 85                  90                  95
Thr Ala Phe Met Gln Leu Ser Ser Leu Thr Pro Asp Asp Ser Ala Val
            100                 105                 110
```

```
Tyr Tyr Cys Ala Arg Gly Thr Gly Gly Phe Leu Arg Ile Ile Ser Lys
            115                 120                 125

Phe Asp Tyr Trp Gly Gln Gly Val Met Val Thr Val Ser Ser Ala Gln
130                 135                 140

Thr Thr Ala Pro Ser Val Tyr Pro Leu Ala Pro Gly Cys Gly Asp Thr
145                 150                 155                 160

Thr Ser Ser Thr Val Thr Leu Gly Cys Leu Val Lys Gly Tyr Phe Pro
                165                 170                 175

Glu Pro Val Thr Val Thr Trp Asn Ser Gly Ala Leu Ser Ser Asp Val
                180                 185                 190

His Thr Phe Pro Ala Val Leu Gln Ser Gly Leu Tyr Thr Leu Thr Ser
                195                 200                 205

Ser Val Thr Ser Ser Thr Trp Pro Ser Gln Thr Val Thr Cys Asn Val
            210                 215                 220

Ala His Pro Ala Ser Ser Thr Lys Val Asp Lys Val Glu Arg Arg
225                 230                 235                 240

Asn Gly Gly Ile Gly His Lys Cys Pro Thr Cys Pro Thr Cys His Lys
                    245                 250                 255

Cys Pro Val Pro Glu Leu Leu Gly Gly Pro Ser Val Phe Ile Phe Pro
                260                 265                 270

Pro Lys Pro Lys Asp Ile Leu Leu Ile Ser Gln Asn Ala Lys Val Thr
            275                 280                 285

Cys Val Val Val Asp Val Ser Glu Glu Pro Asp Val Gln Phe Ser
290                 295                 300

Trp Phe Val Asn Asn Val Glu Val His Thr Ala Gln Thr Gln Pro Arg
305                 310                 315                 320

Glu Glu Gln Tyr Asn Ser Thr Phe Arg Val Val Ser Ala Leu Pro Ile
                325                 330                 335

Gln His Gln Asp Trp Met Ser Gly Lys Glu Phe Lys Cys Lys Val Asn
                340                 345                 350

Asn Lys Ala Leu Pro Ser Pro Ile Glu Lys Thr Ile Ser Lys Pro Lys
            355                 360                 365

Gly Leu Val Arg Lys Pro Gln Val Tyr Val Met Gly Pro Pro Thr Glu
370                 375                 380

Gln Leu Thr Glu Gln Thr Val Ser Leu Thr Cys Leu Thr Ser Gly Phe
385                 390                 395                 400

Leu Pro Asn Asp Ile Gly Val Glu Trp Thr Ser Asn Gly His Ile Glu
                    405                 410                 415

Lys Asn Tyr Lys Asn Thr Glu Pro Val Met Asp Ser Asp Gly Ser Phe
            420                 425                 430

Phe Met Tyr Ser Lys Leu Asn Val Glu Arg Ser Arg Trp Asp Ser Arg
                435                 440                 445

Ala Pro Phe Val Cys Ser Val Val His Glu Gly Leu His Asn His His
450                 455                 460

Val Glu Lys Ser Ile Ser Arg Pro Pro Gly Lys
465                 470                 475

<210> SEQ ID NO 23
<211> LENGTH: 123
<212> TYPE: PRT
<213> ORGANISM: Rattus norvegicus

<400> SEQUENCE: 23

Gln Val Gln Leu Arg Gln Ser Gly Ala Glu Leu Ala Lys Pro Gly Ser
1               5                   10                  15
```

```
Ser Val Lys Ile Ser Cys Lys Ala Ser Gly Tyr Thr Phe Thr Ser Tyr
        20                  25                  30

Tyr Ile Ile Trp Met Lys Gln Thr Ala Gly Gln Gly Leu Gln Tyr Val
            35                  40                  45

Gly Tyr Ile Asn Pro Gly Ser Gly His Thr Asn Tyr Asn Glu Lys Phe
 50                  55                  60

Lys Gly Lys Ala Thr Leu Thr Val Asp Lys Ser Ser Thr Ala Phe
 65                  70                  75                  80

Met Gln Leu Ser Ser Leu Thr Pro Asp Asp Ser Ala Val Tyr Tyr Cys
                85                  90                  95

Ala Arg Gly Thr Gly Gly Phe Leu Arg Ile Ile Ser Lys Phe Asp Tyr
            100                 105                 110

Trp Gly Gln Gly Val Met Val Thr Val Ser Ser
            115                 120
```

<210> SEQ ID NO 24
<211> LENGTH: 10
<212> TYPE: PRT
<213> ORGANISM: Rattus norvegicus

<400> SEQUENCE: 24

```
Gly Tyr Thr Phe Thr Ser Tyr Tyr Ile Ile
1               5                   10
```

<210> SEQ ID NO 25
<211> LENGTH: 10
<212> TYPE: PRT
<213> ORGANISM: Rattus norvegicus

<400> SEQUENCE: 25

```
Tyr Ile Asn Pro Gly Ser Gly His Thr Asn
1               5                   10
```

<210> SEQ ID NO 26
<211> LENGTH: 14
<212> TYPE: PRT
<213> ORGANISM: Rattus norvegicus

<400> SEQUENCE: 26

```
Gly Thr Gly Gly Phe Leu Arg Ile Ile Ser Lys Phe Asp Tyr
1               5                   10
```

<210> SEQ ID NO 27
<211> LENGTH: 233
<212> TYPE: PRT
<213> ORGANISM: Rattus norvegicus
<220> FEATURE:
<221> NAME/KEY: SIGNAL
<222> LOCATION: (1)..(20)

<400> SEQUENCE: 27

```
Met Glu Thr Asp Arg Leu Leu Leu Trp Val Leu Leu Leu Trp Val Pro
1               5                   10                  15

Gly Ser Thr Gly Asp Thr Val Leu Thr Gln Ser Pro Ala Leu Ala Val
            20                  25                  30

Ser Leu Gly Gln Arg Val Thr Ile Ser Cys Arg Ala Ser Lys Ser Val
            35                  40                  45

Ser Thr Tyr Met His Trp Tyr Gln Gln Arg Ser Gly Gln Gln Pro Lys
 50                  55                  60

Leu Leu Ile Tyr Ser Ala Ser Thr Leu Glu Ser Gly Val Pro Ser Arg
```

```
                65                  70                  75                  80
        Phe Ser Gly Ser Gly Ser Gly Thr Asp Phe Thr Leu Thr Ile Asp Pro
                        85                  90                  95

Val Glu Ala Asp Asp Ile Ala Asn Tyr Tyr Cys Gln Gln Ser Asn Glu
                        100                 105                 110

Leu Pro Tyr Thr Phe Gly Ala Gly Thr Lys Leu Glu Leu Lys Arg Ala
                        115                 120                 125

Asp Ala Ala Pro Thr Val Ser Ile Phe Pro Pro Ser Thr Glu Gln Leu
                130                 135                 140

Ala Thr Gly Gly Ala Ser Val Val Cys Leu Met Asn Asn Phe Tyr Pro
        145                 150                 155                 160

Arg Asp Ile Ser Val Lys Trp Lys Ile Asp Gly Thr Glu Arg Arg Asp
                        165                 170                 175

Gly Val Leu Asp Ser Val Thr Asp Gln Asp Ser Lys Asp Ser Thr Tyr
                        180                 185                 190

Ser Met Ser Ser Thr Leu Ser Leu Thr Lys Ala Asp Tyr Glu Ser His
                        195                 200                 205

Asn Leu Tyr Thr Cys Glu Val Val His Lys Thr Ser Ser Pro Val
                210                 215                 220

Val Lys Ser Phe Asn Arg Asn Glu Cys
        225                 230

<210> SEQ ID NO 28
<211> LENGTH: 108
<212> TYPE: PRT
<213> ORGANISM: Rattus norvegicus

<400> SEQUENCE: 28

Asp Thr Val Leu Thr Gln Ser Pro Ala Leu Ala Val Ser Leu Gly Gln
        1               5                   10                  15

Arg Val Thr Ile Ser Cys Arg Ala Ser Lys Ser Val Ser Thr Tyr Met
                        20                  25                  30

His Trp Tyr Gln Gln Arg Ser Gly Gln Gln Pro Lys Leu Leu Ile Tyr
                        35                  40                  45

Ser Ala Ser Thr Leu Glu Ser Gly Val Pro Ser Arg Phe Ser Gly Ser
                50                  55                  60

Gly Ser Gly Thr Asp Phe Thr Leu Thr Ile Asp Pro Val Glu Ala Asp
        65                  70                  75                  80

Asp Ile Ala Asn Tyr Tyr Cys Gln Gln Ser Asn Glu Leu Pro Tyr Thr
                        85                  90                  95

Phe Gly Ala Gly Thr Lys Leu Glu Leu Lys Arg Ala
                        100                 105

<210> SEQ ID NO 29
<211> LENGTH: 11
<212> TYPE: PRT
<213> ORGANISM: Rattus norvegicus

<400> SEQUENCE: 29

Arg Ala Ser Lys Ser Val Ser Thr Tyr Met His
        1               5                   10

<210> SEQ ID NO 30
<211> LENGTH: 7
<212> TYPE: PRT
<213> ORGANISM: Rattus norvegicus

<400> SEQUENCE: 30
```

Ser Ala Ser Thr Leu Glu Ser
1               5

<210> SEQ ID NO 31
<211> LENGTH: 9
<212> TYPE: PRT
<213> ORGANISM: Rattus norvegicus

<400> SEQUENCE: 31

Gln Gln Ser Asn Glu Leu Pro Tyr Thr
1               5

<210> SEQ ID NO 32
<211> LENGTH: 1425
<212> TYPE: DNA
<213> ORGANISM: Rattus norvegicus
<220> FEATURE:
<221> NAME/KEY: sig_peptide
<222> LOCATION: (1)..(57)

<400> SEQUENCE: 32

| | | | | |
|---|---|---|---|---|
| atggaatgga | actgggtctt | tctcttcctc | ctgtcagtaa | ctgcagaggt | ccactcccag | 60 |
| gtccaactgc | agcagtctgg | agctgaactg | gcaaagcctg | gctcttcagt | gaagatttcc | 120 |
| tgcaaggctt | ctggctacac | cttcaccagc | tactatataa | gctggataaa | gcagacgact | 180 |
| ggacagggcc | ttaagtatat | tggatttatt | aatccgggaa | gtggacatac | taactacaat | 240 |
| gagaagttca | agggcaaggc | cacattgact | gtagacaaat | cctctagcac | agccttcatg | 300 |
| caactcagca | gcctgacacc | tgacgactct | gcgatctatt | actgtgcaag | aggggctggg | 360 |
| ggttttctac | ggattattac | taagtttgat | tactggggcc | aaggagtcat | ggtcacagtc | 420 |
| tcctcagccc | aaacaacagc | cccatctgtc | tatccactgg | ctcctggatg | tggtgataca | 480 |
| accagctcca | cggtgactct | gggatgcctg | gtcaagggct | atttccctga | gccagtcacc | 540 |
| gtgacctgga | actctggagc | cctgtccagc | gatgtgcaca | cctttccagc | tgtcctgcag | 600 |
| tctgggctct | acactctcac | cagctcagtg | acctccagca | cctggcccag | ccagaccgtc | 660 |
| acctgcaacg | tagcccaccc | ggccagcagc | accaaggtgg | acaagaaagt | tgagcgcaga | 720 |
| aatggcggca | ttggacacaa | atgccctaca | tgccctacat | gtcacaaatg | cccagttcct | 780 |
| gaactcttgg | gtggaccatc | tgtcttcatc | ttcccgccaa | agcccaagga | catcctcttg | 840 |
| atctcccaga | acgccaaggt | cacgtgtgtg | gtggtggatg | tgagcgagga | ggagccggac | 900 |
| gtccagttca | gctggtttgt | gaacaacgta | gaagtacaca | cagctcagac | acaaccccgt | 960 |
| gaggagcagt | acaacagcac | cttcagagtg | gtcagtgccc | tccccatcca | gcaccaggac | 1020 |
| tggatgagcg | gcaaggagtt | caatgcaag | gtcaacaaca | agccctccc | aagccccatc | 1080 |
| gagaaaacca | tctcaaaacc | caaagggcta | gtcagaaaac | cacaggtata | cgtcatgggt | 1140 |
| ccaccgacag | agcagttgac | tgagcaaacg | gtcagtttga | cctgcttgac | ctcaggcttc | 1200 |
| ctccctaacg | acatcggtgt | ggagtggacc | agcaacgggc | atatagaaaa | gaactacaag | 1260 |
| aacaccgagc | cagtgatgga | ctctgacggt | tctttcttca | tgtacagcaa | gctcaatgtg | 1320 |
| gaaaggagca | ggtgggatag | cagagcgccc | ttcgtctgct | ccgtggtcca | cgagggtctg | 1380 |
| cacaatcacc | acgtggagaa | gagcatctcc | cggcctccgg | gtaaa | | 1425 |

<210> SEQ ID NO 33
<211> LENGTH: 369
<212> TYPE: DNA
<213> ORGANISM: Rattus norvegicus

<400> SEQUENCE: 33

```
caggtccaac tgcagcagtc tggagctgaa ctggcaaagc ctggctcttc agtgaagatt        60
tcctgcaagg cttctggcta caccttcacc agctactata aagctggat aaagcagacg       120 actggacagg gccttaagta tattggattt attaatccgg gaagtggaca tactaactac       180
aatgagaagt tcaagggcaa ggccacattg actgtagaca atcctctag cacagccttc        240 atgcaactca gcagcctgac acctgacgac tctgcgatct attactgtgc aagaggggct       300
gggggttttc tacggattat tactaagttt gattactggg gccaaggagt catggtcaca       360
gtctcctca                                                              369
```

<210> SEQ ID NO 34
<211> LENGTH: 699
<212> TYPE: DNA
<213> ORGANISM: Rattus norvegicus
<220> FEATURE:
<221> NAME/KEY: sig_peptide
<222> LOCATION: (1)..(60)

<400> SEQUENCE: 34

```
atggagacag acagactcct gctatgggtg ctgctgctct gggttccagg ctccactggt        60
gacactgtgc tgacccagtc tcctgctttg gctgtgtctc tagggcagag ggtcaccatc       120
tcctgtaggg ccagcaaaag tgtcagtaca tatatacact ggtaccaaca gaggtcggga       180
cagcaaccca aactcctgat ctatagtgca tccaacctag aatctggagt cccttccagg       240
ttcagtggga gtgggtctgg gacagacttt accctcacca tagatcctgt ggagcctgat       300
gacatagcaa actattactg tcagcagatt aatgaacttc cgtacacgtt tggagctggg       360
accaagctgg aactgaaacg ggctgatgct gcaccaactg tatctatctt cccaccatcc       420
acggaacagt tagcaactgg aggtgcctca gtcgtgtgcc tcatgaacaa cttctatccc       480
agagacatca gtgtcaagtg gaagattgat ggcactgaac gacgagatgg tgtcctggac       540
agtgttactg atcaggacag caaagacagc acgtacagca tgagcagcac cctctcgttg       600
accaaggctg actatgaaag tcataacctc tatacctgtg aggttgttca taagacatca       660
tcctcacccg tcgtcaagag cttcaacagg aatgagtgt                             699
```

<210> SEQ ID NO 35
<211> LENGTH: 324
<212> TYPE: DNA
<213> ORGANISM: Rattus norvegicus

<400> SEQUENCE: 35

```
gacactgtgc tgacccagtc tcctgctttg gctgtgtctc tagggcagag ggtcaccatc        60
tcctgtaggg ccagcaaaag tgtcagtaca tatatacact ggtaccaaca gaggtcggga       120
cagcaaccca aactcctgat ctatagtgca tccaacctag aatctggagt cccttccagg       180
ttcagtggga gtgggtctgg gacagacttt accctcacca tagatcctgt ggagcctgat       240
gacatagcaa actattactg tcagcagatt aatgaacttc cgtacacgtt tggagctggg       300
accaagctgg aactgaaacg ggct                                            324
```

<210> SEQ ID NO 36
<211> LENGTH: 1425
<212> TYPE: DNA
<213> ORGANISM: Rattus norvegicus
<220> FEATURE:
<221> NAME/KEY: sig_peptide

<222> LOCATION: (1)..(57)

<400> SEQUENCE: 36

| | | | | |
|---|---|---|---|---|
| atggagtgga | actgggtctt | tctcttcctc | ctgtcagtaa | ctgcagtcgt | ccactcccag | 60 |
| gtccagctgc | agcagtctgg | agctgagctg | gcaaagcctg | gctcttcagt | gaagatttcc | 120 |
| tgcaaggctt | ctggctacac | cttcaccagc | tactatataa | cctggataaa | gcagacgact | 180 |
| ggacagggcc | ttaagtatat | tggatatatt | aatccgggaa | gtggacatac | taactacaat | 240 |
| gagaagttca | agggcaaggc | cacattgact | gtagacaaat | cctccagcac | agccttcatg | 300 |
| caactcagca | gcctgacacc | tgacgactct | gcggtctatt | actgtgcaag | aggggctggg | 360 |
| ggttttctac | ggattattag | taagtttgat | tactggggcc | aaggagtcat | ggtcacagtc | 420 |
| tcctcagccc | aaacaacagc | cccatctgtc | tatccactgg | ctcctggatg | tggtgataca | 480 |
| accagctcca | cggtgactct | gggatgcctg | gtcaagggct | atttccctga | gccagtcacc | 540 |
| gtgacctgga | actctggagc | cctgtccagc | gatgtgcaca | cctttccagc | tgtcctgcag | 600 |
| tctgggctct | acactctcac | cagctcagtg | acctccagca | cctggcccag | ccagaccgtc | 660 |
| acctgcaacg | tagcccaccc | ggccagcagc | accaaggtgg | acaagaaagt | tgagcgcaga | 720 |
| aatggcggca | ttggacacaa | atgccctaca | tgccctacat | gtcacaaatg | cccagttcct | 780 |
| gaactcttgg | gtggaccatc | tgtcttcatc | ttcccgccaa | agcccaagga | catcctcttg | 840 |
| atctcccaga | cgccaaggt | cacgtgtgtg | gtggtggatg | tgagcgagga | ggagccggac | 900 |
| gtccagttca | gctggtttgt | gaacaacgta | gaagtacaca | cagctcagac | acaaccccgt | 960 |
| gaggagcagt | acaacagcac | cttcagagtg | gtcagtgccc | tccccatcca | gcaccaggac | 1020 |
| tggatgagcg | gcaaggagtt | caaatgcaag | gtcaacaaca | agccctccc | aagccccatc | 1080 |
| gagaaaacca | tctcaaaacc | caagggcta | gtcagaaaac | cacaggtata | cgtcatgggt | 1140 |
| ccaccgacag | agcagttgac | tgagcaaacg | gtcagtttga | cctgcttgac | ctcaggcttc | 1200 |
| ctccctaacg | catcggtgt | ggagtggacc | agcaacgggc | atatagaaaa | gaactacaag | 1260 |
| aacaccgagc | cagtgatgga | ctctgacggt | tctttcttca | tgtacagcaa | gctcaatgtg | 1320 |
| gaaaggagca | ggtgggatag | cagagcgccc | ttcgtctgct | ccgtggtcca | cgagggtctg | 1380 |
| cacaatcacc | acgtggagaa | gagcatctcc | cggcctccgg | gtaaa | | 1425 |

<210> SEQ ID NO 37
<211> LENGTH: 369
<212> TYPE: DNA
<213> ORGANISM: Rattus norvegicus

<400> SEQUENCE: 37

| | | | | |
|---|---|---|---|---|
| caggtccagc | tgcagcagtc | tggagctgag | ctggcaaagc | ctggctcttc | agtgaagatt | 60 |
| tcctgcaagg | cttctggcta | caccttcacc | agctactata | taacctggat | aaagcagacg | 120 |
| actggacagg | gccttaagta | tattggatat | attaatccgg | gaagtggaca | tactaactac | 180 |
| aatgagaagt | tcaagggcaa | ggccacattg | actgtagaca | aatcctccag | cacagccttc | 240 |
| atgcaactca | gcagcctgac | acctgacgac | tctgcggtct | attactgtgc | aagagggget | 300 |
| gggggtttc | tacggattat | tagtaagttt | gattactggg | gccaaggagt | catggtcaca | 360 |
| gtctcctca | | | | | | 369 |

<210> SEQ ID NO 38
<211> LENGTH: 699
<212> TYPE: DNA
<213> ORGANISM: Rattus norvegicus
<220> FEATURE:
<221> NAME/KEY: sig_peptide
<222> LOCATION: (1)..(60)

<400> SEQUENCE: 38

| | | | | | |
|---|---|---|---|---|---|
| atggagacag | acagactcct | gctatgggtg | ctgctgctct | gggttccagg | ctccactggt | 60 |
| gacactgtgc | tgacccagtc | tcctgctttg | gctgtgtctc | tagggcagag | ggtcaccatc | 120 |
| tcttgtaggg | ccagcaaaag | tgtcagtaca | tatatgcact | ggtaccaaca | gaggtcggga | 180 |
| cagcaaccca | aactcctgat | ctatagtgca | tccaacctag | aatctggagt | cccttccagg | 240 |
| ttcagtggga | gtgggtctgg | gacagacttt | accctcacca | tagatcctgt | gaaggctgat | 300 |
| gacataacaa | actattactg | tcagcagagt | aatgaacttc | cgtacacgtt | tggagctggg | 360 |
| accaagctgg | aactgaaacg | ggctgatgct | gcaccaactg | tatctatctt | cccaccatcc | 420 |
| acggaacagt | tagcaactgg | aggtgcctca | gtcgtgtgcc | tcatgaacaa | cttctatccc | 480 |
| agagacatca | gtgtcaagtg | gaagattgat | ggcactgaac | gacgagatgg | tgtcctggac | 540 |
| agtgttactg | atcaggacag | caaagacagc | acgtacagca | tgagcagcac | cctctcgttg | 600 |
| accaaggctg | actatgaaag | tcataacctc | tatacctgtg | aggttgttca | taagacatca | 660 |
| tcctcacccg | tcgtcaagag | cttcaacagg | aatgagtgt | | | 699 |

<210> SEQ ID NO 39
<211> LENGTH: 324
<212> TYPE: DNA
<213> ORGANISM: Rattus norvegicus

<400> SEQUENCE: 39

| | | | | | |
|---|---|---|---|---|---|
| gacactgtgc | tgacccagtc | tcctgctttg | gctgtgtctc | tagggcagag | ggtcaccatc | 60 |
| tcttgtaggg | ccagcaaaag | tgtcagtaca | tatatgcact | ggtaccaaca | gaggtcggga | 120 |
| cagcaaccca | aactcctgat | ctatagtgca | tccaacctag | aatctggagt | cccttccagg | 180 |
| ttcagtggga | gtgggtctgg | gacagacttt | accctcacca | tagatcctgt | gaaggctgat | 240 |
| gacataacaa | actattactg | tcagcagagt | aatgaacttc | cgtacacgtt | tggagctggg | 300 |
| accaagctgg | aactgaaacg | ggct | | | | 324 |

<210> SEQ ID NO 40
<211> LENGTH: 1425
<212> TYPE: DNA
<213> ORGANISM: Rattus norvegicus
<220> FEATURE:
<221> NAME/KEY: sig_peptide
<222> LOCATION: (1)..(57)

<400> SEQUENCE: 40

| | | | | | |
|---|---|---|---|---|---|
| atggaatgga | actgggtctt | tctcttcctc | ctgtcagtaa | ctgcagaagt | ccactcccag | 60 |
| gtccagctgc | ggcagtctgg | agctgagttg | gctaagcctg | gctcttcagt | gaagatttcc | 120 |
| tgcaaggctt | ctggctacac | cttcaccagc | tactatataa | tctggatgaa | acagacggct | 180 |
| ggccagggcc | ttcagtatgt | tggatatatt | aatccgggaa | gtggacatac | taactacaat | 240 |
| gagaagttca | aggcaaggc | cacattgact | gtagacaaat | cctccagcac | agccttcatg | 300 |
| caactcagca | gcctgacacc | tgacgactct | gcggtctatt | actgtgcaag | agggactggg | 360 |
| ggttttctac | ggattattag | taagtttgat | tactggggcc | aaggagtcat | ggtcacagtc | 420 |
| tcctcagccc | aaacaacagc | cccatctgtc | tatccactgg | ctcctggatg | tggtgataca | 480 |
| accagctcca | cggtgactct | gggatgcctg | gtcaagggct | atttccctga | gccagtcacc | 540 |

```
gtgacctgga actctggagc cctgtccagc gatgtgcaca cctttccagc tgtcctgcag      600
tctgggctct acactctcac cagctcagtg acctccagca cctggcccag ccagaccgtc      660
acctgcaacg tagcccaccc ggccagcagc accaaggtgg acaagaaagt tgagcgcaga      720
aatggcggca ttggacacaa atgccctaca tgccctacat gtcacaaatg cccagttcct      780
gaactcttgg gtggaccatc tgtcttcatc ttcccgccaa agcccaagga catcctcttg      840
atctcccaga cgccaaggt cacgtgtgtg gtggtggatg tgagcgagga ggagccggac       900
gtccagttca gctggtttgt gaacaacgta gaagtacaca cagctcagac acaacccgt       960 gaggagcagt acaacagcac cttcagagtg gtcagtgccc tccccatcca gcaccaggac     1020
tggatgagcg gcaaggagtt caaatgcaag gtcaacaaca agccctcccc aagccccatc     1080
gagaaaacca tctcaaaacc caagggcta gtcagaaaac acaggtata cgtcatgggt       1140 ccaccgacag agcagttgac tgagcaaacg gtcagtttga cctgcttgac ctcaggcttc     1200
ctccctaacg acatcggtgt ggagtggacc agcaacgggc atatagaaaa gaactacaag    1260
aacaccgagc cagtgatgga ctctgacggt tctttcttca tgtacagcaa gctcaatgtg    1320
gaaaggagca ggtgggatag cagagcgccc ttcgtctgct ccgtggtcca cgagggtctg    1380
cacaatcacc acgtggagaa gagcatctcc cggcctccgg gtaaa                    1425
```

<210> SEQ ID NO 41
<211> LENGTH: 369
<212> TYPE: DNA
<213> ORGANISM: Rattus norvegicus

<400> SEQUENCE: 41

```
caggtccagc tgcggcagtc tggagctgag ttggctaagc ctggctcttc agtgaagatt       60
tcctgcaagg cttctggcta caccttcacc agctactata taatctggat gaaacagacg      120
gctggccagg ccttcagta tgttggatat attaatccgg gaagtggaca tactaactac       180
aatgagaagt tcaagggcaa ggccacattg actgtagaca atcctccag cacagccttc       240 atgcaactca gcagcctgac acctgacgac tctgcggtct attactgtgc aagagggact     300
gggggttttc tacggattat tagtaagttt gattactggg gccaaggagt catggtcaca     360
gtctcctca                                                             369
```

<210> SEQ ID NO 42
<211> LENGTH: 699
<212> TYPE: DNA
<213> ORGANISM: Rattus norvegicus
<220> FEATURE:
<221> NAME/KEY: sig_peptide
<222> LOCATION: (1)..(60)

<400> SEQUENCE: 42

```
atggagacag acagactcct gctatgggtg ctgctgctct gggttccagg ctccactggt       60
gacactgtgc tgacccagtc tcctgctttg gctgtgtctc tagggcagag ggtcaccatc      120
tcttgtaggg ccagcaaaag tgtcagtaca tatatgcact ggtaccaaca gaggtcggga     180
cagcaaccca aactcctgat ctatagtgct tccaccctag aatctggagt cccttccagg     240
ttcagtggga gtgggtctgg acagactttt accctcacca tagatcctgt ggaggctgat     300
gacatagcaa actattactg tcagcagagt aatgaacttc cgtacacgtt tggagctggg    360
accaagctgg aactgaaacg ggctgatgct gcaccaactg tatctatctt cccaccatcc   420
acggaacagt tagcaactgg aggtgcctca gtcgtgtgcc tcatgaacaa cttctatccc  480
```

-continued

```
agagacatca gtgtcaagtg gaagattgat ggcactgaac gacgagatgg tgtcctggac      540
agtgttactg atcaggacag caaagacagc acgtacagca tgagcagcac cctctcgttg      600
accaaggctg actatgaaag tcataacctc tatacctgtg aggttgttca taagacatca      660
tcctcacccg tcgtcaagag cttcaacagg aatgagtgt                             699
```

<210> SEQ ID NO 43
<211> LENGTH: 324
<212> TYPE: DNA
<213> ORGANISM: Rattus norvegicus

<400> SEQUENCE: 43

```
gacactgtgc tgacccagtc tcctgctttg gctgtgtctc tagggcagag ggtcaccatc       60
tcttgtaggg ccagcaaaag tgtcagtaca tatatgcact ggtaccaaca gaggtcggga      120
cagcaaccca aactcctgat ctatagtgct tccaccctag aatctggagt cccttccagg      180
ttcagtggga gtgggtctgg gacagacttt accctcacca tagatcctgt ggaggctgat      240
gacatagcaa actattactg tcagcagagt aatgaacttc cgtacacgtt tggagctggg      300
accaagctgg aactgaaacg ggct                                             324
```

<210> SEQ ID NO 44
<211> LENGTH: 472
<212> TYPE: PRT
<213> ORGANISM: Artificial Sequence
<220> FEATURE:
<223> OTHER INFORMATION: amino acid sequence of 04-046Ch heavy chain
<220> FEATURE:
<221> NAME/KEY: SIGNAL
<222> LOCATION: (1)..(19)

<400> SEQUENCE: 44

```
Met Lys His Leu Trp Phe Phe Leu Leu Leu Val Ala Ala Pro Arg Trp
1               5                   10                  15

Val Leu Ser Gln Val Gln Leu Gln Gln Ser Gly Ala Glu Leu Ala Lys
            20                  25                  30

Pro Gly Ser Ser Val Lys Ile Ser Cys Lys Ala Ser Gly Tyr Thr Phe
        35                  40                  45

Thr Ser Tyr Tyr Ile Ser Trp Ile Lys Gln Thr Thr Gly Gln Gly Leu
    50                  55                  60

Lys Tyr Ile Gly Phe Ile Asn Pro Gly Ser Gly His Thr Asn Tyr Asn
65                  70                  75                  80

Glu Lys Phe Lys Gly Lys Ala Thr Leu Thr Val Asp Lys Ser Ser Ser
                85                  90                  95

Thr Ala Phe Met Gln Leu Ser Ser Leu Thr Pro Asp Asp Ser Ala Ile
            100                 105                 110

Tyr Tyr Cys Ala Arg Gly Ala Gly Gly Phe Leu Arg Ile Ile Thr Lys
        115                 120                 125

Phe Asp Tyr Trp Gly Gln Gly Val Met Val Thr Val Ser Ser Ala Ser
    130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205
```

Ser Val Val Thr Val Pro Ser Ser Leu Gly Thr Gln Thr Tyr Ile
    210                 215                 220

Cys Asn Val Asn His Lys Pro Ser Asn Thr Lys Val Asp Lys Arg Val
225                 230                 235                 240

Glu Pro Lys Ser Cys Asp Lys Thr His Thr Cys Pro Pro Cys Pro Ala
                245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
    290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
        355                 360                 365

Arg Glu Pro Gln Val Tyr Thr Leu Pro Pro Ser Arg Glu Glu Met Thr
    370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
            420                 425                 430

Ser Lys Leu Thr Val Asp Lys Ser Arg Trp Gln Gln Gly Asn Val Phe
        435                 440                 445

Ser Cys Ser Val Met His Glu Ala Leu His Asn His Tyr Thr Gln Lys
    450                 455                 460

Ser Leu Ser Leu Ser Pro Gly Lys
465                 470

<210> SEQ ID NO 45
<211> LENGTH: 233
<212> TYPE: PRT
<213> ORGANISM: Artificial Sequence
<220> FEATURE:
<223> OTHER INFORMATION: amino acid sequence of 04-046Ch light chain
<220> FEATURE:
<221> NAME/KEY: SIGNAL
<222> LOCATION: (1)..(20)

<400> SEQUENCE: 45

Met Val Leu Gln Thr Gln Val Phe Ile Ser Leu Leu Trp Ile Ser
1               5                   10                  15

Gly Ala Tyr Gly Asp Thr Val Leu Thr Gln Ser Pro Ala Leu Ala Val
            20                  25                  30

Ser Leu Gly Gln Arg Val Thr Ile Ser Cys Arg Ala Ser Lys Ser Val
        35                  40                  45

Ser Thr Tyr Ile His Trp Tyr Gln Gln Arg Ser Gly Gln Gln Pro Lys
    50                  55                  60

Leu Leu Ile Tyr Ser Ala Ser Asn Leu Glu Ser Gly Val Pro Ser Arg
65                  70                  75                  80

```
Phe Ser Gly Ser Gly Ser Gly Thr Asp Phe Thr Leu Thr Ile Asp Pro
                85                  90                  95
Val Glu Pro Asp Asp Ile Ala Asn Tyr Tyr Cys Gln Gln Ile Asn Glu
            100                 105                 110
Leu Pro Tyr Thr Phe Gly Ala Gly Thr Lys Leu Glu Leu Lys Arg Ala
        115                 120                 125
Val Ala Ala Pro Ser Val Phe Ile Phe Pro Pro Ser Asp Glu Gln Leu
    130                 135                 140
Lys Ser Gly Thr Ala Ser Val Val Cys Leu Leu Asn Asn Phe Tyr Pro
145                 150                 155                 160
Arg Glu Ala Lys Val Gln Trp Lys Val Asp Asn Ala Leu Gln Ser Gly
                165                 170                 175
Asn Ser Gln Glu Ser Val Thr Glu Gln Asp Ser Lys Asp Ser Thr Tyr
            180                 185                 190
Ser Leu Ser Ser Thr Leu Thr Leu Ser Lys Ala Asp Tyr Glu Lys His
        195                 200                 205
Lys Val Tyr Ala Cys Glu Val Thr His Gln Gly Leu Ser Ser Pro Val
    210                 215                 220
Thr Lys Ser Phe Asn Arg Gly Glu Cys
225                 230
```

<210> SEQ ID NO 46
<211> LENGTH: 1416
<212> TYPE: DNA
<213> ORGANISM: Artificial Sequence
<220> FEATURE:
<223> OTHER INFORMATION: nucleotide sequence of 04-046Ch heavy chain
<220> FEATURE:
<221> NAME/KEY: sig_peptide
<222> LOCATION: (1)..(57)

<400> SEQUENCE: 46

```
atgaaacacc tgtggttctt cctcctgctg gtggcagctc ccagatgggt gctgagccag     60
gtgcagctgc agcagtctgg cgccgaactg gccaagcctg gcagcagcgt gaagatcagc    120
tgcaaggcca gcggctacac cttcaccagc tactacatca gctggataa gcagaccacc     180
ggccagggcc tgaagtacat cggcttcatc aaccccggca gcggccacac caactacaac    240
gagaagttca agggcaaggc caccctgacc gtggacaaga gcagcagcac cgccttcatg    300
cagctgtcca gcctgacccc cgacgacagc gccatctact actgtgctag aggcgctggc    360
ggcttcctgc ggatcatcac caagttcgac tactggggcc agggcgtgat ggtcaccgtc    420
agctcagcct ccaccaaggg cccaagcgtc ttccccctgg caccctcctc caagagcacc    480
tctggcggca cagccgccct gggctgcctg gtcaaggact acttcccga acccgtgacc    540
gtgagctgga actcaggcgc cctgaccagc ggcgtgcaca ccttcccgc tgtcctgcag    600
tcctcaggac tctactccct cagcagcgtg gtgaccgtgc cctccagcag cttgggcacc    660
cagacctaca tctgcaacgt gaatcacaag cccagcaaca ccaaggtgga caagagagtt    720
gagcccaaat cttgtgacaa aactcacaca tgcccaccct gcccagcacc tgaactcctg    780
gggggaccct cagtcttcct cttcccccca aaacccaagg acaccctcat gatctcccgg    840
acccctgagg tcacatgcgt ggtggtggac gtgagccacg aagaccctga ggtcaagttc    900
aactggtacg tggacggcgt ggaggtgcat aatgccaaga caaagccccg ggaggagcag    960
tacaacagca cgtaccgggt ggtcagcgtc ctcaccgtcc tgcaccagga ctggctgaat   1020
ggcaaggagt acaagtgcaa ggtctccaac aaagccctcc cagcccccat cgagaaaacc   1080
```

-continued

```
atctccaaag ccaaaggcca gccccgggaa ccacaggtgt acaccctgcc cccatcccgg      1140
gaggagatga ccaagaacca ggtcagcctg acctgcctgg tcaaaggctt ctatcccagc      1200
gacatcgccg tggagtggga gagcaatggc cagcccgaga caactacaa gaccacccct       1260 cccgtgctgg actccgacgg ctccttcttc ctctacagca agctcaccgt ggacaagagc      1320
aggtggcagc agggcaacgt cttctcatgc tccgtgatgc atgaggctct gcacaaccac      1380
tacacccaga gagcctctc cctgtctccc ggcaaa                                 1416
```

<210> SEQ ID NO 47
<211> LENGTH: 699
<212> TYPE: DNA
<213> ORGANISM: Artificial Sequence
<220> FEATURE:
<223> OTHER INFORMATION: nucleotide sequence of 04-046Ch light chain
<220> FEATURE:
<221> NAME/KEY: sig_peptide
<222> LOCATION: (1)..(60)

<400> SEQUENCE: 47

```
atggtgctgc agacccaggt gttcatctcc ctgctgctgt ggatctccgg cgcgtacggc      60
gataccgtgc tgacacagtc tccagccctg gccgtgtccc tgggccagag agtgaccatc      120
agctgcagag ccagcaagag cgtgtccacc tacatccact ggtatcagca gcggagcggc      180
cagcagccca gctgctgat ctacagcgcc agcaacctgg aaagcggcgt gcccagcaga      240
ttttccggca gcggctctgg caccgacttc accctgacca tcgacccgt ggaacccgac       300 gatatcgcca actactactg ccagcagatc aacgagctgc cctacacctt cggagccggc      360
accaagctgg aactgaagag agccgtggcc gcccctccg tgttcatctt ccccccctcc       420
gacgagcagc tgaagtccgg caccgcctcc gtggtgtgcc tgctgaataa cttctacccc      480
agagaggcca aggtgcagtg gaaggtggac aacgccctgc agtccgggaa ctcccaggag      540
agcgtgaccg agcaggacag caaggacagc acctacagcc tgagcagcac cctgaccctg      600
agcaaagccg actacgagaa gcacaaggtg tacgcctgcg aggtgaccca ccagggcctg      660 agctccccg tcaccaagag cttcaacagg ggggagtgt                              699
```

<210> SEQ ID NO 48
<211> LENGTH: 472
<212> TYPE: PRT
<213> ORGANISM: Artificial Sequence
<220> FEATURE:
<223> OTHER INFORMATION: amino acid sequence of h046-H4b
<220> FEATURE:
<221> NAME/KEY: SIGNAL
<222> LOCATION: (1)..(19)

<400> SEQUENCE: 48

```
Met Lys His Leu Trp Phe Phe Leu Leu Leu Val Ala Ala Pro Arg Trp
1               5                   10                  15

Val Leu Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Tyr Tyr Ile Ser Trp Ile Arg Gln Ala Pro Gly Gln Gly Leu
    50                  55                  60

Lys Tyr Met Gly Phe Ile Asn Pro Gly Ser Gly His Thr Asn Tyr Asn
65                  70                  75                  80

Glu Lys Phe Lys Gly Arg Val Thr Ile Thr Ala Asp Lys Ser Ser Ser
```

```
                    85                  90                  95
Thr Ala Thr Met Glu Leu Ser Ser Leu Arg Ser Glu Asp Thr Ala Val
                100                 105                 110
Tyr Tyr Cys Ala Arg Gly Ala Gly Phe Leu Arg Ile Ile Thr Lys
            115                 120                 125
Phe Asp Tyr Trp Gly Gln Gly Thr Leu Val Thr Val Ser Ser Ala Ser
        130                 135                 140
Thr Lys Gly Pro Ser Val Phe Pro Leu Ala Pro Ser Ser Lys Ser Thr
145                 150                 155                 160
Ser Gly Gly Thr Ala Ala Leu Gly Cys Leu Val Lys Asp Tyr Phe Pro
                165                 170                 175
Glu Pro Val Thr Val Ser Trp Asn Ser Gly Ala Leu Thr Ser Gly Val
                180                 185                 190
His Thr Phe Pro Ala Val Leu Gln Ser Ser Gly Leu Tyr Ser Leu Ser
            195                 200                 205
Ser Val Val Thr Val Pro Ser Ser Ser Leu Gly Thr Gln Thr Tyr Ile
        210                 215                 220
Cys Asn Val Asn His Lys Pro Ser Asn Thr Lys Val Asp Lys Arg Val
225                 230                 235                 240
Glu Pro Lys Ser Cys Asp Lys Thr His Thr Cys Pro Pro Cys Pro Ala
                245                 250                 255
Pro Glu Leu Leu Gly Gly Pro Ser Val Phe Leu Phe Pro Pro Lys Pro
                260                 265                 270
Lys Asp Thr Leu Met Ile Ser Arg Thr Pro Glu Val Thr Cys Val Val
            275                 280                 285
Val Asp Val Ser His Glu Asp Pro Glu Val Lys Phe Asn Trp Tyr Val
        290                 295                 300
Asp Gly Val Glu Val His Asn Ala Lys Thr Lys Pro Arg Glu Glu Gln
305                 310                 315                 320
Tyr Asn Ser Thr Tyr Arg Val Val Ser Val Leu Thr Val Leu His Gln
                325                 330                 335
Asp Trp Leu Asn Gly Lys Glu Tyr Lys Cys Lys Val Ser Asn Lys Ala
            340                 345                 350
Leu Pro Ala Pro Ile Glu Lys Thr Ile Ser Lys Ala Lys Gly Gln Pro
        355                 360                 365
Arg Glu Pro Gln Val Tyr Thr Leu Pro Pro Ser Arg Glu Glu Met Thr
    370                 375                 380
Lys Asn Gln Val Ser Leu Thr Cys Leu Val Lys Gly Phe Tyr Pro Ser
385                 390                 395                 400
Asp Ile Ala Val Glu Trp Glu Ser Asn Gly Gln Pro Glu Asn Asn Tyr
                405                 410                 415
Lys Thr Thr Pro Pro Val Leu Asp Ser Asp Gly Ser Phe Phe Leu Tyr
            420                 425                 430
Ser Lys Leu Thr Val Asp Lys Ser Arg Trp Gln Gln Gly Asn Val Phe
        435                 440                 445
Ser Cys Ser Val Met His Glu Ala Leu His Asn His Tyr Thr Gln Lys
    450                 455                 460
Ser Leu Ser Leu Ser Pro Gly Lys
465                 470

<210> SEQ ID NO 49
<211> LENGTH: 1416
<212> TYPE: DNA
<213> ORGANISM: Artificial Sequence
```

<220> FEATURE:
<223> OTHER INFORMATION: nucleotide sequence of h046-H4b (1)
<220> FEATURE:
<221> NAME/KEY: sig_peptide
<222> LOCATION: (1)..(57)

<400> SEQUENCE: 49

```
atgaaacacc tgtggttctt cctcctgctg gtggcagctc ccagatgggt gctgagccag     60
gtgcagctgg tgcagtctgg cgccgaagtg aagaaaccag cgccagcgt gaaggtgtcc    120
tgcaaggcca gcggctacac ctttaccagc tactacatca gctggatccg gcaggcccct    180
ggacagggcc tgaagtacat gggcttcatc aaccctggca gcggccacac caactacaac    240
gagaagttca agggcagagt gaccatcacc gccgacaaga gcagcagcac cgccaccatg    300
gaactgagca gcctgagaag cgaggacacc gccgtgtact actgcgctag aggcgctggc    360
ggcttcctgc ggatcatcac caagttcgac tactggggcc agggcaccct cgtgaccgtc    420
agctcagcct ccaccaaggg cccaagcgtc ttcccctgg cacctcctc aagagcacc       480
tctggcggca cagccgccct gggctgcctg gtcaaggact acttccccga acccgtgacc    540
gtgagctgga actcaggcgc cctgaccagc ggcgtgcaca ccttccccgc tgtcctgcag    600
tcctcaggac tctactccct cagcagcgtg gtgaccgtgc cctccagcag cttgggcacc    660
cagacctaca tctgcaacgt gaatcacaag cccagcaaca ccaaggtgga caagagagtt    720
gagcccaaat cttgtgacaa aactcacaca tgcccaccct gcccagcacc tgaactcctg    780
gggggaccct cagtcttcct cttccccca aaacccaagg acaccctcat gatctcccgg    840
acccctgagg tcacatgcgt ggtggtggac gtgagccacg aagaccctga ggtcaagttc    900
aactggtacg tggacggcgt ggaggtgcat aatgccaaga caaagcccg ggaggagcag    960
tacaacagca cgtaccgggt ggtcagcgtc ctcaccgtcc tgcaccagga ctggctgaat   1020
ggcaaggagt acaagtgcaa ggtctccaac aaagccctcc cagcccccat cgagaaaacc   1080
atctccaaag ccaaaggcca gccccgggaa ccacaggtgt acaccctgcc cccatcccgg   1140
gaggagatga ccaagaacca ggtcagcctg acctgcctgg tcaaaggctt ctatcccagc   1200
gacatcgccg tggagtggga gagcaatggc cagcccgaga acaactacaa gaccaccct   1260
cccgtgctgg actccgacgg ctccttcttc ctctacagca agctcaccgt ggacaagagc   1320
aggtggcagc agggcaacgt cttctcatgc tccgtgatgc atgaggctct gcacaaccac   1380
tacacccaga agagcctctc cctgtctccc ggcaaa                             1416
```

<210> SEQ ID NO 50
<211> LENGTH: 472
<212> TYPE: PRT
<213> ORGANISM: Artificial Sequence
<220> FEATURE:
<223> OTHER INFORMATION: amino acid sequence of h046-H4e
<220> FEATURE:
<221> NAME/KEY: SIGNAL
<222> LOCATION: (1)..(19)

<400> SEQUENCE: 50

```
Met Lys His Leu Trp Phe Phe Leu Leu Leu Val Ala Ala Pro Arg Trp
1               5                   10                  15

Val Leu Ser Glu Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Tyr Tyr Ile Ser Trp Ile Arg Gln Ala Pro Gly Gln Gly Leu
```

-continued

```
            50                  55                  60
Lys Tyr Met Gly Phe Ile Asn Pro Gly Ser Gly His Thr Asn Tyr Asn
 65                      70                  75                  80

Glu Lys Phe Lys Gly Arg Val Thr Ile Thr Ala Asp Lys Ser Ser Ser
                     85                  90                  95

Thr Ala Thr Met Glu Leu Ser Ser Leu Arg Ser Glu Asp Thr Ala Val
                100                 105                 110

Tyr Tyr Cys Ala Arg Gly Ala Gly Phe Leu Arg Ile Ile Thr Lys
                115                 120                 125

Phe Asp Tyr Trp Gly Gln Gly Thr Leu Val Thr Val Ser Ser Ala Ser
            130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                    165                 170                 175

Glu Pro Val Thr Val Ser Trp Asn Ser Gly Ala Leu Thr Ser Gly Val
                180                 185                 190

His Thr Phe Pro Ala Val Leu Gln Ser Ser Gly Leu Tyr Ser Leu Ser
            195                 200                 205

Ser Val Val Thr Val Pro Ser Ser Ser Leu Gly Thr Gln Thr Tyr Ile
        210                 215                 220

Cys Asn Val Asn His Lys Pro Ser Asn Thr Lys Val Asp Lys Arg Val
225                 230                 235                 240

Glu Pro Lys Ser Cys Asp Lys Thr His Thr Cys Pro Pro Cys Pro Ala
                    245                 250                 255

Pro Glu Leu Leu Gly Gly Pro Ser Val Phe Leu Phe Pro Pro Lys Pro
                260                 265                 270

Lys Asp Thr Leu Met Ile Ser Arg Thr Pro Glu Val Thr Cys Val Val
                275                 280                 285

Val Asp Val Ser His Glu Asp Pro Glu Val Lys Phe Asn Trp Tyr Val
            290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                    325                 330                 335

Asp Trp Leu Asn Gly Lys Glu Tyr Lys Cys Lys Val Ser Asn Lys Ala
                340                 345                 350

Leu Pro Ala Pro Ile Glu Lys Thr Ile Ser Lys Ala Lys Gly Gln Pro
                355                 360                 365

Arg Glu Pro Gln Val Tyr Thr Leu Pro Pro Ser Arg Glu Glu Met Thr
            370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                    405                 410                 415

Lys Thr Thr Pro Pro Val Leu Asp Ser Asp Gly Ser Phe Phe Leu Tyr
                420                 425                 430

Ser Lys Leu Thr Val Asp Lys Ser Arg Trp Gln Gln Gly Asn Val Phe
            435                 440                 445

Ser Cys Ser Val Met His Glu Ala Leu His Asn His Tyr Thr Gln Lys
        450                 455                 460

Ser Leu Ser Leu Ser Pro Gly Lys
465                 470
```

<210> SEQ ID NO 51
<211> LENGTH: 1416
<212> TYPE: DNA
<213> ORGANISM: Artificial Sequence
<220> FEATURE:
<223> OTHER INFORMATION: nucleotide sequence of h046-H4e
<220> FEATURE:
<221> NAME/KEY: sig_peptide
<222> LOCATION: (1)..(57)

<400> SEQUENCE: 51

```
atgaagcacc tgtggttctt tctgctgctg gtggccgctc ccagatgggt gctgtctgaa      60
gtgcagctgg tgcagtctgg cgccgaagtg aagaaacctg gcgcctccgt gaaggtgtcc     120
tgcaaggcct ccggctacac ctttaccagc tactacatct cctggatccg gcaggcccct     180
ggacagggcc tgaagtacat gggcttcatc aaccccggct ccggccacac caactacaac     240
gagaagttca agggcagagt gaccattacc gccgacaagt cctcctccac cgctaccatg     300
gaactgtcct ccctgcggag cgaggacacc gccgtgtact actgtgctag aggcgctggc     360
ggcttcctgc ggatcatcac caagttcgac tactggggcc agggcaccct cgtgaccgtg     420
tcctctgctt ctaccaaggg cccctccgtg ttccctctgg ccccttccag caagtctacc     480
tctggcggca cagccgctct gggctgcctc gtgaaggact acttccccga gcccgtgaca     540
gtgtcttgga actctggcgc cctgacctcc ggcgtgcaca catttccagc tgtgctgcag     600
tcctccggcc tgtactccct gtcctccgtc gtgactgtgc cctccagctc tctgggcacc     660
cagacctaca tctgcaacgt gaaccacaag ccctccaaca ccaaggtgga caagcgggtg     720
gaacccaagt cctgcgacaa gacccacacc tgtcccccct tgcctgcccc tgaactgctg     780
ggcggaccca gcgtgttcct gttccccccca agcccaagg acaccctgat gatctcccgg     840
acccccgaag tgacctgcgt ggtggtggat gtgtcccacg aggaccctga agtgaagttc     900
aattggtacg tggacggcgt ggaagtgcac aacgccaaga ccaagcctag agaggaacag     960
tacaactcca cctaccgggt ggtgtccgtg ctgaccgtgc tgcaccagga ttggctgaac    1020
ggcaaagagt acaagtgcaa ggtgtccaac aaggctctgc ctgcccccat cgaaaagacc    1080
atctccaagg ccaagggcca gccccgggaa ccccaggtgt acacactgcc ccctagccgg    1140
gaagagatga ccaagaacca ggtgtccctg acctgtctcg tgaaaggctt ctacccctcc    1200
gatatcgccg tggaatggga gtccaacggc cagcctgaga caactacaa gaccaccccc    1260
cctgtgctgg actccgacgg ctcattcttc ctgtacagca agctgacagt ggacaagtcc    1320
cggtggcagc agggcaacgt gttctcctgc tccgtgatgc acgaggccct gcacaaccac    1380
tacacccaga gtccctgtc cctgagcccc ggcaaa                              1416
```

<210> SEQ ID NO 52
<211> LENGTH: 472
<212> TYPE: PRT
<213> ORGANISM: Artificial Sequence
<220> FEATURE:
<223> OTHER INFORMATION: amino acid sequence of h046-H5b

<400> SEQUENCE: 52

```
Met Lys His Leu Trp Phe Phe Leu Leu Leu Val Ala Ala Pro Arg Trp
1               5                   10                  15

Val Leu Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
```

-continued

```
                35                  40                  45
Thr Ser Tyr Tyr Ile Ser Trp Ile Arg Gln Ala Pro Gly Gln Gly Leu
 50                  55                  60
Lys Tyr Met Gly Phe Ile Asn Pro Gly Ser Gly His Thr Asn Tyr Asn
 65                  70                  75                  80
Glu Lys Phe Lys Gly Arg Val Thr Ile Thr Ala Asp Lys Ser Ser Ser
                 85                  90                  95
Thr Ala Asn Met Glu Leu Ser Ser Leu Arg Ser Glu Asp Thr Ala Val
                100                 105                 110
Tyr Tyr Cys Ala Arg Gly Ala Gly Gly Phe Leu Arg Ile Ile Thr Lys
                115                 120                 125
Phe Asp Tyr Trp Gly Gln Gly Thr Leu Val Thr Val Ser Ser Ala Ser
                130                 135                 140
Thr Lys Gly Pro Ser Val Phe Pro Leu Ala Pro Ser Ser Lys Ser Thr
145                 150                 155                 160
Ser Gly Gly Thr Ala Ala Leu Gly Cys Leu Val Lys Asp Tyr Phe Pro
                165                 170                 175
Glu Pro Val Thr Val Ser Trp Asn Ser Gly Ala Leu Thr Ser Gly Val
                180                 185                 190
His Thr Phe Pro Ala Val Leu Gln Ser Ser Gly Leu Tyr Ser Leu Ser
                195                 200                 205
Ser Val Val Thr Val Pro Ser Ser Ser Leu Gly Thr Gln Thr Tyr Ile
210                 215                 220
Cys Asn Val Asn His Lys Pro Ser Asn Thr Lys Val Asp Lys Arg Val
225                 230                 235                 240
Glu Pro Lys Ser Cys Asp Lys Thr His Thr Cys Pro Pro Cys Pro Ala
                245                 250                 255
Pro Glu Leu Leu Gly Gly Pro Ser Val Phe Leu Phe Pro Pro Lys Pro
                260                 265                 270
Lys Asp Thr Leu Met Ile Ser Arg Thr Pro Glu Val Thr Cys Val Val
                275                 280                 285
Val Asp Val Ser His Glu Asp Pro Glu Val Lys Phe Asn Trp Tyr Val
290                 295                 300
Asp Gly Val Glu Val His Asn Ala Lys Thr Lys Pro Arg Glu Glu Gln
305                 310                 315                 320
Tyr Asn Ser Thr Tyr Arg Val Val Ser Val Leu Thr Val Leu His Gln
                325                 330                 335
Asp Trp Leu Asn Gly Lys Glu Tyr Lys Cys Lys Val Ser Asn Lys Ala
                340                 345                 350
Leu Pro Ala Pro Ile Glu Lys Thr Ile Ser Lys Ala Lys Gly Gln Pro
                355                 360                 365
Arg Glu Pro Gln Val Tyr Thr Leu Pro Pro Ser Arg Glu Glu Met Thr
                370                 375                 380
Lys Asn Gln Val Ser Leu Thr Cys Leu Val Lys Gly Phe Tyr Pro Ser
385                 390                 395                 400
Asp Ile Ala Val Glu Trp Glu Ser Asn Gly Gln Pro Glu Asn Asn Tyr
                405                 410                 415
Lys Thr Thr Pro Pro Val Leu Asp Ser Asp Gly Ser Phe Phe Leu Tyr
                420                 425                 430
Ser Lys Leu Thr Val Asp Lys Ser Arg Trp Gln Gln Gly Asn Val Phe
                435                 440                 445
Ser Cys Ser Val Met His Glu Ala Leu His Asn His Tyr Thr Gln Lys
450                 455                 460
```

Ser Leu Ser Leu Ser Pro Gly Lys
465                 470

<210> SEQ ID NO 53
<211> LENGTH: 1416
<212> TYPE: DNA
<213> ORGANISM: Artificial Sequence
<220> FEATURE:
<223> OTHER INFORMATION: nucleotide sequence of h046-H5b (1)
<220> FEATURE:
<221> NAME/KEY: sig_peptide
<222> LOCATION: (1)..(57)

<400> SEQUENCE: 53

| | | |
|---|---|---|
| atgaaacacc tgtggttctt cctcctgctg gtggcagctc ccagatgggt gctgagccag | 60 |
| gtgcagctgg tgcagtctgg cgccgaagtg aagaaaccag cgccagcgt gaaggtgtcc | 120 |
| tgcaaggcca gcggctacac ctttaccagc tactacatca gctggatccg gcaggcccct | 180 |
| ggacagggcc tgaagtacat gggcttcatc aaccctggca gcggcacac caactacaac | 240 |
| gagaagttca aggcagagt gaccatcacc gccgacaaga gcagcagcac cgccaacatg | 300 |
| gaactgagca gcctgcggag cgaggacacc gccgtgtact attgtgctag aggcgctggc | 360 |
| ggcttcctgc ggatcatcac caagttcgac tactggggcc agggcaccct cgtgaccgtc | 420 |
| agctcagcct ccaccaaggg cccaagcgtc ttccccctgg cccctcctc caagagcacc | 480 |
| tctgcggca cagccgccct gggctgcctg gtcaaggact acttccccga cccgtgacc | 540 |
| gtgagctgga ctcaggcgc cctgaccagc ggcgtgcaca ccttcccgc tgtcctgcag | 600 |
| tcctcaggac tctactccct cagcagcgtg gtgaccgtgc cctccagcag cttgggcacc | 660 |
| cagacctaca tctgcaacgt gaatcacaag cccagcaaca ccaaggtgga caagagagtt | 720 |
| gagcccaaat cttgtgacaa aactcacaca tgcccaccct gcccagcacc tgaactcctg | 780 |
| gggggaccct cagtcttcct cttcccccca aaacccaagg acaccctcat gatctcccgg | 840 |
| acccctgagg tcacatgcgt ggtggtggac gtgagccacg aagaccctga ggtcaagttc | 900 |
| aactggtacg tggacggcgt ggaggtgcat aatgccaaga caaagcccg ggaggagcag | 960 |
| tacaacagca cgtaccgggt ggtcagcgtc ctcaccgtcc tgcaccagga ctggctgaat | 1020 |
| ggcaaggagt acaagtgcaa ggtctccaac aaagccctcc cagccccat cgagaaaacc | 1080 |
| atctccaaag ccaaaggcca gccccgggaa ccacaggtgt acaccctgcc cccatcccgg | 1140 |
| gaggagatga ccaagaacca ggtcagcctg acctgcctgg tcaaaggctt ctatcccagc | 1200 |
| gacatcgccg tggagtggga gagcaatggc cagcccgaga caactacaa gaccacccct | 1260 |
| cccgtgctgg actccgacgg ctccttcttc ctctacagca agctcaccgt ggacaagagc | 1320 |
| aggtggcagc agggcaacgt cttctcatgc tccgtgatgc atgaggctct gcacaaccac | 1380 |
| tacacccaga gagcctctc cctgtctccc ggcaaa | 1416 |

<210> SEQ ID NO 54
<211> LENGTH: 472
<212> TYPE: PRT
<213> ORGANISM: Artificial Sequence
<220> FEATURE:
<223> OTHER INFORMATION: amino acid sequece of h046-H8

<400> SEQUENCE: 54

Met Lys His Leu Trp Phe Phe Leu Leu Leu Val Ala Ala Pro Arg Trp
1               5                   10                  15

Val Leu Ser Gln Val Gln Leu Gln Gln Ser Gly Ala Glu Leu Ala Lys

```
                20              25              30
Pro Gly Ser Ser Val Lys Ile Ser Cys Lys Ala Ser Gly Tyr Thr Phe
            35              40              45
Thr Ser Tyr Tyr Ile Ser Trp Ile Lys Gln Thr Thr Gly Gln Gly Leu
        50              55              60
Lys Tyr Ile Gly Phe Ile Asn Pro Gly Ser Gly His Thr Asn Tyr Asn
65              70              75              80
Glu Lys Phe Lys Gly Lys Ala Thr Leu Thr Val Asp Lys Ser Ser Ser
                85              90              95
Thr Ala Asn Met Gln Leu Ser Ser Leu Thr Pro Asp Asp Ser Ala Ile
            100             105             110
Tyr Tyr Cys Ala Arg Gly Ala Gly Phe Leu Arg Ile Ile Thr Lys
            115             120             125
Phe Asp Tyr Trp Gly Gln Gly Val Met Val Thr Val Ser Ser Ala Ser
        130             135             140
Thr Lys Gly Pro Ser Val Phe Pro Leu Ala Pro Ser Ser Lys Ser Thr
145             150             155             160
Ser Gly Gly Thr Ala Ala Leu Gly Cys Leu Val Lys Asp Tyr Phe Pro
                165             170             175
Glu Pro Val Thr Val Ser Trp Asn Ser Gly Ala Leu Thr Ser Gly Val
            180             185             190
His Thr Phe Pro Ala Val Leu Gln Ser Ser Gly Leu Tyr Ser Leu Ser
        195             200             205
Ser Val Val Thr Val Pro Ser Ser Ser Leu Gly Thr Gln Thr Tyr Ile
210             215             220
Cys Asn Val Asn His Lys Pro Ser Asn Thr Lys Val Asp Lys Arg Val
225             230             235             240
Glu Pro Lys Ser Cys Asp Lys Thr His Thr Cys Pro Pro Cys Pro Ala
            245             250             255
Pro Glu Leu Leu Gly Gly Pro Ser Val Phe Leu Phe Pro Pro Lys Pro
        260             265             270
Lys Asp Thr Leu Met Ile Ser Arg Thr Pro Glu Val Thr Cys Val Val
            275             280             285
Val Asp Val Ser His Glu Asp Pro Glu Val Lys Phe Asn Trp Tyr Val
        290             295             300
Asp Gly Val Glu Val His Asn Ala Lys Thr Lys Pro Arg Glu Glu Gln
305             310             315             320
Tyr Asn Ser Thr Tyr Arg Val Val Ser Val Leu Thr Val Leu His Gln
            325             330             335
Asp Trp Leu Asn Gly Lys Glu Tyr Lys Cys Lys Val Ser Asn Lys Ala
            340             345             350
Leu Pro Ala Pro Ile Glu Lys Thr Ile Ser Lys Ala Lys Gly Gln Pro
            355             360             365
Arg Glu Pro Gln Val Tyr Thr Leu Pro Pro Ser Arg Glu Glu Met Thr
            370             375             380
Lys Asn Gln Val Ser Leu Thr Cys Leu Val Lys Gly Phe Tyr Pro Ser
385             390             395             400
Asp Ile Ala Val Glu Trp Glu Ser Asn Gly Gln Pro Glu Asn Asn Tyr
            405             410             415
Lys Thr Thr Pro Pro Val Leu Asp Ser Asp Gly Ser Phe Phe Leu Tyr
            420             425             430
Ser Lys Leu Thr Val Asp Lys Ser Arg Trp Gln Gln Gly Asn Val Phe
            435             440             445
```

Ser Cys Ser Val Met His Glu Ala Leu His Asn His Tyr Thr Gln Lys
            450                 455                 460

Ser Leu Ser Leu Ser Pro Gly Lys
465                 470

<210> SEQ ID NO 55
<211> LENGTH: 1416
<212> TYPE: DNA
<213> ORGANISM: Artificial Sequence
<220> FEATURE:
<223> OTHER INFORMATION: nucleotide sequence of h046-H8 (1)
<220> FEATURE:
<221> NAME/KEY: sig_peptide
<222> LOCATION: (1)..(57)

<400> SEQUENCE: 55
atgaaacacc tgtggttctt cctcctgctg gtggcagctc ccagatgggt gctgagccag      60
gtgcagctgc agcagtctgg cgccgaactg gccaagcctg gcagcagcgt gaagatcagc    120
tgcaaggcca gcggctacac cttcaccagc tactacatca gctggatcaa gcagaccacc    180
ggccagggcc tgaagtacat cggcttcatc aaccccggca gcggccacac caactacaac    240
gagaagttca agggcaaggc caccctgacc gtggacaaga gcagcagcac cgccaacatg    300
cagctgtcca gcctgacccc cgacgacagc gccatctact actgtgctag aggcgctggc    360
ggcttcctgc ggatcatcac caagttcgac tactggggcc agggcgtgat ggtcaccgtc    420
agctcagcct ccaccaaggg cccaagcgtc ttccccctgg caccctcctc caagagcacc    480
tctggcggca cagccgccct gggctgcctg gtcaaggact acttccccga accgtgacc     540 gtgagctgga actcaggcgc cctgaccagc ggcgtgcaca ccttcccgc tgtcctgcag     600 tcctcaggac tctactccct cagcagcgtg gtgaccgtgc cctccagcag cttgggcacc    660
cagacctaca tctgcaacgt gaatcacaag cccagcaaca ccaaggtgga caagagagtt    720
gagcccaaat cttgtgacaa aactcacaca tgcccaccct gcccagcacc tgaactcctg    780
gggggaccct cagtcttcct cttccccca aaacccaagg acaccctcat gatctcccgg     840 accctgagg tcacatgcgt ggtggtggac gtgagccacg aagaccctga ggtcaagttc     900
aactggtacg tggacggcgt ggaggtgcat aatgccaaga caaagccccg ggaggagcag    960
tacaacagca cgtaccgggt ggtcagcgtc ctcaccgtcc tgcaccagga ctggctgaat   1020
ggcaaggagt acaagtgcaa ggtctccaac aaagccctcc cagcccccat cgagaaaacc   1080
atctccaaag ccaaaggcca gccccgggaa ccacaggtgt acaccctgcc cccatcccgg   1140
gaggagatga ccaagaacca ggtcagcctg acctgcctgg tcaaaggctt ctatcccagc   1200
gacatcgccg tggagtggga gagcaatggg cagcccgaga caactacaa gaccacccct   1260 cccgtgctgg actccgacgg ctccttcttc ctctacagca agctcaccgt ggacaagagc   1320
aggtggcagc agggcaacgt cttctcatgc tccgtgatgc atgaggctct gcacaaccac   1380
tacacccaga gagcctctc cctgtctccc ggcaaa                             1416

<210> SEQ ID NO 56
<211> LENGTH: 472
<212> TYPE: PRT
<213> ORGANISM: Artificial Sequence
<220> FEATURE:
<223> OTHER INFORMATION: amino acid sequence of h046-H10
<220> FEATURE:
<221> NAME/KEY: SIGNAL
<222> LOCATION: (1)..(19)

<400> SEQUENCE: 56

```
Met Lys His Leu Trp Phe Phe Leu Leu Leu Val Ala Ala Pro Arg Trp
1               5                   10                  15

Val Leu Ser Gln Val Gln Leu Gln Gln Ser Gly Ala Glu Leu Ala Lys
            20                  25                  30

Pro Gly Ser Ser Val Lys Val Ser Cys Lys Ala Ser Gly Tyr Thr Phe
        35                  40                  45

Thr Ser Tyr Tyr Ile Ser Trp Ile Lys Gln Thr Thr Gly Gln Gly Leu
    50                  55                  60

Lys Tyr Ile Gly Phe Ile Asn Pro Gly Ser Gly His Thr Asn Tyr Asn
65                  70                  75                  80

Glu Lys Phe Lys Gly Lys Ala Thr Leu Thr Val Asp Lys Ser Ser Ser
                85                  90                  95

Thr Ala Asn Met Gln Leu Ser Ser Leu Thr Pro Asp Asp Ser Ala Ile
            100                 105                 110

Tyr Tyr Cys Ala Arg Gly Ala Gly Phe Leu Arg Ile Ile Thr Lys
        115                 120                 125

Phe Asp Tyr Trp Gly Gln Gly Val Met Val Thr Val Ser Ser Ala Ser
    130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Leu Gly Thr Gln Thr Tyr Ile
    210                 215                 220

Cys Asn Val Asn His Lys Pro Ser Asn Thr Lys Val Asp Lys Arg Val
225                 230                 235                 240

Glu Pro Lys Ser Cys Asp Lys Thr His Thr Cys Pro Pro Cys Pro Ala
                245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
    290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
        355                 360                 365

Arg Glu Pro Gln Val Tyr Thr Leu Pro Pro Ser Arg Glu Glu Met Thr
    370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415
```

Lys Thr Thr Pro Pro Val Leu Asp Ser Asp Gly Ser Phe Phe Leu Tyr
            420                 425                 430

Ser Lys Leu Thr Val Asp Lys Ser Arg Trp Gln Gln Gly Asn Val Phe
            435                 440                 445

Ser Cys Ser Val Met His Glu Ala Leu His Asn His Tyr Thr Gln Lys
        450                 455                 460

Ser Leu Ser Leu Ser Pro Gly Lys
465                 470

<210> SEQ ID NO 57
<211> LENGTH: 1416
<212> TYPE: DNA
<213> ORGANISM: Artificial Sequence
<220> FEATURE:
<223> OTHER INFORMATION: nucleotide sequence of h046-H10 (1)
<220> FEATURE:
<221> NAME/KEY: sig_peptide
<222> LOCATION: (1)..(57)

<400> SEQUENCE: 57
atgaaacacc tgtggttctt cctcctgctg gtggcagctc ccagatgggt gctgagccag      60
gtgcagctgc agcagtctgg cgccgaactg gccaagcctg gcagcagcgt gaaggtgagc     120
tgcaaggcca gcggctacac cttcaccagc tactacatca gctggatcaa gcagaccacc     180
ggccagggcc tgaagtacat cggcttcatc aaccccggca gcggccacac caactacaac     240
gagaagttca agggcaaggc cacactgacc gtggacaaga gcagcagcac cgccaacatg     300
cagctgtcca gcctgacccc cgacgacagc gccatctact actgtgctag aggcgctggc     360
ggcttcctgc ggatcatcac caagttcgac tactggggcc agggcgtgat ggtcaccgtc     420
agctcagcct ccaccaaggg cccaagcgtc ttccccctgg caccctcctc aagagcacc     480 tctgcggca gccgccct gggctgcctg gtcaaggact acttccccga accgtgacc     540 gtgagctgga ctcaggcgc cctgaccagc ggcgtgcaca ccttcccgc tgtcctgcag     600 tcctcaggac tctactccct cagcagcgtg gtgaccgtgc cctccagcag cttgggcacc     660
cagacctaca tctgcaacgt gaatcacaag cccagcaaca ccaaggtgga caagagagtt     720
gagcccaaat cttgtgacaa aactcacaca tgcccaccct gcccagcacc tgaactcctg     780 ggggaccct cagtcttcct cttcccccca aaacccaagg acaccctcat gatctcccgg     840
acccctgagg tcacatgcgt ggtggtggac gtgagccacg aagaccctga ggtcaagttc     900
aactggtacg tggacggcgt ggaggtgcat aatgccaaga caaagcccg ggaggagcag     960 tacaacagca cgtaccgggt ggtcagcgtc ctcaccgtcc tgcaccagga ctggctgaat    1020
ggcaaggagt acaagtgcaa ggtctccaac aaagccctcc cagcccccat cgagaaaacc    1080
atctccaaag ccaaaggcca gccccgggaa ccacaggtgt acaccctgcc cccatcccgg    1140
gaggagatga ccaagaacca ggtcagcctg acctgcctgg tcaaaggctt ctatcccagc    1200
gacatcgccg tggagtggga gagcaatggc cagcccgaga acaactacaa gaccaccct    1260 cccgtgctgg actccgacgg ctccttcttc ctctacagca agctcaccgt ggacaagagc    1320
aggtggcagc agggcaacgt cttctcatgc tccgtgatgc atgaggctct gcacaaccac    1380
tacacccaga agagcctctc cctgtctccc ggcaaa                              1416

<210> SEQ ID NO 58
<211> LENGTH: 234
<212> TYPE: PRT
<213> ORGANISM: Artificial Sequence
<220> FEATURE:
<223> OTHER INFORMATION: amino acid sequce of h046-L1
<220> FEATURE:
<221> NAME/KEY: SIGNAL
<222> LOCATION: (1)..(20)

<400> SEQUENCE: 58

Met Val Leu Gln Thr Gln Val Phe Ile Ser Leu Leu Leu Trp Ile Ser
1               5                   10                  15

Gly Ala Tyr Gly Asp Ile Gln Met Thr Gln Ser Pro Ser Ser Leu Ser
            20                  25                  30

Ala Ser Val Gly Asp Arg Val Thr Ile Thr Cys Arg Ala Ser Lys Ser
        35                  40                  45

Val Ser Thr Tyr Ile His Trp Tyr Gln Gln Lys Pro Gly Lys Ala Pro
    50                  55                  60

Lys Leu Leu Ile Tyr Ser Ala Ser Asn Leu Glu Ser Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Gln Gln Ile Asn
            100                 105                 110

Glu Leu Pro Tyr Thr Phe Gly Gln Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 59
<211> LENGTH: 702
<212> TYPE: DNA
<213> ORGANISM: Artificial Sequence
<220> FEATURE:
<223> OTHER INFORMATION: nuceleotide sequence of h046-L1 (1)
<220> FEATURE:
<221> NAME/KEY: sig_peptide
<222> LOCATION: (1)..(60)

<400> SEQUENCE: 59
atggtgctgc agacccaggt gttcatctcc ctgctgctgt ggatctccgg cgcgtacggc    60
gacatccaga tgacccagag ccctagcagc ctgagcgcca gcgtgggcga cagagtgacc   120
atcacctgtc gggccagcaa gagcgtgtcc acctacatcc actggtatca gcagaagccc   180
ggcaaggccc ccaagctgct gatctacagc gccagcaacc tggaaagcgg cgtgcccagc   240 agatttccg gcagcggctc tggcaccgac ttcaccctga caatcagcag cctgcagccc   300
gaggacttcg ccacctacta ctgccagcag atcaacgagc tgccctacac cttcggccag   360
ggcaccaagg tggaaatcaa gcgtacggtg gccgcccct ccgtgttcat cttccccccc   420

-continued

```
tccgacgagc agctgaagtc cggcaccgcc tccgtggtgt gcctgctgaa taacttctac    480
cccagagagg ccaaggtgca gtggaaggtg acaacgccc tgcagtccgg gaactcccag     540
gagagcgtga ccgagcagga cagcaaggac agcacctaca gcctgagcag caccctgacc    600
ctgagcaaag ccgactacga gaagcacaag gtgtacgcct gcgaggtgac ccaccagggc    660
ctgagctccc ccgtcaccaa gagcttcaac agggggggagt gt                      702
```

```
<210> SEQ ID NO 60
<211> LENGTH: 234
<212> TYPE: PRT
<213> ORGANISM: Artificial Sequence
<220> FEATURE:
<223> OTHER INFORMATION: amino acid sequence of h046-L2
<220> FEATURE:
<221> NAME/KEY: SIGNAL
<222> LOCATION: (1)..(20)

<400> SEQUENCE: 60

Met Val Leu Gln Thr Gln Val Phe Ile Ser Leu Leu Trp Ile Ser
1               5                   10                  15

Gly Ala Tyr Gly Asp Ile Gln Met Thr Gln Ser Pro Ser Ser Leu Ser
            20                  25                  30

Ala Ser Val Gly Asp Arg Val Thr Ile Thr Cys Arg Ala Ser Lys Ser
        35                  40                  45

Val Ser Thr Tyr Ile His Trp Tyr Gln Gln Lys Pro Gly Lys Gln Pro
    50                  55                  60

Lys Leu Leu Ile Tyr Ser Ala Ser Asn Leu Glu Ser Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Gln Gln Ile Asn
            100                 105                 110

Glu Leu Pro Tyr Thr Phe Gly Gln Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

```
<210> SEQ ID NO 61
<211> LENGTH: 702
<212> TYPE: DNA
<213> ORGANISM: Artificial Sequence
<220> FEATURE:
<223> OTHER INFORMATION: nucleotide sequence of h046-L2 (1)
<220> FEATURE:
<221> NAME/KEY: sig_peptide
<222> LOCATION: (1)..(60)
```

<400> SEQUENCE: 61

```
atggtgctgc agacccaggt gttcatctcc ctgctgctgt ggatctccgg cgcgtacggc      60
gacatccaga tgacccagag ccctagcagc ctgagcgcca gcgtgggcga cagagtgacc     120
atcacctgtc gggccagcaa gagcgtgtcc acctacatcc actggtatca gcagaagccc     180
ggcaagcagc ccaagctgct gatctacagc gccagcaacc tggaaagcgg cgtgcccagc     240
agatttccg gcagcggctc tggcaccgac ttcaccctga caatcagcag cctgcagccc      300
gaggacttcg ccacctacta ctgccagcag atcaacgagc tgccctacac cttcggccag     360
ggcaccaagg tggaaatcaa gcgtacggtg gccgccccct ccgtgttcat cttcccccc      420
tccgacgagc agctgaagtc cggcaccgcc tccgtggtgt gcctgctgaa taacttctac     480
cccagagagg ccaaggtgca gtggaaggtg gacaacgccc tgcagtccgg gaactcccag     540
gagagcgtga ccgagcagga cagcaaggac agcacctaca gcctgagcag caccctgacc     600
ctgagcaaag ccgactacga gaagcacaag gtgtacgcct gcgaggtgac ccaccagggc     660
ctgagctccc ccgtcaccaa gagcttcaac agggggggagt gt                       702
```

<210> SEQ ID NO 62
<211> LENGTH: 234
<212> TYPE: PRT
<213> ORGANISM: Artificial Sequence
<220> FEATURE:
<223> OTHER INFORMATION: amino acid sequence of h046-L6
<220> FEATURE:
<221> NAME/KEY: SIGNAL
<222> LOCATION: (1)..(20)

<400> SEQUENCE: 62

```
Met Val Leu Gln Thr Gln Val Phe Ile Ser Leu Leu Leu Trp Ile Ser
1               5                   10                  15
Gly Ala Tyr Gly Asp Thr Gln Leu Thr Gln Ser Pro Ser Ser Leu Ser
            20                  25                  30
Ala Ser Val Gly Asp Arg Val Thr Ile Thr Cys Arg Ala Ser Lys Ser
        35                  40                  45
Val Ser Thr Tyr Ile His Trp Tyr Gln Gln Lys Pro Gly Lys Gln Pro
    50                  55                  60
Lys Leu Leu Ile Tyr Ser Ala Ser Asp Arg Glu Ser Gly Val Pro Ser
65                  70                  75                  80
Arg Phe Ser Gly Ser Gly Ser Gly Thr Asp Phe Thr Leu Thr Ile Ser
                85                  90                  95
Ser Leu Gln Pro Glu Asp Phe Ala Asn Tyr Tyr Cys Gln Gln Ile Asn
            100                 105                 110
Glu Leu Pro Tyr Thr Phe Gly Gln Gly Thr Lys Val Glu Ile Lys Arg
        115                 120                 125
Thr Val Ala Ala Pro Ser Val Phe Ile Phe Pro Pro Ser Asp Glu Gln
    130                 135                 140
Leu Lys Ser Gly Thr Ala Ser Val Val Cys Leu Leu Asn Asn Phe Tyr
145                 150                 155                 160
Pro Arg Glu Ala Lys Val Gln Trp Lys Val Asp Asn Ala Leu Gln Ser
                165                 170                 175
Gly Asn Ser Gln Glu Ser Val Thr Glu Gln Asp Ser Lys Asp Ser Thr
            180                 185                 190
Tyr Ser Leu Ser Ser Thr Leu Thr Leu Ser Lys Ala Asp Tyr Glu Lys
        195                 200                 205
```

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 63
<211> LENGTH: 702
<212> TYPE: DNA
<213> ORGANISM: Artificial Sequence
<220> FEATURE:
<223> OTHER INFORMATION: nucleotide sequence of h046-L6 (1)
<220> FEATURE:
<221> NAME/KEY: sig_peptide
<222> LOCATION: (1)..(60)

<400> SEQUENCE: 63
atggtgctgc agacccaggt gttcatctcc ctgctgctgt ggatctccgg cgcgtacggc      60
gatacccagc tgacacagag ccctagcagc ctgtctgcca gcgtgggcga cagagtgacc     120
atcacctgtc gggccagcaa gagcgtgtcc acctacatcc actggtatca gcagaagccc     180
ggcaagcagc ccaagctgct gatctacagc gccagcgaca gagaaagcgg cgtgcccagc     240 agatttccg gcagcggctc tggcaccgac ttcaccctga caatcagcag cctgcagccc     300
gaggacttcg ccaactacta ctgccagcag atcaacgagc tgccctacac cttcggccag     360
ggcaccaagg tggaaatcaa gcgtacggtg gccgccccct ccgtgttcat cttccccccc     420
tccgacgagc agctgaagtc cggcaccgcc tccgtggtgt gcctgctgaa taacttctac     480
cccagagagg ccaaggtgca gtggaaggtg gacaacgccc tgcagtccgg gaactcccag     540
gagagcgtga ccgagcagga cagcaaggac agcacctaca gcctgagcag caccctgacc     600
ctgagcaaag ccgactacga gaagcacaag gtgtacgcct gcgaggtgac ccaccagggc     660
ctgagctccc ccgtcaccaa gagcttcaac agggggagt gt                        702

<210> SEQ ID NO 64
<211> LENGTH: 234
<212> TYPE: PRT
<213> ORGANISM: Artificial Sequence
<220> FEATURE:
<223> OTHER INFORMATION: amino acid sequence of h046-L7
<220> FEATURE:
<221> NAME/KEY: SIGNAL
<222> LOCATION: (1)..(20)

<400> SEQUENCE: 64

Met Val Leu Gln Thr Gln Val Phe Ile Ser Leu Leu Leu Trp Ile Ser
1               5                   10                  15

Gly Ala Tyr Gly Asp Thr Gln Leu Thr Gln Ser Pro Ser Ser Leu Ser
            20                  25                  30

Ala Ser Val Gly Asp Arg Val Thr Ile Thr Cys Arg Ala Ser Lys Ser
        35                  40                  45

Val Ser Thr Tyr Ile His Trp Tyr Gln Gln Lys Pro Gly Lys Gln Pro
    50                  55                  60

Lys Leu Leu Ile Tyr Ser Ala Gly Asn Leu Glu Ser Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Asn Tyr Tyr Cys Gln Gln Ile Asn
            100                 105                 110

Glu Leu Pro Tyr Thr Phe Gly Gln Gly Thr Lys Val Glu Ile Lys Arg
        115                 120                 125

```
Thr Val Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
                180                 185                 190

Tyr Ser Leu Ser Ser Thr Leu Thr Leu Ser Lys Ala Asp Tyr Glu Lys
            195                 200                 205

His Lys Val Tyr Ala Cys Glu Val Thr His Gln Gly Leu Ser Ser Pro
        210                 215                 220

Val Thr Lys Ser Phe Asn Arg Gly Glu Cys
225                 230
```

<210> SEQ ID NO 65
<211> LENGTH: 702
<212> TYPE: DNA
<213> ORGANISM: Artificial Sequence
<220> FEATURE:
<223> OTHER INFORMATION: nucleotide sequence of h046-L7 (1)
<220> FEATURE:
<221> NAME/KEY: sig_peptide
<222> LOCATION: (1)..(60)

<400> SEQUENCE: 65

```
atggtgctgc agacccaggt gttcatctcc ctgctgctgt ggatctccgg cgcgtacggc      60
gatacccagc tgacacagag ccctagcagc ctgtctgcca gcgtgggcga cagagtgacc     120
atcacctgtc gggccagcaa gagcgtgtcc acctacatcc actggtatca gcagaagccc     180
ggcaagcagc ccaagctgct gatctacagc gccggcaacc tggaaagcgg cgtgcccagc     240 agatttccg gcagcggctc tggcaccgac ttcaccctga caatcagcag cctgcagccc     300
gaggacttcg ccaactacta ctgccagcag atcaacgagc tgccctacac cttcggccag     360
ggcaccaagg tggaaatcaa gcgtacggtg gccgcccccct ccgtgttcat cttccccccc     420
tccgacgagc agctgaagtc cggcaccgcc tccgtggtgt gcctgctgaa taacttctac     480
cccagagagg ccaaggtgca gtggaaggtg gacaacgccc tgcagtccgg gaactcccag     540
gagagcgtga ccgagcagga cagcaaggac agcacctaca gcctgagcag cacccctgacc     600 ctgagcaaag ccgactacga gaagcacaag gtgtacgcct gcgaggtgac ccaccagggc     660
ctgagctccc ccgtcaccaa gagcttcaac agggggagt gt                          702
```

<210> SEQ ID NO 66
<211> LENGTH: 37
<212> TYPE: DNA
<213> ORGANISM: Artificial Sequence
<220> FEATURE:
<223> OTHER INFORMATION: PCR primer Nhe-polyC-S
<220> FEATURE:
<221> NAME/KEY: misc_feature
<222> LOCATION: (37)..(37)
<223> OTHER INFORMATION: n is a, c, g, or t

<400> SEQUENCE: 66

```
gctagcgcta ccggactcag atcccccccc cccccdn                                37
```

<210> SEQ ID NO 67
<211> LENGTH: 28
<212> TYPE: DNA

```
<213> ORGANISM: Artificial Sequence
<220> FEATURE:
<223> OTHER INFORMATION: PCR primer rIg gamma-AS1

<400> SEQUENCE: 67
tcactgagct ggtgagagtg tagagccc                                              28

<210> SEQ ID NO 68
<211> LENGTH: 28
<212> TYPE: DNA
<213> ORGANISM: Artificial Sequence
<220> FEATURE:
<223> OTHER INFORMATION: PCR primer rIg gamma-AS2

<400> SEQUENCE: 68
tcaccgagct gctgagggtg tagagccc                                              28

<210> SEQ ID NO 69
<211> LENGTH: 28
<212> TYPE: DNA
<213> ORGANISM: Artificial Sequence
<220> FEATURE:
<223> OTHER INFORMATION: PCR primer rIg kappa-AS

<400> SEQUENCE: 69
tcaccgagct gctgagggtg tagagccc                                              28

<210> SEQ ID NO 70
<211> LENGTH: 19
<212> TYPE: DNA
<213> ORGANISM: Artificial Sequence
<220> FEATURE:
<223> OTHER INFORMATION: PCR primer rIg gamma-seq

<400> SEQUENCE: 70
ctggctcagg gaaatagcc                                                        19

<210> SEQ ID NO 71
<211> LENGTH: 19
<212> TYPE: DNA
<213> ORGANISM: Artificial Sequence
<220> FEATURE:
<223> OTHER INFORMATION: PCR primer rIg kappa-seq

<400> SEQUENCE: 71
tccagttgct aactgttcc                                                        19

<210> SEQ ID NO 72
<211> LENGTH: 41
<212> TYPE: DNA
<213> ORGANISM: Artificial Sequence
<220> FEATURE:
<223> OTHER INFORMATION: PCR primer NFLAG-1

<400> SEQUENCE: 72
gactacaaag acgatgacga caagccctct gtgtctccag c                               41

<210> SEQ ID NO 73
<211> LENGTH: 39
<212> TYPE: DNA
<213> ORGANISM: Artificial Sequence
<220> FEATURE:
<223> OTHER INFORMATION: PCR primer NFLAG-2

<400> SEQUENCE: 73
cttgtcgtca tcgtctttgt agtccatggt ggagcctgc                                  39
```

<210> SEQ ID NO 74
<211> LENGTH: 29
<212> TYPE: DNA
<213> ORGANISM: Artificial Sequence
<220> FEATURE:
<223> OTHER INFORMATION: PCR Primer mEC2-1

<400> SEQUENCE: 74
acgcgcttcg ctgtgttcta cggcgccag                                29

<210> SEQ ID NO 75
<211> LENGTH: 29
<212> TYPE: DNA
<213> ORGANISM: Artificial Sequence
<220> FEATURE:
<223> OTHER INFORMATION: PCR primer mEC2-2

<400> SEQUENCE: 75
ctggcgccgt agaacacagc gaagcgcgt                                29

<210> SEQ ID NO 76
<211> LENGTH: 49
<212> TYPE: DNA
<213> ORGANISM: Artificial Sequence
<220> FEATURE:
<223> OTHER INFORMATION: PCR primer mEC3-1

<400> SEQUENCE: 76
tgtcggtgct gggcgtgaag tcgggtggac gatcatgctg ccgtgtctt          49

<210> SEQ ID NO 77
<211> LENGTH: 49
<212> TYPE: DNA
<213> ORGANISM: Artificial Sequence
<220> FEATURE:
<223> OTHER INFORMATION: PCR primer mEC3-2

<400> SEQUENCE: 77
aagacacggc agcatgatcg tccacccgac ttcacgccca gcaccgaca          49

<210> SEQ ID NO 78
<211> LENGTH: 43
<212> TYPE: DNA
<213> ORGANISM: Artificial Sequence
<220> FEATURE:
<223> OTHER INFORMATION: PCR primer mEC4-1

<400> SEQUENCE: 78
tggcgctgtg gcccaacgta cctaagcaca cgagcctcgt ggt                43

<210> SEQ ID NO 79
<211> LENGTH: 43
<212> TYPE: DNA
<213> ORGANISM: Artificial Sequence
<220> FEATURE:
<223> OTHER INFORMATION: PCR primer mEC4-2

<400> SEQUENCE: 79
accacgaggc tcgtgtgctt aggtacgttg ggccacagcg cca                43

<210> SEQ ID NO 80
<211> LENGTH: 28
<212> TYPE: DNA
<213> ORGANISM: Artificial Sequence
<220> FEATURE:

<223> OTHER INFORMATION: PCR primer mEC1-1

<400> SEQUENCE: 80
gcgctgatgg cggtgcacgg agccatct						28

<210> SEQ ID NO 81
<211> LENGTH: 24
<212> TYPE: DNA
<213> ORGANISM: Artificial Sequence
<220> FEATURE:
<223> OTHER INFORMATION: PCR primer mEC1-2

<400> SEQUENCE: 81
agagggcatg gtggagcctg cttt						24

<210> SEQ ID NO 82
<211> LENGTH: 32
<212> TYPE: DNA
<213> ORGANISM: Artificial Sequence
<220> FEATURE:
<223> OTHER INFORMATION: PCR primer mEC1-3

<400> SEQUENCE: 82
aggctccacc atgccctctg cgttgtctat ga					32

<210> SEQ ID NO 83
<211> LENGTH: 44
<212> TYPE: DNA
<213> ORGANISM: Artificial Sequence
<220> FEATURE:
<223> OTHER INFORMATION: PCR primer mEC1-4

<400> SEQUENCE: 83
caccgccatc agcgcttgcc acaggctggg gaaggtggct tgca			44

<210> SEQ ID NO 84
<211> LENGTH: 449
<212> TYPE: DNA
<213> ORGANISM: Homo sapiens

<400> SEQUENCE: 84
gcctccggac tctagagcca ccatggtgct gcagacccag gtgttcatct ccctgctgct		60
gtggatctcc ggcgcgtacg gcgatatcgt gatgattaaa cgtacggtgg ccgccccctc	120
cgtgttcatc ttcccccccct ccgacgagca gctgaagtcc ggcaccgcct ccgtggtgtg	180
cctgctgaat aacttctacc cagagaggc caaggtgcag tggaaggtgg acaacgccct	240
gcagtccggg aactcccagg agagcgtgac cgagcaggac agcaaggaca gcacctacag	300
cctgagcagc accctgaccc tgagcaaagc cgactacgag aagcacaagg tgtacgcctg	360
cgaggtgacc caccagggcc tgagctcccc cgtcaccaag agcttcaaca ggggggagtg	420
ttaggggccc gtttaaacgg gggaggcta						449

<210> SEQ ID NO 85
<211> LENGTH: 30
<212> TYPE: DNA
<213> ORGANISM: Artificial Sequence
<220> FEATURE:
<223> OTHER INFORMATION: PCR primer 3.3-F1

<400> SEQUENCE: 85
tataccgtcg acctctagct agagcttggc						30

<210> SEQ ID NO 86
<211> LENGTH: 30
<212> TYPE: DNA
<213> ORGANISM: Artificial Sequence
<220> FEATURE:
<223> OTHER INFORMATION: PCR primer 3.3-R1

<400> SEQUENCE: 86

```
gctatggcag ggcctgccgc cccgacgttg                                        30
```

<210> SEQ ID NO 87
<211> LENGTH: 1132
<212> TYPE: DNA
<213> ORGANISM: Homo sapiens

<400> SEQUENCE: 87

```
gcctccggac tctagagcca ccatgaaaca cctgtggttc ttcctcctgc tggtggcagc       60
tcccagatgg gtgctgagcc aggtgcaatt gtgcaggcgg ttagctcagc ctccaccaag      120
ggcccaagcg tcttcccct ggcaccctcc tccaagagca cctctggcgg cacagccgcc      180
ctgggctgcc tggtcaagga ctacttcccc gaacccgtga ccgtgagctg gaactcaggc     240
gccctgacca gcggcgtgca caccttcccc gctgtcctgc agtcctcagg actctactcc      300
ctcagcagcg tggtgaccgt gccctccagc agcttgggca cccagaccta catctgcaac      360
gtgaatcaca gcccagcaa caccaaggtg gacaagagag ttgagcccaa atcttgtgac      420
aaaactcaca catgcccacc ctgcccagca cctgaactcc tggggggacc ctcagtcttc      480
ctcttcccc caaaacccaa ggacaccctc atgatctccc ggacccctga ggtcacatgc      540
gtggtggtgg acgtgagcca cgaagaccct gaggtcaagt tcaactggta cgtggacggc      600
gtggaggtgc ataatgccaa gacaaagccc cgggaggagc agtacaacag cacgtaccgg     660
gtggtcagcg tcctcaccgt cctgcaccag gactggctga atggcaagga gtacaagtgc      720
aaggtctcca acaaagccct cccagccccc atcgagaaaa ccatctccaa agccaaaggc      780
cagccccggg aaccacaggt gtacaccctg cccccatccc gggaggagat gaccaagaac      840
caggtcagcc tgacctgcct ggtcaaaggc ttctatccca gcgacatcgc cgtggagtgg      900
gagagcaatg gccagcccga gaacaactac aagaccaccc ctcccgtgct ggactccgac      960
ggctccttct cctctacag caagctcacc gtggacaaga gcaggtggca gcagggcaac     1020
gtcttctcat gctccgtgat gcatgaggct ctgcacaacc actacaccca gaagagcctc     1080
tccctgtctc cggcaaatg agatatcggg cccgtttaaa cggggggaggc ta            1132
```

<210> SEQ ID NO 88
<211> LENGTH: 22
<212> TYPE: DNA
<213> ORGANISM: Artificial Sequence
<220> FEATURE:
<223> OTHER INFORMATION: PCR primer EG-Inf-F

<400> SEQUENCE: 88

```
agctcccaga tgggtgctga gc                                                22
```

<210> SEQ ID NO 89
<211> LENGTH: 22
<212> TYPE: DNA
<213> ORGANISM: Artificial Sequence
<220> FEATURE:
<223> OTHER INFORMATION: PCR primer EG1-Inf-R

<400> SEQUENCE: 89

```
gggccccttgg tggaggctga gc                                             22

<210> SEQ ID NO 90
<211> LENGTH: 24
<212> TYPE: DNA
<213> ORGANISM: Artificial Sequence
<220> FEATURE:
<223> OTHER INFORMATION: PCR primer CM-LKF

<400> SEQUENCE: 90
ctgtggatct ccggcgcgta cggc                                            24

<210> SEQ ID NO 91
<211> LENGTH: 30
<212> TYPE: DNA
<213> ORGANISM: Artificial Sequence
<220> FEATURE:
<223> OTHER INFORMATION: PCR primer 046L-R

<400> SEQUENCE: 91
ggagggggcg gccacggctc tcttcagttc                                      30

<210> SEQ ID NO 92
<211> LENGTH: 7
<212> TYPE: PRT
<213> ORGANISM: Artificial Sequence
<220> FEATURE:
<223> OTHER INFORMATION: amino acid sequence of h046-L6 CDRL2

<400> SEQUENCE: 92

Ser Ala Ser Asp Arg Glu Ser
1               5

<210> SEQ ID NO 93
<211> LENGTH: 7
<212> TYPE: PRT
<213> ORGANISM: Artificial Sequence
<220> FEATURE:
<223> OTHER INFORMATION: amiono acid sequence of h046-L7 CDRL2

<400> SEQUENCE: 93

Ser Ala Gly Asn Leu Glu Ser
1               5

<210> SEQ ID NO 94
<211> LENGTH: 408
<212> TYPE: DNA
<213> ORGANISM: Artificial Sequence
<220> FEATURE:
<223> OTHER INFORMATION: DNA fragment A

<400> SEQUENCE: 94
agctcccaga tgggtgctga gccaggtgca gctggtgcag tctggcgccg aagtgaagaa      60
accaggcgcc agcgtgaagg tgtcctgcaa ggccagcggc tacaccttta ccagctacta    120
catcagctgg atccggcagg cccctggaca gggcctgaag tacatgggct ggatcaaccc    180
tggcagcggc cacaccaact acaacgagaa gttcaagggc agagtgacca tcaccgccga    240
caagagcagc agcaccgcca ccatggaact gagcagcctg agaagcgagg acaccgccgt    300
gtactactgc gctagaggcg ctggcggctt cctgcggatc atcaccaagt cgactactg     360 gggccagggc accctcgtga ccgtcagctc agcctccacc aagggccc                 408

<210> SEQ ID NO 95
<211> LENGTH: 30
```

<212> TYPE: DNA
<213> ORGANISM: Artificial Sequence
<220> FEATURE:
<223> OTHER INFORMATION: PCR primer Hb-F

<400> SEQUENCE: 95
atcaaccctg gcagcggcca caccaactac                                        30

<210> SEQ ID NO 96
<211> LENGTH: 32
<212> TYPE: DNA
<213> ORGANISM: Artificial Sequence
<220> FEATURE:
<223> OTHER INFORMATION: PCR primer Hb-R

<400> SEQUENCE: 96
gaagcccatg tacttcaggc cctgtccagg gg                                     32

<210> SEQ ID NO 97
<211> LENGTH: 408
<212> TYPE: DNA
<213> ORGANISM: Artificial Sequence
<220> FEATURE:
<223> OTHER INFORMATION: DNA fragment B

<400> SEQUENCE: 97
agctcccaga tgggtgctga gccaggtgca gctggtgcag tctggcgccg aagtgaagaa        60
accaggcgcc agcgtgaagg tgtcctgcaa ggccagcggc tacacctta ccagctacta       120 catcagctgg atccggcagg cccctggaca gggcctgaag tacatgggct ggatcaaccc       180
tggcagcggc cacaccaact acaacgagaa gttcaagggc agagtgacca tcaccgccga       240
caagagcagc agcaccgcca acatggaact gagcagcctg cggagcgagg acaccgccgt       300
gtactattgt gctagaggcg ctggcggctt cctgcggatc atcaccaagt tcgactactg       360
gggccagggc accctcgtga ccgtcagctc agcctccacc aagggccc                    408

<210> SEQ ID NO 98
<211> LENGTH: 33
<212> TYPE: DNA
<213> ORGANISM: Artificial Sequence
<220> FEATURE:
<223> OTHER INFORMATION: H08-F

<400> SEQUENCE: 98
aacatgcagc tgtccagcct gaccccgac gac                                    33

<210> SEQ ID NO 99
<211> LENGTH: 30
<212> TYPE: DNA
<213> ORGANISM: Artificial Sequence
<220> FEATURE:
<223> OTHER INFORMATION: H08-R

<400> SEQUENCE: 99
ggcggtgctg ctgctcttgt ccacggtcag                                        30

<210> SEQ ID NO 100
<211> LENGTH: 33
<212> TYPE: DNA
<213> ORGANISM: Artificial Sequence
<220> FEATURE:
<223> OTHER INFORMATION: H10-F

<400> SEQUENCE: 100

```
gtgagctgca aggccagcgg ctacaccttc acc                                    33

<210> SEQ ID NO 101
<211> LENGTH: 30
<212> TYPE: DNA
<213> ORGANISM: Artificial Sequence
<220> FEATURE:
<223> OTHER INFORMATION: H10-R

<400> SEQUENCE: 101
cttcacgctg ctgccaggct tggccagttc                                        30

<210> SEQ ID NO 102
<211> LENGTH: 21
<212> TYPE: DNA
<213> ORGANISM: Artificial Sequence
<220> FEATURE:
<223> OTHER INFORMATION: PCR primer KCL-Inf-R

<400> SEQUENCE: 102 ggaggggggcg gccaccgtac g                                                21

<210> SEQ ID NO 103
<211> LENGTH: 1416
<212> TYPE: DNA
<213> ORGANISM: Artificial Sequence
<220> FEATURE:
<223> OTHER INFORMATION: nucleotide sequence of h046-H4b (2)
<220> FEATURE:
<221> NAME/KEY: sig_peptide
<222> LOCATION: (1)..(57)

<400> SEQUENCE: 103
atgaagcacc tgtggttctt tctgctgctg gtggccgctc ccagatgggt gctgtctcag       60
gtgcagctgg tgcagtctgg cgccgaagtg aagaaacctg gcgcctccgt gaaggtgtcc      120
tgcaaggcct ccggctacac ctttaccagc tactacatct cctggatccg gcaggcccct      180
ggacagggcc tgaagtacat gggcttcatc aaccccggct ccggccacac caactacaac      240
gagaagttca aggcagagt gaccattacc gccgacaagt cctcctccac cgctaccatg      300
gaactgtcct ccctgcggag cgaggacacc gccgtgtact actgtgctag aggcgctggc      360
ggcttcctgc ggatcatcac caagttcgac tactggggcc agggcaccct cgtgaccgtg      420
tcctctgctt ctaccaaggg ccctccgtg ttccctctgg ccccttccag caagtctacc       480
tctggcggca cagccgctct gggctgcctc gtgaaggact acttccccga gcccgtgaca      540
gtgtcttgga actctggcgc cctgacctcc ggcgtgcaca catttccagc tgtgctgcag      600
tcctccggcc tgtactccct gtcctccgtc gtgactgtgc cctccagctc tctgggcacc      660
cagacctaca tctgcaacgt gaaccacaag ccctccaaca ccaaggtgga caagcgggtg      720
gaacccaagt cctgcgacaa gacccacacc tgtcccccctt gtcctgcccc tgaactgctg      780
ggcggaccca gcgtgttcct gttcccccca aagcccaagg acaccctgat gatctcccgg      840
acccccgaag tgacctgcgt ggtggtggat gtgtcccacg aggaccctga agtgaagttc      900
aattggtacg tggacggcgt ggaagtgcac aacgccaaga ccaagcctag agaggaacag      960
tacaactcca cctaccgggt ggtgtccgtg ctgaccgtgc tgcaccagga ttggctgaac     1020
ggcaaagagt acaagtgcaa ggtgtccaac aaggctctgc ctgcccccat cgaaaagacc     1080
atctccaagg ccaagggcca gccccgggaa cccagtgt acacactgcc cctagccgg      1140 gaagagatga ccaagaacca ggtgtccctg acctgtctcg tgaaaggctt ctaccctcc      1200
```

-continued

| | |
|---|---|
| gatatcgccg tggaatggga gtccaacggc cagcctgaga acaactacaa gaccaccccc | 1260 |
| cctgtgctgg actccgacgg ctcattcttc ctgtacagca agctgacagt ggacaagtcc | 1320 |
| cggtggcagc agggcaacgt gttctcctgc tccgtgatgc acgaggccct gcacaaccac | 1380 |
| tacacccaga agtccctgtc cctgagcccc ggcaaa | 1416 |

<210> SEQ ID NO 104
<211> LENGTH: 1416
<212> TYPE: DNA
<213> ORGANISM: Artificial Sequence
<220> FEATURE:
<223> OTHER INFORMATION: nucleotide sequence of h046-H5b (2)
<220> FEATURE:
<221> NAME/KEY: sig_peptide
<222> LOCATION: (1)..(57)

<400> SEQUENCE: 104

| | |
|---|---|
| atgaagcacc tgtggttctt tctgctgctg gtggccgctc ccagatgggt gctgtctcag | 60 |
| gtgcagctgg tgcagtctgg cgccgaagtg aagaaacctg gcgcctccgt gaaggtgtcc | 120 |
| tgcaaggctt ccggctacac ctttaccagc tactacatct cctggatccg gcaggcccct | 180 |
| ggacagggcc tgaagtacat gggcttcatc aaccccggct ccggccacac caactacaac | 240 |
| gagaagttca agggcagagt gaccattacc gccgacaagt cctcctccac cgccaacatg | 300 |
| gaactgtcct ccctgcggag cgaggacacc gccgtgtact actgtgctag aggcgctggc | 360 |
| ggcttcctgc ggatcatcac caagttcgac tactggggcc agggcaccct cgtgaccgtg | 420 |
| tcctctgctt ctaccaaggg cccctccgtg ttccctctgg ccccttccag caagtctacc | 480 |
| tctgcggca cagccgctct gggctgcctc gtgaaggact acttccccga gcccgtgaca | 540 |
| gtgtcttgga ctctggcgc cctgaccctcc ggcgtgcaca catttccagc tgtgctgcag | 600 |
| tcctccggcc tgtactccct gtcctccgtc gtgactgtgc cctccagctc tctgggcacc | 660 |
| cagacctaca tctgcaacgt gaaccacaag ccctccaaca ccaaggtgga caagcgggtg | 720 |
| gaacccaagt cctgcgacaa gacccacacc tgtcccccctt gtcctgcccc tgaactgctg | 780 |
| ggcggaccca gcgtgttcct gttccccca aagcccaagg acaccctgat gatctcccgg | 840 |
| accccgaag tgacctgcgt ggtggtggat gtgtcccacg aggaccctga agtgaagttc | 900 |
| aattggtacg tggacggcgt ggaagtgcac aacgccaaga ccaagcctag agaggaacag | 960 |
| tacaactcca cctaccgggt ggtgtccgtg ctgaccgtgc tgcaccagga ttggctgaac | 1020 |
| ggcaaagagt acaagtgcaa ggtgtccaac aaggccctgc ctgcccccat cgaaaagacc | 1080 |
| atctccaagg ccaagggcca gccccgggaa ccccaggtgt acacactgcc cctagccgg | 1140 |
| gaagagatga ccaagaacca ggtgtccctg acctgtctcg tgaaaggctt ctacccctcc | 1200 |
| gatatcgccg tggaatggga gtccaacggc cagcctgaga acaactacaa gaccaccccc | 1260 |
| cctgtgctgg actccgacgg ctcattcttc ctgtacagca agctgacagt ggacaagtcc | 1320 |
| cggtggcagc agggcaacgt gttctcctgc tccgtgatgc acgaggccct gcacaaccac | 1380 |
| tacacccaga agtccctgtc cctgagcccc ggcaaa | 1416 |

<210> SEQ ID NO 105
<211> LENGTH: 1416
<212> TYPE: DNA
<213> ORGANISM: Artificial Sequence
<220> FEATURE:
<223> OTHER INFORMATION: nucleotide sequence of h046-Hwt (2)

<400> SEQUENCE: 105

```
atgaagcacc tgtggttctt tctgctgctg gtggccgctc ccagatgggt gctgtctcag   60
gtgcagctgc agcagtctgg cgccgagctg gctaagcctg gctcctccgt gaagatctcc  120
tgcaaggcct ccggctacac ctttaccagc tactacatct cctggatcaa gcagaccacc  180
ggccagggcc tgaagtacat cggcttcatc aaccccggct ccggccacac caactacaac  240
gagaagttca agggcaaggc caccctgacc gtggacaagt cctcctccac cgccttcatg  300
cagctgtcct ccctgacccc tgacgactcc gccatctact actgcgctag aggcgctggc  360
ggcttcctgc ggatcatcac caagttcgac tactggggcc agggcgtgat ggtcaccgtg  420
tcctctgctt ccaccaaggg ccccgccgtg tttcctctgg ccccttccag caagtccacc  480
tctggcggaa cagccgctct gggctgcctc gtgaaggact acttccccga gcctgtgacc  540
gtgtcttgga actctggcgc cctgacatcc ggcgtgcaca ccttccctgc tgtgctgcag  600
tctagcggcc tgtactccct gtcctccgtc gtgaccgtgc cttccagctc tctgggcacc  660
cagacctaca tctgcaacgt gaaccacaag ccctccaaca ccaaggtgga caagcgggtg  720
gaacccaagt cctgcgacaa gacccacacc tgtcccccct gtcctgcccc tgaactgctg  780
ggcggacctt ccgtgttcct gttccccccc aagcccaagg ataccctgat gatctcccgg  840
acccccgaag tgacctgcgt ggtggtggat gtgtcccacg aggaccctga agtgaagttc  900
aattggtacg tggacggcgt ggaagtgcac aacgccaaga ccaagcctag agaggaacag  960
tacaactcca cctaccgggt ggtgtccgtg ctgaccgtgc tgcaccagga ttggctgaac 1020
ggcaaagagt acaagtgcaa ggtgtccaac aaggccctgc ctgcccccat cgaaaagacc 1080
atctccaagg ccaagggcca gccccgggaa ccccaggtgt acacactgcc ccctagccgg 1140
gaagagatga ccaagaacca ggtgtccctg acctgtctcg tgaaaggctt ctaccccctc 1200
cgatatcgccg tggaatggga gtccaacggc agcctgaga acaactacaa gaccacccc 1260
cctgtgctgg actccgacgg ctcattcttc ctgtacagca agctgacagt ggataagagc 1320
cggtggcagc agggcaacgt gttctcctgc tccgtgatgc acgaggccct gcacaaccac 1380
tacacccaga gtccctgtc cctgagcccc ggcaaa                            1416
```

<210> SEQ ID NO 106
<211> LENGTH: 1416
<212> TYPE: DNA
<213> ORGANISM: Artificial Sequence
<220> FEATURE:
<223> OTHER INFORMATION: nucleotide sequence of h046-H8 (2)
<220> FEATURE:
<221> NAME/KEY: sig_peptide
<222> LOCATION: (1)..(57)

<400> SEQUENCE: 106

```
atgaagcacc tgtggttctt tctgctgctg gtggccgctc ccagatgggt gctgtctcag   60
gtgcagctgc agcagtctgg cgccgagctg gctaagcctg gctcctccgt gaagatctcc  120
tgcaaggcct ccggctacac ctttaccagc tactacatct cctggatcaa gcagaccacc  180
ggccagggcc tgaagtacat cggcttcatc aaccccggct ccggccacac caactacaac  240
gagaagttca agggcaaggc caccctgacc gtggacaagt cctcctccac cgccaacatg  300
cagctgtcct ccctgacccc tgacgactcc gccatctact actgcgctag aggcgctggc  360
ggcttcctgc ggatcatcac caagttcgac tactggggcc agggcgtgat ggtcaccgtg  420
tcctctgctt ccaccaaggg ccccgccgtg tttcctctgg ccccttccag caagtccacc  480
tctggcggaa cagccgctct gggctgcctc gtgaaggact acttccccga gcctgtgacc  540
```

```
gtgtcttgga actctggcgc cctgacatcc ggcgtgcaca ccttccctgc tgtgctgcag      600
tctagcggcc tgtactccct gtcctccgtc gtgaccgtgc cttccagctc tctgggcacc      660
cagacctaca tctgcaacgt gaaccacaag ccctccaaca ccaaggtgga caagcgggtg      720
gaacccaagt cctgcgacaa gacccacacc tgtcccccTt gtcctgcccc tgaactgctg      780
ggcggacctt ccgtgttcct gttccccCca agcccaagg ataccctgat gatctcccgg       840
accccCgaag tgacctgcgt ggtggtggat gtgtcccacg aggaccctga agtgaagttc      900
aattggtacg tggacggcgt ggaagtgcac aacgccaaga ccaagcctag agaggaacag      960
tacaactcca cctaccgggt ggtgtccgtg ctgaccgtgc tgcaccagga ttggctgaac     1020
ggcaaagagt acaagtgcaa ggtgtccaac aaggccctgc ctgcccccat cgaaaagacc     1080
atctccaagg ccaagggcca gccccgggaa ccccaggtgt acacactgcc ccctagccgg     1140
gaagagatga ccaagaacca ggtgtccctg acctgtctcg tgaaaggctt ctaccctcc      1200 gatatcgccg tggaatggga gtccaacggc cagcctgaga caactacaa gaccaccccc     1260 cctgtgctgg actccgacgg ctcattcttc ctgtacagca agctgacagt ggataagagc     1320
cggtggcagc agggcaacgt gttctcctgc tccgtgatgc acgaggccct gcacaaccac     1380
tacacccaga gtccctgtc cctgagcccc ggcaaa                                1416

<210> SEQ ID NO 107
<211> LENGTH: 1416
<212> TYPE: DNA
<213> ORGANISM: Artificial Sequence
<220> FEATURE:
<223> OTHER INFORMATION: nucleotide sequence of h046-H10 (2)
<220> FEATURE:
<221> NAME/KEY: sig_peptide
<222> LOCATION: (1)..(57)

<400> SEQUENCE: 107
atgaagcacc tgtggttctt tctgctgctg gtggccgctc ccagatgggt gctgtctcag       60
gtgcagctgc agcagtctgg cgccgagctg gctaagcctg gctcctctgt gaaggtgtcc      120
tgcaaggcct ccggctacac ctttaccagc tactacatct cctggatcaa gcagaccacc      180
ggccagggcc tgaagtacat cggcttcatc aaccccggct ccggcacac caactacaac      240 gagaagttca gggcaaggc caccctgacc gtggacaagt cctcctccac cgccaacatg      300
cagctgtcct ccctgaccc ctgacgactcc gccatctact actgcgctag aggcgctggc      360
ggcttcctgc ggatcatcac caagttcgac tactggggcc agggcgtgat ggtcaccgtg      420
tcctctgctt ccaccaaggg cccctccgtg tttcctctgg cccccttccag caagtccacc      480 tctggcggaa cagccgctct gggctgcctc gtgaaggact acttccccga gcctgtgacc      540
gtgtcttgga actctggcgc cctgacatcc ggcgtgcaca ccttccctgc tgtgctgcag      600
tctagcggcc tgtactccct gtcctccgtc gtgaccgtgc cttccagctc tctgggcacc      660
cagacctaca tctgcaacgt gaaccacaag ccctccaaca ccaaggtgga caagcgggtg      720
gaacccaagt cctgcgacaa gacccacacc tgtcccccTt gtcctgcccc tgaactgctg      780
ggcggacctt ccgtgttcct gttccccca agcccaagg ataccctgat gatctcccgg       840
accccCgaag tgacctgcgt ggtggtggat gtgtcccacg aggaccctga agtgaagttc      900
aattggtacg tggacggcgt ggaagtgcac aacgccaaga ccaagcctag agaggaacag      960
tacaactcca cctaccgggt ggtgtccgtg ctgaccgtgc tgcaccagga ttggctgaac     1020
ggcaaagagt acaagtgcaa ggtgtccaac aaggctctgc ctgcccccat cgaaaagacc     1080
```

| | |
|---|---|
| atctccaagg ccaagggcca gccccgggaa ccccaggtgt acacactgcc ccctagccgg | 1140 |
| gaagagatga ccaagaacca ggtgtccctg acctgtctcg tgaaaggctt ctacccctcc | 1200 |
| gatatcgccg tggaatggga gtccaacggc cagcctgaga caactacaa gaccaccccc | 1260 |
| cctgtgctgg actccgacgg ctcattcttc ctgtacagca agctgacagt ggataagagc | 1320 |
| cggtggcagc agggcaacgt gttctcctgc tccgtgatgc acgaggccct gcacaaccac | 1380 |
| tacacccaga gtccctgtc cctgagcccc ggcaaa | 1416 |

<210> SEQ ID NO 108
<211> LENGTH: 702
<212> TYPE: DNA
<213> ORGANISM: Artificial Sequence
<220> FEATURE:
<223> OTHER INFORMATION: nucleotide sequence of h046-L1 (2)
<220> FEATURE:
<221> NAME/KEY: sig_peptide
<222> LOCATION: (1)..(60)

<400> SEQUENCE: 108

| | |
|---|---|
| atggtgctgc agacccaggt gttcatctcc ctgctgctgt ggatctccgg cgcctacggc | 60 |
| gacatccaga tgacccagag cccttccagc ctgtccgctt ccgtgggcga cagagtgacc | 120 |
| atcacctgtc gggcctccaa gtccgtgtcc acctacatcc actggtatca gcagaagccc | 180 |
| ggcaaggccc ccaagctgct gatctactcc gcctccaacc tggaatccgg cgtgccctcc | 240 |
| agattctccg gctctggctc tggcaccgac tttaccctga ccatctccag cctgcagccc | 300 |
| gaggacttcg ccacctacta ctgccagcag atcaacgagc tgcccctacac cttcggccag | 360 |
| ggcaccaagg tggaaatcaa gcggaccgtg gccgctccct ccgtgtttat cttcccaccc | 420 |
| tccgacgagc agctgaagtc cggcacagct tctgtcgtgt gcctgctgaa caacttctac | 480 |
| ccccgcgagg ccaaggtgca gtggaaggtg gacaacgccc tgcagtccgg caactcccag | 540 |
| gaatccgtga ccgagcagga ctccaaggac agcacctact ccctgtcctc caccctgacc | 600 |
| ctgtccaagg ccgactacga aagcacaag gtgtacgcct gcgaagtgac ccaccagggc | 660 |
| ctgtctagcc ccgtgaccaa gtctttcaac cggggcgagt gc | 702 |

<210> SEQ ID NO 109
<211> LENGTH: 702
<212> TYPE: DNA
<213> ORGANISM: Artificial Sequence
<220> FEATURE:
<223> OTHER INFORMATION: nucleotide sequence of h046-L-2 (2)
<220> FEATURE:
<221> NAME/KEY: sig_peptide
<222> LOCATION: (1)..(60)

<400> SEQUENCE: 109

| | |
|---|---|
| atggtgctgc agacccaggt gttcatctcc ctgctgctgt ggatctccgg cgcctacggc | 60 |
| gacatccaga tgacccagag cccttccagc ctgtccgctt ccgtgggcga cagagtgacc | 120 |
| atcacctgtc gggcctccaa gtccgtgtcc acctacatcc actggtatca gcagaagccc | 180 |
| ggcaagcagc ccaagctgct gatctactcc gcctccaacc tggaatccgg cgtgccctcc | 240 |
| agattctccg gctctggctc tggcaccgac tttaccctga ccatctccag cctgcagccc | 300 |
| gaggacttcg ccacctacta ctgccagcag atcaacgagc tgcccctacac cttcggccag | 360 |
| ggcaccaagg tggaaatcaa gcggaccgtg gccgctccct ccgtgtttat cttcccaccc | 420 |
| tccgacgagc agctgaagtc cggcacagct tctgtcgtgt gcctgctgaa caacttctac | 480 |
| ccccgcgagg ccaaggtgca gtggaaggtg gacaacgccc tgcagtccgg caactcccag | 540 |

```
gaatccgtga ccgagcagga ctccaaggac agcacctact ccctgtcctc caccctgacc    600
ctgtccaagg ccgactacga aagcacaag gtgtacgcct gcgaagtgac ccaccagggc    660
ctgtctagcc ccgtgaccaa gtctttcaac cggggcgagt gc                      702
```

<210> SEQ ID NO 110
<211> LENGTH: 702
<212> TYPE: DNA
<213> ORGANISM: Artificial Sequence
<220> FEATURE:
<223> OTHER INFORMATION: nucleotide sequence of h046-L6 (2)
<220> FEATURE:
<221> NAME/KEY: sig_peptide
<222> LOCATION: (1)..(60)

<400> SEQUENCE: 110

```
atggtgctgc agacccaggt gttcatctcc ctgctgctgt ggatctccgg cgcctacggc     60
gatacacagc tgacccagag cccttccagc ctgtctgctt ccgtgggcga cagagtgacc   120
atcacctgtc gggcctccaa gtccgtgtcc acctacatcc actggtatca gcagaagccc   180
ggcaagcagc ccaagctgct gatctactct gcctccgacc gcgagtctgg cgtgccctct   240
agattctccg gctctggctc tggcaccgac tttaccctga ccatctccag cctgcagccc   300
gaggacttcg ccaactacta ctgccagcag atcaacagca gcccctacac ttcggccag    360 ggcaccaagg tggaaatcaa gcggaccgtg gccgctccct ccgtgtttat cttcccaccc   420
tccgacgagc agctgaagtc cggcacagct tctgtcgtgt gcctgctgaa caacttctac   480
ccccgcgagg ccaaggtgca gtggaaggtg acaacgccc tgcagtccgg caactcccag    540
gaatccgtga ccgagcagga ctccaaggac agcacctact ccctgtcctc caccctgacc   600
ctgtccaagg ccgactacga gaagcacaag gtgtacgcct gcgaagtgac ccaccagggc   660
ctgtctagcc ccgtgaccaa gtctttcaac cggggcgagt gc                      702
```

<210> SEQ ID NO 111
<211> LENGTH: 702
<212> TYPE: DNA
<213> ORGANISM: Artificial Sequence
<220> FEATURE:
<223> OTHER INFORMATION: nucleotide sequence of h046-L7 (2)
<220> FEATURE:
<221> NAME/KEY: sig_peptide
<222> LOCATION: (1)..(60)

<400> SEQUENCE: 111

```
atggtgctgc agacccaggt gttcatctcc ctgctgctgt ggatctccgg cgcctacggc     60
gatacacagc tgacccagag cccttccagc ctgtctgctt ccgtgggcga cagagtgacc   120
atcacctgtc gggcctccaa gtccgtgtcc acctacatcc actggtatca gcagaagccc   180
ggcaagcagc ccaagctgct gatctactct gccggcaacc tggaatccgg cgtgccctcc   240
agattctccg gctctggctc tggcaccgac tttaccctga ccatctccag cctgcagccc   300
gaggacttcg ccaactacta ctgccagcag atcaacagca gcccctacac ttcggccag    360 ggcaccaagg tggaaatcaa gcggaccgtg gccgctccct ccgtgtttat cttcccaccc   420
tccgacgagc agctgaagtc cggcacagct tctgtcgtgt gcctgctgaa caacttctac   480
ccccgcgagg ccaaggtgca gtggaaggtg acaacgccc tgcagtccgg caactcccag    540
gaatccgtga ccgagcagga ctccaaggac agcacctact ccctgtcctc caccctgacc   600
ctgtccaagg ccgactacga gaagcacaag gtgtacgcct gcgaagtgac ccaccagggc   660
```

```
ctgtctagcc ccgtgaccaa gtctttcaac cggggcgagt gc                         702

<210> SEQ ID NO 112
<211> LENGTH: 37
<212> TYPE: DNA
<213> ORGANISM: Artificial Sequence
<220> FEATURE:
<223> OTHER INFORMATION: PCR primer LPCX-1

<400> SEQUENCE: 112
ctcaagcttc gaattcacca tgccctctgt gtctcca                               37

<210> SEQ ID NO 113
<211> LENGTH: 37
<212> TYPE: DNA
<213> ORGANISM: Artificial Sequence
<220> FEATURE:
<223> OTHER INFORMATION: PCR primer LPCX-2

<400> SEQUENCE: 113
ttggccgagg cggcctccta agcctcgggc ccattag                               37
```

ANTI-GPR20 ANTIBODY AND ANTI-GPR20 ANTIBODY-DRUG CONJUGATE

CROSS-REFERENCE TO RELATED APPLICATIONS

The present application is a Continuation of U.S. patent application Ser. No. 16/330,085, filed on Mar. 2, 2019, which is a U.S. National Phase Application of International Patent Application No. PCT/JP2018/001065, filed Jan. 16, 2018, which claims priority to and the benefit of Japanese Patent Application No. 2017-006004, filed on Jan. 17, 2017. The contents of these applications are hereby incorporated by reference in their entireties.

SEQUENCE LISTING

The instant application contains a Sequence Listing which has been submitted in ASCII format via EFS-Web and is hereby incorporated by reference in its entirety. Said ASCII copy, created on Jan. 17, 2017, is named 098065-0276 SL.txt and is 121 kb in size.

TECHNICAL FIELD

The present invention relates to an anti-GPR20 antibody binding to GPR20 and having an internalization effect, a method for producing the anti-GPR20 antibody, an antibody-drug conjugate comprising the antibody, an antitumor agent comprising the antibody-drug conjugate, and the like.

BACKGROUND ART

Cancers rank high in causes of death. Although the number of cancer patients is expected to increase with aging of the population, treatment needs have not yet been sufficiently satisfied. The problems of conventional chemotherapeutics are that: due to their low selectivity, these chemotherapeutics are toxic not only to tumor cells but also to normal cells and thereby have adverse reactions; and the chemotherapeutics cannot be administered in sufficient amounts and thus cannot sufficiently produce their effects. Hence, in recent years, more highly selective molecular targeted drugs or antibody drugs have been developed, which target molecules that exhibit mutations or high expression characteristic of cancer cells, or specific molecules involved in malignant transformation of cells.

Gastrointestinal stromal tumor (GIST) is a mesenchymal tumor that develops in the gastrointestinal tract from the esophagus to the rectum and the mesenterium, and its incidence is reportedly 1 to 2 persons per 100,000 per year (Non Patent Literature 1). Activating mutations in the receptor tyrosine kinase KIT or PDGFRA are found in approximately 86% of GIST patients, and these mutations contribute to proliferation of tumor cells. GIST treatment is based on surgical resection. Meanwhile, tyrosine kinase inhibitors (TKIs) such as imatinib, sunitinib, or regorafenib are prescribed for unresectable and progressive or metastatic GIST (Non Patent Literature 2). These TKIs often exhibit significant efficacy for GIST having the above-described mutations, but need to be continuously administered. In addition, in many cases, GIST cannot completely disappear by the TKIs, and eventually becomes unresponsive to the drugs due to secondary mutations in the target KIT or PDGFRA, activating mutations in RAS, BRAF, and the like, and activation of other signaling pathways, so that the disease progresses. Furthermore, these TKIs rarely exhibit therapeutic effects on wild type GIST found to have no mutation in KIT or PDGFRA, albeit in a small number of cases (Non Patent Literature 3). Hence, there has been a demand for the development of treatment methods effective for TKI-resistant GIST.

GPR20 (G protein-coupled receptor 20) is a seven-transmembrane protein composed of 358 amino acids, which belongs to class A of the G protein-coupled receptor (GPCR) family, and this protein has N-terminal extracellular and C-terminal intracellular domains. The human GPR20 gene was cloned for the first time in 1997 (Non Patent Literature 4). Its putative amino acid sequence was then found to partially differ from that encoded by the human GPR20 gene cloned by another researcher in 2008 (Non Patent Literature 5). The latter sequence, which is identical to a sequence registered in the NCBI database of human complete genomic sequence analysis, is currently disclosed as the DNA sequence encoding human GPR20 and the amino acid sequence thereof in a public database. The DNA sequence and the amino acid sequence can be referred to under, for example, accession Nos. NM_005293 and NP_005284 (NCBI).

GPR20 has an amino acid sequence similar to that of GPCR which recognizes a nucleotide or a lipid. However, neither physiological functions nor in vivo ligands have not been identified for GPR20. From an experiment that GPR20 was exogenously expressed in HEK293 cells, it has been reported that GPR20 constitutively activates Gi trimeric G proteins under conditions without ligand stimulation (Non Patent Literature 5).

GPR20 has been confirmed to express messenger RNA (mRNA) in heart, brain, placenta, lung, liver, skeletal muscle, kidney, pancreas, spleen, thymus, prostate, testis, ovary, small intestine, rectum, and leukocytes, and, in particular, its high expression in small intestine has been reported (Non Patent Literature 5). In brain, the expression in thalamus, putamen, and caudate nuclei has been reported (Non Patent Literature 4). GPR20-deficient mice have exhibited the phenotype of hyperactivity disorder characterized by increase in total distance travelled in open field tests, suggesting that GPR20 is associated with spontaneous activity in the central nervous system (Patent Literature 1). It has also been reported that GPR20 is highly expressed in GIST (Non Patent Literature 6). It has been reported that the expression of GPR20 is controlled by ets variant 1 (ETV1), which is a major transcriptional factor of GIST (Non Patent Literature 7).

Antibodies are highly stable in blood, and specifically bind to their target antigens. For these reasons, reduction in adverse reaction is expected, and a large number of antibody drugs targeting molecules highly expressed on cancer cell surface have been developed. Examples of the mechanism of action of antibody drugs directly targeting tumor cells include antibody-dependent cellular cytotoxicity (ADCC), complement-dependent cytotoxicity (CDC), blocking of signals of receptors involved in tumor growth, and apoptosis induction.

One of the techniques using the antigen-binding ability of antibodies is an antibody-drug conjugate (ADC). ADC for cancer is an antibody conjugated with a cytotoxic drug in which the antibody binds to an antigen expressed on cancer cell surface and can internalize the antigen into the cell through the binding. ADC for cancer can efficiently deliver the drug to cancer cells, and can thereby be expected to kill the cancer cells by accumulating the drug in the cancer cells (Non Patent Literature 8). With regard to ADC, for example, Adcetris (brentuximab vedotin) comprising an anti-CD30 monoclonal antibody conjugated to monomethyl auristatin E has been approved as a therapeutic drug for Hodgkin's lymphoma and anaplastic large cell lymphoma. Also, Kadcyla (trastuzumab emtansine) comprising an anti-HER2 monoclonal antibody conjugated to emtansine is used in the treatment of HER2-positive progressive or recurrent breast cancer.

The features of the target antigen suitable for ADC as an antitumor drug are that: the antigen is specifically highly expressed on cancer cell surface but is low or not expressed in normal cells; the antigen can be internalized into cells; the antigen is not secreted from cell surface; etc. Important features of the antibody suitable for ADC are that the antibody specifically binds to the target antigen as well as has high internalization ability. The internalization ability of the antibody depends on the properties of both the target antigen and the antibody. It is difficult to predict an antigen-binding site suitable for internalization from the molecular structure of a target or to easily predict an antibody having high internalization ability from binding strength, physical properties, and the like of the antibody. Hence, an important challenge to develop ADC having high efficacy is the obtainment of an antibody having high internalization ability against the target antigen (Non Patent Literature 9).

Any antitumor therapeutic drug targeting GPR20 has not been known so far. Furthermore, there has been no report on an anti-GPR20 antibody binding to GPR20 expressed on cell membrane surface and having internalization activity, and ADC containing the antibody.

CITATION LIST

Patent Literature

Patent Literature 1: US 2003/0018989

Non Patent Literature

Non Patent Literature 1: Corless C. L., et al., Nat Rev Cancer (2011) 11, 865-878
Non Patent Literature 2: Demetri G. D., et al., NCCN Task Force report, J Natl Compr Canc Netw. (2010) 8, Suppl 2: S1-41
Non Patent Literature 3: Bauer S., Joensuu H., Drugs. (2015) 75, 1323-1334
Non Patent Literature 4: O'Dowd B. F., Gene 187 (1997) 75-81
Non Patent Literature 5: Hase M., et al., J Biol Chem. (2008) 283, 12747-12755
Non Patent Literature 6: Allander S. V., et al., CANCER RESEARCH (2001) 61, 8624-8628
Non Patent Literature 7: Chi P., et al., Nature. (2010) 467 (7317): 849-853
Non Patent Literature 8: Heidi L. Perez, et al., Drug Discov. Today (2014) 19, 869-881
Non Patent Literature 9: Peters C., Brown S., Bioscience Reports (2015) 35, e00225

SUMMARY OF INVENTION

Technical Problem

It is an object of the present invention to provide an antibody specifically binding to GPR20-positive tumor cells such as GIST, an antibody-drug conjugate comprising the antibody, a pharmaceutical product comprising the antibody-drug conjugate and having therapeutic effects on a tumor, a method for treating a tumor using the aforementioned pharmaceutical product, methods for producing the antibody and the antibody-drug conjugate, and the like.

Solution to Problem

The present inventors have conducted intensive studies directed towards achieving the above-described object, and hypothesized that GPR20 is one of the molecules characterizing GIST, and this molecule is capable of serving as a therapeutic target specific for GIST. As a result of examining the internalization activity and binding pattern of an anti-human GPR20 antibody, the inventors have found an anti-GPR20 antibody having high internalization activity among antibodies that exhibit a specific binding pattern. The inventors have further found that an anti-GPR20 antibody-drug conjugate comprising the aforementioned anti-GPR20 antibody conjugated to a drug exerting toxicity in cells via a linker having a specific structure exerts an antitumor effect on a GPR20-positive malignant tumor, such as GIST, expressing GPR20, thereby completing the present invention. Specifically, the present invention includes the following aspects of the invention.

Specifically, the invention of the present application provides:
(1) an antibody or a functional fragment of the antibody having the following properties (a) and (b):
(a) specifically binding to GPR20, and
(b) having internalization ability that permits cellular uptake after binding to GPR20;
(2) the antibody or the functional fragment of the antibody according to (1), wherein the GPR20 is a polypeptide consisting of the amino acid sequence shown in SEQ ID NO: 1;
(3) the antibody or the functional fragment of the antibody according to (1) or (2), which specifically binds to a polypeptide consisting of the amino acid sequence shown in SEQ ID NO: 1 and does not specifically bind to a polypeptide with the amino acid Y (tyrosine) at amino acid position 113 substituted with a different amino acid;
(4) the antibody or the functional fragment of the antibody according to any one of (1) to (3), which specifically binds to a polypeptide consisting of the amino acid sequence shown in SEQ ID NO: 1 and does not specifically bind to a polypeptide with the amino acid Y (tyrosine) at amino acid position 113 substituted with F (phenylalanine);
(5) the antibody or the functional fragment of the antibody according to any one of (1) to (4), which specifically binds to a conformation consisting of the amino acid sequence at amino acid positions 1 to 48 and the amino acid sequence at amino acid positions 108 to 125 in SEQ ID NO: 1;
(6) the antibody or the functional fragment of the antibody according to any one of (1) to (5), which specifically binds to at least one amino acid residue selected from the amino acid sequence at amino acid positions 1 to 48 and at least one amino acid residue selected from the amino acid sequence at amino acid positions 108 to 125 in SEQ ID NO: 1;
(7) the antibody or the functional fragment of the antibody according to any one of (1) to (6), wherein at least one of the amino acids to which the antibody or the functional fragment specifically binds is the amino acid at amino acid position 113 of SEQ ID NO: 1;
(8) the antibody or the functional fragment of the antibody according to any one of (1) to (7), which has competitive inhibitory activity, for binding to GPR20, against any one antibody selected from the group consisting of the following antibodies (a) to (c):

(a) an antibody having a heavy chain consisting of the amino acid sequence at amino acid positions 20 to 475 of SEQ ID NO: 2 and a light chain consisting of the amino acid sequence at amino acid positions 21 to 233 of SEQ ID NO: 7,
(b) an antibody having a heavy chain consisting of the amino acid sequence at amino acid positions 20 to 475 of SEQ ID NO: 12 and a light chain consisting of the amino acid sequence at amino acid positions 21 to 233 of SEQ ID NO: 17, and
(c) an antibody having a heavy chain consisting of the amino acid sequence at amino acid positions 20 to 475 of SEQ ID NO: 22 and a light chain consisting of the amino acid sequence at amino acid positions 21 to 233 of SEQ ID NO: 27;
(9) the antibody or the functional fragment of the antibody according to any one of (1) to (8), which comprises CDRH1, CDRH2 and CDRH3 in any one combination selected from the group consisting of the following combinations (a) to (c), and CDRL1, CDRL2 and CDRL3 in any one combination selected from the following combinations (d) to (h):
(a) CDRH1 consisting of the amino acid sequence shown in SEQ ID NO: 4, CDRH2 consisting of the amino acid sequence shown in SEQ ID NO: 5, and CDRH3 consisting of the amino acid sequence shown in SEQ ID NO: 6,
(b) CDRH1 consisting of the amino acid sequence shown in SEQ ID NO: 14, CDRH2 consisting of the amino acid sequence shown in SEQ ID NO: 15, and CDRH3 consisting of the amino acid sequence shown in SEQ ID NO: 16,
(c) CDRH1 consisting of the amino acid sequence shown in SEQ ID NO: 24, CDRH2 consisting of the amino acid sequence shown in SEQ ID NO: 25, and CDRH3 consisting of the amino acid sequence shown in SEQ ID NO: 26,
(d) CDRL1 consisting of the amino acid sequence shown in SEQ ID NO: 9, CDRL2 consisting of the amino acid sequence shown in SEQ ID NO: 10, and CDRL3 consisting of the amino acid sequence shown in SEQ ID NO: 11,
(e) CDRL1 consisting of the amino acid sequence shown in SEQ ID NO: 9, CDRL2 consisting of the amino acid sequence shown in SEQ ID NO: 92, and CDRL3 consisting of the amino acid sequence shown in SEQ ID NO: 11,
(f) CDRL1 consisting of the amino acid sequence shown in SEQ ID NO: 9, CDRL2 consisting of the amino acid sequence shown in SEQ ID NO: 93, and CDRL3 consisting of the amino acid sequence shown in SEQ ID NO: 11,
(g) CDRL1 consisting of the amino acid sequence shown in SEQ ID NO: 19, CDRL2 consisting of the amino acid sequence shown in SEQ ID NO: 20, and CDRL3 consisting of the amino acid sequence shown in SEQ ID NO: 21, and
(h) CDRL1 consisting of the amino acid sequence shown in SEQ ID NO: 29, CDRL2 consisting of the amino acid sequence shown in SEQ ID NO: 30, and CDRL3 consisting of the amino acid sequence shown in SEQ ID NO: 31;
(10) the antibody or the functional fragment of the antibody according to any one of (1) to (9), which comprises CDRH1, CDRH2 and CDRH3, and CDRL1, CDRL2 and CDRL3 in any one combination selected from the following combinations (a) to (e):
(a) CDRH1 consisting of the amino acid sequence shown in SEQ ID NO: 4, CDRH2 consisting of the amino acid sequence shown in SEQ ID NO: 5, and CDRH3 consisting of the amino acid sequence shown in SEQ ID NO: 6, and CDRL1 consisting of the amino acid sequence shown in SEQ ID NO: 9, CDRL2 consisting of the amino acid sequence shown in SEQ ID NO: 10, and CDRL3 consisting of the amino acid sequence shown in SEQ ID NO: 11,
(b) CDRH1 consisting of the amino acid sequence shown in SEQ ID NO: 4, CDRH2 consisting of the amino acid sequence shown in SEQ ID NO: 5, and CDRH3 consisting of the amino acid sequence shown in SEQ ID NO: 6, and CDRL1 consisting of the amino acid sequence shown in SEQ ID NO: 9, CDRL2 consisting of the amino acid sequence shown in SEQ ID NO: 92, and CDRL3 consisting of the amino acid sequence shown in SEQ ID NO: 11,
(c) CDRH1 consisting of the amino acid sequence shown in SEQ ID NO: 4, CDRH2 consisting of the amino acid sequence shown in SEQ ID NO: 5, and CDRH3 consisting of the amino acid sequence shown in SEQ ID NO: 6, and CDRL1 consisting of the amino acid sequence shown in SEQ ID NO: 9, CDRL2 consisting of the amino acid sequence shown in SEQ ID NO: 93, and CDRL3 consisting of the amino acid sequence shown in SEQ ID NO: 11,
(d) CDRH1 consisting of the amino acid sequence shown in SEQ ID NO: 14, CDRH2 consisting of the amino acid sequence shown in SEQ ID NO: 15, and CDRH3 consisting of the amino acid sequence shown in SEQ ID NO: 16, and CDRL1 consisting of the amino acid sequence shown in SEQ ID NO: 19, CDRL2 consisting of the amino acid sequence shown in SEQ ID NO: 20, and CDRL3 consisting of the amino acid sequence shown in SEQ ID NO: 21,
(e) CDRH1 consisting of the amino acid sequence shown in SEQ ID NO: 24, CDRH2 consisting of the amino acid sequence shown in SEQ ID NO: 25, and CDRH3 consisting of the amino acid sequence shown in SEQ ID NO: 26, and CDRL1 consisting of the amino acid sequence shown in SEQ ID NO: 29, CDRL2 consisting of the amino acid sequence shown in SEQ ID NO: 30, and CDRL3 consisting of the amino acid sequence shown in SEQ ID NO: 31;
(11) the antibody or the functional fragment of the antibody according to any one of (1) to (10), which has any one heavy chain variable region selected from the group consisting of the following variable regions (a) to (c), and any one light chain variable region selected from the following variable regions (d) to (h):
a heavy chain variable region selected from the group consisting of
(a) a heavy chain variable region consisting of the amino acid sequence shown in SEQ ID NO: 3,
(b) a heavy chain variable region consisting of the amino acid sequence shown in SEQ ID NO: 13, and
(c) a heavy chain variable region consisting of the amino acid sequence shown in SEQ ID NO: 23,
(d) a light chain variable region consisting of the amino acid sequence shown in SEQ ID NO: 8,
(e) a light chain variable region consisting of the amino acid sequence at amino acid positions 21 to 129 in SEQ ID NO: 62,
(f) a light chain variable region consisting of the amino acid sequence at amino acid positions 21 to 129 in SEQ ID NO: 64,
(g) a light chain variable region consisting of the amino acid sequence shown in SEQ ID NO: 18, and
(h) a light chain variable region consisting of the amino acid sequence shown in SEQ ID NO: 28;
(12) the antibody or the functional fragment of the antibody according to any one of (1) to (11), which comprises a heavy chain variable region and a light chain variable region in any one combination selected from the following combinations (a) to (e):
(a) a heavy chain variable region consisting of the amino acid sequence shown in SEQ ID NO: 3, and a light chain variable region consisting of the amino acid sequence shown in SEQ ID NO: 8, (b) a heavy chain variable region consisting of the amino acid sequence shown in SEQ ID NO: 3, and a light chain variable region consisting of the amino acid sequence at amino acid positions 21 to 129 in SEQ ID NO: 62,
(c) a heavy chain variable region consisting of the amino acid sequence shown in SEQ ID NO: 3, and a light chain variable region consisting of the amino acid sequence at amino acid positions 21 to 129 in SEQ ID NO: 64,
(d) a heavy chain variable region consisting of the amino acid sequence shown in SEQ ID NO: 13, and a light chain variable region consisting of the amino acid sequence shown in SEQ ID NO: 18, and
(e) a heavy chain variable region consisting of the amino acid sequence shown in SEQ ID NO: 23, and a light chain variable region consisting of the amino acid sequence shown in SEQ ID NO: 28;
(13) the antibody or the functional fragment of the antibody according to any one of (1) to (12), wherein the constant region is a human-derived constant region;
(14) the antibody or the functional fragment of the antibody according to (13), which comprises a heavy chain consisting of the amino acid sequence shown in SEQ ID NO: 44 and a light chain consisting of the amino acid sequence shown in SEQ ID NO: 45;
(15) the antibody or the functional fragment of the antibody according to any one of (1) to (14), which is humanized;
(16) the antibody or the functional fragment of the antibody according to (15), which has a heavy chain variable region consisting of any one amino acid sequence selected from the group consisting of the following amino acid sequences (a) to (h), and a light chain variable region consisting of any one amino acid sequence selected from the group consisting of the following amino acid sequences (i) to (o):
(a) the amino acid sequence at amino acid positions 20 to 142 in SEQ ID NO: 48,
(b) the amino acid sequence at amino acid positions 20 to 142 in SEQ ID NO: 50,
(c) the amino acid sequence at amino acid positions 20 to 142 in SEQ ID NO: 52,
(d) the amino acid sequence at amino acid positions 20 to 142 in SEQ ID NO: 54,
(e) the amino acid sequence at amino acid positions 20 to 142 in SEQ ID NO: 56,
(f) the amino acid sequence at amino acid positions 20 to 142 in SEQ ID NO: 44,
(g) an amino acid sequence having a homology of at least 95% or more to the sequence of a framework region other than at each CDR sequence in the sequences of (a) to (f),
(h) an amino acid sequence comprising a deletion, substitution or addition of one or several amino acids in the sequence of a framework region other than at each CDR sequence in the sequences of (a) to (g),
(i) the amino acid sequence at amino acid positions 21 to 129 in SEQ ID NO: 58,
(j) the amino acid sequence at amino acid positions 21 to 129 in SEQ ID NO: 60,
(k) the amino acid sequence at amino acid positions 21 to 129 in SEQ ID NO: 62,
(l) the amino acid sequence at amino acid positions 21 to 129 in SEQ ID NO: 64,
(m) the amino acid sequence at amino acid positions 21 to 128 in SEQ ID NO: 45,
(n) an amino acid sequence having a homology of at least 95% or more to the sequence of a framework region other than at each CDR sequence in the sequences of (i) to (m), and
(o) an amino acid sequence comprising a deletion, substitution or addition of one or several amino acids in the sequence of a framework region other than at each CDR sequence in the sequences of (i) to (n);
(17) the antibody or the functional fragment of the antibody according to (16), which comprises a heavy chain variable region and a light chain variable region in any one combination selected from the group consisting of the following combinations (a) to (t):
(a) a heavy chain variable region consisting of the amino acid sequence at amino acid positions 20 to 142 in SEQ ID NO: 48 and a light chain variable region consisting of the amino acid sequence at amino acid positions 21 to 129 in SEQ ID NO: 58,
(b) a heavy chain variable region consisting of the amino acid sequence at amino acid positions 20 to 142 in SEQ ID NO: 48 and a light chain variable region consisting of the amino acid sequence at amino acid positions 21 to 129 in SEQ ID NO: 60,
(c) a heavy chain variable region consisting of the amino acid sequence at amino acid positions 20 to 142 in SEQ ID NO: 48 and a light chain variable region consisting of the amino acid sequence at amino acid positions 21 to 129 in SEQ ID NO: 62,
(d) a heavy chain variable region consisting of the amino acid sequence at amino acid positions 20 to 142 in SEQ ID NO: 48 and a light chain variable region consisting of the amino acid sequence at amino acid positions 21 to 129 in SEQ ID NO: 64,
(e) a heavy chain variable region consisting of the amino acid sequence at amino acid positions 20 to 142 in SEQ ID NO: 50 and a light chain variable region consisting of the amino acid sequence at amino acid positions 21 to 129 in SEQ ID NO: 58,
(f) a heavy chain variable region consisting of the amino acid sequence at amino acid positions 20 to 142 in SEQ ID NO: 50 and a light chain variable region consisting of the amino acid sequence at amino acid positions 21 to 129 in SEQ ID NO: 60,
(g) a heavy chain variable region consisting of the amino acid sequence at amino acid positions 20 to 142 in SEQ ID NO: 50 and a light chain variable region consisting of the amino acid sequence at amino acid positions 21 to 129 in SEQ ID NO: 62,
(h) a heavy chain variable region consisting of the amino acid sequence at amino acid positions 20 to 142 in SEQ ID NO: 50 and a light chain variable region consisting of the amino acid sequence at amino acid positions 21 to 129 in SEQ ID NO: 64,
(i) a heavy chain variable region consisting of the amino acid sequence at amino acid positions 20 to 142 in SEQ ID NO: 52 and a light chain variable region consisting of the amino acid sequence at amino acid positions 21 to 129 in SEQ ID NO: 58,
(j) a heavy chain variable region consisting of the amino acid sequence at amino acid positions 20 to 142 in SEQ ID NO: 52 and a light chain variable region consisting of the amino acid sequence at amino acid positions 21 to 129 in SEQ ID NO: 60,
(k) a heavy chain variable region consisting of the amino acid sequence at amino acid positions 20 to 142 in SEQ ID NO: 52 and a light chain variable region consisting of the amino acid sequence at amino acid positions 21 to 129 in SEQ ID NO: 62,
(l) a heavy chain variable region consisting of the amino acid sequence at amino acid positions 20 to 142 in SEQ ID NO:

52 and a light chain variable region consisting of the amino acid sequence at amino acid positions 21 to 129 in SEQ ID NO: 64,
(m) a heavy chain variable region consisting of the amino acid sequence at amino acid positions 20 to 142 in SEQ ID NO: 54 and a light chain variable region consisting of the amino acid sequence at amino acid positions 21 to 129 in SEQ ID NO: 58,
(n) a heavy chain variable region consisting of the amino acid sequence at amino acid positions 20 to 142 in SEQ ID NO: 54 and a light chain variable region consisting of the amino acid sequence at amino acid positions 21 to 129 in SEQ ID NO: 60,
(o) a heavy chain variable region consisting of the amino acid sequence at amino acid positions 20 to 142 in SEQ ID NO: 54 and a light chain variable region consisting of the amino acid sequence at amino acid positions 21 to 129 in SEQ ID NO: 62,
(p) a heavy chain variable region consisting of the amino acid sequence at amino acid positions 20 to 142 in SEQ ID NO: 54 and a light chain variable region consisting of the amino acid sequence at amino acid positions 21 to 129 in SEQ ID NO: 64,
(q) a heavy chain variable region consisting of the amino acid sequence at amino acid positions 20 to 142 in SEQ ID NO: 56 and a light chain variable region consisting of the amino acid sequence at amino acid positions 21 to 129 in SEQ ID NO: 58,
(r) a heavy chain variable region consisting of the amino acid sequence at amino acid positions 20 to 142 in SEQ ID NO: 56 and a light chain variable region consisting of the amino acid sequence at amino acid positions 21 to 129 in SEQ ID NO: 60,
(s) a heavy chain variable region consisting of the amino acid sequence at amino acid positions 20 to 142 in SEQ ID NO: 56 and a light chain variable region consisting of the amino acid sequence at amino acid positions 21 to 129 in SEQ ID NO: 62, and
(t) a heavy chain variable region consisting of the amino acid sequence at amino acid positions 20 to 142 in SEQ ID NO: 56 and a light chain variable region consisting of the amino acid sequence at amino acid positions 21 to 129 in SEQ ID NO: 64;
(18) the antibody or the functional fragment of the antibody according to (16) or (17), which comprises a heavy chain and a light chain in any one combination selected from the following combinations (a) to (x):
(a) a heavy chain consisting of the amino acid sequence at amino acid positions 20 to 472 in SEQ ID NO: 48 and a light chain consisting of the amino acid sequence at amino acid positions 21 to 234 in SEQ ID NO: 58,
(b) a heavy chain consisting of the amino acid sequence at amino acid positions 20 to 472 in SEQ ID NO: 48 and a light chain consisting of the amino acid sequence at amino acid positions 21 to 234 in SEQ ID NO: 60,
(c) a heavy chain consisting of the amino acid sequence at amino acid positions 20 to 472 in SEQ ID NO: 48 and a light chain consisting of the amino acid sequence at amino acid positions 21 to 234 in SEQ ID NO: 62,
(d) a heavy chain consisting of the amino acid sequence at amino acid positions 20 to 472 in SEQ ID NO: 48 and a light chain consisting of the amino acid sequence at amino acid positions 21 to 234 in SEQ ID NO: 64,
(e) a heavy chain consisting of the amino acid sequence at amino acid positions 20 to 472 in SEQ ID NO: 50 and a light chain consisting of the amino acid sequence at amino acid positions 21 to 234 in SEQ ID NO: 58,
(f) a heavy chain consisting of the amino acid sequence at amino acid positions 20 to 472 in SEQ ID NO: 50 and a light chain consisting of the amino acid sequence at amino acid positions 21 to 234 in SEQ ID NO: 60,
(g) a heavy chain consisting of the amino acid sequence at amino acid positions 20 to 472 in SEQ ID NO: 50 and a light chain consisting of the amino acid sequence at amino acid positions 21 to 234 in SEQ ID NO: 62,
(h) a heavy chain consisting of the amino acid sequence at amino acid positions 20 to 472 in SEQ ID NO: 50 and a light chain consisting of the amino acid sequence at amino acid positions 21 to 234 in SEQ ID NO: 64,
(i) a heavy chain consisting of the amino acid sequence at amino acid positions 20 to 472 in SEQ ID NO: 52 and a light chain consisting of the amino acid sequence at amino acid positions 21 to 234 in SEQ ID NO: 58,
(j) a heavy chain consisting of the amino acid sequence at amino acid positions 20 to 472 in SEQ ID NO: 52 and a light chain consisting of the amino acid sequence at amino acid positions 21 to 234 in SEQ ID NO: 60,
(k) a heavy chain consisting of the amino acid sequence at amino acid positions 20 to 472 in SEQ ID NO: 52 and a light chain consisting of the amino acid sequence at amino acid positions 21 to 234 in SEQ ID NO: 62,
(l) a heavy chain consisting of the amino acid sequence at amino acid positions 20 to 472 in SEQ ID NO: 52 and a light chain consisting of the amino acid sequence at amino acid positions 21 to 234 in SEQ ID NO: 64,
(m) a heavy chain consisting of the amino acid sequence at amino acid positions 20 to 474 in SEQ ID NO: 54 and a light chain consisting of the amino acid sequence at amino acid positions 21 to 234 in SEQ ID NO: 58,
(n) a heavy chain consisting of the amino acid sequence at amino acid positions 20 to 474 in SEQ ID NO: 54 and a light chain consisting of the amino acid sequence at amino acid positions 21 to 234 in SEQ ID NO: 60,
(o) a heavy chain consisting of the amino acid sequence at amino acid positions 20 to 474 in SEQ ID NO: 54 and a light chain consisting of the amino acid sequence at amino acid positions 21 to 234 in SEQ ID NO: 62,
(p) a heavy chain consisting of the amino acid sequence at amino acid positions 20 to 474 in SEQ ID NO: 54 and a light chain consisting of the amino acid sequence at amino acid positions 21 to 234 in SEQ ID NO: 64,
(q) a heavy chain consisting of the amino acid sequence at amino acid positions 20 to 474 in SEQ ID NO: 56 and a light chain consisting of the amino acid sequence at amino acid positions 21 to 234 in SEQ ID NO: 58,
(r) a heavy chain consisting of the amino acid sequence at amino acid positions 20 to 474 in SEQ ID NO: 56 and a light chain consisting of the amino acid sequence at amino acid positions 21 to 234 in SEQ ID NO: 60,
(s) a heavy chain consisting of the amino acid sequence at amino acid positions 20 to 474 in SEQ ID NO: 56 and a light chain consisting of the amino acid sequence at amino acid positions 21 to 234 in SEQ ID NO: 62,
(t) a heavy chain consisting of the amino acid sequence at amino acid positions 20 to 474 in SEQ ID NO: 56 and a light chain consisting of the amino acid sequence at amino acid positions 21 to 234 in SEQ ID NO: 64,
(u) a heavy chain consisting of the amino acid sequence at amino acid positions 20 to 472 in SEQ ID NO: 44 and a light chain consisting of the amino acid sequence at amino acid positions 21 to 234 in SEQ ID NO: 58,
(v) a heavy chain consisting of the amino acid sequence at amino acid positions 20 to 472 in SEQ ID NO: 44 and a light chain consisting of the amino acid sequence at amino acid positions 21 to 234 in SEQ ID NO: 60,
(w) a heavy chain consisting of the amino acid sequence at amino acid positions 20 to 472 in SEQ ID NO: 44 and a light chain consisting of the amino acid sequence at amino acid positions 21 to 234 in SEQ ID NO: 62; and
(x) a heavy chain consisting of the amino acid sequence at amino acid positions 20 to 472 in SEQ ID NO: 44 and a light chain consisting of the amino acid sequence at amino acid positions 21 to 234 in SEQ ID NO: 64;
(19) the functional fragment of the antibody according to any one of (1) to (18), wherein the functional fragment is selected from the group consisting of Fab, F(ab)2, Fab' and Fv;
(20) a polynucleotide encoding the antibody or the functional fragment of the antibody according to any one of (1) to (19);
(21) the polynucleotide according to (20), which comprises polynucleotides in any one combination selected from the group consisting of the following combinations (a) to (e):
(a) a polynucleotide encoding CDRH1 consisting of the amino acid sequence shown in SEQ ID NO: 4, CDRH2 consisting of the amino acid sequence shown in SEQ ID NO: 5 and CDRH3 consisting of the amino acid sequence shown in SEQ ID NO: 6, and a polynucleotide encoding CDRL1 consisting of the amino acid sequence shown in SEQ ID NO: 9, CDRL2 consisting of the amino acid sequence shown in SEQ ID NO: 10 and CDRL3 consisting of the amino acid sequence shown in SEQ ID NO: 11,
(b) a polynucleotide encoding CDRH1 consisting of the amino acid sequence shown in SEQ ID NO: 4, CDRH2 consisting of the amino acid sequence shown in SEQ ID NO: 5 and CDRH3 consisting of the amino acid sequence shown in SEQ ID NO: 6, and a polynucleotide encoding CDRL1 consisting of the amino acid sequence shown in SEQ ID NO: 9, CDRL2 consisting of the amino acid sequence shown in SEQ ID NO: 92 and CDRL3 consisting of the amino acid sequence shown in SEQ ID NO: 11,
(c) a polynucleotide encoding CDRH1 consisting of the amino acid sequence shown in SEQ ID NO: 4, CDRH2 consisting of the amino acid sequence shown in SEQ ID NO: 5 and CDRH3 consisting of the amino acid sequence shown in SEQ ID NO: 6, and a polynucleotide encoding CDRL1 consisting of the amino acid sequence shown in SEQ ID NO: 9, CDRL2 consisting of the amino acid sequence shown in SEQ ID NO: 93 and CDRL3 consisting of the amino acid sequence shown in SEQ ID NO: 11,
(d) a polynucleotide encoding CDRH1 consisting of the amino acid sequence shown in SEQ ID NO: 14, CDRH2 consisting of the amino acid sequence shown in SEQ ID NO: 15 and CDRH3 consisting of the amino acid sequence shown in SEQ ID NO: 16, and a polynucleotide encoding CDRL1 consisting of the amino acid sequence shown in SEQ ID NO: 19, CDRL2 consisting of the amino acid sequence shown in SEQ ID NO: 20 and CDRL3 consisting of the amino acid sequence shown in SEQ ID NO: 21, and
(e) a polynucleotide encoding CDRH1 consisting of the amino acid sequence shown in SEQ ID NO: 24, CDRH2 consisting of the amino acid sequence shown in SEQ ID NO: 25 and CDRH3 consisting of the amino acid sequence shown in SEQ ID NO: 26, and a polynucleotide encoding CDRL1 consisting of the amino acid sequence shown in SEQ ID NO: 29, CDRL2 consisting of the amino acid sequence shown in SEQ ID NO: 30 and CDRL3 consisting of the amino acid sequence shown in SEQ ID NO: 31;
(22) the polynucleotide according to (20) or (21), which comprises polynucleotides in any one combination selected from the group consisting of the following combinations (a) to (e):

(a) a polynucleotide encoding a heavy chain variable region consisting of the amino acid sequence shown in SEQ ID NO: 3, and a polynucleotide encoding a light chain variable region consisting of the amino acid sequence shown in SEQ ID NO: 8,
(b) a polynucleotide encoding a heavy chain variable region consisting of the amino acid sequence shown in SEQ ID NO: 3, and a polynucleotide encoding a light chain variable region consisting of the amino acid sequence at amino acid positions 21 to 129 in SEQ ID NO: 62,
(c) a polynucleotide encoding a heavy chain variable region consisting of the amino acid sequence shown in SEQ ID NO: 3, and a polynucleotide encoding a light chain variable region consisting of the amino acid sequence at amino acid positions 21 to 129 in SEQ ID NO: 64,
(d) a polynucleotide encoding a heavy chain variable region consisting of the amino acid sequence shown in SEQ ID NO: 13, and a polynucleotide encoding a light chain variable region consisting of the amino acid sequence shown in SEQ ID NO: 18, and
(e) a polynucleotide encoding a heavy chain variable region consisting of the amino acid sequence shown in SEQ ID NO: 23, and a polynucleotide encoding a light chain variable region consisting of the amino acid sequence shown in SEQ ID NO: 28;
(23) an expression vector comprising the polynucleotide according to any one of (20) to (22);
(24) a host cell transformed with the expression vector according to (23);
(25) the host cell according to (23), wherein the host cell is a eukaryotic cell;
(26) a method for producing an antibody of interest or a functional fragment of the antibody, which comprises a step of culturing the host cell according to (24) or (25), and a step of collecting an antibody of interest or a functional fragment of the antibody from the culture obtained by the aforementioned step;
(27) an antibody or a functional fragment of the antibody obtained by the production method according to (26);
(28) the functional fragment of the antibody according to (27), wherein the functional fragment is selected from the group consisting of Fab, F(ab)2, Fab' and Fv;
(29) the antibody or the functional fragment of the antibody according to any one of (1) to (19), (27) and (28), which comprises one or two or more modifications selected from the group consisting of N-linked glycosylation, O-linked glycosylation, N-terminal processing, C-terminal processing, deamidation, isomerization of aspartic acid, oxidation of methionine, addition of a methionine residue to the N-terminus, amidation of a proline residue, and a heavy chain comprising a deletion of one or two amino acids at the carboxyl terminus;
(30) the antibody according to (29), wherein one or two amino acids are deleted at the carboxyl terminus of a heavy chain thereof;
(31) the antibody according to (30), wherein one amino acid is deleted at each of the carboxyl termini of both of the heavy chains thereof;
(32) the antibody according to any one of (29) to (31), wherein a proline residue at the carboxyl terminus of a heavy chain thereof is further amidated;
(33) the antibody or the functional fragment of the antibody according to any one of (1) to (19) and (26) to (31), wherein sugar chain modification is regulated in order to enhance antibody-dependent cellular cytotoxic activity;
(34) an antibody-drug conjugate comprising the antibody or the functional fragment of the antibody according to any one of (1) to (19) and (27) to (33) conjugated to a drug;
(35) the antibody-drug conjugate according to (34), wherein the drug is an antitumor compound;

(36) the antibody-drug conjugate according to (35), wherein the antitumor compound is an antitumor compound represented by the following formula:

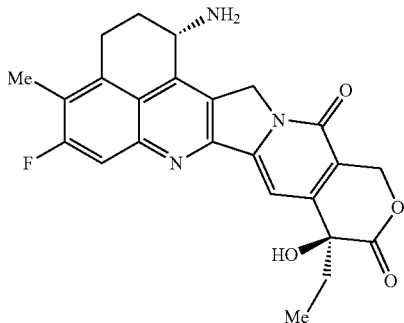

[Formula 1]

(37) the antibody-drug conjugate according to (36), wherein the antibody is conjugated to the antitumor compound via a linker having a structure represented by any of the following formulas (a) to (f):
(a)-(Succinimid-3-yl-N)—CH$_2$CH$_2$—C(=O)-GGFG-NH—CH$_2$CH$_2$CH$_2$—C(=O)—,
(b)-(Succinimid-3-yl-N)—CH$_2$CH$_2$CH$_2$CH$_2$CH$_2$—C(=O)-GGFG-NH—CH$_2$CH$_2$CH$_2$—C(=O)—,
(c)-(Succinimid-3-yl-N)—CH$_2$CH$_2$CH$_2$CH$_2$CH$_2$—C(=O)-GGFG-NH—CH$_2$—O—CH$_2$—C(=O)—,
(d)-(Succinimid-3-yl-N)—CH$_2$CH$_2$CH$_2$CH$_2$CH$_2$—C(=O)-GGFG-NH—CH$_2$CH$_2$—O—CH$_2$—C(=O)—,
(e)-(Succinimid-3-yl-N)—CH$_2$CH$_2$—C(=O)—NH—CH$_2$CH$_2$O—CH$_2$CH$_2$O—CH$_2$CH$_2$—C(=O)-GGFG-NH—CH$_2$CH$_2$CH$_2$—C(=O)—, and
(f)-(Succinimid-3-yl-N)—CH$_2$CH$_2$—C(=O)—NH—CH$_2$CH$_2$O—CH$_2$CH$_2$O—CH$_2$CH$_2$O—CH$_2$CH$_2$O—CH$_2$CH$_2$—C(=O)-GGFG-NH—CH$_2$CH$_2$CH$_2$—C(=O)—,
wherein the antibody is connected to the terminus of -(Succinimid-3-yl-N), the antitumor compound is connected to the carbonyl group of the —(CH$_2$)n$^2$-C(=O)— moiety with the nitrogen atom of the amino group at position 1 as a connecting position, GGFG represents an amino acid sequence consisting of glycine-glycine-phenylalanine-glycine linked through peptide bonds, and -(Succinimid-3-yl-N)— has a structure represented by the following formula:

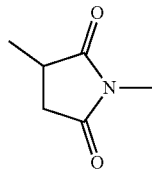

[Formula 2]

which is connected to the antibody at position 3 thereof and is connected to a methylene group in the linker structure containing this structure on the nitrogen atom at position 1;
(38) the antibody-drug conjugate according to any one of (34) to (37), wherein the linker is represented by any formula selected from the following formulas (a) to (c):
(a)-(Succinimid-3-yl-N)—CH$_2$CH$_2$CH$_2$CH$_2$CH$_2$—C(=O)-GGFG-NH—CH$_2$—O—CH$_2$—C(=O)—,
(b)-(Succinimid-3-yl-N)—CH$_2$CH$_2$CH$_2$CH$_2$CH$_2$—C(=O)-GGFG-NH—CH$_2$CH$_2$—O—CH$_2$—C(=O)—, and
(c)-(Succinimid-3-yl-N)—CH$_2$CH$_2$—C(=O)—NH—CH$_2$CH$_2$O—CH$_2$CH$_2$O—CH$_2$CH$_2$—C(=O)-GGFG-NH—CH$_2$CH$_2$CH$_2$—C(=O)—.
(39) the antibody-drug conjugate according to any one of (34) to (38), wherein the linker is represented by the following formula (a) or (b):
(a)-(Succinimid-3-yl-N)—CH$_2$CH$_2$CH$_2$CH$_2$CH$_2$—C(=O)-GGFG-NH—CH$_2$—O—CH$_2$—C(=O)—, and
(b)-(Succinimid-3-yl-N)—CH$_2$CH$_2$—C(=O)—NH—CH$_2$CH$_2$O—CH$_2$CH$_2$O—CH$_2$CH$_2$—C(=O)-GGFG-NH—CH$_2$CH$_2$CH$_2$—C(=O)—.
(40) the antibody-drug conjugate according to any one of (34) to (39), wherein the linker is represented by the following formula (a):
(a)-(Succinimid-3-yl-N)—CH$_2$CH$_2$CH$_2$CH$_2$CH$_2$—C(=O)-GGFG-NH—CH$_2$—O—CH$_2$—C(=O)—;
(41) the antibody-drug conjugate according to any one of (34) to (40), wherein the antibody is conjugated to a drug linker structure represented by the following formula [Formula 3] (wherein A represents a connecting position to the antibody) by a thioether bond:

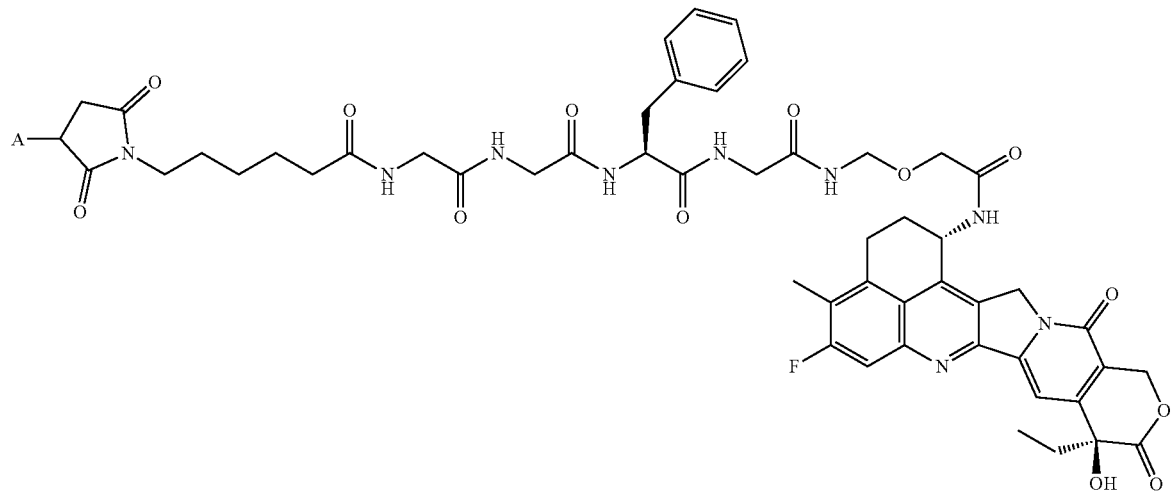

[Formula 3]

(42) the antibody-drug conjugate according to any one of (34) to (40), which has a structure represented by the following formula [Formula 4],
wherein AB represents the antibody or the functional fragment of the antibody, n represents an average number of units of the drug-linker structure conjugated to the antibody per antibody, and the antibody is connected to the linker via a sulfhydryl group derived from the antibody:

[Formula 4]

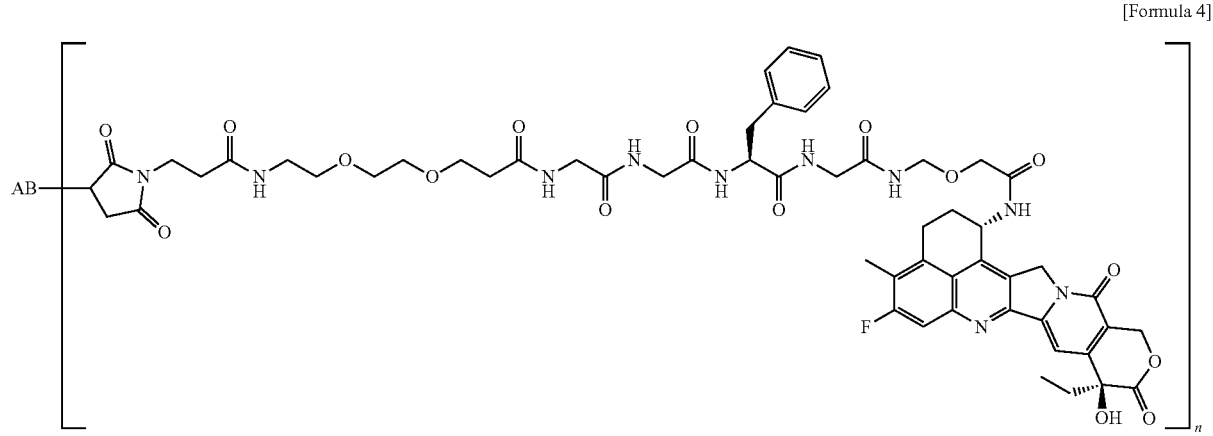

(43) the antibody-drug conjugate according to any one of (34) to (39), which is represented by the following formula [Formula 5],
wherein AB represents the antibody or the functional fragment of the antibody, n represents an average number of units of the drug-linker structure conjugated to the antibody per antibody, and the antibody is connected to the linker via a sulfhydryl group derived from the antibody:

[Formula 5]

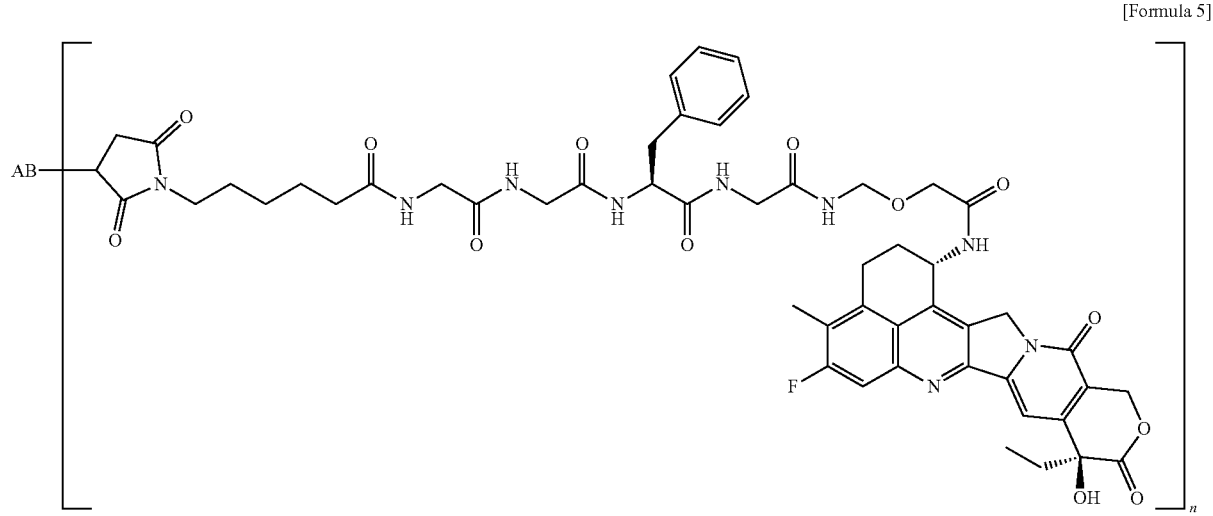

(44) the antibody-drug conjugate according to any one of (41) to (43), wherein the antibody is an antibody comprising a heavy chain and a light chain in any one combination selected from the group consisting of the following combinations (a) to (x), or a functional fragment of the antibody:
(a) a heavy chain consisting of the amino acid sequence at amino acid positions 20 to 472 in SEQ ID NO: 48, and a light chain consisting of the amino acid sequence at amino acid positions 21 to 234 in SEQ ID NO: 58,
(b) a heavy chain consisting of the amino acid sequence at amino acid positions 20 to 472 in SEQ ID NO: 48, and a light chain consisting of the amino acid sequence at amino acid positions 21 to 234 in SEQ ID NO: 60,
(c) a heavy chain consisting of the amino acid sequence at amino acid positions 20 to 472 in SEQ ID NO: 48, and a light chain consisting of the amino acid sequence at amino acid positions 21 to 234 in SEQ ID NO: 62,
(d) a heavy chain consisting of the amino acid sequence at amino acid positions 20 to 472 in SEQ ID NO: 48, and a light chain consisting of the amino acid sequence at amino acid positions 21 to 234 in SEQ ID NO: 64,
(e) a heavy chain consisting of the amino acid sequence at amino acid positions 20 to 472 in SEQ ID NO: 50, and a light chain consisting of the amino acid sequence at amino acid positions 21 to 234 in SEQ ID NO: 58,
(f) a heavy chain consisting of the amino acid sequence at amino acid positions 20 to 472 in SEQ ID NO: 50, and a light chain consisting of the amino acid sequence at amino acid positions 21 to 234 in SEQ ID NO: 60, (g) a heavy chain consisting of the amino acid sequence at amino acid positions 20 to 472 in SEQ ID NO: 50, and a light chain consisting of the amino acid sequence at amino acid positions 21 to 234 in SEQ ID NO: 62,
(h) a heavy chain consisting of the amino acid sequence at amino acid positions 20 to 472 in SEQ ID NO: 50, and a light chain consisting of the amino acid sequence at amino acid positions 21 to 234 in SEQ ID NO: 64,
(i) a heavy chain consisting of the amino acid sequence at amino acid positions 20 to 472 in SEQ ID NO: 52, and a light chain consisting of the amino acid sequence at amino acid positions 21 to 234 in SEQ ID NO: 58,
(j) a heavy chain consisting of the amino acid sequence at amino acid positions 20 to 472 in SEQ ID NO: 52, and a light chain consisting of the amino acid sequence at amino acid positions 21 to 234 in SEQ ID NO: 60,
(k) a heavy chain consisting of the amino acid sequence at amino acid positions 20 to 472 in SEQ ID NO: 52, and a light chain consisting of the amino acid sequence at amino acid positions 21 to 234 in SEQ ID NO: 62,
(l) a heavy chain consisting of the amino acid sequence at amino acid positions 20 to 472 in SEQ ID NO: 52, and a light chain consisting of the amino acid sequence at amino acid positions 21 to 234 in SEQ ID NO: 64,
(m) a heavy chain consisting of the amino acid sequence at amino acid positions 20 to 474 in SEQ ID NO: 54, and a light chain consisting of the amino acid sequence at amino acid positions 21 to 234 in SEQ ID NO: 58,
(n) a heavy chain consisting of the amino acid sequence at amino acid positions 20 to 474 in SEQ ID NO: 54, and a light chain consisting of the amino acid sequence at amino acid positions 21 to 234 in SEQ ID NO: 60,
(o) a heavy chain consisting of the amino acid sequence at amino acid positions 20 to 474 in SEQ ID NO: 54, and a light chain consisting of the amino acid sequence at amino acid positions 21 to 234 in SEQ ID NO: 62,
(p) a heavy chain consisting of the amino acid sequence at amino acid positions 20 to 474 in SEQ ID NO: 54, and a light chain consisting of the amino acid sequence at amino acid positions 21 to 234 in SEQ ID NO: 64,
(q) a heavy chain consisting of the amino acid sequence at amino acid positions 20 to 474 in SEQ ID NO: 56, and a light chain consisting of the amino acid sequence at amino acid positions 21 to 234 in SEQ ID NO: 58,
(r) a heavy chain consisting of the amino acid sequence at amino acid positions 20 to 474 in SEQ ID NO: 56, and a light chain consisting of the amino acid sequence at amino acid positions 21 to 234 in SEQ ID NO: 60,
(s) a heavy chain consisting of the amino acid sequence at amino acid positions 20 to 474 in SEQ ID NO: 56, and a light chain consisting of the amino acid sequence at amino acid positions 21 to 234 in SEQ ID NO: 62,
(t) a heavy chain consisting of the amino acid sequence at amino acid positions 20 to 474 in SEQ ID NO: 56, and a light chain consisting of the amino acid sequence at amino acid positions 21 to 234 in SEQ ID NO: 64,
(u) a heavy chain consisting of the amino acid sequence at amino acid positions 20 to 472 in SEQ ID NO: 44, and a light chain consisting of the amino acid sequence at amino acid positions 21 to 234 in SEQ ID NO: 58,
(v) a heavy chain consisting of the amino acid sequence at amino acid positions 20 to 472 in SEQ ID NO: 44, and a light chain consisting of the amino acid sequence at amino acid positions 21 to 234 in SEQ ID NO: 60,
(w) a heavy chain consisting of the amino acid sequence at amino acid positions 20 to 472 in SEQ ID NO: 44, and a light chain consisting of the amino acid sequence at amino acid positions 21 to 234 in SEQ ID NO: 62, and
(x) a heavy chain consisting of the amino acid sequence at amino acid positions 20 to 472 in SEQ ID NO: 44, and a light chain consisting of the amino acid sequence at amino acid positions 21 to 234 in SEQ ID NO: 64;
(45) the antibody-drug conjugate according to (44), wherein the heavy chain of the antibody comprises one or two or more modifications selected from the group consisting of N-linked glycosylation, O-linked glycosylation, N-terminal processing, C-terminal processing, deamidation, isomerization of aspartic acid, oxidation of methionine, addition of a methionine residue to the N-terminus, amidation of a proline residue, and a heavy chain comprising a deletion of one or two amino acids at the carboxyl terminus;
(46) the antibody-drug conjugate according to any one of (34) to (45), wherein the average number of the selected drug-linker structure conjugated per antibody is in a range of from 1 to 10;
(47) the antibody-drug conjugate according to any one of (34) to (46), wherein the average number of the selected drug-linker structure conjugated per antibody is in a range of from 2 to 8;
(48) the antibody-drug conjugate according to any one of (34) to (47), wherein the average number of the selected drug-linker structure conjugated per antibody is in a range of from 3 to 8;
(49) the antibody-drug conjugate according to any one of (34) to (48), wherein the average number of the selected drug-linker structure conjugated per antibody is in a range of from 7 to 8;
(50) the antibody-drug conjugate according to any one of (34) to (49), wherein the average number of the selected drug-linker structure conjugated per antibody is 8;
(51) a pharmaceutical composition comprising any component selected from the antibodies or the functional fragments of the antibodies according to (1) to (19) and (27) to (33) and the antibody-drug conjugates according to (34) to (50), a salt of the component, or a hydrate of the component or the salt;
(52) the pharmaceutical composition according to (51), which is an antitumor drug;
(53) the antitumor drug according to (52), wherein the tumor is a tumor expressing GPR20;
(54) the antitumor drug according to (52) or (53), wherein the tumor is gastrointestinal stromal tumor;
(55) the pharmaceutical composition or the antitumor drug according to any one of (51) to (54), further comprising an additional antitumor drug;
(56) a method for treating a tumor, which comprises administering any component selected from the antibodies or the functional fragments of the antibodies according to (1) to (19) and (27) to (33), the antibody-drug conjugates according to (34) to (50), salts of these components, and hydrates of these components or the salts to an individual;
(57) the treatment method according to (56), wherein the tumor is gastrointestinal stromal tumor;
(58) the treatment method according to (56) or (57), wherein the tumor is a tumor that exhibits resistance to a tyrosine kinase inhibitor;
(59) a method for treating a tumor, which comprises administering a pharmaceutical composition comprising at least one component selected from the antibodies or the functional fragments of the antibodies according to (1) to (19) and (27) to (33), the antibody-drug conjugates according to (34) to (50), salts of these components, and hydrates of these components or the salts, and at least one antitumor drug to an individual, simultaneously, separately, or continuously;

(60) the method for treating a tumor according to (59), wherein the antitumor drug is a tyrosine kinase inhibitor;
(61) the method for treating a tumor according to (60), wherein the tyrosine kinase inhibitor is at least one selected from sunitinib, imatinib, and regorafenib;
(62) the method for treating a tumor according to any one of (56) to (61), wherein the tumor is gastrointestinal stromal tumor that exhibits resistance to a tyrosine kinase inhibitor; and
(63) a method for producing an antibody-drug conjugate, which comprises a step of culturing the host cell according to (24) or (25), a step of collecting an antibody of interest or a functional fragment of the antibody from the culture obtained by the aforementioned step, and a step of reacting the antibody or the functional fragment of the antibody obtained by the aforementioned step with a drug-linker intermediate compound.

Advantageous Effects of Invention

Features of the anti-GPR20 antibody of the present invention are to recognize a conformation consisting of two extracellular regions having the amino acid sequence at positions 1 to 48 and the amino acid sequence at positions 108 to 125, respectively, from the N-terminus of GPR20, and to have internalization activity. An anti-GPR20 antibody-drug conjugate comprising the anti-GPR20 antibody of the present invention conjugated to a drug exerting toxicity in cells via a linker having a specific structure can be expected to achieve an excellent antitumor effect and safety by administration to patients having cancer cells expressing GPR20. Specifically, the anti-GPR20 antibody-drug conjugate of the present invention is useful as an antitumor agent.

BRIEF DESCRIPTION OF DRAWINGS

FIG. 1 shows the amino acid sequence (SEQ ID NO: 2) of the heavy chain of rat anti-GPR20 antibody 04-046 and the nucleotide sequence (SEQ ID NO: 32) of cDNA encoding the heavy chain.

FIG. 2 shows the amino acid sequence (SEQ ID NO: 7) of the light chain of the rat anti-GPR20 antibody 04-046 and the nucleotide sequence (SEQ ID NO: 34) of cDNA encoding the light chain.

FIG. 3 shows the amino acid sequence (SEQ ID NO: 12) of the heavy chain of rat anti-GPR20 antibody 04-079 and the nucleotide sequence (SEQ ID NO: 36) of cDNA encoding the heavy chain.

FIG. 4 shows the amino acid sequence (SEQ ID NO: 17) of the light chain of the rat anti-GPR20 antibody 04-079 and the nucleotide sequence (SEQ ID NO: 38) of cDNA encoding the light chain.

FIG. 5 shows the amino acid sequence (SEQ ID NO: 22) of the heavy chain of rat anti-GPR20 antibody 04-126 and the nucleotide sequence (SEQ ID NO: 40) of cDNA encoding the heavy chain.

FIG. 6 shows the amino acid sequence (SEQ ID NO: 27) of the light chain of the rat anti-GPR20 antibody 04-126 and the nucleotide sequence (SEQ ID NO: 42) of cDNA encoding the light chain.

FIG. 7 shows the amino acid sequence (SEQ ID NO: 44) of the heavy chain of human chimeric anti-GPR20 antibody 04-046Ch and the nucleotide sequence (SEQ ID NO: 46) of cDNA encoding the heavy chain.

FIG. 8 shows the amino acid sequence (SEQ ID NO: 45) of the light chain of the human chimeric anti-GPR20 antibody 04-046Ch and the nucleotide sequence (SEQ ID NO: 47) of cDNA encoding the light chain.

FIG. 9 shows the amino acid sequence (SEQ ID NO: 48) of a humanized h046-H4b type heavy chain.

FIG. 10 shows the amino acid sequence (SEQ ID NO: 50) of a humanized h046-H4e type heavy chain.

FIG. 11 shows the amino acid sequence (SEQ ID NO: 52) of a humanized h046-H5b type heavy chain.

FIG. 12 shows the amino acid sequence (SEQ ID NO: 54) of a humanized h046-H8 type heavy chain.

FIG. 13 shows the amino acid sequence (SEQ ID NO: 56) of a humanized h046-H10 type heavy chain.

FIG. 14 shows the amino acid sequence (SEQ ID NO: 58) of a humanized h046-L1 type light chain.

FIG. 15 shows the amino acid sequence (SEQ ID NO: 60) of a humanized h046-L2 type light chain.

FIG. 16 shows the amino acid sequence (SEQ ID NO: 62) of a humanized h046-L6 type light chain.

FIG. 17 shows the amino acid sequence (SEQ ID NO: 64) of a humanized h046-L7 type light chain.

FIG. 18 shows flow cytometry analysis results when a culture supernatant of a hybridoma producing an anti-human GPR20 antibody was reacted with a cell line transiently expressing human GPR20.

FIG. 19-1 shows the concentration-dependent binding of a rat anti-human GPR20 antibody to a human GPR20-expressing cell line in flow cytometry analysis.

FIG. 19-2 shows the concentration-dependent binding of a rat anti-human GPR20 antibody to a human GPR20-expressing cell line in flow cytometry analysis.

FIG. 19-3 shows the concentration-dependent binding of a rat anti-human GPR20 antibody to a human GPR20-expressing cell line in flow cytometry analysis.

FIG. 20 shows the internalization ability of a rat anti-GPR20 antibody. The ordinate depicts a survival rate (relative ratio to a cell survival rate without antibody addition defined as 100%) when the rat anti-GPR20 antibody and a saporin-labeled anti-rat IgG antibody were added to a human GPR20-expressing cell line.

FIG. 21 shows a diagram of the comparison between the amino acid sequences of human GPR20 and mouse GPR20. The amino acid sequences indicated by EC1, EC2, EC3, and EC4 represent extracellular regions, and the numbers within the parentheses represent regional sites based on human GPR20 amino acid positions. The shaded characters represent the same amino acids between humans and mice.

FIG. 22-a shows the binding properties of various anti-GPR20 antibodies. This drawing shows the binding activity of each anti-GPR20 antibody against human GPR20, mouse GPR20, and human/mouse chimeric GPR20 proteins in which one of the extracellular regions EC1, EC2, EC3, and EC4 of human GPR20 was substituted with the corresponding sequence of mouse GPR20.

FIG. 22-b shows the binding properties of various anti-GPR20 antibodies. This drawing shows the binding activity of each anti-GPR20 antibody against human GPR20, mouse GPR20, and human/mouse chimeric GPR20 proteins in which one of the extracellular regions EC1, EC2, EC3, and EC4 of human GPR20 was substituted with the corresponding sequence of mouse GPR20.

FIG. 23-a shows a negative control.

FIG. 23-b shows the human GPR20-specific binding of the human chimeric anti-GPR20 antibody 04-046Ch.

FIG. 24 shows the GPR20-binding activity of a humanized anti-GPR20 antibody.

FIG. 25 shows the GPR20-binding activity of a humanized anti-GPR20 antibody and an antibody-drug conjugate.

FIG. 26 shows the in vitro cell proliferation-suppressive activity of an antibody-drug conjugate (1) against GPR20-expressing cells.

FIG. 27 shows the in vitro cell proliferation-suppressive activity of antibody-drug conjugates (7), (8), and (9) against GPR20-expressing cells.

FIG. 28 shows the antitumor effects of antibody-drug conjugates (1) and (2) in subcutaneously GIST-T1/GPR20 cell-transplanted nude mouse models.

FIG. 29 shows the antitumor effects of antibody-drug conjugates (1) and (2) in subcutaneously GIST430 cell-transplanted nude mouse models.

FIG. 30 shows the antitumor effects of antibody-drug conjugates (6) and (9) in subcutaneously GIST-T1/GPR20 cell-transplanted nude mouse models.

FIG. 31 shows the antitumor effects of antibody-drug conjugates (3), (5), (6), (10), (11), and (12) in subcutaneously GIST-T1/GPR20 cell-transplanted nude mouse models.

FIG. 32 shows the antitumor effects of antibody-drug conjugate (13) in subcutaneously GIST-T1/GPR20 cell-transplanted nude mouse models.

FIG. 33 shows the antitumor effects of antibody-drug conjugates (4) and (13) in subcutaneously GIST020-transplanted nude mouse models.

FIG. 34 shows the antitumor effect of antibody-drug conjugate (13) in subcutaneously GIST1-transplanted nude mouse models.

FIG. 35 shows the antitumor effects of antibody-drug conjugate (14) and an antibody-drug conjugate targeting HER2 in subcutaneously stomach-cancer-cell-line-NCI-N87-cell-transplanted nude mouse models.

FIG. 36 shows the antitumor effect of antibody-drug conjugate (14) in models prepared by subcutaneously transplanting, into nude mice, a tumor GIST074 derived from a patient with gastrointestinal stromal tumor in the stomach that had become unresponsive to regorafenib treatment.

FIG. 37 shows the effect of combined use of antibody-drug conjugate (3) and sunitinib in models prepared by subcutaneously transplanting, into nude mice, a human gastrointestinal stromal tumor cell line GIST430/654 having an imatinib-resistant mutation.

DESCRIPTION OF EMBODIMENTS

Hereinafter, the preferred embodiments for carrying out the present invention will be described with reference to the drawings. It is to be noted that the embodiments described below merely illustrate the representative embodiments of the present invention, and the scope of the present invention shall not be narrowly interpreted due to these examples.

In the present description, the term "cancer" is used to have the same meaning as that of the term "tumor".

In the present description, the term "gene" is used to include not only DNA but also its mRNA and cDNA, and cRNA thereof.

In the present description, the term "polynucleotide" is used to have the same meaning as that of a nucleic acid, and also includes DNA, RNA, a probe, an oligonucleotide, and a primer.

In the present description, the terms "polypeptide" and "protein" are used without being distinguished from each other.

In the present description, the term "cell" includes cells in an individual animal, and cultured cells.

In the present description, the term "GPR20" is used to have the same meaning as that of GPR20 protein.

In the present description, the term "cytotoxic activity" is used to mean that a pathologic change is caused to cells in any given way. The term not only means a direct trauma, but also means all types of structural or functional damage caused to cells, such as DNA cleavage, formation of a base dimer, chromosomal cleavage, damage to cell mitotic apparatus, and a reduction in the activities of various types of enzymes.

In the present description, the phrase "exerting toxicity in cells" is used to mean that toxicity is exhibited in cells in any given way. The term not only means a direct trauma, but also means all types of structural, functional, or metabolic influences caused to cells, such as DNA cleavage, formation of a base dimer, chromosomal cleavage, damage to cell mitotic apparatus, a reduction in the activities of various types of enzymes, and suppression of effects of cell growth factors.

In the present description, the term "epitope" is used to mean the partial peptide or partial three-dimensional structure of GPR20, to which a specific anti-GPR20 antibody binds. Such an epitope, which is the above-described partial peptide of GPR20, can be determined by a method well known to a person skilled in the art, such as an immunoassay. First, various partial structures of an antigen are produced. As regards production of such partial structures, a known oligopeptide synthesis technique can be applied. For example, a series of polypeptides, in which GPR20 has been successively truncated at an appropriate length from the C-terminus or N-terminus thereof, are produced by a genetic recombination technique well known to a person skilled in the art. Thereafter, the reactivity of an antibody to such polypeptides is studied, and recognition sites are roughly determined. Thereafter, further shorter peptides are synthesized, and the reactivity thereof to these peptides can then be studied, so as to determine an epitope. When an antibody binding to a membrane protein having a plurality of extracellular domains is directed to a three-dimensional structure composed of a plurality of domains as an epitope, the domain to which the antibody binds can be determined by modifying the amino acid sequence of a specific extracellular domain, and thereby modifying the three-dimensional structure. The epitope, which is a partial three-dimensional structure of an antigen that binds to a specific antibody, can also be determined by specifying the amino acid residues of an antigen adjacent to the above-described antibody by X-ray structural analysis.

In the present description, the phrase "antibodies binding to the same epitope" is used to mean antibodies that bind to a common epitope. If a second antibody binds to a partial peptide or a partial three-dimensional structure to which a first antibody binds, it can be determined that the first antibody and the second antibody bind to the same epitope. In addition, by confirming that a second antibody competes with a first antibody for the binding of the first antibody to an antigen (i.e., a second antibody interferes with the binding of a first antibody to an antigen), it can be determined that the first antibody and the second antibody bind to the same epitope, even if the specific sequence or structure of the epitope has not been determined. Furthermore, when a first antibody and a second antibody bind to the same epitope and further, the first antibody has special effects such as antitumor activity or internalization activity, the second antibody can be expected to have the same activity as that of the first antibody. Accordingly, by confirming that the second anti-GPR20 antibody competes with the first anti-GPR20 antibody for the binding of the first anti-GPR20 antibody to a partial peptide of GPR20, it can be determined that the first antibody and the second antibody are antibodies binding to the same epitope of GPR20.

In the present description, the term "CDR" is used to mean a complementarity determining region. It is known that the heavy chain and light chain of an antibody molecule each have three CDRs. Such a CDR is also referred to as a hypervariable region, and is located in the variable regions of the heavy chain and light chain of an antibody. These regions have a particularly highly variable primary structure and are separated into three sites on the primary structure of the polypeptide chain in each of the heavy chain and light chain. In the present description, with regard to the CDR of an antibody, the CDRs of a heavy chain are referred to as CDRH1, CDRH2 and CDRH3, respectively, from the amino-terminal side of the amino acid sequence of the heavy chain, whereas the CDRs of a light chain are referred to as CDRL1, CDRL2 and CDRL3, respectively, from the amino-terminal side of the amino acid sequence of the light chain. These sites are located close to one another on the three-dimensional structure, and determine the specificity of the antibody to an antigen to which the antibody binds.

In the present invention, the phrase "hybridizing under stringent conditions" is used to mean that hybridization is carried out in the commercially available hybridization solution ExpressHyb Hybridization Solution (manufactured by Clontech Laboratories, Inc.) at 68° C., or that hybridization is carried out under conditions in which hybridization is carried out using a DNA-immobilized filter in the presence of 0.7 to 1.0 M NaCl at 68° C., and the resultant is then washed at 68° C. with a 0.1- to 2-fold concentration of SSC solution (wherein 1-fold concentration of SSC consists of 150 mM NaCl and 15 mM sodium citrate) for identification, or conditions equivalent thereto.

1. GPR20

GPR20 is a seven-pass transmembrane protein composed of 358 amino acids, which belongs to class A of the G protein-coupled receptor (GPCR) family, and this protein has N-terminal extracellular and C-terminal intracellular domains.

The GPR20 protein used in the present invention can be directly purified from the GPR20-expressing cells of a human or a non-human mammal (e.g., a rat or a mouse) and can then be used, or a cell membrane fraction of the aforementioned cells can be prepared and can be used as the GPR20 protein. Alternatively, GPR20 can also be obtained by synthesizing it in vitro, or by allowing host cells to produce GPR20 by genetic manipulation. According to such genetic manipulation, the GPR20 protein can be obtained, specifically, by incorporating GPR20 cDNA into a vector capable of expressing the GPR20 cDNA, and then synthesizing GPR20 in a solution containing enzymes, substrate and energetic materials necessary for transcription and translation, or by transforming the host cells of other prokaryotes or eukaryotes, so as to allow them to express GPR20. Also, the GPR20-expressing cells based on the above-described genetic manipulation, or a cell line expressing GPR20 may be used as the GPR20 protein. Alternatively, the expression vector into which GPR20 cDNA has been incorporated can be directly administered to an animal to be immunized, and GPR20 can be expressed in the body of the animal thus immunized.

The DNA sequence and amino acid sequence of human GPR20 are disclosed in a public database, and can be referred to under, for example, accession Nos. NM_005293 and NP_005284 (NCBI).

Moreover, a protein which consists of an amino acid sequence comprising a substitution, deletion and/or addition of one or several amino acids in the above-described amino acid sequence of GPR20, and has a biological activity equivalent to that of the GPR20 protein, is also included in GPR20.

The amino acid sequence of the human GPR20 protein is shown in SEQ ID NO: 1 in the sequence listing. The extracellular regions are constituted by an extracellular domain consisting of amino acid positions 1 to 48 (EC1), an extracellular domain consisting of amino acid positions 108 to 125 (EC2), an extracellular domain (EC3) consisting of amino acid positions 190 to 196, and an extracellular domain (EC4) consisting of amino acid positions 260 to 275, in SEQ ID NO: 1 in the sequence listing.

2. Production of Anti-GPR20 Antibody

One example of the anti-GPR20 antibody of the present invention can include an anti-GPR20 antibody which recognizes a conformation consisting of two extracellular regions having the amino acid sequence at positions 1 to 48 and the amino acid sequence at positions 108 to 125, respectively, from the N-terminus of GPR20 shown in SEQ ID NO: 1 in the sequence listing, and has internalization activity.

Another example of the anti-GPR20 antibody of the present invention can include an anti-GPR20 antibody which recognizes a conformation consisting of two extracellular regions having the amino acid sequence at positions 1 to 48 and the amino acid sequence at positions 108 to 125, respectively, from the N-terminus of GPR20 shown in SEQ ID NO: 1 in the sequence listing, binds to at least tyrosine at position 113, and has internalization activity.

A further example of the anti-GPR20 antibody of the present invention can include an anti-GPR20 antibody which specifically binds to a polypeptide consisting of the amino acid sequence shown in SEQ ID NO: 1 in the sequence listing, does not bind to a polypeptide with the amino acid tyrosine at amino acid position 113 of SEQ ID NO: 1 in the sequence listing substituted with a different amino acid (e.g., phenylalanine), and has internalization activity.

The anti-GPR20 antibody of the present invention may be derived from any species. Preferred examples of the species can include humans, rats, mice and rabbits. When the anti-GPR20 antibody of the present invention is derived from a species other than human, it is preferred to chimerize or humanize the anti-GPR20 antibody by a well-known technique. The antibody of the present invention may be a polyclonal antibody or may be a monoclonal antibody, and a monoclonal antibody is preferred.

The anti-GPR20 antibody of the present invention is an antibody that can target tumor cells. Specifically, the anti-GPR20 antibody of the present invention possesses a property of being able to recognize tumor cells, a property of being able to bind to tumor cells, a property of being internalized into tumor cells by cellular uptake, and the like. Accordingly, the anti-GPR20 antibody of the present invention can be conjugated to a compound having antitumor activity via a linker to prepare an antibody-drug conjugate.

The binding activity of an antibody against tumor cells can be confirmed by flow cytometry. The uptake of an antibody into tumor cells can be confirmed by (1) an assay of visualizing a cellularly taken-up antibody under a fluorescent microscope using a secondary antibody (fluorescently labeled) binding to a therapeutic antibody (Cell Death and Differentiation (2008) 15, 751-761), (2) an assay of measuring the amount of cellularly taken-up fluorescence using a secondary antibody (fluorescently labeled) binding to a therapeutic antibody (Molecular Biology of the Cell Vol.

15, 5268-5282, December 2004) or (3) Mab-ZAP assay using an immunotoxin binding to a therapeutic antibody, wherein the toxin is released upon cellular uptake, so as to suppress cell proliferation (Bio Techniques 28: 162-165, January 2000). A recombinant complex protein of a catalytic region of diphtheria toxin and protein G may be used as the immunotoxin.

In the present description, the term "high internalization ability" is used to mean that the survival rate (which is indicated by a relative ratio to a cell survival rate without antibody addition defined as 100%) of GPR20-expressing cells to which the aforementioned antibody and a saporin-labeled anti-rat IgG antibody have been administered is preferably 70% or less, and more preferably 60% or less.

The antitumor antibody-drug conjugate of the present invention comprises a conjugated compound exerting an antitumor effect. Therefore, it is preferred, but not essential, that the antibody itself should have an antitumor effect. For the purpose of specifically and selectively exerting the cytotoxicity of the antitumor compound in tumor cells, it is important and preferred that the antibody should have a property of being internalized and transferred into tumor cells.

The anti-GPR20 antibody can be obtained by immunizing an animal with a polypeptide serving as an antigen by a method usually performed in this field, and then collecting and purifying an antibody produced in a living body thereof. Since GPR20 is a seven-pass transmembrane protein, it is preferred to use GPCR retaining a three-dimensional structure as an antigen. Examples of such a method can include a DNA immunization method.

The origin of the antigen is not limited to a human, and thus, an animal can also be immunized with an antigen derived from a non-human animal such as a mouse or a rat. In this case, an antibody applicable to the disease of a human can be selected by examining the cross-reactivity of the obtained antibody binding to the heterologous antigen with the human antigen.

Furthermore, antibody-producing cells that produce an antibody against the antigen can be fused with myeloma cells according to a known method (e.g., Kohler and Milstein, Nature (1975) 256, p. 495-497; and Kennet, R. ed., Monoclonal Antibodies, p. 365-367, Plenum Press, N. Y. (1980)) to establish hybridomas, so as to obtain a monoclonal antibody.

Hereinafter, the method for obtaining an antibody against GPR20 will be specifically described.

(1) Preparation of Antigen

The antigen can be obtained by allowing host cells to produce a gene encoding the antigen protein according to genetic manipulation. Specifically, a vector capable of expressing the antigen gene is produced, and the vector is then introduced into host cells, so that the gene is expressed therein, and thereafter, the expressed antigen may be purified. The antibody can also be obtained by a method of immunizing an animal with the antigen-expressing cells based on the above-described genetic manipulation, or a cell line expressing the antigen.

Alternatively, the antibody can also be obtained, without the use of the antigen protein, by incorporating cDNA of the antigen protein into an expression vector, then administering the expression vector to an animal to be immunized, and expressing the antigen protein in the body of the animal thus immunized, so that an antibody against the antigen protein is produced therein.

(2) Production of Anti-GPR20 Monoclonal Antibody

The anti-GPR20 antibody used in the present invention is not particularly limited. For example, an antibody specified by an amino acid sequence shown in the sequence listing of the present application can be suitably used. The anti-GPR20 antibody used in the present invention is desirably an antibody having the following properties:

(1) an antibody having the following properties:
(a) specifically binding to GPR20, and
(b) having activity of being internalized into GPR20-expressing cells by binding to GPR20;
(2) the antibody according to the above (1) or the aforementioned antibody, wherein the GPR20 is human GPR20; and
(3) recognizing a conformation consisting of two extracellular regions having the amino acid sequence at positions 1 to 48 and the amino acid sequence at positions 108 to 125, respectively, from the N-terminus of human GPR20, and having internalization activity.

The method for obtaining the antibody against GPR20 of the present invention is not particularly limited as long as the anti-GPR20 antibody can be obtained. Since GPR20 is a transmembrane protein, it is preferred to use GPR20 retaining the conformation as an antigen.

One preferred example of the method for obtaining the antibody can include a DNA immunization method. The DNA immunization method is an approach which involves transfecting an animal (e.g., mouse or rat) individual with an antigen expression plasmid, and then expressing the antigen in the individual to induce immunity against the antigen. The transfection approach includes a method of directly injecting the plasmid to the muscle, a method of injecting a transfection reagent such as a liposome or polyethylenimine to the vein, an approach using a viral vector, an approach of injecting gold particles attached with the plasmid using a gene gun, a hydrodynamic method of rapidly injecting a plasmid solution in a large amount to the vein, and the like. With regard to the transfection method of injecting the expression plasmid to the muscle, a technique called in vivo electroporation, which involves applying electroporation to the intramuscular injection site of the plasmid, is known as an approach for improving an expression level (Aihara H, Miyazaki J. Nat Biotechnol. 1998 September; 16 (9): 867-70 or Mir L M, Bureau M F, Gehl J, Rangara R, Rouy D, Caillaud J M, Delaere P, Branellec D, Schwartz B, Scherman D. Proc Natl Acad Sci USA. 1999 Apr. 13; 96 (8): 4262-7). This approach further improves the expression level by treating the muscle with hyaluronidase before the intramuscular injection of the plasmid (McMahon J M 1, Signori E, Wells K E, Fazio V M, Wells D J., Gene Ther. 2001 August; 8 (16): 1264-70). Furthermore, the hybridoma production can be performed by a known method, and can also be performed using, for example, Hybrimune Hybridoma Production System (Cyto Pulse Sciences, Inc.).

Specific examples of the obtainment of a monoclonal antibody can also include the following procedures:

(a) immune response can be immunized by incorporating GPR20 cDNA into an expression vector (e.g., pcDNA3.1; Thermo Fisher Scientific Inc.), and directly administering the vector to an animal (e.g., a rat or a mouse) to be immunized by a method such as electroporation or a gene gun, so as to express GPR20 in the body of the animal. The administration of the vector by electroporation or the like may be performed one or more times, preferably a plurality of times, if necessary for enhancing an antibody titer;

(b) collection of a tissue (e.g., a lymph node) containing antibody-producing cells from the aforementioned animal in which the immune response has been induced;

(c) preparation of myeloma cells (hereinafter, referred to as "myelomas") (e.g., mouse myeloma SP2/0-ag14 cells); (d) cell fusion between the antibody-producing cells and the myelomas;
(e) selection of a hybridoma group producing an antibody of interest;
(f) division into single cell clones (cloning);
(g) optionally, the culture of hybridomas for the mass production of monoclonal antibodies, or the breeding of animals into which the hybridomas are transplanted; and
(h) study on the physiological activity (internalization activity) and binding specificity of the monoclonal antibody thus produced, or examination of the properties of the antibody as a labeling reagent.

Examples of the method for measuring the antibody titer used herein can include, but are not limited to, flow cytometry and Cell-ELISA.

Examples of the hybridoma strain thus established can include anti-GPR20 antibody-producing hybridomas 04-046, 04-079 and 04-126. It is to be noted that, in the present description, an antibody produced by the anti-GPR20 antibody-producing hybridoma 04-046 is referred to as a "04-046 antibody" or simply "04-046", an antibody produced by the hybridoma 04-079 is referred to as a "04-079 antibody" or simply "04-079", and an antibody produced by the hybridoma 04-126 is referred to as a "04-126 antibody" or simply "04-126".

The heavy chain of the 04-046 antibody has the amino acid sequence shown in SEQ ID NO: 2 in the sequence listing. In the heavy chain amino acid sequence shown in SEQ ID NO: 2 in the sequence listing, the amino acid sequence consisting of the amino acid residues at positions 1 to 19 is a signal sequence, the amino acid sequence consisting of the amino acid residues at positions 20 to 142 is a variable region, and the amino acid sequence consisting of the amino acid residues at positions 143 to 475 is a constant region. The aforementioned variable region has CDRH1 consisting of an amino acid sequence consisting of the amino acid residues at positions 45 to 54, CDRH2 consisting of an amino acid sequence consisting of the amino acid residues at positions 69 to 78, and CDRH3 consisting of an amino acid sequence consisting of the amino acid residues at positions 118 to 131, in SEQ ID NO: 2 in the sequence listing. The heavy chain variable region of the 04-046 antibody has the amino acid sequence shown in SEQ ID NO: 3 in the sequence listing. The CDRH1 of the 04-046 antibody has the amino acid sequence shown in SEQ ID NO: 4 in the sequence listing, the amino acid sequence of the CDRH2 has the amino acid sequence shown in SEQ ID NO: 5 in the sequence listing, and the amino acid sequence of the CDRH3 has the amino acid sequence shown in SEQ ID NO: 6 in the sequence listing. Furthermore, the sequence of the heavy chain of the 04-046 antibody is shown in FIG. 1.

The light chain of the 04-046 antibody has the amino acid sequence shown in SEQ ID NO: 7 in the sequence listing. In the light chain amino acid sequence shown in SEQ ID NO: 7 in the sequence listing, the amino acid sequence consisting of the amino acid residues at positions 1 to 20 is a signal sequence, the amino acid sequence consisting of the amino acid residues at positions 21 to 128 is a variable region, and the amino acid sequence consisting of the amino acid residues at positions 129 to 233 is a constant region. The aforementioned variable region has CDRL1 consisting of an amino acid sequence consisting of the amino acid residues at positions 43 to 53, CDRL2 consisting of an amino acid sequence consisting of the amino acid residues at positions 69 to 75, and CDRL3 consisting of an amino acid sequence consisting of the amino acid residues at positions 108 to 116, in SEQ ID NO: 7 in the sequence listing. The light chain variable region of the 04-046 antibody has the amino acid sequence shown in SEQ ID NO: 8 in the sequence listing. The CDRL1 of the 04-046 antibody has the amino acid sequence shown in SEQ ID NO: 9 in the sequence listing, the amino acid sequence of the CDRL2 has the amino acid sequence shown in SEQ ID NO: 10 in the sequence listing, and the amino acid sequence of the CDRL3 has the amino acid sequence shown in SEQ ID NO: 11 in the sequence listing. Furthermore, the sequence of the light chain of the 04-046 antibody is shown in FIG. 2.

The heavy chain of the 04-079 antibody has the amino acid sequence shown in SEQ ID NO: 12 in the sequence listing. In the heavy chain amino acid sequence shown in SEQ ID NO: 12 in the sequence listing, the amino acid sequence consisting of the amino acid residues at positions 1 to 19 is a signal sequence, the amino acid sequence consisting of the amino acid residues at positions 20 to 142 is a variable region, and the amino acid sequence consisting of the amino acid residues at positions 143 to 475 is a constant region. The aforementioned variable region has CDRH1 consisting of an amino acid sequence consisting of the amino acid residues at positions 45 to 54, CDRH2 consisting of an amino acid sequence consisting of the amino acid residues at positions 69 to 78, and CDRH3 consisting of an amino acid sequence consisting of the amino acid residues at positions 118 to 131, in SEQ ID NO: 12 in the sequence listing. The heavy chain variable region of the 04-079 antibody has the amino acid sequence shown in SEQ ID NO: 13 in the sequence listing. The CDRH1 of the 04-079 antibody has the amino acid sequence shown in SEQ ID NO: 14 in the sequence listing, the amino acid sequence of the CDRH2 has the amino acid sequence shown in SEQ ID NO: 15 in the sequence listing, and the amino acid sequence of the CDRH3 has the amino acid sequence shown in SEQ ID NO: 16 in the sequence listing. Furthermore, the sequence of the heavy chain of the 04-079 antibody is shown in FIG. 3.

The light chain of the 04-079 antibody has the amino acid sequence shown in SEQ ID NO: 17 in the sequence listing. In the light chain amino acid sequence shown in SEQ ID NO: 17 in the sequence listing, the amino acid sequence consisting of the amino acid residues at positions 1 to 20 is a signal sequence, the amino acid sequence consisting of the amino acid residues at positions 21 to 128 is a variable region, and the amino acid sequence consisting of the amino acid residues at positions 129 to 233 is a constant region. The aforementioned variable region has CDRL1 consisting of an amino acid sequence consisting of the amino acid residues at positions 43 to 53, CDRL2 consisting of an amino acid sequence consisting of the amino acid residues at positions 69 to 75, and CDRL3 consisting of an amino acid sequence consisting of the amino acid residues at positions 108 to 116, in SEQ ID NO: 17 in the sequence listing. The light chain variable region of the 04-079 antibody has the amino acid sequence shown in SEQ ID NO: 18 in the sequence listing. The CDRL1 of the 04-079 antibody has the amino acid sequence shown in SEQ ID NO: 19 in the sequence listing, the amino acid sequence of the CDRL2 has the amino acid sequence shown in SEQ ID NO: 20 in the sequence listing, and the amino acid sequence of the CDRL3 has the amino acid sequence shown in SEQ ID NO: 21 in the sequence listing. Furthermore, the sequence of the light chain of the 04-079 antibody is shown in FIG. 4.

The heavy chain of the 04-126 antibody has the amino acid sequence shown in SEQ ID NO: 22 in the sequence listing. In the heavy chain amino acid sequence shown in SEQ ID NO: 22 in the sequence listing, the amino acid sequence consisting of the amino acid residues at positions 1 to 19 is a signal sequence, the amino acid sequence consisting of the amino acid residues at positions 20 to 142 is a variable region, and the amino acid sequence consisting of the amino acid residues at positions 143 to 475 is a constant region. The aforementioned variable region has CDRH1 consisting of an amino acid sequence consisting of the amino acid residues at positions 45 to 54, CDRH2 consisting of an amino acid sequence consisting of the amino acid residues at positions 69 to 78, and CDRH3 consisting of an amino acid sequence consisting of the amino acid residues at positions 118 to 131, in SEQ ID NO: 22 in the sequence listing. The heavy chain variable region of the 04-126 antibody has the amino acid sequence shown in SEQ ID NO: 23 in the sequence listing. The CDRH1 of the 04-126 antibody has the amino acid sequence shown in SEQ ID NO: 24 in the sequence listing, the amino acid sequence of the CDRH2 has the amino acid sequence shown in SEQ ID NO: 25 in the sequence listing, and the amino acid sequence of the CDRH3 has the amino acid sequence shown in SEQ ID NO: 26 in the sequence listing. Furthermore, the sequence of the heavy chain of the 04-126 antibody is shown in FIG. 5.

The light chain of the 04-126 antibody has the amino acid sequence shown in SEQ ID NO: 27 in the sequence listing. In the light chain amino acid sequence shown in SEQ ID NO: 27 in the sequence listing, the amino acid sequence consisting of the amino acid residues at positions 1 to 20 is a signal sequence, the amino acid sequence consisting of the amino acid residues at positions 21 to 128 is a variable region, and the amino acid sequence consisting of the amino acid residues at positions 129 to 233 is a constant region. The aforementioned variable region has CDRL1 consisting of an amino acid sequence consisting of the amino acid residues at positions 43 to 53, CDRL2 consisting of an amino acid sequence consisting of the amino acid residues at positions 69 to 75, and CDRL3 consisting of an amino acid sequence consisting of the amino acid residues at positions 108 to 116, in SEQ ID NO: 27 in the sequence listing. The light chain variable region of the 04-126 antibody has the amino acid sequence shown in SEQ ID NO: 28 in the sequence listing. The CDRL1 of the 04-126 antibody has the amino acid sequence shown in SEQ ID NO: 29 in the sequence listing, the amino acid sequence of the CDRL2 has the amino acid sequence shown in SEQ ID NO: 30 in the sequence listing, and the amino acid sequence of the CDRL3 has the amino acid sequence shown in SEQ ID NO: 31 in the sequence listing. Furthermore, the sequence of the light chain of the 04-126 antibody is shown in FIG. 6.

The heavy chain amino acid sequence of the 04-046 antibody is encoded by the nucleotide sequence shown in SEQ ID NO: 32 in the sequence listing. In the nucleotide sequence shown in SEQ ID NO: 32 in the sequence listing, the nucleotide sequence consisting of the nucleotides at positions 1 to 57 is a signal sequence, the nucleotide sequence consisting of the nucleotides at positions 58 to 426 encodes the heavy chain variable region of the 04-046 antibody, and the nucleotide sequence consisting of the nucleotides at positions 427 to 1425 encodes the heavy chain constant region of the 04-046 antibody. The nucleotide sequence encoding the aforementioned variable region has a polynucleotide consisting of the nucleotide sequence at nucleotide positions 133 to 162 encoding CDRH1, a polynucleotide consisting of the nucleotide sequence at nucleotide positions 205 to 234 encoding CDRH2, and a polynucleotide consisting of the nucleotide sequence at nucleotide positions 352 to 393 encoding CDRH3, in SEQ ID NO: 32. The nucleotide sequence of the heavy chain variable region of the 04-046 antibody is also shown in SEQ ID NO: 33 in the sequence listing. Furthermore, the sequence of SEQ ID NO: 32 is shown in FIG. 1.

The light chain amino acid sequence of the 04-046 antibody is encoded by the nucleotide sequence shown in SEQ ID NO: 34 in the sequence listing. In the nucleotide sequence shown in SEQ ID NO: 34 in the sequence listing, the nucleotide sequence consisting of the nucleotides at positions 1 to 60 encodes a signal sequence, the nucleotide sequence consisting of the nucleotides at positions 61 to 384 encodes the light chain variable region of the 04-046 antibody, and the nucleotide sequence consisting of the nucleotides at positions 385 to 699 encodes the light chain constant region of the 04-046 antibody. The nucleotide sequence encoding the aforementioned variable region has a polynucleotide consisting of the nucleotide sequence at nucleotide positions 127 to 159 encoding CDRL1, a polynucleotide consisting of the nucleotide sequence at nucleotide positions 205 to 225 encoding CDRL2, and a polynucleotide consisting of the nucleotide sequence at nucleotide positions 322 to 348 encoding CDRL3, in SEQ ID NO: 34. The nucleotide sequence of the light chain variable region of the 04-046 antibody is also shown in SEQ ID NO: 35 in the sequence listing. Furthermore, the sequence of SEQ ID NO: 34 is shown in FIG. 2.

The heavy chain amino acid sequence of the 04-079 antibody is encoded by the nucleotide sequence shown in SEQ ID NO: 36 in the sequence listing. In the nucleotide sequence shown in SEQ ID NO: 36 in the sequence listing, the nucleotide sequence consisting of the nucleotides at positions 1 to 57 encodes a signal sequence, the nucleotide sequence consisting of the nucleotides at positions 58 to 426 encodes the heavy chain variable region of the 04-079 antibody, and the nucleotide sequence consisting of the nucleotides at positions 427 to 1425 encodes the heavy chain constant region of the 04-079 antibody. The nucleotide sequence encoding the aforementioned variable region has a polynucleotide consisting of the nucleotide sequence at nucleotide positions 133 to 162 encoding CDRH1, a polynucleotide consisting of the nucleotide sequence at nucleotide positions 205 to 234 encoding CDRH2, and a polynucleotide consisting of the nucleotide sequence at nucleotide positions 352 to 393 encoding CDRH3, in SEQ ID NO: 36. The nucleotide sequence of the heavy chain variable region of the 04-079 antibody is also shown in SEQ ID NO: 37 in the sequence listing. Furthermore, the sequence of SEQ ID NO: 36 is shown in FIG. 3.

The light chain amino acid sequence of the 04-079 antibody is encoded by the nucleotide sequence shown in SEQ ID NO: 38 in the sequence listing. In the nucleotide sequence shown in SEQ ID NO: 38 in the sequence listing, the nucleotide sequence consisting of the nucleotides at positions 1 to 60 encodes a signal sequence, the nucleotide sequence consisting of the nucleotides at positions 61 to 384 encodes the light chain variable region of the 04-079 antibody, and the nucleotide sequence consisting of the nucleotides at positions 385 to 699 encodes the light chain constant region of the 04-079 antibody. The nucleotide sequence encoding the aforementioned variable region has a polynucleotide consisting of the nucleotide sequence at nucleotide positions 127 to 159 encoding CDRL1, a polynucleotide consisting of the nucleotide sequence at nucleotide positions 205 to 225 encoding CDRL2, and a polynucleotide consisting of the nucleotide sequence at nucleotide positions 322 to 348 encoding CDRL3, in SEQ ID NO: 38. The nucleotide sequence of the light chain variable region of the 04-079 antibody is also shown in SEQ ID NO: 39 in the sequence listing. Furthermore, the sequence of SEQ ID NO: 38 is shown in FIG. 4.

The heavy chain amino acid sequence of the 04-126 antibody is encoded by the nucleotide sequence shown in SEQ ID NO: 40 in the sequence listing. In the nucleotide sequence shown in SEQ ID NO: 40 in the sequence listing, the nucleotide sequence consisting of the nucleotides at positions 1 to 57 encodes a signal sequence, the nucleotide sequence consisting of the nucleotides at positions 58 to 426 encodes the heavy chain variable region of the 04-126 antibody, and the nucleotide sequence consisting of the nucleotides at positions 427 to 1425 encodes the heavy chain constant region of the 04-126 antibody. The nucleotide sequence encoding the aforementioned variable region has a polynucleotide consisting of the nucleotide sequence at nucleotide positions 133 to 162 encoding CDRH1, a polynucleotide consisting of the nucleotide sequence at nucleotide positions 205 to 234 encoding CDRH2, and a polynucleotide consisting of the nucleotide sequence at nucleotide positions 352 to 393 encoding CDRH3, in SEQ ID NO: 40. The nucleotide sequence of the heavy chain variable region of the 04-126 antibody is also shown in SEQ ID NO: 41 in the sequence listing. Furthermore, the sequence of SEQ ID NO: 40 is shown in FIG. 5.

The light chain amino acid sequence of the 04-126 antibody is encoded by the nucleotide sequence shown in SEQ ID NO: 42 in the sequence listing. In the nucleotide sequence shown in SEQ ID NO: 42 in the sequence listing, the nucleotide sequence consisting of the nucleotides at positions 1 to 60 encodes a signal sequence, the nucleotide sequence consisting of the nucleotides at positions 61 to 384 encodes the light chain variable region of the 04-126 antibody, and the nucleotide sequence consisting of the nucleotides at positions 385 to 699 encodes the light chain constant region of the 04-126 antibody. The nucleotide sequence encoding the aforementioned variable region has a polynucleotide consisting of the nucleotide sequence at nucleotide positions 127 to 159 encoding CDRL1, a polynucleotide consisting of the nucleotide sequence at nucleotide positions 205 to 225 encoding CDRL2, and a polynucleotide consisting of the nucleotide sequence at nucleotide positions 322 to 348 encoding CDRL3, in SEQ ID NO: 42. The nucleotide sequence of the light chain variable region of the 04-126 antibody is also shown in SEQ ID NO: 43 in the sequence listing. Furthermore, the sequence of SEQ ID NO: 42 is shown in FIG. 6.

Furthermore, also in the case where the steps (a) to (h) in the above "(2) Production of anti-GPR20 monoclonal antibody" are carried out again to obtain a monoclonal antibody separately and in the case where a monoclonal antibody is obtained separately by other methods, an antibody having internalization activity equivalent to that of the 04-046 antibody, the 04-079 antibody or the 04-126 antibody can be obtained. One example of such an antibody can include an antibody binding to the same epitope to which the 04-046 antibody, the 04-079 antibody or the 04-126 antibody binds. If a newly prepared monoclonal antibody binds to a partial peptide or a partial three-dimensional structure to which the 04-046 antibody, the 04-079 antibody or the 04-126 antibody binds, it can be determined that the monoclonal antibody binds to the same epitope to which the 04-046 antibody, the 04-079 antibody or the 04-126 antibody binds.

Moreover, by confirming that the monoclonal antibody competes with the 04-046 antibody, the 04-079 antibody or the 04-126 antibody in the binding of the antibody to GPR20 (i.e., the monoclonal antibody interferes with the binding of the 04-046 antibody, the 04-079 antibody or the 04-126 antibody to GPR20), it can be determined that the monoclonal antibody binds to the same epitope to which the anti-GPR20 antibody binds, even if the specific sequence or structure of the epitope has not been determined. When it is confirmed that the monoclonal antibody binds to the same epitope to which the 04-046 antibody, the 04-079 antibody or the 04-126 antibody binds, then it is strongly expected that the monoclonal antibody should have antigen-binding ability, biological activity and/or internalization activity equivalent to that of the 04-046 antibody, the 04-079 antibody or the 04-126 antibody.

(3) Other Antibodies

The antibody of the present invention also includes genetically recombinant antibodies that have been artificially modified for the purpose of reducing heterogenetic antigenicity to humans, such as a chimeric antibody, a humanized antibody and a human antibody, as well as the above-described monoclonal antibody against GPR20. These antibodies can be produced by known methods.

Example of the chimeric antibody can include antibodies in which a variable region and a constant region are heterologous to each other, such as a chimeric antibody formed by conjugating the variable region of a mouse- or rat-derived antibody to a human-derived constant region (see Proc. Natl. Acad. Sci. U.S.A., 81, 6851-6855, (1984)).

The chimeric antibody derived from the rat anti-human GPR20 antibody 04-046 antibody is an antibody consisting of a heavy chain comprising a heavy chain variable region consisting of the amino acid sequence shown in SEQ ID NO: 3, and a light chain comprising a light chain variable region shown in SEQ ID NO: 8, and this chimeric antibody may have any given human-derived constant region.

The chimeric antibody derived from the rat anti-human GPR20 antibody 04-079 antibody is an antibody consisting of a heavy chain comprising a heavy chain variable region consisting of the amino acid sequence shown in SEQ ID NO: 13, and a light chain comprising a light chain variable region shown in SEQ ID NO: 18, and this chimeric antibody may have any given human-derived constant region.

The chimeric antibody derived from the rat anti-human GPR20 antibody 04-126 antibody is an antibody consisting of a heavy chain comprising a heavy chain variable region consisting of the amino acid sequence shown in SEQ ID NO: 23, and a light chain comprising a light chain variable region shown in SEQ ID NO: 28, and this chimeric antibody may have any given human-derived constant region.

Specific examples of the chimeric antibody derived from the rat anti-human GPR20 antibody 04-046 antibody can include chimeric antibody 04-046Ch (hereinafter, also referred to as "04-046Ch") derived from the rat anti-human GPR20 antibody 04-046 antibody. The amino acid sequence of the 04-046Ch antibody can be an antibody consisting of a heavy chain having an amino acid sequence consisting of the amino acid residues at positions 20 to 472 of SEQ ID NO: 44 in the sequence listing, and a light chain having an amino acid sequence consisting of positions 21 to 233 of SEQ ID NO: 45 in the sequence listing. It is to be noted that, in the heavy chain sequence shown in SEQ ID NO: 44 in the sequence listing, the amino acid sequence consisting of the amino acid residues at positions 1 to 19 is a signal sequence, the amino acid sequence consisting of the amino acid residues at positions 20 to 142 is a variable region, and the amino acid sequence consisting of the residues at positions 143 to 472 is a constant region. The sequence of SEQ ID NO: 44 is shown in FIG. 7. Furthermore, in the light chain sequence shown in SEQ ID NO: 45 in the sequence listing, the amino acid sequence consisting of the amino acid residues at positions 1 to 20 is a signal sequence, the amino acid sequence consisting of the amino acid residues at positions 21 to 128 is a variable region, and the amino acid sequence consisting of the amino acid residues at positions 129 to 233 is a constant region. The sequence of SEQ ID NO: 45 is shown in FIG. 8.

The heavy chain amino acid sequence of the 04-046Ch antibody is encoded by the nucleotide sequence shown in SEQ ID NO: 46 in the sequence listing. The nucleotide sequence consisting of the nucleotides at positions 1 to 57 in the nucleotide sequence shown in SEQ ID NO: 46 in the sequence listing encodes the signal sequence of the 04-046Ch antibody. The nucleotide sequence consisting of the nucleotides at positions 58 to 426 in the nucleotide sequence shown in SEQ ID NO: 46 in the sequence listing encodes the heavy chain variable region sequence of the 04-046Ch antibody. The nucleotide sequence consisting of the nucleotides at positions 427 to 1416 in the nucleotide sequence shown in SEQ ID NO: 46 in the sequence listing encodes the heavy chain constant region of the 04-046Ch antibody. The sequence of SEQ ID NO: 46 is shown in FIG. 7. The light chain amino acid sequence of the 04-046Ch antibody is encoded by the nucleotide sequence shown in SEQ ID NO: 47 in the sequence listing. The nucleotide sequence consisting of the nucleotides at positions 1 to 60 in the nucleotide sequence shown in SEQ ID NO: 47 in the sequence listing encodes the signal sequence of the 04-046Ch antibody. The nucleotide sequence consisting of the nucleotides at positions 61 to 384 in the nucleotide sequence shown in SEQ ID NO: 47 in the sequence listing encodes the light chain variable region sequence of the 04-046Ch antibody. The nucleotide sequence consisting of the nucleotides at positions 385 to 699 in the nucleotide sequence shown in SEQ ID NO: 47 in the sequence listing encodes the light chain constant region of the 04-046Ch antibody. The sequence of SEQ ID NO: 47 is shown in FIG. 8.

Examples of the humanized antibody can include an antibody formed by incorporating only complementarity determining regions (CDRs) into a human-derived antibody (see Nature (1986) 321, p. 522-525), an antibody formed by transplanting the amino acid residues in some frameworks, as well as CDR sequences, into a human antibody according to a CDR grafting method (International Publication No. WO90/07861), and an antibody formed by modifying the amino acid sequences of some CDRs while maintaining antigen-binding ability.

However, the humanized antibody derived from the 04-046 antibody, 04-079, or the 04-126 antibody is not limited to a specific humanized antibody as long as it retains all 6 CDR sequences of the 04-046 antibody, the 04-079 antibody or the 04-126 antibody and has internalization activity. Moreover, this humanized antibody is not limited to a specific humanized antibody as long as it has internalization activity while the amino acid sequences of some CDRs of the 04-046 antibody, the 04-079 antibody or the 04-126 antibody are modified.

Concrete examples of the humanized antibody of the rat antibody 04-046 can include any given combination of: a heavy chain comprising a heavy chain variable region consisting of any one of (1) an amino acid sequence consisting of the amino acid residues at positions 20 to 142 in SEQ ID NO: 48, 50, 52, 54 or 56 in the sequence listing, (2) an amino acid sequence having a homology of at least 95% or more to the above-described amino acid sequence (1), and (3) an amino acid sequence comprising a deletion, substitution or addition of one or several amino acids in the above-described amino acid sequence (1); and a light chain comprising a light chain variable region consisting of any one of (4) an amino acid sequence consisting of the amino acid residues at positions 21 to 129 in SEQ ID NO: 58, 60, 62 or 64, (5) an amino acid sequence having a homology of at least 95% or more to the above-described amino acid sequence (4), and (6) an amino acid sequence comprising a deletion, substitution or addition of one or several amino acids in the above-described amino acid sequence (4).

Alternatively, an antibody having a humanized heavy chain or light chain and the other chain derived from a rat antibody or a chimeric antibody can also be used. Examples of such an antibody can include any given combination of: a heavy chain consisting of any one of (1) an amino acid sequence consisting of the amino acid residues at positions 20 to 472 in SEQ ID NO: 44 in the sequence listing, (2) an amino acid sequence having a homology of at least 95% or more to the above-described amino acid sequence (1), and (3) an amino acid sequence comprising a deletion, substitution or addition of one or several amino acids in the above-described amino acid sequence (1); and a light chain comprising a light chain variable region consisting of any one of (4) an amino acid sequence consisting of the amino acid residues at positions 21 to 129 in SEQ ID NO: 58, 60, 62 or 64, (5) an amino acid sequence having a homology of at least 95% or more to the above-described amino acid sequence (4), and (6) an amino acid sequence comprising a deletion, substitution or addition of one or several amino acids in the above-described amino acid sequence (4). Other examples of such an antibody can include any given combination of: a heavy chain comprising a heavy chain variable region consisting of any one of (1) an amino acid sequence consisting of the amino acid residues at positions 20 to 142 in SEQ ID NO: 48, 50, 52, 54 or 56 in the sequence listing, (2) an amino acid sequence having a homology of at least 95% or more to the above-described amino acid sequence (1), and (3) an amino acid sequence comprising a deletion, substitution or addition of one or several amino acids in the above-described amino acid sequence (1); and a light chain comprising a light chain variable region consisting of any one of (4) an amino acid sequence consisting of the amino acid residues at positions 21 to 233 in SEQ ID NO: 45 in the sequence listing, (5) an amino acid sequence having a homology of at least 95% or more to the above-described amino acid sequence (4), and (6) an amino acid sequence comprising a deletion, substitution or addition of one or several amino acids in the above-described amino acid sequence (4). Further alternative examples thereof can include an antibody consisting of any combination of a heavy chain and a light chain selected from the following combinations (7) to (10): (7) a heavy chain consisting of the amino acid sequence at amino acid positions 20 to 472 in SEQ ID NO: 44, and a light chain consisting of the amino acid sequence at amino acid positions 21 to 234 in SEQ ID NO: 58, (8) a heavy chain consisting of the amino acid sequence at amino acid positions 20 to 472 in SEQ ID NO: 44, and a light chain consisting of the amino acid sequence at amino acid positions 21 to 234 in SEQ ID NO: 60, (9) a heavy chain consisting of the amino acid sequence at amino acid positions 20 to 472 in SEQ ID NO: 44, and a light chain consisting of the amino acid sequence at amino acid positions 21 to 234 in SEQ ID NO: 62, and (10) a heavy chain consisting of the amino acid sequence at amino acid positions 20 to 472 in SEQ ID NO: 44, and a light chain consisting of the amino acid sequence at amino acid positions 21 to 234 in SEQ ID NO: 64.

In SEQ ID NO: 48, the sequence consisting of the amino acid residues at positions 45 to 54 (GYTFTSYYIS) corresponds to CDRH1, the sequence consisting of the amino acid residues at positions 69 to 78 (FINPGSGHTN) corresponds to CDRH2, and the sequence consisting of the amino acid residues at positions 118 to 131 (GAGGFLRIITKFDY) corresponds to CDRH3. In SEQ ID NO: 50, the sequence consisting of the amino acid residues at positions 45 to 54 (GYTFTSYYIS) corresponds to CDRH1, the sequence consisting of the amino acid residues at positions 69 to 78 (FINPGSGHTN) corresponds to CDRH2, and the sequence consisting of the amino acid residues at positions 118 to 131 (GAGGFLRIITKFDY) corresponds to CDRH3. In SEQ ID NO: 52, the sequence consisting of the amino acid residues at positions 45 to 54 (GYTFTSYYIS) corresponds to CDRH1, the sequence consisting of the amino acid residues at positions 69 to 78 (FINPGSGHTN) corresponds to CDRH2, and the sequence consisting of the amino acid residues at positions 118 to 131 (GAGGFLRIITKFDY) corresponds to CDRH3. In SEQ ID NO: 54, the sequence consisting of the amino acid residues at positions 45 to 54 (GYTFTSYYIS) corresponds to CDRH1, the sequence consisting of the amino acid residues at positions 69 to 78 (FINPGSGHTN) corresponds to CDRH2, and the sequence consisting of the amino acid residues at positions 118 to 131 (GAGGFLRIITKFDY) corresponds to CDRH3. In SEQ ID NO: 56, the sequence consisting of the amino acid residues at positions 45 to 54 (GYTFTSYYIS) corresponds to CDRH1, the sequence consisting of the amino acid residues at positions 69 to 78 (FINPGSGHTN) corresponds to CDRH2, and the sequence consisting of the amino acid residues at positions 118 to 131 (GAGGFLRIITKFDY) corresponds to CDRH3.

In SEQ ID NO: 58, the sequence consisting of the amino acid residues at positions 44 to 54 (RASKSVSTYIH) corresponds to CDRL1, the sequence consisting of the amino acid residues at positions 70 to 76 (SASNLES) corresponds to CDRL2, and the sequence consisting of the amino acid residues at amino acid positions 109 to 117 (QQINELPYT) corresponds to CDRL3. In SEQ ID NO: 60, the sequence consisting of the amino acid residues at positions 44 to 54 (RASKSVSTYIH) corresponds to CDRL1, the sequence consisting of the amino acid residues at positions 70 to 76 (SASNLES) corresponds to CDRL2, and the sequence consisting of the amino acid residues at amino acid positions 109 to 117 (QQINELPYT) corresponds to CDRL3. In SEQ ID NO: 62, the sequence consisting of the amino acid residues at positions 44 to 54 (RASKSVSTYIH) corresponds to CDRL1, the sequence consisting of the amino acid residues at positions 70 to 76 (SASDRES) corresponds to CDRL2, and the sequence consisting of the amino acid residues at amino acid positions 109 to 117 (QQINELPYT) corresponds to CDRL3. In SEQ ID NO: 64, the sequence consisting of the amino acid residues at positions 44 to 54 (RASKSVSTYIH) corresponds to CDRL1, the sequence consisting of the amino acid residues at positions 70 to 76 (SAGNLES) corresponds to CDRL2, and the sequence consisting of the amino acid residues at amino acid positions 109 to 117 (QQINELPYT) corresponds to CDRL3.

It is to be noted that the term "several" is used in the present description to mean 1 to 10, 1 to 9, 1 to 8, 1 to 7, 1 to 6, 1 to 5, 1 to 4, 1 to 3, or 1 or 2.

The amino acid substitution in the present description is preferably a conservative amino acid substitution. The conservative amino acid substitution is a substitution occurring within an amino acid group associated with amino acid side chains. Preferred amino acid groups are the following: acidic group=aspartic acid and glutamic acid; basic group=lysine, arginine, and histidine; non-polar group=alanine, valine, leucine, isoleucine, proline, phenylalanine, methionine, and tryptophan; and uncharged polar family=glycine, asparagine, glutamine, cysteine, serine, threonine, and tyrosine. Other preferred amino acid groups are the following: aliphatic hydroxy group=serine and threonine; amide-containing group=asparagine and glutamine; aliphatic group=alanine, valine, leucine and isoleucine; and aromatic group=phenylalanine, tryptophan and tyrosine. Such amino acid substitution is preferably carried out without impairing the properties of a substance having the original amino acid sequence.

Examples of the antibody having a preferred combination of the above-described heavy chains and light chains can include an antibody consisting of a heavy chain having a variable region consisting of the amino acid sequence at amino acid positions 20 to 142 in SEQ ID NO: 48, and a light chain having a variable region consisting of the amino acid sequence at amino acid positions 21 to 129 in SEQ ID NO: 64, an antibody consisting of a heavy chain having a variable region consisting of the amino acid sequence at amino acid positions 20 to 142 in SEQ ID NO: 52, and a light chain having a variable region consisting of the amino acid sequence at amino acid positions 21 to 129 in SEQ ID NO: 60, an antibody consisting of a heavy chain having a variable region consisting of the amino acid sequence at amino acid positions 20 to 142 in SEQ ID NO: 54, and a light chain having a variable region consisting of the amino acid sequence at amino acid positions 21 to 129 in SEQ ID NO: 58, an antibody consisting of a heavy chain having a variable region consisting of the amino acid sequence at amino acid positions 20 to 142 in SEQ ID NO: 56, and a light chain having a variable region consisting of the amino acid sequence at amino acid positions 21 to 129 in SEQ ID NO: 58, an antibody consisting of a heavy chain having a variable region consisting of the amino acid sequence at amino acid positions 20 to 142 in SEQ ID NO: 56, and a light chain having a variable region consisting of the amino acid sequence at amino acid positions 21 to 129 in SEQ ID NO: 62, and an antibody consisting of a heavy chain having a variable region consisting of the amino acid sequence at amino acid positions 20 to 142 in SEQ ID NO: 50, and a light chain having a variable region consisting of the amino acid sequence at amino acid positions 21 to 129 in SEQ ID NO: 64.

Examples of the antibody having a more preferred combination can include an antibody consisting of a heavy chain consisting of the amino acid sequence at amino acid positions 20 to 472 in SEQ ID NO: 48, and a light chain consisting of the amino acid sequence at amino acid positions 21 to 234 in SEQ ID NO: 64, an antibody consisting of a heavy chain consisting of the amino acid sequence at amino acid positions 20 to 472 in SEQ ID NO: 52, and a light chain consisting of the amino acid sequence at amino acid positions 21 to 234 in SEQ ID NO: 60, an antibody consisting of a heavy chain consisting of the amino acid sequence at amino acid positions 20 to 472 in SEQ ID NO: 54, and a light chain consisting of the amino acid sequence at amino acid positions 21 to 234 in SEQ ID NO: 58, an antibody consisting of a heavy chain consisting of the amino acid sequence at amino acid positions 20 to 472 in SEQ ID NO: 56, and a light chain consisting of the amino acid sequence at amino acid positions 21 to 234 in SEQ ID NO: 58, an antibody consisting of a heavy chain consisting of the amino acid sequence at amino acid positions 20 to 472 in SEQ ID NO: 56, and a light chain consisting of the amino acid sequence at amino acid positions 21 to 234 in SEQ ID NO: 62, and an antibody consisting of a heavy chain consisting of the amino acid sequence at amino acid positions 20 to 472 in SEQ ID NO: 50, and a light chain consisting of the amino acid sequence at amino acid positions 21 to 234 in SEQ ID NO: 64.

By combining together sequences showing a high homology to the above-described heavy chain amino acid sequences and light chain amino acid sequences, it is possible to select an antibody having a biological activity equivalent to that of each of the above-described antibodies. Such a homology is a homology of generally 80% or more, preferably 90% or more, more preferably 95% or more, and most preferably 99% or more. Moreover, also by combining with one another, amino acid sequences comprising a substitution, deletion or addition of one or several amino acid residues with respect to the amino acid sequence of a heavy chain or a light chain, it is possible to select an antibody having a biological activity equivalent to that of each of the above-described antibodies.

The homology between two types of amino acid sequences can be determined using default parameters of Blast algorithm version 2.2.2 (Altschul, Stephen F., Thomas L. Madden, Alejandro A. Schaffer, Jinghui Zhang, Zheng Zhang, Webb Miller, and David J. Lipman (1997), "Gapped BLAST and PSI-BLAST: a new generation of protein database search programs", Nucleic Acids Res. 25: 3389-3402). The Blast algorithm can also be used by accessing www.ncbi.nlm.nih.gov/blast through the internet.

It is to be noted that, in the heavy chain amino acid sequence shown in SEQ ID NO: 48, 50, 52, 54 or 56 in the sequence listing, the amino acid sequence consisting of the amino acid residues at positions 1 to 19 is a signal sequence, the amino acid sequence consisting of the amino acid residues at positions 20 to 142 is a variable region, and the amino acid sequence consisting of the amino acid residues at positions 143 to 472 is a constant region. The sequence of SEQ ID NO: 48 is shown in FIG. 9, the sequence of SEQ ID NO: 50 is shown in FIG. 10, the sequence of SEQ ID NO: 52 is shown in FIG. 11, the sequence of SEQ ID NO: 54 is shown in FIG. 12, and the sequence of SEQ ID NO: 56 is shown in FIG. 13.

Furthermore, in the light chain amino acid sequence shown in SEQ ID NO: 58, 60, 62 or 64 in the sequence listing, the amino acid sequence consisting of the amino acid residues at positions 1 to 20 is a signal sequence, the amino acid sequence consisting of the amino acid residues at positions 21 to 129 is a variable region, and the amino acid sequence consisting of the amino acid residues at positions 130 to 234 is a constant region. The sequence of SEQ ID NO: 58 is shown in FIG. 14, the sequence of SEQ ID NO: 60 is shown in FIG. 15, the sequence of SEQ ID NO: 62 is shown in FIG. 16, and the sequence of SEQ ID NO: 64 is shown in FIG. 17.

Further examples of the antibody of the present invention can include a human antibody binding to GPR20. The anti-GPR20 human antibody means a human antibody having only the gene sequence of an antibody derived from human chromosomes. The anti-GPR20 human antibody can be obtained by a method using a human antibody-producing mouse having a human chromosomal fragment comprising the heavy chain and light chain genes of a human antibody (see Tomizuka, K. et al., Nature Genetics (1997) 16, p. 133-143; Kuroiwa, Y. et al., Nucl. Acids Res. (1998) 26, p. 3447-3448; Yoshida, H. et al., Animal Cell Technology: Basic and Applied Aspects vol. 10, p. 69-73 (Kitagawa, Y., Matsuda, T. and Iijima, S. eds.), Kluwer Academic Publishers, 1999; Tomizuka, K. et al., Proc. Natl. Acad. Sci. USA (2000) 97, p. 722-727; etc.).

Such a human antibody-producing mouse can be specifically produced by using a genetically modified animal, the gene loci of endogenous immunoglobulin heavy chain and light chain of which have been disrupted and instead the gene loci of human immunoglobulin heavy chain and light chain have been then introduced using a yeast artificial chromosome (YAC) vector or the like, then producing a knock-out animal and a transgenic animal from such a genetically modified animal, and then breeding such animals with one another.

Otherwise, the anti-GPR20 human antibody can also be obtained by transforming eukaryotic cells with cDNA encoding each of the heavy chain and light chain of such a human antibody, or preferably with a vector comprising the cDNA, according to genetic recombination techniques, and then culturing the transformed cells producing a genetically modified human monoclonal antibody, so that the antibody can be obtained from the culture supernatant.

In this context, eukaryotic cells, and preferably, mammalian cells such as CHO cells, lymphocytes or myelomas can, for example, be used as a host.

Furthermore, a method of obtaining a phage display-derived human antibody that has been selected from a human antibody library (see Wormstone, I. M. et al., Investigative Ophthalmology & Visual Science. (2002) 43 (7), p. 2301-2308; Carmen, S. et al., Briefings in Functional Genomics and Proteomics (2002), 1 (2), p. 189-203; Siriwardena, D. et al., Ophthalmology (2002) 109 (3), p. 427-431; etc.) is also known.

For example, a phage display method, which comprises allowing the variable regions of a human antibody to express as a single chain antibody (scFv) on the surface of phages, and then selecting a phage binding to an antigen, can be applied (Nature Biotechnology (2005), 23, (9), p. 1105-1116).

By analyzing the phage gene that has been selected because of its binding ability to the antigen, DNA sequences encoding the variable regions of a human antibody binding to the antigen can be determined.

Once the DNA sequence of scFv binding to the antigen is determined, an expression vector having the aforementioned sequence is produced, and the produced expression vector is then introduced into an appropriate host and can be allowed to express therein, thereby obtaining a human antibody (International Publication Nos. WO92/01047, WO92/20791, WO93/06213, WO93/11236, WO93/19172, WO95/01438, and WO95/15388, Annu. Rev. Immunol (1994) 12, p. 433-455, Nature Biotechnology (2005) 23 (9), p. 1105-1116).

If a newly produced human antibody binds to a partial peptide or a partial three-dimensional structure to which the 04-046 antibody, the 04-079 antibody or the 04-126 antibody described in the present description binds, it can be determined that the human antibody binds to the same epitope to which the 04-046 antibody, the 04-079 antibody or the 04-126 antibody binds. Moreover, by confirming that the human antibody competes with the 04-046 antibody, the 04-079 antibody or the 04-126 antibody in the binding of the antibody to GPR20 (i.e., the human antibody interferes with the binding of the 04-046 antibody, the 04-079 antibody or the 04-126 antibody to GPR20), it can be determined that the human antibody binds to the same epitope to which the 04-046 antibody, the 04-079 antibody or the 04-126 antibody binds, even if the specific sequence or structure of the epitope has not been determined. When it is confirmed that the human antibody binds to the same epitope to which the 04-046 antibody, the 04-079 antibody or the 04-126 antibody binds, then it is strongly expected that the human antibody should have a biological activity equivalent to that of the 04-046 antibody, the 04-079 antibody or the 04-126 antibody.

The chimeric antibodies, the humanized antibodies, or the human antibodies obtained by the above-described methods are evaluated for their binding activity against the antigen according to a known method, etc., so that a preferred antibody can be selected.

One example of another indicator for comparison of the properties of antibodies can include the stability of an antibody. A differential scanning calorimetry (DSC) is an apparatus capable of promptly and exactly measuring a thermal denaturation midpoint (Tm) serving as a good indicator for the relative structural stability of a protein. By using DSC to measure Tm values and making a comparison regarding the obtained values, differences in the thermal stability can be compared. It is known that the preservation stability of an antibody has a certain correlation with the thermal stability of the antibody (Lori Burton, et al., Pharmaceutical Development and Technology (2007) 12, p. 265-273), and thus, a preferred antibody can be selected using thermal stability as an indicator. Other examples of the indicator for selection of an antibody can include high yield in suitable host cells and low agglutination in an aqueous solution. For example, since an antibody with the highest yield does not always exhibit the highest thermal stability, it is necessary to select an antibody most suitable for administration to a human by comprehensively determining it based on the aforementioned indicators.

The antibody of the present invention also includes a modification of an antibody. The modification is used to mean the antibody of the present invention, which is chemically or biologically modified. Examples of such a chemical modification include the binding of a chemical moiety to an amino acid skeleton, and the chemical modification of an N-linked or O-linked carbohydrate chain. Examples of such a biological modification include antibodies which have undergone a posttranslational modification (e.g., N-linked or O-linked glycosylation, N-terminal or C-terminal processing, deamidation, isomerization of aspartic acid, and oxidation of methionine), and antibodies, to the N-terminus of which a methionine residue is added as a result of having been allowed to be expressed using prokaryote host cells. In addition, such a modification is meant to also include labeled antibodies for enabling detection or isolation of the antibody of the present invention or an antigen, for example, an enzymatically labeled antibody, a fluorescently labeled antibody, and an affinity-labeled antibody. Such a modification of the antibody of the present invention is useful for the improvement of the stability and retention in blood of an antibody, a reduction in antigenicity, detection or isolation of an antibody or an antigen, etc.

Moreover, by regulating a sugar chain modification (glycosylation, de-fucosylation, etc.) that binds to the antibody of the present invention, antibody-dependent cellular cytotoxic activity can be enhanced. As techniques of regulating the sugar chain modification of an antibody, those described in International Publication Nos. WO1999/54342, WO2000/61739, and WO2002/31140, etc. are known, though the techniques are not limited thereto. The antibody of the present invention also includes antibodies in which the aforementioned sugar chain modification has been regulated.

Once an antibody gene is isolated, the gene can be introduced into an appropriate host to produce an antibody, using an appropriate combination of a host and an expression vector. A specific example of the antibody gene can be a combination of a gene encoding the heavy chain sequence of the antibody described in the present description and a gene encoding the light chain sequence of the antibody described therein. Upon transformation of host cells, such a heavy chain sequence gene and a light chain sequence gene may be inserted into a single expression vector, or these genes may instead each be inserted into different expression vectors.

When eukaryotic cells are used as hosts, animal cells, plant cells or eukaryotic microorganisms can be used. In particular, examples of the animal cells can include mammalian cells such as COS cells which are monkey cells (Gluzman, Y., Cell (1981) 23, p. 175-182, ATCC CRL-1650), mouse fibroblasts NIH3T3 (ATCC No. CRL-1658), a dihydrofolate reductase-deficient cell line of Chinese hamster ovary cells (CHO cells, ATCC CCL-61) (Urlaub, G. and Chasin, L. A. Proc. Natl. Acad. Sci. U.S.A. (1980) 77, p. 4126-4220), and FreeStyle 293F cells (Invitrogen Corp.).

When prokaryotic cells are used as hosts, *Escherichia coli* or *Bacillus subtilis* can be used, for example.

An antibody gene of interest is introduced into these cells for transformation, and the transformed cells are then cultured in vitro to obtain an antibody. In the aforementioned culture, there are cases where yield is different depending on the sequence of the antibody, and thus, it is possible to select an antibody, which is easily produced as a medicament, from antibodies having equivalent binding activity, using the yield as an indicator. Accordingly, the antibody of the present invention also includes an antibody obtained by the above-described method for producing an antibody, which comprises a step of culturing the transformed host cells and a step of collecting an antibody of interest or a functional fragment of the antibody from the culture obtained in the aforementioned step.

It is known that the lysine residue at the carboxyl terminus of the heavy chain of an antibody produced in cultured mammalian cells is deleted (Journal of Chromatography A, 705: 129-134 (1995)), and also, it is known that the two amino acid residues at the heavy chain carboxyl terminus, glycine and lysine, are deleted, and that the proline residue positioned at the carboxyl terminus is newly amidated (Analytical Biochemistry, 360: 75-83 (2007)). However, such deletion and modification of these heavy chain sequences do not have an influence on the antigen-binding activity and effector function (activation of complement, antibody-dependent cellular cytotoxicity, etc.) of an antibody. Accordingly, the antibody according to the present invention also includes an antibody that has undergone the aforementioned modification, and a functional fragment of the antibody, and specific examples of such an antibody include a deletion mutant comprising a deletion of 1 or 2 amino acids at the heavy chain carboxyl terminus, and a deletion mutant formed by amidating the aforementioned deletion mutant (e.g., a heavy chain in which the proline residue at the carboxyl-terminal site is amidated). However, deletion mutants involving a deletion at the carboxyl terminus of the heavy chain of the antibody according to the present invention are not limited to the above-described deletion mutants, as long as they retain antigen-binding activity and effector function. Two heavy chains constituting the antibody according to the present invention may be any one type of heavy chain selected from the group consisting of a full-length antibody and the above-described deletion mutants, or may be a combination of any two types selected from the aforementioned group. The ratio of individual deletion mutants can be influenced by the types of cultured mammalian cells that produce the antibody according to the present invention, and the culture conditions. Examples of the main ingredient of the antibody according to the present invention can include antibodies where one amino acid residue is deleted at each of the carboxyl termini of the two heavy chains.

Examples of the isotype of the antibody of the present invention can include IgG (IgG1, IgG2, IgG3, and IgG4). Among others, IgG1 and IgG2 are preferable.

Examples of the biological activity of an antibody can generally include antigen-binding activity, activity of being internalized into cells expressing an antigen by binding to the antigen, activity of neutralizing the activity of an antigen, activity of enhancing the activity of an antigen, antibody-dependent cellular cytotoxic (ADCC) activity, complement-dependent cytotoxic (CDC) activity, and antibody-dependent cellular phagocytosis (ADCP). The function of the antibody according to the present invention is binding activity against GPR20 and is preferably activity of being internalized into GPR20-expressing cells by binding to GPR20. Moreover, the antibody of the present invention may have ADCC activity, CDC activity and/or ADCP activity, as well as cellular internalization activity.

The obtained antibody can be purified to a homogenous state. For separation and purification of the antibody, separation and purification methods used for ordinary proteins may be used. For example, column chromatography, filtration, ultrafiltration, salting-out, dialysis, preparative polyacrylamide gel electrophoresis, and isoelectric focusing are appropriately selected and combined with one another, so that the antibody can be separated and purified (Strategies for Protein Purification and Characterization: A Laboratory Course Manual, Daniel R. Marshak et al. eds., Cold Spring Harbor Laboratory Press (1996); and Antibodies: A Laboratory Manual. Ed Harlow and David Lane, Cold Spring Harbor Laboratory (1988)), though examples of the separation and purification methods are not limited thereto.

Examples of the chromatography can include affinity chromatography, ion exchange chromatography, hydrophobic chromatography, gel filtration chromatography, reverse phase chromatography, and absorption chromatography.

These chromatographic techniques can be carried out using liquid chromatography such as HPLC or FPLC.

Examples of the column used in the affinity chromatography can include a Protein A column and a Protein G column. Examples of the column involving the use of Protein A can include Hyper D, POROS, and Sepharose F. F. (Pharmacia).

Also, using an antigen-immobilized carrier, the antibody can be purified by utilizing the binding activity of the antibody to the antigen.

3. Anti-GPR20 antibody-drug conjugate (1) Drug

The anti-GPR20 antibody obtained in the above "2. Production of anti-GPR20 antibody" can be conjugated to a drug via a linker structure moiety to prepare an anti-GPR20 antibody-drug conjugate. The drug is not particularly limited as long as it has a substituent or a partial structure that can be connected to a linker structure. The anti-GPR20 antibody-drug conjugate can be used for various purposes according to the conjugated drug. Examples of such a drug can include substances having antitumor activity, substances effective for blood diseases, substances effective for autoimmune diseases, anti-inflammatory substances, antimicrobial substances, antifungal substances, antiparasitic substances, antiviral substances, and anti-anesthetic substances.

(1)-1 Antitumor Compound

An example using an antitumor compound as a compound to be conjugated in the anti-GPR20 antibody-drug conjugate of the present invention will be described below. The antitumor compound is not particularly limited as long as the compound has an antitumor effect and has a substituent or a partial structure that can be connected to a linker structure. Upon cleavage of a part or the whole of the linker in tumor cells, the antitumor compound moiety is released so that the antitumor compound exhibits an antitumor effect. As the linker is cleaved at a connecting position with the drug, the antitumor compound is released in its original structure to exert its original antitumor effect.

The anti-GPR20 antibody obtained in the above "2. Production of anti-GPR20 antibody" can be conjugated to the antitumor compound via a linker structure moiety to prepare an anti-GPR20 antibody-drug conjugate.

As one example of the antitumor compound used in the present invention, exatecan, a camptothecin derivative ((1S,9S)-1-amino-9-ethyl-5-fluoro-2,3-dihydro-9-hydroxy-4-methyl-1H,12H-benzo[de]pyrano[3',4':6,7]indolizino[1,2-b]quinoline-10,13(9H,15H)-dione represented by the following formula) can be preferably used.

[Formula 6]

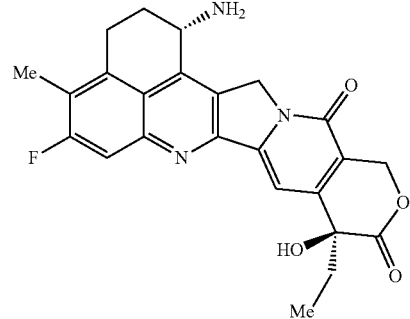

The compound can be easily obtained by, for example, a method described in U.S. Patent Publication No. US2016/0297890 or other known methods, and the amino group at position 1 can be preferably used as a connecting position to the linker structure. Further, exatecan may be released in tumor cells while a part of the linker is still attached thereto. However, the compound exerts an excellent antitumor effect even in such a state.

Since exatecan has a camptothecin structure, it is known that the equilibrium shifts to a structure with a formed lactone ring (closed ring) in an acidic aqueous medium (e.g., on the order of pH 3) whereas the equilibrium shifts to a structure with an opened lactone ring (open ring) in a basic aqueous medium (e.g., on the order of pH 10). A drug conjugate into which exatecan residues corresponding to such a closed ring structure and an open ring structure have been introduced is also expected to have an equivalent antitumor effect, and it is needless to say that any of such drug conjugates is included in the scope of the present invention.

Other examples of the antitumor compound can include antitumor compounds described in the literature (Pharmacological Reviews, 68, p. 3-19, 2016). Specific examples thereof can include doxorubicin, calicheamicin, dolastatin 10, auristatins such as monomethyl auristatin E (MMAE) and monomethyl auristatin F (MMAF), maytansinoids such as DM1 and DM4, a pyrrolobenzodiazepine dimer SG2000 (SJG-136), a camptothecin derivative SN-38, duocarmycins such as CC-1065, amanitin, daunorubicin, mitomycin C, bleomycin, cyclocytidine, vincristine, vinblastine, methotrexate, platinum-based antitumor agents (cisplatin and derivatives thereof), and Taxol and derivatives thereof.

In the antibody-drug conjugate, the number of conjugated drug molecules per antibody molecule is a key factor having an influence on the efficacy and safety thereof. The production of the antibody-drug conjugate is carried out by specifying reaction conditions such as the amounts of starting materials and reagents used for reaction, so as to attain a constant number of conjugated drug molecules. Unlike the chemical reaction of a low-molecular-weight compound, a mixture containing different numbers of conjugated drug molecules is usually obtained. The number of conjugated drug molecules per antibody molecule is defined and indicated as an average value, i.e., the average number of conjugated drug molecules. Unless otherwise specified, i.e., except in the case of representing an antibody-drug conjugate having a specific number of conjugated drug molecules that is included in an antibody-drug conjugate mixture having different numbers of conjugated drug molecules, the number of conjugated drug molecules according to the present invention also means an average value as a rule. The number of exatecan molecules conjugated to an antibody molecule is controllable, and as an average number of conjugated drug molecules per antibody, approximately 1 to 10 exatecan molecules can be conjugated. The number of exatecan molecules is preferably 2 to 8, more preferably 5 to 8, further preferably 7 to 8, still further preferably 8. It is to be noted that a person skilled in the art can design a reaction for conjugating a required number of drug molecules to an antibody molecule based on the description of Examples of the present application, and can obtain an antibody-drug conjugate with a controlled number of conjugated exatecan molecules.

(2) Linker Structure

The linker structure which conjugates the drug to the anti-GPR20 antibody in the anti-GPR20 antibody-drug conjugate of the present invention will be described.

In the antibody-drug conjugate of the present application, the linker structure which conjugates the anti-GPR20 antibody to the drug is not particularly limited as long as the resulting antibody-drug conjugate can be used. The linker structure can be appropriately selected and used according to the purpose of use. One example of the linker structure can include a linker described in a known literature (Pharmacol Rev 68: 3-19, January 2016, Protein Cell DOI 10.1007/s13238-016-0323-0, etc.). Further specific examples thereof can include VC (valine-citrulline), MC (maleimidocaproyl), SMCC (succinimidyl 4-(N-maleimidomethyl) cyclohexane-1-carboxylate), SPP (N-succinimidyl 4-(2-pyridyldithio) pentanoate, SS (disulfide), SPDB (N-succinimidyl 4-(2-pyridyldithio)butyrate, SS/hydrazone, hydrazone and carbonate.

Another example of the linker structure can include a linker structure described in U.S. Patent Publication No. US2016/0297890 (as one example, those described in the paragraphs [0260] to [0289]). Any linker structure given below can be preferably used. It is to be noted that the left terminus of the structure is a connecting position to the antibody, and the right terminus thereof is a connecting position to the drug. Furthermore, GGFG in the linker structures given below represents an amino acid sequence consisting of glycine-glycine-phenylalanine-glycine linked through peptide bonds.

-(Succinimid-3-yl-N)—$CH_2CH_2$—C(=O)-GGFG-NH—$CH_2CH_2CH_2$—C(=O)—,

-(Succinimid-3-yl-N)—$CH_2CH_2CH_2CH_2CH_2$—C(=O)-GGFG-NH—$CH_2CH_2CH_2$—C(=O)—, -(Succinimid-3-yl-N)—$CH_2CH_2CH_2CH_2CH_2$—C(=O)-GGFG-NH—$CH_2$—O—$CH_2$—C(=O)—, -(Succinimid-3-yl-N)—$CH_2CH_2CH_2CH_2CH_2$—C(=O)-GGFG-NH—$CH_2CH_2$—O—$CH_2$—C(=O)—, -(Succinimid-3-yl-N)—$CH_2CH_2$—C(=O)—NH—$CH_2CH_2O$—$CH_2CH_2O$—$CH_2CH_2$—C(=O)-GGFG-NH—$CH_2CH_2CH_2$—C(=O)—, and -(Succinimid-3-yl-N)—$CH_2CH_2$—C(=O)—NH—$CH_2CH_2O$—$CH_2CH_2O$—$CH_2CH_2O$—$CH_2CH_2O$—$CH_2CH_2$—C(=O)-GGFG-NH—$CH_2CH_2CH_2$—C(=O)—.

More preferred are the following:

-(Succinimid-3-yl-N)—$CH_2CH_2CH_2CH_2CH_2$—C(=O)-GGFG-NH—$CH_2$—O—$CH_2$—C(=O)—, -(Succinimid-3-yl-N)—$CH_2CH_2CH_2CH_2CH_2$—C(=O)-GGFG-NH—$CH_2CH_2$—O—$CH_2$—C(=O)—, and -(Succinimid-3-yl-N)—$CH_2CH_2$—C(=O)—NH—$CH_2CH_2O$—$CH_2CH_2O$—$CH_2CH_2$—C(=O)-GGFG-NH—$CH_2CH_2CH_2$—C(=O)—.

Still more preferred are the following:

-(Succinimid-3-yl-N)—$CH_2CH_2CH_2CH_2CH_2$—C(=O)-GGFG-NH—$CH_2$—O—$CH_2$—C(=O)—, and -(Succinimid-3-yl-N)—$CH_2CH_2$—C(=O)—NH—$CH_2CH_2O$—$CH_2CH_2O$—$CH_2CH_2$—C(=O)-GGFG-NH—$CH_2CH_2CH_2$—C(=O)—.

The antibody is connected to the terminus of -(Succinimid-3-yl-N) (e.g., a terminus opposite (left terminus) to the terminus to which (—$CH_2CH_2CH_2CH_2CH_2$— is connected in "-(Succinimid-3-yl-N)—$CH_2CH_2CH_2CH_2CH_2$—C(=O)-GGFG-NH—$CH_2$—O—$CH_2$—C(=O)—") is connected), and the antitumor compound is connected to a terminus opposite to the terminus to which -(Succinimid-3-yl-N) is connected (the carbonyl group of $CH_2$—O—$CH_2$—C(=O)— at the right terminus in the above-described example. "-(Succinimid-3-yl-N)—" has a structure represented by the following formula:

[Formula 7]

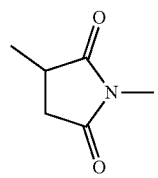

Position 3 of this partial structure is the connecting position to the anti-GPR20 antibody. This connection to the antibody at position 3 is characterized by forming a thioether bond. The nitrogen atom at position 1 of this structure moiety is connected to the carbon atom of methylene which is present within the linker including the structure.

In the antibody-drug conjugate of the present invention having exatecan as the drug, a drug-linker structure moiety having any structure given below is preferred for the conjugation to the antibody. For these drug-linker structure moieties, the average conjugated number per antibody may be 1 to 10 and is preferably 2 to 8, more preferably 5 to 8, further preferably 7 to 8, and still further preferably 8.

-(Succinimid-3-yl-N)—CH$_2$CH$_2$—C(=O)-GGFG-NH—CH$_2$CH$_2$CH$_2$—C(=O)—(NH-DX), -(Succinimid-3-yl-N)—CH$_2$CH$_2$CH$_2$CH$_2$CH$_2$—C(=O)-GGFG-NH—CH$_2$CH$_2$CH$_2$—C(=O)—(NH-DX), -(Succinimid-3-yl-N)—CH$_2$CH$_2$CH$_2$CH$_2$CH$_2$—C(=O)-GGFG-NH—CH$_2$—O—CH$_2$—C(=O)—(NH-DX), -(Succinimid-3-yl-N)—CH$_2$CH$_2$CH$_2$CH$_2$CH$_2$—C(=O)-GGFG-NH—CH$_2$CH$_2$—O—CH$_2$—C(=O)—(NH-DX), -(Succinimid-3-yl-N)—CH$_2$CH$_2$—C(=O)—NH—CH$_2$CH$_2$O—CH$_2$CH$_2$O—CH$_2$CH$_2$—C(=O)-GGFG-NH—CH$_2$CH$_2$CH$_2$—C(=O)—(NH-DX), and -(Succinimid-3-yl-N)—CH$_2$CH$_2$—C(=O)—NH—CH$_2$CH$_2$O—CH$_2$CH$_2$O—CH$_2$CH$_2$O—CH$_2$CH$_2$O—CH$_2$CH$_2$—C(=O)-GGFG-NH—CH$_2$CH$_2$CH$_2$—C(=O)—(NH-DX).

More preferred are the following:

-(Succinimid-3-yl-N)—CH$_2$CH$_2$CH$_2$CH$_2$CH$_2$—C(=O)-GGFG-NH—CH$_2$—O—CH$_2$—C(=O)—(NH-DX), -(Succinimid-3-yl-N)—CH$_2$CH$_2$CH$_2$CH$_2$CH$_2$—C(=O)-GGFG-NH—CH$_2$CH$_2$—O—CH$_2$—C(=O)—(NH-DX), and -(Succinimid-3-yl-N)—CH$_2$CH$_2$—C(=O)—NH—CH$_2$CH$_2$O—CH$_2$CH$_2$O—CH$_2$CH$_2$—C(=O)-GGFG-NH—CH$_2$CH$_2$CH$_2$—C(=O)—(NH-DX).

Still more preferred are the following:

-(Succinimid-3-yl-N)—CH$_2$CH$_2$CH$_2$CH$_2$CH$_2$—C(=O)-GGFG-NH—CH$_2$—O—CH$_2$—C(=O)—(NH-DX), and -(Succinimid-3-yl-N)—CH$_2$CH$_2$—C(=O)—NH—CH$_2$CH$_2$O—CH$_2$CH$_2$O—CH$_2$CH$_2$—C(=O)-GGFG-NH—CH$_2$CH$_2$CH$_2$—C(=O)—(NH-DX).

Further preferred is the following:

-(Succinimid-3-yl-N)—CH$_2$CH$_2$CH$_2$CH$_2$CH$_2$—C(=O)-GGFG-NH—CH$_2$—O—CH$_2$—C(=O)—(NH-DX)

(3) Method for Producing Antibody-Drug Conjugate

The antibody that can be used in the antibody-drug conjugate of the present invention is not particularly limited as long as it is an anti-GPR20 antibody having internalization activity or a functional fragment of the antibody, described in the above section "2. Production of anti-GPR20 antibody" and Examples.

Next, the method for producing the antibody-drug conjugate of the present invention will be described with reference to specific examples. It is to be noted that, in the description below, compound No. shown in each reaction scheme is used to represent a compound. Specifically, each compound is referred to as a "compound of the formula (1)", "compound (1)", or the like. The same holds true for the other compound Nos.

(3)-1 Production Method 1

The antibody-drug conjugate represented by the formula (1) given below in which the anti-GPR20 antibody is connected to the linker structure via thioether can be produced by reacting an antibody having a sulfhydryl group converted from a disulfide bond by the reduction of the anti-GPR20 antibody, with the compound (2) obtainable by a known method (e.g., obtainable by a method described in the patent publication literature US2016/297890 (e.g., a method described in the paragraphs [0336] to [0374])). This antibody-drug conjugate can be produced by the following method, for example.

[Formula 8]

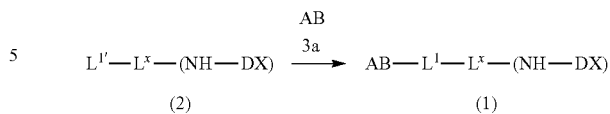

wherein AB represents an antibody with a sulfhydryl group, wherein

L$^1$ has a structure represented by -(Succinimid-3-yl-N)—, and

L$^{1'}$ represents a maleimidyl group represented by the following formula.

[Formula 9]

-L$^1$-L$^x$ has a structure represented by any of the following formulas:

-(Succinimid-3-yl-N)—CH$_2$CH$_2$—C(=O)-GGFG-NH—CH$_2$CH$_2$CH$_2$—C(=O)—,

-(Succinimid-3-yl-N)—CH$_2$CH$_2$CH$_2$CH$_2$CH$_2$—C(=O)-GGFG-NH—CH$_2$CH$_2$CH$_2$—C(=O)—, -(Succinimid-3-yl-N)—CH$_2$CH$_2$CH$_2$CH$_2$CH$_2$—C(=O)-GGFG-NH—CH$_2$—O—CH$_2$—C(=O)—, -(Succinimid-3-yl-N)—CH$_2$CH$_2$CH$_2$CH$_2$CH$_2$—C(=O)-GGFG-NH—CH$_2$CH$_2$—O—CH$_2$—C(=O)—, -(Succinimid-3-yl-N)—CH$_2$CH$_2$—C(=O)—NH—CH$_2$CH$_2$O—CH$_2$CH$_2$O—CH$_2$CH$_2$—C(=O)-GGFG-NH—CH$_2$CH$_2$CH$_2$—C(=O)—, and -(Succinimid-3-yl-N)—CH$_2$CH$_2$—C(=O)—NH—CH$_2$CH$_2$O—CH$_2$CH$_2$O—CH$_2$CH$_2$O—CH$_2$CH$_2$O—CH$_2$CH$_2$—C(=O)-GGFG-NH—CH$_2$CH$_2$CH$_2$—C(=O)—.

Among them, more preferred are the following:

-(Succinimid-3-yl-N)—CH$_2$CH$_2$CH$_2$CH$_2$CH$_2$—C(=O)-GGFG-NH—CH$_2$—O—CH$_2$—C(=O)—, -(Succinimid-3-yl-N)—CH$_2$CH$_2$CH$_2$CH$_2$CH$_2$—C(=O)-GGFG-NH—CH$_2$CH$_2$—O—CH$_2$—C(=O)—, and -(Succinimid-3-yl-N)—CH$_2$CH$_2$—C(=O)—NH—CH$_2$CH$_2$O—CH$_2$CH$_2$O—CH$_2$CH$_2$—C(=O)-GGFG-NH—CH$_2$CH$_2$CH$_2$—C(=O)—.

Further preferred are the following:

-(Succinimid-3-yl-N)—CH$_2$CH$_2$CH$_2$CH$_2$CH$_2$—C(=O)-GGFG-NH—CH$_2$—O—CH$_2$—C(=O)—, and -(Succinimid-3-yl-N)—CH$_2$CH$_2$—C(=O)—NH—CH$_2$CH$_2$O—CH$_2$CH$_2$O—CH$_2$CH$_2$—C(=O)-GGFG-NH—CH$_2$CH$_2$CH$_2$—C(=O)—.

—(NH-DX) has a structure represented by the following formula:

[Formula 10]

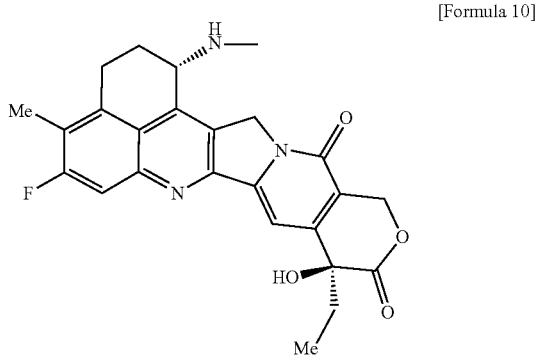 [SMILES: CC[C@@]1(O)C(=O)OCc2c1cc1n(c2=O)Cc2c-1nc1cc(F)c(C)c3c1c2[C@@H](NC)CC3]

and it represents a group that is derived by removing one hydrogen atom of the amino group at position 1 of exatecan. In the above-described reaction scheme, the compound of the formula (1) can be interpreted as having a structure in which one structure moiety from the drug to the linker terminus is connected to one antibody. However, this description is given for the sake of convenience, and there are actually many cases in which a plurality of the aforementioned structure moieties is connected to one antibody molecule. The same holds true for the explanation of the production method described below.

Specifically, the antibody-drug conjugate (1) can be produced by reacting the compound (2) obtainable by a known method (e.g., obtainable by a method described in the patent publication literature US2016/297890 (e.g., a method described in the paragraphs [0336] to [0374])), with the antibody (3a) having a sulfhydryl group.

The antibody (3a) having a sulfhydryl group can be obtained by a method well known to a person skilled in the art (Hermanson, G. T, Bioconjugate Techniques, pp. 56-136, pp. 456-493, Academic Press (1996)). Examples of the method can include, but are not limited to: Traut's reagent is reacted with the amino group of the antibody; N-succinimidyl S-acetylthioalkanoates are reacted with the amino group of the antibody followed by reaction with hydroxylamine; N-succinimidyl 3-(pyridyldithio)propionate is reacted with the antibody, followed by reaction with a reducing agent; the antibody is reacted with a reducing agent such as dithiothreitol, 2-mercaptoethanol, or tris(2-carboxyethyl)phosphine hydrochloride (TCEP) to reduce the interchain disulfide bond in the antibody, so as to form a sulfhydryl group.

Specifically, an antibody with interchain disulfide bonds partially or completely reduced can be obtained by using 0.3 to 3 molar equivalents of TCEP as a reducing agent per interchain disulfide bond in the antibody, and reacting the reducing agent with the antibody in a buffer solution containing a chelating agent. Examples of the chelating agent can include ethylenediaminetetraacetic acid (EDTA) and diethylenetriaminepentaacetic acid (DTPA). The chelating agent can be used at a concentration of 1 mM to 20 mM. A solution of sodium phosphate, sodium borate, sodium acetate, or the like can be used as the buffer solution. As a specific example, the antibody (3a) having partially or completely reduced sulfhydryl groups can be obtained by reacting the antibody with TCEP at 4° C. to 37° C. for 1 to 4 hours.

It is to be noted that by carrying out an addition reaction of a sulfhydryl group to a drug-linker moiety, the drug-linker moiety can be conjugated by a thioether bond.

Then, using 2 to 20 molar equivalents of the compound (2) per antibody (3a) having a sulfhydryl group, the antibody-drug conjugate (1) in which 2 to 8 drug molecules are conjugated per antibody can be produced. Specifically, a solution containing the compound (2) dissolved therein may be added to a buffer solution containing the antibody (3a) having a sulfhydryl group for the reaction. In this context, a sodium acetate solution, sodium phosphate, sodium borate, or the like can be used as the buffer solution. pH for the reaction is 5 to 9, and more preferably, the reaction may be performed near pH 7. An organic solvent such as dimethyl sulfoxide (DMSO), dimethylformamide (DMF), dimethylacetamide (DMA), or N-methyl-2-pyrrolidone (NMP) can be used as a solvent for dissolving the compound (2). The reaction may be performed by adding the solution containing the compound (2) dissolved in the organic solvent at 1 to 20% v/v to a buffer solution containing the antibody (3a) having a sulfhydryl group. The reaction temperature is 0 to 37° C., more preferably 10 to 25° C., and the reaction time is 0.5 to 2 hours. The reaction can be terminated by deactivating the reactivity of unreacted compound (2) with a thiol-containing reagent. The thiol-containing reagent is, for example, cysteine or N-acetyl-L-cysteine (NAC). More specifically, the reaction can be terminated by adding 1 to 2 molar equivalents of NAC to the compound (2) used, and incubating the obtained mixture at room temperature for 10 to 30 minutes.

(4) Identification of Antibody-Drug Conjugate

The produced antibody-drug conjugate (e.g., antibody-drug conjugate (1)) can be subjected to concentration, buffer exchange, purification, and measurement of antibody concentration and an average number of conjugated drug molecules per antibody molecule according to common procedures described below, to identify the antibody-drug conjugate (1).

(4)-1 Common Procedure A: Concentration of Aqueous Solution of Antibody or Antibody-Drug Conjugate To Amicon Ultra (50,000 MWCO, Millipore Corporation) container, a solution of an antibody or an antibody-drug conjugate was added, and the solution of the antibody or the antibody-drug conjugate was concentrated by centrifugation (centrifugation at 2000 G to 3800 G for 5 to 20 minutes) using a centrifuge (Allegra X-15R, Beckman Coulter, Inc.)

(4)-2 Common Procedure B: Measurement of Antibody Concentration

Using a UV detector (Nanodrop 1000, Thermo Fisher Scientific Inc.), measurement of the antibody concentration was carried out according to the method defined by the manufacturer. In this respect, 280 nm absorption coefficient differing among antibodies (1.3 mLmg$^{-1}$cm$^{-1}$ to 1.8 mLmg$^{-1}$cm$^{-1}$) was used.

(4)-3 Common Procedure C: Buffer Exchange for Antibody

NAP-25 column (Cat. No. 17-0852-02, GE Healthcare Japan Corporation) using Sephadex G-25 carrier was equilibrated with a phosphate buffer (50 mM, pH 6.0) (referred to as PBS6.0/EDTA in the present description) containing sodium chloride (50 mM) and EDTA (2 mM) according to the method defined by the manufacturer. An aqueous solution of the antibody was applied in an amount of 2.5 mL per NAP-25 column, and thereafter, a fraction (3.5 mL) eluted with 3.5 mL of PBS6.0/EDTA was collected. This fraction was concentrated by the common procedure A. After measurement of the concentration of the antibody using the common procedure B, the antibody concentration was adjusted to 20 mg/mL using PBS6.0/EDTA.

(4)-4 Common Procedure D: Purification of Antibody-Drug Conjugate

NAP-25 column was equilibrated with any commercially available buffer solution such as an acetate buffer containing sorbitol (5%) (10 mM, pH 5.5; referred to as ABS in the present description). An aqueous reaction solution of the antibody-drug conjugate (approximately 2.5 mL) was applied to the NAP-25 column, and thereafter, elution was carried out with the buffer solution in an amount defined by the manufacturer, so as to collect an antibody fraction. A gel filtration purification process, in which the collected fraction was applied again to the NAP-25 column, and elution was carried out with the buffer solution, was repeated a total of 2 or 3 times to obtain the antibody-drug conjugate excluding non-conjugated drug linker and low-molecular-weight compounds (tris(2-carboxyethyl)phosphine hydrochloride (TCEP), N-acetyl-L-cysteine (NAC), and dimethyl sulfoxide).

(4)-5 Common Procedure E: Measurement of Antibody Concentration in Antibody-Drug Conjugate and Average Number of Conjugated Drug Molecules Per Antibody Molecule The conjugated drug concentration in the antibody-drug conjugate can be calculated by measuring UV absorbance of an aqueous solution of the antibody-drug conjugate at two wavelengths of 280 nm and 370 nm, and thereafter performing a calculation shown below.

The total absorbance at any given wavelength is equal to the sum of the absorbance of all light-absorbing chemical species that are present in a system [additivity of absorbance]. Therefore, based on the hypothesis that the molar absorption coefficients of the antibody and the drug do not vary between before and after conjugation between the antibody and the drug, the antibody concentration and the drug concentration in the antibody-drug conjugate are represented by the following equations.

$$A_{280}=A_{D,280}+A_{A,280}=E_{D,280}C_D+E_{A,280}C_A \quad \text{Equation (1)}$$

$$A_{370}=A_{D,370}+A_{A,370}=E_{D,370}C_D+E_{A,370}C_A \quad \text{Equation (2)}$$

In this context, $A_{280}$ represents the absorbance of an aqueous solution of the antibody-drug conjugate at 280 nm, $A_{370}$ represents the absorbance of an aqueous solution of the antibody-drug conjugate at 370 nm, $A_{A,280}$ represents the absorbance of the antibody at 280 nm, $A_{A,370}$ represents the absorbance of the antibody at 370 nm, $A_{D,280}$ represents the absorbance of a conjugate precursor at 280 nm, $A_{D,370}$ represents the absorbance of a conjugate precursor at 370 nm, $\varepsilon_{A,280}$ represents the molar absorption coefficient of the antibody at 280 nm, $\varepsilon_{A,370}$ represents the molar absorption coefficient of the antibody at 370 nm, $\varepsilon_{D,280}$ represents the molar absorption coefficient of a conjugate precursor at 280 nm, $\varepsilon_{D,370}$ represents the molar absorption coefficient of a conjugate precursor at 370 nm, $C_A$ represents the antibody concentration in the antibody-drug conjugate, and CD represent the drug concentration in the antibody-drug conjugate.

In this context, with regard to $\varepsilon_{A,280}$, $\varepsilon_{A,370}$, $\varepsilon_{D,280}$, and $\varepsilon_{D,370}$, preliminarily prepared values (estimated values based on calculation or measurement values obtained by UV measurement of the compound) are used. For example, $\varepsilon_{A,280}$ can be estimated from the amino acid sequence of the antibody by a known calculation method (Protein Science, 1995, vol. 4, 2411-2423). $\varepsilon_{A,370}$ is generally zero. $\varepsilon_{D,280}$ and $\varepsilon_{D,370}$ can be obtained according to the Lambert-Beer's law (Absorbance=Molar concentration x Molar absorption coefficient x Cell path length) by measuring the absorbance of a solution in which the conjugate precursor used is dissolved at a certain molar concentration. CA and CD can be determined by measuring $A_{280}$ and $A_{370}$ of an aqueous solution of the antibody-drug conjugate, and then solving the simultaneous equations (1) and (2) by substitution of these values. Further, by diving $C_D$ by $C_A$, the average number of conjugated drug molecules per antibody can be determined.

(4)-6 Common Procedure F: Measurement of Average Number of Conjugated Drug Molecules Per Antibody Molecule in Antibody-Drug Conjugate—(2)

The average number of conjugated drug molecules per antibody molecule in the antibody-drug conjugate can also be determined by high-performance liquid chromatography (HPLC) analysis using the following method, in addition to the aforementioned "(4)-5 Common procedure E". Hereinafter, the method for measuring the average number of conjugated drug molecules by HPLC when the antibody is conjugated to the drug linker by a disulfide bond will be described. A person skilled in the art is capable of appropriately measuring the average number of conjugated drug molecules by HPLC, depending on the connecting pattern between the antibody and the drug linker, with reference to this method.

F-1. Preparation of Sample for HPLC Analysis (Reduction of Antibody-Drug Conjugate)

An antibody-drug conjugate solution (approximately 1 mg/mL, 60 μL) is mixed with an aqueous solution of dithiothreitol (DTT) (100 mM, 15 μL). By incubating the mixture at 37° C. for 30 minutes, the disulfide bond between the light chain and heavy chain of the antibody-drug conjugate is cleaved. The resulting sample is used in HPLC analysis.

F-2. HPLC Analysis

The HPLC analysis is carried out under the following measurement conditions.

HPLC system: Agilent 1290 HPLC system (Agilent Technologies, Inc.)

Detector: Ultraviolet absorption spectrometer (measurement wavelength: 280 nm)

Column: ACQUITY UPLC BEH Phenyl (2.1×50 mm, 1.7 μm, 130 angstroms; Waters Corp., P/N 186002884)

Column temperature: 80° C.

Mobile phase A: Aqueous solution containing 0.10% trifluoroacetic acid (TFA) and 15% 2-propanol Mobile phase B: Acetonitrile solution containing 0.075% TFA and 15% 2-propanol Gradient program: 140-360 (0 min-15 min), 360-800 (15 min-17 min), 800-140 (17 min-17.01 min.), and 140 (17.01 min-25 min)

Sample injection: 10 μL or

HPLC system: Agilent 1290 HPLC system (Agilent Technologies, Inc.)

Detector: Ultraviolet absorption spectrometer (measurement wavelength: 280 nm)

Column: PLRP-S (2.1×50 mm, 8 μm, 1000 angstroms; Agilent Technologies, Inc., P/N PL1912-1802)

Column temperature: 80° C.

Mobile phase A: 0.04% aqueous TFA solution Mobile phase B: Acetonitrile solution containing 0.04% TFA Gradient program: 29%-36% (0 min-12.5 min), 36%-42% (12.5 min-15 min), 42%-29% (15 min-15.1 min), and 29%-29% (15.1 min-25 min)

Sample injection: 15 μL

F-3. Data Analysis

F-3-1. The light chain and heavy chain of the antibody are represented by $L_i$ and $H_i$, respectively, according to the number of conjugated drug molecules (wherein i represents the number of conjugated drug molecules, i.e., the number of conjugated drug molecules according to the present invention is represented by $L_0$, $L_1$, $H_0$, $H_1$, $H_2$, $H_3$, etc.)

Compared with non-conjugated antibody light ($L_0$) and heavy ($H_0$) chains, a light chain bound to one drug molecule ($L_1$), a heavy chain bound to one drug molecule ($H_1$), a heavy chain bound to two drug molecules ($H_2$), and a heavy chain bound to three drug molecules ($H_3$) exhibit higher hydrophobicity in proportion to the number of conjugated drug molecules and thus have a larger retention time. These chains are therefore eluted in the order of $L_0$ and $L_1$ or $H_0$, $H_1$, $H_2$, and $H_3$. Detection peaks can be assigned to any of $L_0$, $L_1$, $H_0$, $H_1$, $H_2$, and $H_3$ by the comparison of retention times with $L_0$ and $H_0$.

F-3-2. Since the drug linker has UV absorption, peak area values are corrected in response to the number of conjugated drug linker molecules according to the following expression using the molar absorption coefficients of the light chain or heavy chain and the drug linker.

$$\text{Corrected value of peak area of light chain bound to } i \text{ drug molecule(s)}(A_{Li}) = \text{Peak area} \times \frac{\text{Molar absorption coefficient of light chain}}{\text{Molar absorption coefficient of light chain} + \text{The number of conjugated drug molecules}(i) \times \text{Molar absorption coefficient of drug linker}} \quad \text{[Expression 1]}$$

$$\text{Corrected value of peak area of heavy chain bound to } i \text{ drug molecule(s)}(A_{Hi}) = \text{Peak area} \times \frac{\text{Molar absorption coefficient of heavy chain}}{\text{Molar absorption coefficient of heavy chain} + \text{The number of conjugated drug molecules}(i) \times \text{Molar absorption coefficient of drug linker}} \quad \text{[Expression 2]}$$

In this context, a value estimated from the amino acid sequence of the light chain or heavy chain of each antibody by a known calculation method (Protein Science, 1995, vol. 4, 2411-2423) can be used as the molar absorption coefficient (280 nm) of the light chain or heavy chain of the antibody. In the case of h046-H4e/L7, a molar absorption coefficient of 26210 and a molar absorption coefficient of 68990 were used as estimated values for the light chain and heavy chain, respectively, according to the amino acid sequence of the antibody. The actually measured molar absorption coefficient (280 nm) of a compound in which the maleimide group has been converted to succinimide thioether by the reaction of each drug linker with mercaptoethanol or N-acetylcysteine was used as the molar absorption coefficient (280 nm) of the drug linker. The wavelength for absorbance measurement can be appropriately set by a person skilled in the art, but is preferably a wavelength at which the peak of the antibody can be measured, and more preferably 280 nm.

F-3-3. The peak area ratio (%) of each chain is calculated for the total of the corrected values of peak areas according to the following expression.

$$\text{Peak area ratio of light chain bound to } i \text{ drug molecule(s)} = \frac{A_{Li}}{A_{L0} + A_{L1}} \times 100 \quad \text{[Expression 3]}$$

$$\text{Peak area ratio of heavy chain bound to i drug molecule(s)} = \frac{A_{Hi}}{A_{H0} + A_{H1} + A_{H2} + A_{H3}} \times 100$$

$A_{Li}$ and $A_{Hi}$: Corrected values of peak areas of $L_i$ and $H_i$, respectively F-3-4. The average number of conjugated drug molecules per antibody molecule in the antibody-drug conjugate is calculated according to the following expression.

Average number of conjugated drug molecules=($L_0$ peak area ratio×0+$L_0$ peak area ratio×1+$H_0$ peak area ratio×0+$H_1$ peak area ratio×1+$H_2$ peak area ratio×2+$H_3$ peak area ratio×3)/100×2

It is to be noted that, in order to secure the amount of the conjugate, a plurality of conjugates having almost the same average number of conjugated drug molecules (e.g., on the order of ±1), which have been produced under similar conditions, can be mixed to prepare a new lot. In this case, the average number of drug molecules falls between the average numbers of drug molecules before the mixing.

One specific example of the antibody-drug conjugate used in the present invention can include an antibody-drug conjugate in which a drug-linker structure moiety represented by the formula:

[Formula 11]

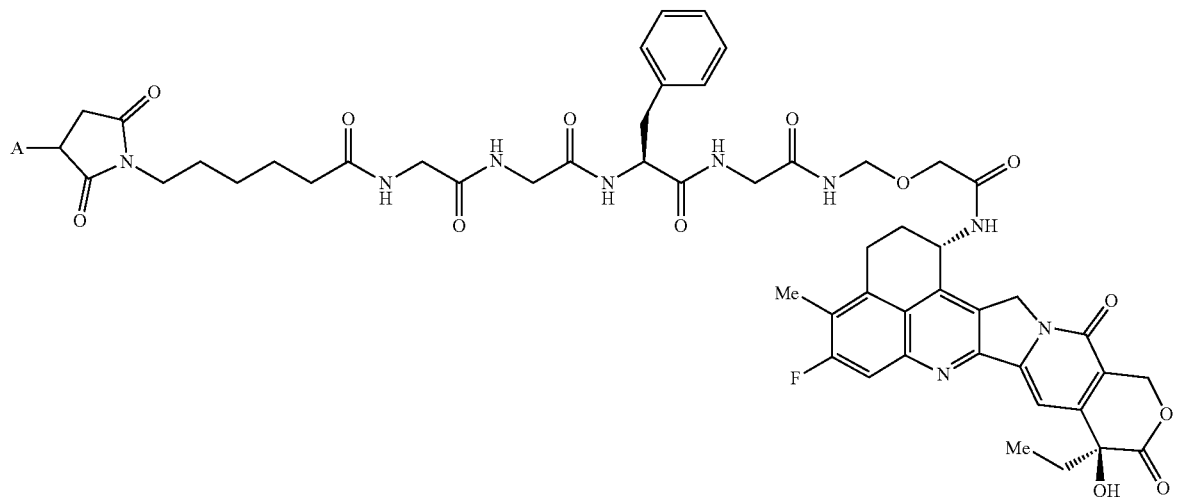

wherein A represents a connecting position to the antibody, is conjugated to the anti-GPR20 antibody disclosed in the present description by a thioether bond.

In the present invention, the partial structure consisting of the linker and the drug in the antibody-drug conjugate is also referred to as a "drug-linker structure", a "drug-linker structure moiety" or a "drug linker". This drug linker is connected to a thiol group (in other words, a sulfur atom of a cysteine residue) formed at an interchain disulfide bond site (two heavy chain-heavy chain positions and two heavy chain-light chain positions) of the antibody.

One specific example of the antibody-drug conjugate of the present invention can include an antibody-drug conjugate having a structure represented by the following formula:

[Formula 12] of the present invention, n can be 2 to 8 and is preferably 5 to 8, more preferably 7 to 8, and still more preferably 8, in measurement by common procedure F.

One example of the antibody-drug conjugate of the present invention can include an antibody-drug conjugate having a structure represented by the above-described formula [Formula 12] or [Formula 13] wherein the antibody represented by AB is an antibody having a heavy chain and a light chain in any one combination selected from the group consisting of the following combinations (a) to (y), or a functional fragment of the antibody, or a pharmacologically acceptable salt of the antibody-drug conjugate:

(a) a heavy chain consisting of the amino acid sequence at amino acid positions 20 to 472 in SEQ ID NO: 48 and a light chain consisting of the amino acid sequence at amino acid positions 21 to 234 in SEQ ID NO: 58,

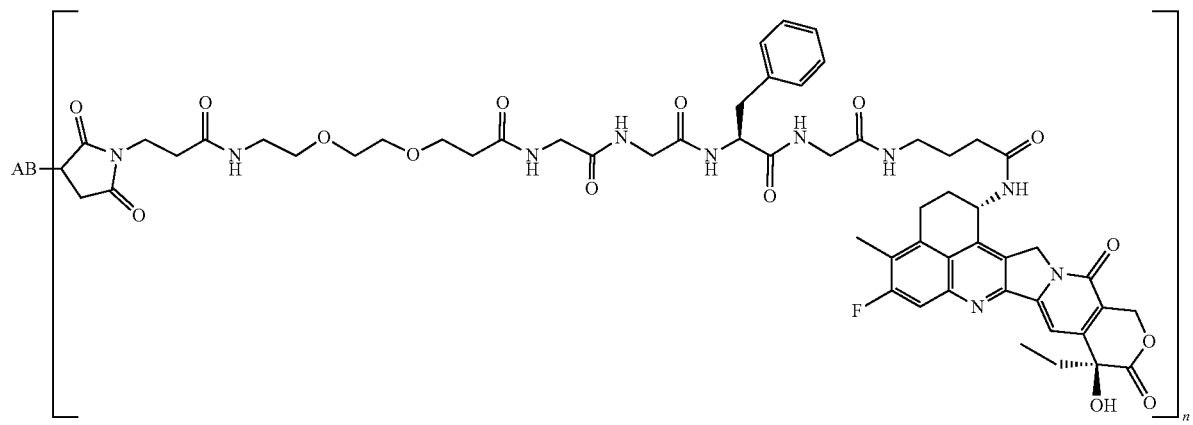

or the following formula:

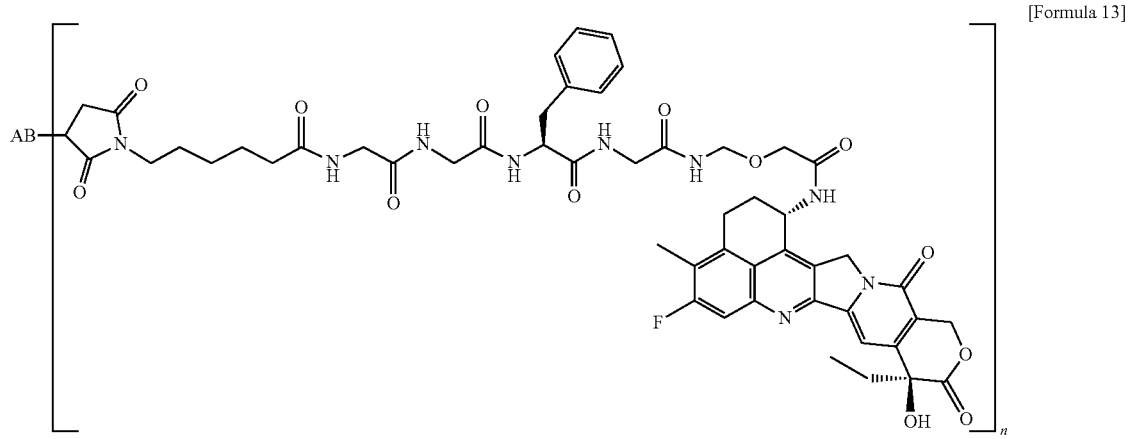

[Formula 13]

In this context, AB represents the anti-GPR20 antibody disclosed in the present description, and the antibody is conjugated to the drug linker via a sulfhydryl group derived from the antibody. In this context, n has the same meaning as that of so-called DAR (drug-to-antibody Ratio), and represents a drug-to-antibody ratio per antibody. Specifically, n represents the number of conjugated drug molecules per antibody molecule, which is a numeric value defined and indicated as an average value, i.e., the average number of conjugated drug molecules. In the case of the antibody-drug conjugate represented by [Formula 5 (i.e. Formula 13)] or (b) a heavy chain consisting of the amino acid sequence at amino acid positions 20 to 472 in SEQ ID NO: 48 and a light chain consisting of the amino acid sequence at amino acid positions 21 to 234 in SEQ ID NO: 60, (c) a heavy chain consisting of the amino acid sequence at amino acid positions 20 to 472 in SEQ ID NO: 48 and a light chain consisting of the amino acid sequence at amino acid positions 21 to 234 in SEQ ID NO: 62, (d) a heavy chain consisting of the amino acid sequence at amino acid positions 20 to 472 in SEQ ID NO: 48 and a light chain consisting of the amino acid sequence at amino acid positions 21 to 234 in SEQ ID NO: 64,
(e) a heavy chain consisting of the amino acid sequence at amino acid positions 20 to 472 in SEQ ID NO: 50 and a light chain consisting of the amino acid sequence at amino acid positions 21 to 234 in SEQ ID NO: 58,
(f) a heavy chain consisting of the amino acid sequence at amino acid positions 20 to 472 in SEQ ID NO: 50 and a light chain consisting of the amino acid sequence at amino acid positions 21 to 234 in SEQ ID NO: 60,
(g) a heavy chain consisting of the amino acid sequence at amino acid positions 20 to 472 in SEQ ID NO: 50 and a light chain consisting of the amino acid sequence at amino acid positions 21 to 234 in SEQ ID NO: 62,
(h) a heavy chain consisting of the amino acid sequence at amino acid positions 20 to 472 in SEQ ID NO: 50 and a light chain consisting of the amino acid sequence at amino acid positions 21 to 234 in SEQ ID NO: 64,
(i) a heavy chain consisting of the amino acid sequence at amino acid positions 20 to 472 in SEQ ID NO: 52 and a light chain consisting of the amino acid sequence at amino acid positions 21 to 234 in SEQ ID NO: 58,
(j) a heavy chain consisting of the amino acid sequence at amino acid positions 20 to 472 in SEQ ID NO: 52 and a light chain consisting of the amino acid sequence at amino acid positions 21 to 234 in SEQ ID NO: 60,
(k) a heavy chain consisting of the amino acid sequence at amino acid positions 20 to 472 in SEQ ID NO: 52 and a light chain consisting of the amino acid sequence at amino acid positions 21 to 234 in SEQ ID NO: 62,
(l) a heavy chain consisting of the amino acid sequence at amino acid positions 20 to 472 in SEQ ID NO: 52 and a light chain consisting of the amino acid sequence at amino acid positions 21 to 234 in SEQ ID NO: 64,
(m) a heavy chain consisting of the amino acid sequence at amino acid positions 20 to 474 in SEQ ID NO: 54 and a light chain consisting of the amino acid sequence at amino acid positions 21 to 234 in SEQ ID NO: 58,
(n) a heavy chain consisting of the amino acid sequence at amino acid positions 20 to 474 in SEQ ID NO: 54 and a light chain consisting of the amino acid sequence at amino acid positions 21 to 234 in SEQ ID NO: 60,
(o) a heavy chain consisting of the amino acid sequence at amino acid positions 20 to 474 in SEQ ID NO: 54 and a light chain consisting of the amino acid sequence at amino acid positions 21 to 234 in SEQ ID NO: 62,
(p) a heavy chain consisting of the amino acid sequence at amino acid positions 20 to 474 in SEQ ID NO: 54 and a light chain consisting of the amino acid sequence at amino acid positions 21 to 234 in SEQ ID NO: 64,
(q) a heavy chain consisting of the amino acid sequence at amino acid positions 20 to 474 in SEQ ID NO: 56 and a light chain consisting of the amino acid sequence at amino acid positions 21 to 234 in SEQ ID NO: 58,
(r) a heavy chain consisting of the amino acid sequence at amino acid positions 20 to 474 in SEQ ID NO: 56 and a light chain consisting of the amino acid sequence at amino acid positions 21 to 234 in SEQ ID NO: 60,
(s) a heavy chain consisting of the amino acid sequence at amino acid positions 20 to 474 in SEQ ID NO: 56 and a light chain consisting of the amino acid sequence at amino acid positions 21 to 234 in SEQ ID NO: 62,
(t) a heavy chain consisting of the amino acid sequence at amino acid positions 20 to 474 in SEQ ID NO: 56 and a light chain consisting of the amino acid sequence at amino acid positions 21 to 234 in SEQ ID NO: 64,
(u) a heavy chain consisting of the amino acid sequence at amino acid positions 20 to 472 in SEQ ID NO: 44 and a light chain consisting of the amino acid sequence at amino acid positions 21 to 234 in SEQ ID NO: 58,
(v) a heavy chain consisting of the amino acid sequence at amino acid positions 20 to 472 in SEQ ID NO: 44 and a light chain consisting of the amino acid sequence at amino acid positions 21 to 234 in SEQ ID NO: 60,
(w) a heavy chain consisting of the amino acid sequence at amino acid positions 20 to 472 in SEQ ID NO: 44 and a light chain consisting of the amino acid sequence at amino acid positions 21 to 234 in SEQ ID NO: 62,
(x) a heavy chain consisting of the amino acid sequence at amino acid positions 20 to 472 in SEQ ID NO: 44 and a light chain consisting of the amino acid sequence at amino acid positions 21 to 234 in SEQ ID NO: 64, and
(y) an antibody having any one combination selected from the group consisting of (a) to (x), wherein the heavy chain or the light chain comprises one or two or more modifications selected from the group consisting of N-linked glycosylation, O-linked glycosylation, N-terminal processing, C-terminal processing, deamidation, isomerization of aspartic acid, oxidation of methionine, addition of a methionine residue to the N-terminus, amidation of a proline residue, and a deletion of one or two amino acids at the carboxyl terminus.

4. Medicament

Since the anti-GPR20 antibody of the present invention or the functional fragment of the antibody described in the above section "2. Production of anti-GPR20 antibody" and Examples binds to GPR20 on tumor cell surface and has internalization activity, it can be used as a medicament, and in particular, as a therapeutic agent for cancer such as gastrointestinal stromal tumor, either alone or in combination with an additional drug.

Furthermore, the anti-GPR20 antibody of the present invention or the functional fragment of the antibody can be used in the detection of cells expressing GPR20.

Moreover, since the anti-GPR20 antibody of the present invention or the functional fragment of the antibody has internalization activity, it can be applied to an antibody for an antibody-drug conjugate.

The anti-GPR20 antibody-drug conjugate of the present invention described in the above section "3. Anti-GPR20 antibody-drug conjugate" and Examples, when a drug having antitumor activity such as cytotoxic activity is used as the drug, is a conjugate of the anti-GPR20 antibody and/or the functional fragment of the antibody having internalization activity, and the drug having antitumor activity such as cytotoxic activity. Since this anti-GPR20 antibody-drug conjugate exhibits antitumor activity against cancer cells expressing GPR20, it can be used as a medicament, and in particular, as a therapeutic agent and/or a prophylactic agent for cancer.

The anti-GPR20 antibody-drug conjugate of the present invention may absorb moisture or have adsorption water, for example, to turn into a hydrate when it is left in air or subjected to recrystallization or purification procedures. Such a compound or a pharmacologically acceptable salt containing water is also included in the present invention.

When the anti-GPR20 antibody-drug conjugate of the present invention has a basic group such as an amino group, it can form a pharmacologically acceptable acid-addition salt, if desired. Examples of such an acid-addition salt can include: hydrohalides such as hydrofluoride, hydrochloride, hydrobromide, and hydroiodide; inorganic acid salts such as nitrate, perchlorate, sulfate, and phosphate; lower alkanesulfonates such as methanesulfonate, trifluoromethanesulfonate, and ethanesulfonate; arylsulfonates such as benzenesulfonate and p-toluenesulfonate; organic acid salts such as formate, acetate, trifluoroacetate, malate, fumarate, succinate, citrate, tartrate, oxalate, and maleate; and amino acid salts such as ornithine salt, glutamate, and aspartate.

When the anti-GPR20 antibody-drug conjugate of the present invention has an acidic group such as a carboxy group, it can form a pharmacologically acceptable base-addition salt, if desired. Examples of such a base-addition salt can include: alkali metal salts such as a sodium salt, a potassium salt, and a lithium salt; alkaline earth metal salts such as a calcium salt and a magnesium salt; inorganic salts such as an ammonium salt; and organic amine salts such as a dibenzylamine salt, a morpholine salt, a phenylglycine alkyl ester salt, an ethylenediamine salt, an N-methylglucamine salt, a diethylamine salt, a triethylamine salt, a cyclohexylamine salt, a dicyclohexylamine salt, an N,N'-dibenzylethylenediamine salt, a diethanolamine salt, an N-benzyl-N-(2-phenylethoxy)amine salt, a piperazine salt, a tetramethylammonium salt, and a tris(hydroxymethyl)aminomethane salt.

The present invention can also include an anti-GPR20 antibody-drug conjugate in which one or more atoms constituting the antibody-drug conjugate are replaced with isotopes of the atoms. There exist two types of isotopes: radioisotopes and stable isotopes. Examples of the isotope can include isotypes of hydrogen ($^2$H and $^3$H), isotopes of carbon ($^{11}$C, $^{13}$C and $^{14}$C), isotopes of nitrogen ($^{13}$N and $^{15}$N), isotopes of oxygen ($^{15}$O, $^{17}$O and $^{18}$O), and isotopes of fluorine ($^{18}$F). A composition comprising the antibody-drug conjugate labeled with such an isotope is useful as, for example, a therapeutic agent, a prophylactic agent, a research reagent, an assay reagent, a diagnostic agent, and an in vivo diagnostic imaging agent. Each of every antibody-drug conjugate labeled with an isotope, and mixtures of antibody-drug conjugates labeled with an isotope at any given ratio are included in the present invention. The antibody-drug conjugate labeled with an isotope can be produced, for example, by using a starting material labeled with an isotope instead of a starting material for the production method of the present invention mentioned earlier according to a method known in the art.

In vitro cytotoxicity can be measured based on the activity of suppressing the proliferative responses of cells, for example. For example, a cancer cell line overexpressing GPR20 is cultured, and the anti-GPR20 antibody-drug conjugate is added at different concentrations to the culture system. Thereafter, its suppressive activity against focus formation, colony formation and spheroid growth can be measured. In this context, by using a gastrointestinal stromal tumor (GIST)-derived cancer cell line, cell proliferation-suppressive activity against gastrointestinal stromal tumor can be examined.

In vivo therapeutic effects on cancer in an experimental animal can be measured, for example, by administering the anti-GPR20 antibody-drug conjugate to a nude mouse into which a tumor cell line highly expressing GPR20 has been transplanted, and then measuring a change in the cancer cells. In this context, by using an animal model derived from an immunodeficient mouse by the transplantation of gastrointestinal stromal tumor-derived cells, therapeutic effects on gastrointestinal stromal tumor can be measured.

The type of the cancer to which the anti-GPR20 antibody-drug conjugate of the present invention is applied is not particularly limited as long as the cancer expresses GPR20 in cancer cells to be treated. Examples thereof can include cancer in digestive organs such as the esophagus, the stomach, the small intestine, and the large intestine, though the cancer is not limited thereto as long as the cancer expresses GPR20. More preferred examples of the cancer can include gastrointestinal stromal tumor (GIST).

The anti-GPR20 antibody-drug conjugate of the present invention can be preferably administered to a mammal, and more preferably to a human.

A substance used in a pharmaceutical composition comprising the anti-GPR20 antibody-drug conjugate of the present invention can be appropriately selected and used from pharmaceutical additives and others usually used in this field, in terms of an applied dose or an applied concentration.

The anti-GPR20 antibody-drug conjugate of the present invention can be administered as a pharmaceutical composition comprising one or more pharmaceutically compatible components. For example, the pharmaceutical composition typically comprises one or more pharmaceutical carriers (e.g., sterilized liquids (e.g., water and oil (including petroleum oil and oil of animal origin, plant origin, or synthetic origin (e.g., peanut oil, soybean oil, mineral oil, and sesame oil))). Water is a more typical carrier when the pharmaceutical composition is intravenously administered. An aqueous saline solution, an aqueous dextrose solution, and an aqueous glycerol solution can also be used as a liquid carrier, in particular, for an injection solution. A suitable pharmaceutical vehicle is known in the art. If desired, the composition may also comprise a trace amount of a moisturizing agent, an emulsifying agent, or a pH buffering agent. Examples of suitable pharmaceutical carriers are disclosed in "Remington's Pharmaceutical Sciences" by E. W. Martin. The prescription corresponds to an administration mode.

Various delivery systems are known, and they can be used for administering the anti-GPR20 antibody-drug conjugate of the present invention. Examples of the administration route can include, but are not limited to, intradermal, intramuscular, intraperitoneal, intravenous, and subcutaneous routes. The administration can be made by injection or bolus injection, for example. According to a specific preferred embodiment, the administration of the above-described antibody-drug conjugate is performed by injection. Parenteral administration is a preferred administration route.

According to a representative embodiment, the pharmaceutical composition is prescribed, as a pharmaceutical composition suitable for intravenous administration to a human, according to the conventional procedures. The composition for intravenous administration is typically a solution in a sterile and isotonic aqueous buffer solution. If necessary, the medicament may also contain a solubilizing agent and a local anesthetic to alleviate pain at an injection area (e.g., lignocaine). In general, the above-described ingredients are provided, either separately or together in a mixture in a unit dosage form, as a freeze-dried powder or an anhydrous concentrate contained in a container which is obtained by sealing in (for example, an ampoule or a sachet indicating the amount of the active agent. When the medicament is to be administered by injection, it may be administered using, for example, an injection bottle containing water or saline of sterile pharmaceutical grade. When the medicament is to be administered by injection, an ampoule of sterile water or saline for injection may be provided such that the above-described ingredients are admixed with one another before administration.

The pharmaceutical composition of the present invention may be a pharmaceutical composition comprising only the anti-GPR20 antibody-drug conjugate of the present application, or may be a pharmaceutical composition comprising the anti-GPR20 antibody-drug conjugate and at least one of other therapeutic agents for cancer. The anti-GPR20 antibody-drug conjugate of the present invention can also be administered together with an additional therapeutic agent for cancer, and can thereby enhance an anticancer effect. The additional anticancer agent used for such a purpose may be administered to an individual, simultaneously, separately, or continuously, together with the antibody-drug conjugate. Otherwise, the additional anticancer agent and the anti-GPR20 antibody-drug conjugate may each be administered to the subject at different administration intervals. Examples of such a therapeutic agent for cancer can include tyrosine kinase inhibitors including imatinib, sunitinib, and regorafenib, CDK4/6 inhibitors including palbociclib, HSP90 inhibitors including TAS-116, MEK inhibitors including MEK162, and immune checkpoint inhibitors including nivolumab, pembrolizumab, and ipilimumab, though the therapeutic agent for cancer is not limited thereto as long as the drug has antitumor activity.

Such a pharmaceutical composition can be prepared as a formulation having a selected composition and a necessary purity in the form of a freeze-dried formulation or a liquid formulation. The pharmaceutical composition prepared as a freeze-dried formulation may be a formulation containing an appropriate pharmaceutical additive used in this field. Likewise, the liquid formulation can be prepared such that the liquid formulation contains various pharmaceutical additives used in this field.

The composition and concentration of the pharmaceutical composition also vary depending on the administration method. With regard to the affinity of the anti-GPR20 antibody-drug conjugate comprised in the pharmaceutical composition of the present invention for the antigen, i.e., the dissociation constant (Kd value) of the anti-GPR20 antibody-drug conjugate to the antigen, as the affinity increases (i.e., the Kd value is low), the pharmaceutical composition can exert medicinal effects, even if the applied dose thereof is decreased. Accordingly, the applied dose of the antibody-drug conjugate can also be determined by setting the applied dose based on the status of the affinity of the antibody-drug conjugate for the antigen. When the antibody-drug conjugate of the present invention is administered to a human, it may be administered at a dose of, for example, from approximately 0.001 to 100 mg/kg once or a plurality of times at intervals of 1 to 180 days. It can be administered preferably at a dose of from 0.1 to 50 mg/kg and more preferably 1 to 15 mg/kg a plurality of times at intervals of 2 to 3 weeks.

EXAMPLES

Hereinafter, the present invention will be specifically described in the following examples. However, these examples are not intended to limit the scope of the present invention. Furthermore, these examples should not be construed in a limited manner by any means. It is to be noted that, in the following examples, unless otherwise specified, individual operations regarding genetic manipulation have been carried out according to the method described in "Molecular Cloning" (Sambrook, J., Fritsch, E. F. and Maniatis, T., published by Cold Spring Harbor Laboratory Press in 1989) or other methods described in experimental manuals used by persons skilled in the art, or when commercially available reagents or kits have been used, the examples have been carried out in accordance with the instructions included in the commercially available products. In the present description, reagents, solvents and starting materials are readily available from commercially available sources, unless otherwise specified.

Example 1: Obtainment of Rat Anti-Human GPR20 Antibody Having Internalization Activity 1)-1 Construction of Human GPR20 Expression Vector Using human brain-derived cDNA as a template, cDNA encoding human GPR20 protein (NP_005284) was amplified by PCR according to a method known to a person skilled in the art, and the amplification product was incorporated into a vector for mammalian expression to produce human GPR20 expression vector pcDNA3.1-hGPR20. The amino acid sequence of the human GPR20 is shown in SEQ ID NO: 1 in the sequence listing. EndoFree Plasmid Giga Kit (Qiagen N.V.) was used in the large scale preparation of pcDNA3.1-hGPR20 plasmid DNA.

1)-2 Immunization of Rats

For immunization, 6-week-old WKY/Izm female rats (Japan SLC, Inc.) were used. First, the lower legs of each rat were pre-treated with Hyaluronidase (Sigma-Aldrich Co. LLC), and thereafter, the human GPR20 expression vector pcDNA3.1-hGPR20 was intramuscularly injected into the same sites. Subsequently, employing ECM830 (BTX), in vivo electroporation was carried out on the same sites using a two-needle electrode. Once every two weeks, the same in vivo electroporation was repeated. On the 79th day, lymph nodes were collected from the rat, and then used in hybridoma preparation.

1)-3 Hybridoma Preparation

The lymph node cells were electrically fused with mouse myeloma SP2/0-ag14 cells using Hybrimune Hybridoma Production System (Cyto Pulse Sciences, Inc.), and the cells were then suspended and diluted with ClonaCell-HY Selection Medium D (StemCell Technologies Inc.), and then cultured under conditions of 37° C. and 5% CO2. Individual hybridoma colonies that appeared in the culture were collected as monoclonal hybridomas, then suspended in Clona-Cell-HY Selection Medium E (StemCell Technologies Inc.), and then cultured under conditions of 37° C. and 5% CO2. After moderate proliferation of cells, frozen stocks of individual hybridoma cells were produced, while a culture supernatant was collected from each hybridoma, and used to screen for anti-GPR20 antibody-producing hybridomas.

1)-4 Antibody-Producing Hybridoma Screening by Cell-ELISA Method

1)-4-1 Preparation of Antigen Gene-Expressing Cells for Use in Cell-ELISA

293α cells (a stable expression cell line derived from HEK293 cells expressing integrin αv and integrin β3) were prepared at $5 \times 10^3$ cells/10 mL in DMEM medium supplemented with 10% FBS. In accordance with transfection procedures for using Lipofectamine 2000 (Invitrogen Corp.), DNA of pcDNA3.1-hGPR20 or pcDNA3.1 as a negative control was introduced into the 293α cells, and the cells were dispensed in an amount of 100 µL/well to a 96-well plate (Corning Inc.). Thereafter, the cells were cultured under conditions of 37° C. and 5% CO2 in DMEM medium supplemented with 10% FBS for 24 to 27 hours. The obtained transfected cells were used for Cell-ELISA in an adhesive state.

1)-4-2 Cell-ELISA

The culture supernatant of the 293α cells transfected with the expression vector prepared in Example 1)-4-1 was removed, and the culture supernatant from each hybridoma was then added to the 293α cells transfected either with pcDNA3.1-hGPR20 or pcDNA3.1. The cells were left standing at 4° C. for 1 hour. The cells in the wells were washed once with PBS (+) supplemented with 5% FBS, and thereafter, Anti-Rat IgG-Peroxidase antibody produced in rabbit (Sigma-Aldrich Co. LLC) that had been 500-fold diluted with PBS (+) supplemented with 5% FBS was added to the wells. The cells were left standing at 4° C. for 1 hour. The cells in the wells were washed three times with PBS (+) supplemented with 5% FBS, and thereafter, OPD chormogenic solution (which had been prepared by dissolving o-phenylenediamine dihydrochloride (Wako Pure Chemical Industries, Ltd.) and $H_2O_2$ in an OPD solution (0.05 M trisodium citrate, 0.1 M disodium hydrogen phosphate 12-water; pH 4.5), so that the substances became 0.4 mg/ml and 0.6% (v/v), respectively) was added in an amount of 100 µL/well to the wells. A coloring reaction was carried out with occasional stirring. Thereafter, 1 M HCl was added to the plate (100 µL/well) to terminate the coloring reaction, followed by measurement of the absorbance at 490 nm using a plate reader (ENVISION: PerkinElmer, Inc.). In order to select hybridomas that produce an antibody specifically binding to human GPR20 expressed on the cell membrane surface, hybridomas that produced a culture supernatant exhibiting higher absorbance in the 293α cells transfected with the pcDNA3.1-hGPR20 expression vector than that in the 293α cells transfected with the control pcDNA3.1 were selected.

1)-5 Human GPR20-Binding Antibody Screening by Flow Cytometry

1)-5-1 Preparation of Antigen Gene-Expressing Cells for Use in Flow Cytometry Analysis 293T cells were seeded in a 225-cm² flask (Sumitomo Bakelite Co., Ltd.) at 5×10⁴ cells/cm², and the cells were then cultured overnight under conditions of 37° C. and 5% $CO_2$ in DMEM medium supplemented with 10% FBS. pcDNA3.1-hGPR20 or pcDNA3.1 as a negative control was introduced into the 293T cells using Lipofectamine 2000, and the cells were further cultured overnight under conditions of 37° C. and 5% $CO_2$. The 293T cells transfected with each expression vector were treated with TrypLE Express (Life Technologies Corp.), and the cells were washed with DMEM supplemented with 10% FBS, and then suspended in PBS supplemented with 5% FBS. The obtained cell suspension was used in flow cytometry analysis.

1)-5-2 Flow Cytometry Analysis

The binding specificity to human GPR20 of an antibody produced from hybridomas that had been determined to be positive by Cell-ELISA in Example 1)-4-2 was further confirmed by flow cytometry. The suspension of the transiently expressing 293T cells prepared in Example 1)-5-1 was centrifuged, and a supernatant was then removed. Thereafter, the cells were suspended by the addition of the culture supernatant from each hybridoma. The cells were left standing at 4° C. for 1 hour. The cells were washed twice with PBS supplemented with 5% FBS, and thereafter, the cells were suspended by the addition of Anti-Rat IgG FITC conjugate (Sigma-Aldrich Co. LLC) that had been 500-fold diluted with PBS supplemented with 5% FBS. The cells were left standing at 4° C. for 1 hour. The cells were washed twice with PBS supplemented with 5% FBS, and then re-suspended in PBS supplemented with 5% FBS and 2 µg/ml 7-aminoactinomycin D (Molecular Probes, Inc.), followed by detection using a flow cytometer (FC500; Beckman Coulter, Inc.). The data was analyzed using Flowjo (Tree Star, Inc.). After dead cells were removed from analysis by gating out 7-aminoactinomycin D-positive cells, a histogram of the FITC fluorescence intensity of live cells was generated. Hybridomas producing human GPR20-binding antibodies (178 clones) were selected based on results where the histogram for the antibody shifted to the strong fluorescence intensity side in the 293T cells transfected with pcDNA3.1-hGPR20 compared with the 293T cells transfected with the control pcDNA3.1. FIG. 18 shows results about clone Nos. 04-002, 04-006, 04-013, 04-014, 04-020, 04-021, 04-037, 04-046, 04-047, 04-060, 04-067, 04-068, 04-079, 04-084, 04-114, 04-115, 04-117, 04-125, 04-126, 04-127, 04-133, 04-139, 04-143, 04-145, 04-151 and 04-163, and the control (W/O 1st Ab) as examples of antibodies specifically binding to human GPR20. The abscissa of FIG. 18 depicts clone No., and the ordinate thereof depicts the amount of the antibody bound based on MFI (mean fluorescence intensity).

1)-6 Screening for Hybridoma Producing Anti-GPR20 Antibody Having Internalization Activity The internalization activity of the anti-GPR20 antibodies was evaluated using an anti-rat IgG antibody reagent Rat-ZAP (Advanced Targeting Systems) conjugated with a toxin (saporin) inhibiting protein synthesis. Specifically, 293α cells caused to transiently express human GPR20 were seeded at 3×10³ cells/well over a 96-well plate, and then cultured overnight under conditions of 37° C. and 5% $CO_2$. After the plate was cooled on ice, 20 µL of the culture supernatant of each anti-GPR20 antibody-producing hybridoma was added to each well, and the plate was left standing at 4° C. for 1 hour. After removal of the culture supernatant by suction, DMEM supplemented with 10% FBS and 500 ng/mL Rat-ZAP was added to the plate, and the cells were cultured under conditions of 37° C. and 5% $CO_2$ for 3 days. The number of live cells was measured by the quantification of ATP using CellTiter-Glo (registered trademark) Luminescent Cell Viability Assay. In this screening, Rat-ZAP is taken up into cells in a manner dependent on the internalization activity of the rat anti-GPR20 antibody, so that saporin inhibiting protein synthesis is released into the cells, so as to suppress cell proliferation. As a result of making a selection using a cell proliferation suppression rate of 60% or more as an indicator, 19 hybridomas (clone Nos: 04-002, 04-006, 04-013, 04-014, 04-021, 04-037, 04-046, 04-047, 04-067, 04-068, 04-079, 04-114, 04-115, 04-125, 04-126, 04-127, 04-133, 04-139 and 04-163) producing anti-GPR20 antibodies having internalization activity were selected.

1)-7 Determination of Subclass and Type of Rat Monoclonal Antibody

The heavy chain subclasses and light chain types of the rat anti-human GPR20 monoclonal antibodies were determined using RAT MONOCLONAL ANTIBODY ISOTYPING TEST KIT (DS Pharma Biomedical Co., Ltd.). As a result, it was confirmed that clone Nos. 04-047 and 04-068 had IgG2a and κ chains, and that clone Nos. 04-002, 04-006, 04-013, 04-014, 04-021, 04-037, 04-046, 04-067, 04-079, 04-114, 04-115, 04-125, 04-126, 04-127, 04-133, 04-139 and 04-163 had IgG2b and κ chains.

1)-8 Preparation of Rat Anti-Human GPR20 Antibody

The rat anti-human GPR20 monoclonal antibodies were purified from the hybridoma culture supernatants.

First, the volume of each rat anti-GPR20 monoclonal antibody-producing hybridoma was sufficiently increased with ClonaCell-HY Selection Medium E (StemCell Technologies Inc.), and thereafter, the medium was exchanged with Hybridoma SFM (Life Technologies Corp.) supplemented with 20% of Ultra Low IgG FBS (Life Technologies Corp.). Thereafter, the hybridoma was cultured for 4 to 5 days. The resulting culture supernatant was harvested, and insoluble matter was removed therefrom by passing through a 0.8-μm filter, and through a 0.2-μm filter.

An antibody was purified from the hybridoma supernatant by Protein G affinity chromatography (4 to 6° C.) in one step. A buffer replacement step after the Protein G affinity chromatography purification was carried out at 4 to 6° C. First, the culture supernatant of the hybridoma was applied to a column that had been packed with Protein G (GE Healthcare Biosciences Corp.) equilibrated with PBS. After the entire culture solution had entered the column, the column was washed with PBS in an amount of two or more times the volume of the column. Subsequently, the antibody was eluted with a 0.1 M glycine/HCl aqueous solution (pH 2.7), so that a fraction containing an antibody was collected. Immediately, the pH of the collected fraction was adjusted to 7.0 to 7.5 by the addition of 1 M Tris-HCl (pH 9.0). Thereafter, using Centrifugal UF Filter Device VIVAS-PIN20 (molecular weight cutoff: UF30K, Sartorius Inc., 4 to 6° C.), the buffer was replaced with PBS, while the antibody was concentrated, so that the concentration of the antibody was adjusted to 0.2 mg/mL or more. Finally, the antibody was filtrated through Minisart-Plus filter (Sartorius Inc.) to obtain a purified Antibody Sample.

Example 2: In Vitro Evaluation of Rat Anti-GPR20 Antibody

2)-1 Evaluation of Binding Ability of Rat Anti-GPR20 Antibody by Flow Cytometry

In order to evaluate GPR20-binding ability, the suspension of the 293T cells transfected with pcDNA3.1-hGPR20, which had been produced by the method shown in 1)-5-1, was centrifuged, and a supernatant was then removed. Thereafter, the cells were suspended by the addition of each of the 19 rat anti-human GPR20 monoclonal antibodies (clone Nos: 04-002, 04-006, 04-013, 04-014, 04-021, 04-037, 04-046, 04-047, 04-067, 04-068, 04-079, 04-114, 04-115, 04-125, 04-126, 04-127, 04-133, 04-139 and 04-163) having internalization activity, and the 2 rat anti-human GPR20 monoclonal antibodies (13-024 and 13-048), which had been prepared in 1)-8, or rat IgG control (R&D Systems, Inc.). The cells were left standing at 4° C. for 1 hour. The cells were washed twice with PBS supplemented with 5% FBS, and then suspended by the addition of Goat Anti-Rat IgG (H+L), PE conjugate (Beckman Coulter, Inc.) that had been 320-fold diluted with PBS supplemented with 5% FBS. The cells were left standing at 4° C. for 1 hour. The cells were washed twice with PBS supplemented with 5% FBS, followed by detection using a flow cytometer (FC500; Beckman Coulter, Inc.). The results are shown in FIG. 19. In FIG. 19, the abscissa depicts an antibody concentration (nM), and the ordinate depicts the amount of the antibody bound based on MFI (mean fluorescence intensity). As shown in FIG. 19, all the amounts of the rat anti-human GPR20 antibodies bound to the 293T cells transfected with pcDNA3.1-hGPR20 were increased in a concentration-dependent manner. On the other hand, rat IgG2a and IgG2b isotype control antibodies did not exhibit GPR20-binding activity.

2)-2 Internalization Activity of Rat Anti-GPR20 Antibody

The internalization activity of the purified rat anti-GPR20 antibodies was evaluated using an anti-rat IgG antibody reagent Rat-ZAP (Advanced Targeting Systems) conjugated with a toxin (saporin) inhibiting protein synthesis, in the same manner as that applied in 1)-6. Specifically, HEK293 cells stably expressing GPR20-EGFP protein comprising human GPR20 linked at its C-terminus to EGFP were seeded at $2.5 \times 10^3$ cells/well, and then cultured overnight under conditions of 37° C. and 5% $CO_2$. Thereafter, each rat anti-GPR20 antibody (final concentration: 0.012 to 1 μg/mL) and Rat-ZAP (final concentration: 0.5 μg/mL) were added to the culture. The cells were cultured for 5 days, and thereafter, the number of live cells was measured by the quantification of ATP using CellTiter-Glo (registered trademark) Luminescent Cell Viability Assay. A cell proliferation-suppressive effect brought about by the addition of each anti-GPR20 antibody was indicated by relative activity to the number of live cells without antibody addition defined as 100%. Each anti-GPR20 antibody exhibited the maximum suppression of cell proliferation, when added at a final concentration of 0.11 or 0.33 μg/mL. FIG. 20 shows a cell survival rate at the concentration at which each antibody exhibited the maximum suppression of cell proliferation. It is believed that antibodies having strong internalization activity in this experiment exhibit a low cell survival rate. Rat IgG2a and IgG2b isotype control antibodies (R&D Systems, Inc.) were used as negative control antibodies recognizing an antigen unrelated to GPR20.

Example 3: Determination of Nucleotide Sequence of cDNA Encoding Variable Region of Rat Anti-GPR20 Antibody The nucleotide sequence of cDNA encoding each of the variable regions of the 21 rat anti-GPR20 antibodies (04-002, 04-006, 04-013, 04-014, 04-021, 04-037, 04-046, 04-047, 04-067, 04-068, 04-079, 04-114, 04-115, 04-125, 04-126, 04-127, 04-133, 04-139, 04-163, 13-024, and 13-048) evaluated for their internalization activity in Example 2 was determined by the following method.

3)-1 cDNA Synthesis

A cell lysate of each anti-GPR20 antibody-producing hybridoma (50 mM Tris-HCl (pH 7.5), 250 mM LiCl, 5 mM EDTA (pH 8), 0.5% lithium dodecyl sulfate (LiDS), 2.5 mM dithiothreitol (DTT)) was mixed with oligo dT25-conjugated magnetic beads (Dynabeads mRNA DIRECT Kit, Life Technologies Corp.), so that mRNA was bound to the magnetic beads. Subsequently, the magnetic beads were washed once each with mRNA washing solution A (10 mM Tris-HCl (pH 7.5), 0.15 M LiCl, 1 mM EDTA, 0.1% LiDS, 0.1% Triton X-100) and with a solution for cDNA synthesis (50 mM Tris-HCl (pH 8.3), 75 mM KCl, 3 mM MgCl2, 5 mM DTT, 0.5 mM dNTP, 0.2% Triton X-100, 1.2 units of RNase inhibitor (Life Technologies Corp.)), followed by cDNA synthesis in a solution for cDNA synthesis to which 12 units of SuperScript III Reverse Transcriptase (Life Technologies Corp.) had been added. Subsequently, the magnetic beads were washed with a 3' tailing reaction solution (50 mM potassium phosphate, 4 mM MgCl2, 0.5 mM dGTP, 0.2% Triton X-100, 1.2 units of RNase inhibitor (Life Technologies Corp.)), and thereafter, a 3' tailing reaction was carried out using a reaction solution to which 48 units of Terminal Transferase, recombinant (F. Hoffmann-La Roche, Ltd.) had been added.

3)-2 Amplification and Sequencing of Rat Immunoglobulin Heavy and Light Chain Variable Region Gene Fragments The magnetic beads were washed with a TE solution (10 mM Tris-HCl (pH 7.5), 1 mM EDTA, 0.1% Triton X-100), and thereafter, the rat immunoglobulin heavy chain and light chain genes were amplified by 5'-RACE PCR. Specifically, the magnetic beads were transferred to a PCR reaction solution (0.2 μM each primer, 0.2 mM each dNTP, 0.25 units of PrimeSTAR HS DNA Polymerase (Takara Bio Inc.)), and reaction was carried out at 35 cycles each involving 94° C. for 30 seconds and 68° C. for 90 seconds. The primer sets used were as described below. In the primer sequences, D represents a mixed base consisting of A, G, and T, and N represents a mixed base of A, C, G, and T.

PCR primer set (for heavy chain)
5'-GCTAGCGCTACCGGACTCA-GATCCCCCCCCCCCCCDN-3' (Nhe-polyC-S) (SEQ ID NO: 66)
5'-TCACTGAGCTGGTGAGAGTGTAGAGCCC-3' (rIgγ-AS1) (SEQ ID NO: 67)
5'-TCACCGAGCTGCTGAGGGTGTAGAGCCC-3' (rIgγ-AS2) (SEQ ID NO: 68)

PCR primer set (for light chain)
5'-GCTAGCGCTACCGGACTCA-GATCCCCCCCCCCCCCDN-3' (Nhe-polyC-S) (SEQ ID NO: 66) (which was the same as that for the heavy chain)
5'-TCAGTAACACTGTCCAGGACACCATCTC-3' (rIgκ-AS) (SEQ ID NO: 69)

The fragments amplified by the above-described PCR reaction were sequenced to analyze their nucleotide sequences. Oligonucleotides having the nucleotide sequences 5'-CTGGCTCAGGGAAATAGCC-3' (rIgγ-seq) (SEQ ID NO: 70) and 5'-TCCAGTTGCTAACTGTTCC-3' (rIgκ-seq) (SEQ ID NO: 71) were used as a sequencing primer for the heavy chain and a sequencing primer for the light chain, respectively.

The sequencing was carried out using a gene sequence analysis apparatus ("ABI PRISM 3700 DNA Analyzer; Applied Biosystems, Inc." or "Applied Biosystems 3730x1 Analyzer; Applied Biosystems, Inc."). In the sequencing reaction, Dye Terminator Cycle Sequencing System with AmpliTaq DNA polymerase (Life Technologies Corp.) and GeneAmp 9700 (Applied Biosystems, Inc.) were used.

As a result of comparing, with one another, amino acid sequences predicted from the determined nucleotide sequences encoding the heavy chain and light chain variable regions of the 22 rat anti-GPR20 antibodies, the antibodies were classified into the following 3 groups:
group A (04-002, 04-006, 04-013, 04-014, 04-037, 04-046, 04-047, 04-067, 04-068, 04-079, 04-114, 04-125, 04-126, 04-127, 04-133, 04-139, and 04-163), group B (04-021 and 04-115), and group C (13-024 and 13-048).

The full-length sequences of the heavy chain and light chain of each antibody were determined by linking them to known constant region sequences. The nucleotide sequence and amino acid sequence of the constant region of rat heavy chain IgG2b were used with reference to the nucleotide sequence and the amino acid sequence of AABRO3048905 (IGHG2B*01) disclosed in IMGT, the international ImMunoGeneTics information system (registered trademark). The nucleotide sequence and the amino acid sequence of the constant region of rat light chain IgK were used with reference to the nucleotide sequence and amino acid sequence of V01241 (IGKC*01) also disclosed in this system.

The heavy chain of the 04-046 antibody has the amino acid sequence shown in SEQ ID NO: 2 in the sequence listing. In the heavy chain amino acid sequence shown in SEQ ID NO: 2 in the sequence listing, the amino acid sequence consisting of the amino acid residues at positions 1 to 19 is a signal sequence, the amino acid sequence consisting of the amino acid residues at positions 20 to 142 is a variable region, and the amino acid sequence consisting of the amino acid residues at positions 143 to 475 is a constant region. The aforementioned variable region has CDRH1 consisting of the amino acid sequence at positions 45 to 54, CDRH2 consisting of the amino acid sequence at positions 69 to 78, and CDRH3 consisting of the amino acid sequence at positions 118 to 131, in SEQ ID NO: 2 in the sequence listing. The heavy chain variable region of the 04-046 antibody has the amino acid sequence shown in SEQ ID NO: 3 in the sequence listing. The CDRH1 of the 04-046 antibody has the amino acid sequence shown in SEQ ID NO: 4 in the sequence listing, the amino acid sequence of the CDRH2 has the amino acid sequence shown in SEQ ID NO: 5 in the sequence listing, and the amino acid sequence of the CDRH3 has the amino acid sequence shown in SEQ ID NO: 6 in the sequence listing. Furthermore, the sequence of the heavy chain of the 04-046 antibody is shown in FIG. 1.

The light chain of the 04-046 antibody has the amino acid sequence shown in SEQ ID NO: 7 in the sequence listing. In the light chain amino acid sequence shown in SEQ ID NO: 7 in the sequence listing, the amino acid sequence consisting of the amino acid residues at positions 1 to 20 is a signal sequence, the amino acid sequence consisting of the amino acid residues at positions 21 to 128 is a variable region, and the amino acid sequence consisting of the amino acid residues at positions 129 to 233 is a constant region. The aforementioned variable region has CDRL1 consisting of the amino acid sequence at positions 43 to 53, CDRL2 consisting of the amino acid sequence at positions 69 to 75, and CDRL3 consisting of the amino acid sequence at positions 108 to 116, in SEQ ID NO: 7 in the sequence listing. The light chain variable region of the 04-046 antibody has the amino acid sequence shown in SEQ ID NO: 8 in the sequence listing. The CDRL1 of the 04-046 antibody has the amino acid sequence shown in SEQ ID NO: 9 in the sequence listing, the amino acid sequence of the CDRL2 has the amino acid sequence shown in SEQ ID NO: 10 in the sequence listing, and the amino acid sequence of the CDRL3 has the amino acid sequence shown in SEQ ID NO: 11 in the sequence listing. Furthermore, the sequence of the light chain of the 04-046 antibody is shown in FIG. 2.

The heavy chain of the 04-079 antibody has the amino acid sequence shown in SEQ ID NO: 12 in the sequence listing. In the heavy chain amino acid sequence shown in SEQ ID NO: 12 in the sequence listing, the amino acid sequence consisting of the amino acid residues at positions 1 to 19 is a signal sequence, the amino acid sequence consisting of the amino acid residues at positions 20 to 142 is a variable region, and the amino acid sequence consisting of the amino acid residues at positions 143 to 475 is a constant region. The aforementioned variable region has CDRH1 consisting of the amino acid sequence at positions 45 to 54, CDRH2 consisting of the amino acid sequence at positions 69 to 78, and CDRH3 consisting of the amino acid sequence at positions 118 to 131, in SEQ ID NO: 12 in the sequence listing. The heavy chain variable region of the 04-079 antibody has the amino acid sequence shown in SEQ ID NO: 13 in the sequence listing. The CDRH1 of the 04-079 antibody has the amino acid sequence shown in SEQ ID NO: 14 in the sequence listing, the amino acid sequence of the CDRH2 has the amino acid sequence shown in SEQ ID NO: 15 in the sequence listing, and the amino acid sequence of the CDRH3 has the amino acid sequence shown in SEQ ID NO: 16 in the sequence listing. Furthermore, the sequence of the heavy chain of the 04-079 antibody is shown in FIG. 3.

The light chain of the 04-079 antibody has the amino acid sequence shown in SEQ ID NO: 17 in the sequence listing. In the light chain amino acid sequence shown in SEQ ID NO: 17 in the sequence listing, the amino acid sequence consisting of the amino acid residues at positions 1 to 20 is a signal sequence, the amino acid sequence consisting of the amino acid residues at positions 21 to 128 is a variable region, and the amino acid sequence consisting of the amino acid residues at positions 129 to 233 is a constant region. The aforementioned variable region has CDRL1 consisting of the amino acid sequence at positions 43 to 53, CDRL2 consisting of the amino acid sequence at positions 69 to 75, and CDRL3 consisting of the amino acid sequence at positions 108 to 116, in SEQ ID NO: 17 in the sequence listing. The light chain variable region of the 04-079 antibody has the amino acid sequence shown in SEQ ID NO: 18 in the sequence listing. The CDRL1 of the 04-079 antibody has the amino acid sequence shown in SEQ ID NO: 19 in the sequence listing, the amino acid sequence of the CDRL2 has the amino acid sequence shown in SEQ ID NO: 20 in the sequence listing, and the amino acid sequence of the CDRL3 has the amino acid sequence shown in SEQ ID NO: 21 in the sequence listing. Furthermore, the sequence of the light chain of the 04-079 antibody is shown in FIG. 4.

The heavy chain of the 04-126 antibody has the amino acid sequence shown in SEQ ID NO: 22 in the sequence listing. In the heavy chain amino acid sequence shown in SEQ ID NO: 22 in the sequence listing, the amino acid sequence consisting of the amino acid residues at positions 1 to 19 is a signal sequence, the amino acid sequence consisting of the amino acid residues at positions 20 to 142 is a variable region, and the amino acid sequence consisting of the amino acid residues at positions 143 to 475 is a constant region. The aforementioned variable region has CDRH1 consisting of the amino acid sequence at positions 45 to 54, CDRH2 consisting of the amino acid sequence at positions 69 to 78, and CDRH3 consisting of the amino acid sequence at positions 118 to 131, in SEQ ID NO: 22 in the sequence listing. The heavy chain variable region of the 04-126 antibody has the amino acid sequence shown in SEQ ID NO: 23 in the sequence listing. The CDRH1 of the 04-126 antibody has the amino acid sequence shown in SEQ ID NO: 24 in the sequence listing, the amino acid sequence of the CDRH2 has the amino acid sequence shown in SEQ ID NO: 25 in the sequence listing, and the amino acid sequence of the CDRH3 has the amino acid sequence shown in SEQ ID NO: 26 in the sequence listing. Furthermore, the sequence of the heavy chain of the 04-126 antibody is shown in FIG. 5.

The light chain of the 04-126 antibody has the amino acid sequence shown in SEQ ID NO: 27 in the sequence listing. In the light chain amino acid sequence shown in SEQ ID NO: 27 in the sequence listing, the amino acid sequence consisting of the amino acid residues at positions 1 to 20 is a signal sequence, the amino acid sequence consisting of the amino acid residues at positions 21 to 128 is a variable region, and the amino acid sequence consisting of the amino acid residues at positions 129 to 233 is a constant region. The aforementioned variable region has CDRL1 consisting of the amino acid sequence at positions 43 to 53, CDRL2 consisting of the amino acid sequence at positions 69 to 75, and CDRL3 consisting of the amino acid sequence at positions 108 to 116, in SEQ ID NO: 27 in the sequence listing. The light chain variable region of the 04-126 antibody has the amino acid sequence shown in SEQ ID NO: 28 in the sequence listing. The CDRL1 of the 04-126 antibody has the amino acid sequence shown in SEQ ID NO: 29 in the sequence listing, the amino acid sequence of the CDRL2 has the amino acid sequence shown in SEQ ID NO: 30 in the sequence listing, and the amino acid sequence of the CDRL3 has the amino acid sequence shown in SEQ ID NO: 31 in the sequence listing. Furthermore, the sequence of the light chain of the 04-126 antibody is shown in FIG. 6.

The heavy chain amino acid sequence of the 04-046 antibody is encoded by the nucleotide sequence shown in SEQ ID NO: 32 in the sequence listing. In the nucleotide sequence shown in SEQ ID NO: 32 in the sequence listing, the nucleotide sequence consisting of the nucleotides at positions 58 to 426 encodes the heavy chain variable region of the 04-046 antibody, and the nucleotide sequence consisting of the nucleotides at positions 427 to 1425 encodes the heavy chain constant region of the 04-046 antibody. The nucleotide sequence encoding the aforementioned variable region has a polynucleotide consisting of the nucleotide sequence at nucleotide positions 133 to 162 encoding CDRH1, a polynucleotide consisting of the nucleotide sequence at nucleotide positions 205 to 234 encoding CDRH2, and a polynucleotide consisting of the nucleotide sequence at nucleotide positions 352 to 393 encoding CDRH3, in SEQ ID NO: 32. The nucleotide sequence of the heavy chain variable region of the 04-046 antibody is also shown in SEQ ID NO: 33 in the sequence listing. Furthermore, the sequence of SEQ ID NO: 32 is shown in FIG. 1.

The light chain amino acid sequence of the 04-046 antibody is encoded by the nucleotide sequence shown in SEQ ID NO: 34 in the sequence listing. In the nucleotide sequence shown in SEQ ID NO: 34 in the sequence listing, the nucleotide sequence consisting of the nucleotides at positions 61 to 384 encodes the light chain variable region of the 04-046 antibody, and the nucleotide sequence consisting of the nucleotides at positions 385 to 699 encodes the light chain constant region of the 04-046 antibody. The nucleotide sequence encoding the aforementioned variable region has a polynucleotide consisting of the nucleotide sequence at nucleotide positions 127 to 159 encoding CDRL1, a polynucleotide consisting of the nucleotide sequence at nucleotide positions 205 to 225 encoding CDRL2, and a polynucleotide consisting of the nucleotide sequence at nucleotide positions 322 to 348 encoding CDRL3, in SEQ ID NO: 34. The nucleotide sequence of the light chain variable region of the 04-046 antibody is also shown in SEQ ID NO: 35 in the sequence listing. Furthermore, the sequence of SEQ ID NO: 34 is shown in FIG. 2.

The heavy chain amino acid sequence of the 04-079 antibody is encoded by the nucleotide sequence shown in SEQ ID NO: 36 in the sequence listing. In the nucleotide sequence shown in SEQ ID NO: 36 in the sequence listing, the nucleotide sequence consisting of the nucleotides at positions 58 to 426 encodes the heavy chain variable region of the 04-079 antibody, and the nucleotide sequence consisting of the nucleotides at positions 427 to 1425 encodes the heavy chain constant region of the 04-079 antibody. The nucleotide sequence encoding the aforementioned variable region has a polynucleotide consisting of the nucleotide sequence at nucleotide positions 133 to 162 encoding CDRH1, a polynucleotide consisting of the nucleotide sequence at nucleotide positions 205 to 234 encoding CDRH2, and a polynucleotide consisting of the nucleotide sequence at nucleotide positions 352 to 393 encoding CDRH3, in SEQ ID NO: 36. The nucleotide sequence of the heavy chain variable region of the 04-079 antibody is also shown in SEQ ID NO: 37 in the sequence listing. Furthermore, the sequence of SEQ ID NO: 37 is shown in FIG. 10.

The light chain amino acid sequence of the 04-079 antibody is encoded by the nucleotide sequence shown in SEQ ID NO: 38 in the sequence listing. In the nucleotide sequence shown in SEQ ID NO: 38 in the sequence listing, the nucleotide sequence consisting of the nucleotides at positions 61 to 384 encodes the light chain variable region of the 04-079 antibody, and the nucleotide sequence consisting of the nucleotides at positions 385 to 699 encodes the light chain constant region of the 04-079 antibody. The nucleotide sequence encoding the aforementioned variable region has a polynucleotide consisting of the nucleotide sequence at nucleotide positions 127 to 159 encoding CDRL1, a polynucleotide consisting of the nucleotide sequence at nucleotide positions 205 to 225 encoding CDRL2, and a polynucleotide consisting of the nucleotide sequence at nucleotide positions 322 to 348 encoding CDRL3, in SEQ ID NO: 38. The nucleotide sequence of the light chain variable region of the 04-079 antibody is also shown in SEQ ID NO: 39 in the sequence listing. Furthermore, the sequence of SEQ ID NO: 38 is shown in FIG. 4.

The heavy chain amino acid sequence of the 04-126 antibody is encoded by the nucleotide sequence shown in SEQ ID NO: 40 in the sequence listing. In the nucleotide sequence shown in SEQ ID NO: 40 in the sequence listing, the nucleotide sequence consisting of the nucleotides at positions 58 to 426 encodes the heavy chain variable region of the 04-126 antibody, and the nucleotide sequence consisting of the nucleotides at positions 427 to 1425 encodes the heavy chain constant region of the 04-126 antibody. The nucleotide sequence encoding the aforementioned variable region has a polynucleotide consisting of the nucleotide sequence at nucleotide positions 133 to 162 encoding CDRH1, a polynucleotide consisting of the nucleotide sequence at nucleotide positions 205 to 234 encoding CDRH2, and a polynucleotide consisting of the nucleotide sequence at nucleotide positions 352 to 393 encoding CDRH3, in SEQ ID NO: 40. The nucleotide sequence of the heavy chain variable region of the 04-126 antibody is also shown in SEQ ID NO: 41 in the sequence listing. Furthermore, the sequence of SEQ ID NO: 40 is shown in FIG. 5.

The light chain amino acid sequence of the 04-126 antibody is encoded by the nucleotide sequence shown in SEQ ID NO: 42 in the sequence listing. In the nucleotide sequence shown in SEQ ID NO: 42 in the sequence listing, the nucleotide sequence consisting of the nucleotides at positions 61 to 384 encodes the light chain variable region of the 04-126 antibody, and the nucleotide sequence consisting of the nucleotides at positions 385 to 699 encodes the light chain constant region of the 04-126 antibody. The nucleotide sequence encoding the aforementioned variable region has a polynucleotide consisting of the nucleotide sequence at nucleotide positions 127 to 159 encoding CDRL1, a polynucleotide consisting of the nucleotide sequence at nucleotide positions 205 to 225 encoding CDRL2, and a polynucleotide consisting of the nucleotide sequence at nucleotide positions 322 to 348 encoding CDRL3, in SEQ ID NO: 42. The nucleotide sequence of the light chain variable region of the 04-126 antibody is also shown in SEQ ID NO: 43 in the sequence listing. Furthermore, the sequence of SEQ ID NO: 42 is shown in FIG. 6.

Example 4: Analysis of GPR20-Binding Site of Anti-GPR20 Monoclonal Antibody

Binding sites of anti-human GPR20 antibodies were classified by measuring their binding activity against mouse GPR20, N-terminally FLAG-tagged human GPR20, and human/mouse chimeric GPR20 in which each of four extracellular regions (EC1, EC2, EC3, and EC4) of human GPR20 was substituted with a mouse GPR20-derived sequence, respectively, by Cell-ELISA. FIG. 21 is a diagram of the comparison between the amino acid sequences of human GPR20 (NP_005284) and mouse GPR20 (NP_775541). The four extracellular regions EC1 to EC4 are represented by positions in the amino acid sequence of human GPR20. EC1 corresponds to positions 1 to 48, EC2 corresponds to positions 108 to 125, EC3 corresponds to positions 190 to 196, and EC4 corresponds to positions 260 to 275.

4)-1 Construction of Mouse GPR20 Expression Vector

According to a method known to a person skilled in the art, cDNA was artificially synthesized based on Ref Seq sequence NM_173365 of mouse GPR20, and then cloned into pcDNA-DEST40 expression vector (Invitrogen Corp.) to construct mouse GPR20 expression vector pcDNA-mGPR20.

4)-2 Construction of N-Terminally FLAG-Tagged Human GPR20 and Human/Mouse Chimeric GPR20 Expression Vectors

4)-2-1

In the construction of expression vectors given below, using the full-length human GPR20 expression vector pcDNA3.1-hGPR20 produced in Example 1 as a template, each PCR reaction was carried out with the primer set given below. In this reaction, KOD FX DNA polymerase (Toyobo Co., Ltd.) was used, and the reaction was carried out at 15 cycles or 10 cycles each involving 98° C. for 10 seconds, 58° C. for 30 seconds, and 68° C. for 7 minutes. Thereafter, the obtained PCR product was treated with the restriction enzyme Dpnl. *Escherichia coli* TOP10 (Invitrogen Corp.) was transformed with this Dpnl-digested DNA to construct expression vectors for N-terminally FLAG-tagged human GPR20 and human GPR20 with EC2 or EC3 or EC4 substituted with a mouse GPR20-derived sequence. The primer set used in each PCR reaction was as follows.

PCR primer set (for N-terminally FLAG-tagged human GPR20)
5'-GACTACAAAGACGATGACGACAAGCCCTCT-GIGTCTCCAGC-3' (NFLAG-1; SEQ ID NO: 72)
5'-CTTGTCGTCATCGTCTTTGTAGTCCATGGTG-GAGCCTGC-3' (NFLAG-2; SEQ ID NO: 73)

PCR primer set (for human GPR20 with EC2 substituted with a mouse GPR20-derived sequence)
5'-ACGCGCTTCGCTGTGTTCTACGGCGCCAG-3' (mEC2-1; SEQ ID NO: 74)
5'-CTGGCGCCGTAGAACACAGCGAAGCGCGT-3' (mEC2-2; SEQ ID NO: 75)

PCR primer set (for human GPR20 with EC3 substituted with a mouse GPR20-derived sequence)
5'-TGTCGGTGCTGGGCGTGAAGTCGGGTGGACGAT-CATGCTGCCGTGTCTT-3' (mEC3-1; SEQ ID NO: 76)
5'-AAGACACGGCAGCATGATCGTCCACCCGACTI-CACGCCCAGCACCGACA-3' (mEC3-2; SEQ ID NO: 77)

PCR primer set (for human GPR20 with EC4 substituted with a mouse GPR20-derived sequence)
5'-TGGCGCTGIGGCC-CAACGTACCTAAGCACACGAGCCTCGTGGT-3' (mEC4-1; SEQ ID NO: 78)
5'-ACCACGAGGCTCGTGTGCTTAGGTACGTTGGGC-CACAGCGCCA-3' (mEC4-2; SEQ ID NO: 79)

4)-2-2

An expression vector for human GPR20 with EC1 substituted with a mouse GPR20-derived sequence was constructed using In-Fusion (registered trademark) HD Cloning Kit (Clontech Laboratories, Inc.). Specifically, using the full-length human GPR20 expression vector pcDNA3.1-hGPR20 produced in Example 1 as a template, PCR reaction was carried out with the primer set given below and KOD FX DNA polymerase (Toyobo Co., Ltd.) at 10 cycles each involving 98° C. for 10 seconds, 58° C. for 30 seconds, and 68° C. for 7 minutes to amplify a DNA fragment comprising the vector sequence.

PCR primer set (for human GPR20 with EC1 substituted with a mouse GPR20-derived sequence—1)
5'-GCGCTGATGGCGGTGCACGGAGCCATCT-3' (mEC1-1; SEQ ID NO: 80)
5'-AGAGGGCATGGTGGAGCCTGCTTT-3' (mEC1-2; SEQ ID NO: 81)

Also, using the full-length mouse GPR20 expression vector pcDNA-mGPR20 constructed in 4)-1 as a template, PCR reaction was carried out with the primer set given below at 20 cycles in the same manner as above to amplify a DNA fragment encoding the EC1 region of mouse GPR20.

PCR primer set (for human GPR20 with EC1 substituted with a mouse GPR20-derived sequence—2)
5'-AGGCTCCACCATGCCCTCTGCGTTGTCTATGA-3' (mEC1-3; SEQ ID NO: 82)
5'-CACCGCCATCAGCGCTTGCCACAGGCTGGG-GAAGGIGGCTTGCA-3' (mEC1-4; SEQ ID NO: 83)

The above-described two DNA fragments were subjected to agarose gel electrophoresis according to the standard method, and DNA fragments having the size of interest were isolated using QlAquick Gel Extraction Kit (Promega Corp.). These two DNA fragments were annealed together through the reaction of In-Fusion HD enzyme (Clontech Laboratories, Inc.), and *Escherichia coli* TOP10 (Invitrogen Corp.) was transformed with the ligation product to construct an expression vector for human GPR20 with EC1 substituted with a mouse GPR20-derived sequence.

4)-3 Evaluation of Binding Properties of Anti-Human GPR20 Antibody by Cell-ELISA The binding activity of the anti-GPR20 antibodies 04-046, 04-079, 04-126, 04-021, 13-024, and 13-048 against 293α cells into which different GPR20 expression vectors were transiently introduced was examined by the same method as the Cell-ELISA method shown in Example 1. The measurement results are shown in FIGS. 22(a) and 22(b). On the abscissa of FIG. 22, EV depicts a control, human GPR20 depicts cells expressing human full-length GPR20, FLAG-huGPR20 depicts cells expressing N-terminally FLAG-tagged human GPR20, mouse GPR20 depicts cells expressing mouse GPR20, hGPR20 mECD1 depicts cells expressing chimeric GPR20 in which ECD1 of human GPR20 was substituted with ECD1 of mouse GPR20, hGPR20 mECD2 depicts cells expressing chimeric GPR20 in which ECD2 of human GPR20 was substituted with ECD2 of mouse GPR20, hGPR20 mECD3 depicts cells expressing chimeric GPR20 in which ECD3 of human GPR20 was substituted with ECD3 of mouse GPR20, and hGPR20 mECD4 depicts cells expressing chimeric GPR20 in which ECD4 of human GPR20 was substituted with ECD4 of mouse GPR20.

Among the three classifications based on antibody sequence similarity shown in Example 3, 04-046, 04-079 and 04-126 in group A did not bind to mouse GPR20, and lost binding activity as a result of substituting EC1 (also referred to as ECD1) or EC2 (also referred to as ECD2) of human GPR20 with that of mouse-derived GPR20. This indicates that 04-046, 04-079 and 04-126 recognize a conformation consisting of EC1 and EC2 of GPR20.

04-021 in group B exhibited weak binding activity against mouse GPR20, and the binding activity was attenuated to the same level as the binding activity against mouse GPR20 as a result of substituting EC1 of human GPR20 with that of mouse-derived GPR20. Furthermore, 04-021 did not exhibit binding activity against N-terminally FLAG-tagged human GPR20, indicating that this antibody recognizes the N-terminus or its neighborhood of GPR20 EC1.

13-024 and 13-048 in group C did not bind to mouse GPR20, and the binding activity was remarkably decreased as a result of substituting EC1 of human GPR20 with that of mouse-derived GPR20, indicating that these antibodies bind to EC1.

From the above-described experiment, Table 1 shows the correspondence between the GPR20 extracellular region recognized by each antibody and the internalization activity (the internalization activity is stronger as the cell survival rate is lower) of the antibody shown in FIG. 20.

TABLE 1

| Group classification based on amino acid sequence of antibody | Antibody No. | Subclass | Cell survival rate (%) in internalization activity evaluation | GPR20 extracellular region recognized |
|---|---|---|---|---|
| A | 04-126 | IgG2b | 54 | EC1, EC2 |
| A | 04-114 | IgG2b | 57 | EC1, EC2 |
| A | 04-046 | IgG2b | 57 | EC1, EC2 |
| A | 04-067 | IgG2b | 58 | EC1, EC2 |
| A | 04-002 | IgG2b | 60 | EC1, EC2 |
| A | 04-014 | IgG2b | 60 | EC1, EC2 |
| A | 04-163 | IgG2b | 61 | EC1, EC2 |
| A | 04-139 | IgG2b | 61 | EC1, EC2 |
| A | 04-079 | IgG2b | 62 | EC1, EC2 |
| A | 04-006 | IgG2b | 63 | EC1, EC2 |
| A | 04-127 | IgG2b | 63 | EC1, EC2 |
| A | 04-125 | IgG2b | 64 | EC1, EC2 |
| A | 04-013 | IgG2b | 67 | EC1, EC2 |
| A | 04-133 | IgG2b | 67 | EC1, EC2 |
| A | 04-047 | IgG2a | 69 | EC1, EC2 |
| B | 04-021 | IgG2b | 70 | EC1 N-terminus |
| A | 04-037 | IgG2b | 71 | EC1, EC2 |
| C | 13-048 | IgG2b | 74 | EC1 |
| A | 04-068 | IgG2a | 76 | EC1, EC2 |
| C | 13-024 | IgG2b | 77 | EC1 |
| B | 04-115 | IgG2b | 86 | EC1 N-terminus |

When the "GPR20 extracellular region recognized" in the table is indicated by the range of the amino acid sequence of human GPR20, EC1 corresponds to positions 1 to 48, EC2 corresponds to positions 108 to 125, EC3 corresponds to positions 190 to 196, and EC4 corresponds to positions 260 to 275. As a result of studying the relationship between the internalization activity (the internalization activity is higher as the cell survival rate is lower) of each antibody and the region recognized by the anti-GPR20 antibody, it was found that all the antibodies that exhibited a cell survival rate of less than 70% and thus seemed to have high internalization activity were antibodies derived from group A. Therefore, it was demonstrated that antibodies that exhibit high internalization activity are concentrated in antibodies of group A which recognize a conformation consisting of EC1 and EC2 of human GPR20. EC2 of human GPR20 differed only in tyrosine residue at position 113 from that (phenylalanine) of mouse GPR20, suggesting that antibodies of group A which recognize a conformation consisting of EC1 and EC2 recognize this tyrosine residue.

Example 5: Preparation of Human Chimeric Anti-GPR20 Antibody 04-046Ch

5)-1 Construction of Human Chimeric Anti-GPR20 Antibody Expression Vector

5)-1-1 Construction of Chimeric and Humanized Antibody Light Chain Expression Vector pCMA-LK An approx. 5.4-kb fragment, which had been obtained by digesting plasmid pcDNA3.3-TOPO/LacZ (Invitrogen Corp.) with the restriction enzymes XbaI and PmeI, was ligated with a DNA fragment comprising a DNA sequence (SEQ ID NO: 84) encoding a human κ chain secretion signal and a human κ chain constant region, using In-Fusion Advantage PCR cloning kit (Clontech Laboratories, Inc.), to prepare pcDNA3.3/LK.

Using pcDNA3.3/LK as a template, PCR was carried out with the primer set given below, and the obtained approx. 3.8-kb fragment was phosphorylated and then self-ligated to construct chimeric and humanized antibody light chain expression vector pCMA-LK having a signal sequence, a cloning site, and the DNA sequence of the human κ chain constant region downstream of CMV promoter.

Primer Set
5'-TATACCGTCGACCTCTAGCTAGAGCTTGGC-3' (3.3-F1; SEQ ID NO: 85)
5'-GCTATGGCAGGGCCTGCCGCCCCGACGTTG-3' (3.3-R1; SEQ ID NO: 86)

5)-1-2 Construction of Chimeric and Humanized Antibody IgG1 Type Heavy Chain Expression Vector pCMA-G1

A DNA fragment, which had been obtained by digesting pCMA-LK with XbaI and PmeI to remove the DNA sequence encoding the κ chain secretion signal and the human κ chain constant region therefrom, was ligated to a DNA fragment comprising a DNA sequence (SEQ ID NO: 87) encoding a human heavy chain signal sequence and the amino acids in a human IgG1 constant region, using In-Fusion Advantage PCR cloning kit (Clontech Laboratories, Inc.), to construct chimeric and humanized antibody IgG1 type heavy chain expression vector pCMA-G1 having a signal sequence, a cloning site, and the DNA sequence of the human IgG1 heavy chain constant region downstream of CMV promoter.

5)-1-3 Construction of Human Chimeric Anti-GPR20 Antibody Heavy Chain Expression Vector A human chimeric antibody heavy chain expression vector was constructed based on the amino acid sequence (SEQ ID NO: 3) of the heavy chain variable region of the rat anti-GPR20 antibody 04-046 determined in Example 3)-2. A DNA fragment corresponding to nucleotide positions 36 to 443 including a DNA sequence encoding the variable region in the nucleotide sequence (SEQ ID NO: 46) of the heavy chain of the human chimeric anti-GPR20 antibody 04-046Ch was synthesized (GENEART, artificial gene synthesis service). Using the synthesized DNA fragment as a template, a DNA fragment comprising a DNA sequence encoding the heavy chain variable region of the human chimeric anti-GPR20 antibody was amplified with KOD-Plus- (Toyobo Co., Ltd.) and the primer set given below. Using In-Fusion HD PCR cloning kit (Clontech Laboratories, Inc.), the amplified DNA fragment was inserted into a site of the chimeric and humanized antibody IgG1 type heavy chain expression vector pCMA-G1 that had been cleaved with the restriction enzyme BlpI, so as to construct a human chimeric anti-GPR20 antibody 04-046Ch heavy chain expression vector. The obtained expression vector was named "pCMA/04-046Ch-H". The amino acid sequence of the heavy chain of the human chimeric anti-GPR20 antibody 04-046Ch is shown in SEQ ID NO: 44. The nucleotide sequence of SEQ ID NO: 46 and the amino acid sequence of SEQ ID NO: 44 are also shown in FIG. 7.

Primer Set
5'-AGCTCCCAGATGGGTGCTGAGC-3' (EG-Inf-F; SEQ ID NO: 88)
5'-GGGCCCTTGGTGGAGGCTGAGC-3' (EG1-Inf-R; SEQ ID NO: 89)

5)-1-4 Construction of Human Chimeric Anti-GPR20 Antibody Light Chain Expression Vector A human chimeric antibody light chain expression vector was constructed based on the amino acid sequence (SEQ ID NO: 8) of the light chain variable region of the rat anti-GPR20 antibody 04-046 determined in Example 3)-2. A DNA fragment corresponding to nucleotide positions 38 to 399 including a DNA sequence encoding the variable region in the nucleotide sequence (SEQ ID NO: 47) of the light chain of the human chimeric anti-GPR20 antibody 04-046Ch was synthesized (GENEART, artificial gene synthesis service). Using the synthesized DNA fragment as a template, a DNA fragment comprising a DNA sequence encoding the light chain variable region of the human chimeric anti-GPR20 antibody was amplified with KOD-Plus- (Toyobo Co., Ltd.) and the primer set given below. Using In-Fusion HD PCR cloning kit (Clontech Laboratories, Inc.), the amplified DNA fragment was inserted into a site of the chimeric and humanized antibody light chain expression vector pCMA-LK that had been cleaved with the restriction enzyme BsiWI, so as to construct a human chimeric anti-GPR20 antibody 04-046Ch light chain expression vector. The obtained expression vector was named "pCMA/04-046Ch-L". The amino acid sequence of the light chain of the human chimeric anti-GPR20 antibody 04-046Ch is shown in SEQ ID NO: 45. The nucleotide sequence of SEQ ID NO: 47 and the amino acid sequence of SEQ ID NO: 45 are also shown in FIG. 8.

Primer Set
5'-CTGTGGATCTCCGGCGCGTACGGC-3' (CM-LKF; SEQ ID NO: 90)
5'-GGAGGGGGCGGCCACGGCTCTCTTCAGTTC-3' (046L-R; SEQ ID NO: 91)

5)-2 Expression and Purification of Human Chimeric Anti-GPR20 Antibody

5)-2-1 Expression of Human Chimeric Anti-GPR20 Antibody

In accordance with the manual, FreeStyle 293F cells (Invitrogen Corp.) were cultured and passaged. $1.2 \times 10^9$ FreeStyle 293F cells (Invitrogen Corp.) in the logarithmic growth phase were seeded on 3-L Fernbach Erlenmeyer Flask (Corning Inc.), then diluted with FreeStyle 293 expression medium (Invitrogen Corp.) at $2.0 \times 10^6$ cells/mL, and shake-cultured at 90 rpm in an 8% CO2 incubator at 37° C. for 1 hour. 1.8 mg of Polyethyleneimine (Polyscience #24765) was dissolved in 20 mL of Opti-Pro SFM medium (Invitrogen Corp.). Meanwhile, the heavy chain expression vector (0.24 mg) and the light chain expression vector (0.36 mg) prepared using NucleoBond Xtra (Takara Bio Inc.) were added to 20 mL of Opti-Pro SFM medium (Invitrogen Corp.). To 20 mL of the Polyethyleneimine/Opti-Pro SFM mixed solution, 20 mL of the expression vector/Opti-Pro SFM mixed solution was added, and the obtained mixture was gently stirred. After incubation for 5 minutes, the mixture was added to the FreeStyle 293F cells. The cells were shake-cultured at 90 rpm in an 8% CO2 incubator at 37° C. for 4 hours, and thereafter, 600 mL of EX-CELL VPRO medium (SAFC Biosciences Inc.), 18 mL of Gluta-MAX I (GIBCO), and 30 mL of Yeastolate Ultrafiltrate (GIBCO) were added to the culture. The cells were further shake-cultured at 90 rpm in an 8% CO2 incubator at 37° C. for 7 days. The obtained culture supernatant was filtrated through Disposable Capsule Filter (Advantec #CCS-045-E1H).

A human chimeric anti-GPR20 antibody obtained by the combination of pCMA/04-046Ch-H and pCMA/04-046Ch-L was named "04-046Ch".

5)-2-2 Purification of 04-046Ch by Two-Step Process

The antibody was purified from the culture supernatant obtained in Example 5)-2-1, by a two-step process, namely, by rProtein A affinity chromatography (at 4 to 6° C.) and ceramic hydroxyapatite (at room temperature). Buffer replacement after the rProtein A affinity chromatography purification and after the ceramic hydroxyapatite purification was carried out at 4 to 6° C. The culture supernatant was applied to MabSelectSuRe (GE Healthcare Biosciences Corp., HiTrap column) that had been equilibrated with PBS. After the entire culture solution had entered the column, the column was washed with PBS in an amount of two or more times the volume of the column. Subsequently, elution was carried out using a 2 M arginine hydrochloride solution (pH 4.0), so that a fraction containing an antibody was collected. This fraction was dialyzed (Thermo Fisher Scientific Inc., Slide-A-Lyzer Dialysis Cassette), so that the buffer was replaced with PBS. Thereafter, an antibody solution that had been 5-fold diluted with a buffer of 5 mM sodium phosphate/50 mM MES/pH 7.0 was applied to a ceramic hydroxyapatite column (Bio-Rad Laboratories, Inc., Bio-Scale CHT Type-1 Hydroxyapatite Column) that had been equilibrated with a buffer of 5 mM NaPi/50 mM MES/30 mM NaCl/pH 7.0. Elution was carried out on a linear concentration gradient of sodium chloride, so that a fraction containing an antibody was collected. This fraction was dialyzed (Thermo Fisher Scientific Inc., Slide-A-Lyzer Dialysis Cassette), so that the buffer was replaced with HBSor (25 mM histidine/5% sorbitol, pH 6.0). The antibody was concentrated with Centrifugal UF Filter Device VIVASPIN20 (molecular weight cutoff: UF10K, Sartorius Inc., 4° C.), thereby adjusting the IgG concentration to 20 mg/mL or more. Finally, the antibody was filtrated through Minisart-Plus filter (Sartorius Inc.) to obtain a purified sample.

5)-3 Evaluation of Binding Activity of Human Chimeric Anti-GPR20 Antibody

The GPR20-binding activity of the produced human chimeric anti-GPR20 antibody 04-046Ch was confirmed by flow cytometry. Using Lipofectamine 2000, pcDNA3.1-hGPR20 or pcDNA3.1 was transiently introduced into 293T cells by the same method as that applied in Example 1)-5-1. The cells were cultured overnight under conditions of 37° C. and 5% CO2, and thereafter, a cell suspension was prepared. To the obtained cell suspension, the human chimeric anti-GPR20 antibody 04-046Ch or human IgG as a negative control was added, and the obtained mixture was left standing at 4° C. for 1 hour. Thereafter, the cells were washed twice with PBS supplemented with 5% FBS, and then suspended by the addition of PE-labeled F(ab')2 Fragment anti-human IgG, Fcγ antibody (Jackson ImmunoResearch Inc.) that had been 320-fold diluted with PBS supplemented with 5% FBS. The cells were left standing at 4° C. for 1 hour. The cells were washed twice with PBS supplemented with 5% FBS, and then re-suspended in PBS supplemented with 5% FBS, followed by detection using a flow cytometer (FC500; Beckman Coulter, Inc.). The data was analyzed using Flowjo (Tree Star, Inc.). 04-046Ch bound to the 293T cells transfected with pcDNA3.1-hGPR20 in an antibody concentration-dependent manner (FIG. 23(a)), without binding to the 293T cells transfected with the negative control pcDNA3.1 (FIG. 23(b)). The abscissa in FIG. 23 depicts an antibody concentration, and the ordinate depicts mean fluorescent intensity indicating the amount of the antibody bound.

Example 6: Production of Humanized Anti-GPR20 Antibody

6)-1 Design of Humanized Form of Anti-GPR20 Antibody 04-046

6)-1-1 Molecular Modeling of 04-046 Variable Region

The molecular modeling of the variable regions of 04-046 was carried out according to a method known as homology modeling (Methods in Enzymology, 203, 121-153, (1991)). The primary sequences of the variable regions of human immunoglobulins registered in Protein Data Bank (Nuc. Acid Res. 35, D301-D303 (2007)) (three-dimensional structures inferred from X-ray crystal structures are available) were compared with the variable regions of 04-046 determined in Example 3)-2. 1SY6 and 1LK3 were selected as sequences having the highest sequence identity to the heavy chain and light chain variable regions of 04-046. The three-dimensional structures of framework regions were produced by combining, with one another, the coordinates of 1SY6 and 1LK3 corresponding to the heavy chain and light chain of 04-046, so as to obtain a "framework model". After that, the representative conformation of each CDR was incorporated into the framework model. Finally, in order to obtain a molecular model with possible variable regions of 04-046, an energy calculation for eliminating atomic contact that was disadvantageous in terms of energy was carried out. The above-described procedures were carried out using a commercially available protein three-dimensional structure analysis program Discovery Studio (Accelrys Inc.).

6)-1-2 Design of Amino Acid Sequence of Humanized h046

A humanized antibody of 04-046 (hereinafter, referred to as "humanized h046") was constructed according to a method generally known as CDR grafting (Proc. Natl. Acad. Sci. USA 86, 10029-10033 (1989)). An acceptor antibody was selected based on amino acid identity in the framework regions.

The sequences of the framework regions of 04-046 were compared with the framework regions of human subgroup consensus sequences determined by KABAT et al. (Sequences of Proteins of Immunological Interest, 5th Ed. Public Health Service National Institutes of Health, Bethesda, Md. (1991)). The consensus sequences of human γ chain subgroup 1 and human κ chain subgroup 1 had high sequence identity in their framework regions as to the heavy chain and light chain, respectively, and based on this, they were selected as acceptors. With regard to the acceptors, the amino acid residues in the framework regions were aligned with the amino acid residues of 04-046, so that the positions, at which different amino acids were used, were identified. The positions of these residues were analyzed using the three-dimensional model of 04-046 constructed above, and donor residues to be grafted onto the acceptors were selected based on the criteria given by Queen et al. (Proc. Natl. Acad. Sci. USA 86, 10029-10033 (1989)). The thus-selected several donor residues were introduced into an acceptor antibody, so as to construct the sequence of humanized h046 as in the manner described in the following examples.

6)-2 Humanization of 04-046_Heavy Chain

6)-2-1 Humanized h046-H4b Type Heavy Chain

A humanized h046 heavy chain designed by substituting glutamine at amino acid position 24 with valine, leucine at amino acid position 30 with valine, alanine at amino acid position 31 with lysine, serine at amino acid position 35 with alanine, isoleucine at amino acid position 39 with valine, lysine at amino acid position 57 with arginine, threonine at amino acid positions 40 and 59) with alanine, threonine at amino acid position 60) with proline, isoleucine at amino acid position 67 with methionine, lysine at amino acid position 86 with arginine, alanine at amino acid position 87 with valine, leucine at amino acid position 89 with isoleucine, valine at amino acid position 91 with alanine, phenylalanine at amino acid position 99 with threonine, glutamine at amino acid position 101 with glutamic acid, threonine at amino acid position 106 with arginine, proline at amino acid position 107 with serine, aspartic acid at amino acid position 108 with glutamic acid, serine at amino acid position 120 with threonine, isoleucine at amino acid position 122 with valine, valine at amino acid position 136 with threonine, and methionine at amino acid position 137 with leucine in SEQ ID NO: 44 as to the variable region moiety (amino acid sequence consisting of the amino acid residues at positions 20 to 142 in the amino acid sequence shown in SEQ ID NO: 44) in the human chimeric antibody 04-046Ch heavy chain shown in SEQ ID NO: 44, was named "humanized h046-H4b type heavy chain" (also referred to as "h046-H4b").

The amino acid sequence of the humanized h046-H4b type heavy chain is shown in SEQ ID NO: 48 in the sequence listing. In the amino acid sequence shown in SEQ ID NO: 48, the sequence consisting of the amino acid residues at positions 1 to 19 corresponds to a signal sequence, the sequence consisting of the amino acid residues at positions 20 to 142 corresponds to a heavy chain variable region, and the sequence consisting of the amino acid residues at positions 143 to 472 corresponds to a heavy chain constant region. The nucleotide sequence encoding the amino acid sequence of SEQ ID NO: 48 is shown in SEQ ID NO: 49 in the sequence listing. In the nucleotide sequence of SEQ ID NO: 49, the sequence consisting of the nucleotides at positions 1 to 57 corresponds to a signal sequence, the sequence consisting of the nucleotides at positions 58 to 426 corresponds to a sequence encoding the heavy chain variable region, and the sequence consisting of the nucleotides at positions 427 to 1416 corresponds to a sequence encoding the heavy chain constant region. The amino acid sequence of SEQ ID NO: 48 is also shown in FIG. 9.

6)-2-2 Humanized h046-H4e Type Heavy Chain

A humanized h046 heavy chain designed by substituting glutamine at amino acid position 20 with glutamic acid, glutamine at amino acid position 24 with valine, leucine at amino acid position 30 with valine, alanine at amino acid position 31 with lysine, serine at amino acid position 35 with alanine, isoleucine at amino acid position 39 with valine, lysine at amino acid position 57 with arginine, threonine at amino acid position 59 with alanine, threonine at amino acid position 60 with proline, isoleucine at amino acid position 67 with methionine, lysine at amino acid position 86 with arginine, alanine at amino acid positions 68 and 87 with valine, leucine at amino acid position 89 with isoleucine, valine at amino acid position 91 with alanine, phenylalanine at amino acid position 99 with threonine, glutamine at amino acid position 101 with glutamic acid, threonine at amino acid position 106) with arginine, proline at amino acid position 107) with serine, aspartic acid at amino acid position 108 with glutamic acid, serine at amino acid position 120 with threonine, isoleucine at amino acid position 122 with valine, valine at amino acid position 136 with threonine, and methionine at amino acid position 137 with leucine in SEQ ID NO: 44 as to the variable region moiety in the human chimeric antibody 04-046Ch heavy chain shown in SEQ ID NO: 44, was named "humanized h046-H4e type heavy chain" (also referred to as "h046-H4e").

The amino acid sequence of the humanized h046-H4e type heavy chain is shown in SEQ ID NO: 50 in the sequence listing. In the amino acid sequence of SEQ ID NO: 50, the sequence consisting of the amino acid residues at positions 1 to 19 corresponds to a signal sequence, the sequence consisting of the amino acid residues at positions 20 to 142 corresponds to a heavy chain variable region, and the sequence consisting of the amino acid residues at positions 143 to 472 corresponds to a heavy chain constant region. The nucleotide sequence encoding the amino acid sequence of SEQ ID NO: 50 is shown in SEQ ID NO: 51 in the sequence listing. In the nucleotide sequence of SEQ ID NO: 51, the sequence consisting of the nucleotides at positions 1 to 57 corresponds to a signal sequence, the sequence consisting of the nucleotides at positions 58 to 426 corresponds to a sequence encoding the heavy chain variable region, and the sequence consisting of the nucleotides at positions 427 to 1416 corresponds to a sequence encoding the heavy chain constant region. The amino acid sequence of SEQ ID NO: 50 is also shown in FIG. 10.

6)-2-3 Humanized h046-H5b Type Heavy Chain

A humanized h046 heavy chain designed by substituting glutamine at amino acid position 24 with valine, leucine at amino acid position 30 with valine, alanine at amino acid position 31 with lysine, serine at amino acid position 35 with alanine, isoleucine at amino acid position 39 with valine, lysine at amino acid position 57 with arginine, threonine at amino acid position 59 with alanine, threonine at amino acid position 60 with proline, isoleucine at amino acid position 67 with methionine, lysine at amino acid position 86 with arginine, alanine at amino acid position 87 with valine, leucine at amino acid position 89 with isoleucine, valine at amino acid position 91 with alanine, phenylalanine at amino acid position 99 with asparagine, glutamine at amino acid position 101 with glutamic acid, threonine at amino acid position 106) with arginine, proline at amino acid position 107 with serine, aspartic acid at amino acid position 108 with glutamic acid, serine at amino acid position 120 with threonine, isoleucine at amino acid position 122 with valine, valine at amino acid position 136) with threonine, and methionine at amino acid position 137 with leucine in SEQ ID NO: 44 as to the variable region moiety in the human chimeric antibody 04-046Ch heavy chain shown in SEQ ID NO: 44, was named "humanized h046-H5b type heavy chain" (also referred to as "h046-H5b").

The amino acid sequence of the humanized h046-H5b type heavy chain is shown in SEQ ID NO: 52 in the sequence listing. In the amino acid sequence of SEQ ID NO: 52, the sequence consisting of the amino acid residues at positions 1 to 19 corresponds to a signal sequence, the sequence consisting of the amino acid residues at positions 20 to 142 corresponds to a heavy chain variable region, and the sequence consisting of the amino acid residues at positions 143 to 472 corresponds to a heavy chain constant region. The nucleotide sequence encoding the amino acid sequence of SEQ ID NO: 52 is shown in SEQ ID NO: 53 in the sequence listing. In the nucleotide sequence of SEQ ID NO: 53, the sequence consisting of the nucleotides at positions 1 to 57 corresponds to a signal sequence, the sequence consisting of the nucleotides at positions 58 to 426 corresponds to a sequence encoding the heavy chain variable region, and the sequence consisting of the nucleotides at positions 427 to 1416 corresponds to a sequence encoding the heavy chain constant region. The amino acid sequence of SEQ ID NO: 52 is also shown in FIG. 11.

6)-2-4 Humanized h046-H8 Type Heavy Chain

A humanized h046 heavy chain designed by substituting phenylalanine at amino acid position 80 with asparagine as to the variable region moiety in the human chimeric antibody 04-046Ch heavy chain shown in SEQ ID NO: 44, was named "humanized h046-H8 type heavy chain" (also referred to as "h046-H8").

The amino acid sequence of the humanized h046-H8 type heavy chain is shown in SEQ ID NO: 54 in the sequence listing. In the amino acid sequence of SEQ ID NO: 54, the sequence consisting of the amino acid residues at positions 1 to 19, the sequence consisting of the amino acid residues at positions 20 to 142, and the sequence consisting of the amino acid residues at positions 143 to 472 correspond to a signal sequence, a heavy chain variable region, and a heavy chain constant region, respectively. The nucleotide sequence encoding the amino acid sequence of SEQ ID NO: 54 is shown in SEQ ID NO: 55 in the sequence listing. In the nucleotide sequence of SEQ ID NO: 55, the sequence consisting of the nucleotides at positions 1 to 57, the sequence consisting of the nucleotides at positions 58 to 426, and the sequence consisting of the nucleotides at positions 427 to 1416 encode the signal sequence, the heavy chain variable region sequence, and the heavy chain constant region sequence, respectively. The amino acid sequence of SEQ ID NO: 54 is also shown in FIG. 12.

6)-2-5 Humanized h046-H10 Type Heavy Chain

A humanized h046 heavy chain designed by substituting isoleucine at amino acid position 39 with valine and phenylalanine at amino acid position 99 with asparagine in SEQ ID NO: 44 as to the variable region moiety in the human chimeric antibody 04-046Ch heavy chain shown in SEQ ID NO: 44, was named "humanized h046-H10 type heavy chain" (also referred to as "h046-H10").

The amino acid sequence of the humanized h046-H10 type heavy chain is shown in SEQ ID NO: 56 in the sequence listing. In the amino acid sequence of SEQ ID NO: 56, the sequence consisting of the amino acid residues at positions 1 to 19 corresponds to a signal sequence, the sequence consisting of the amino acid residues at positions 20 to 142 corresponds to a heavy chain variable region, and the sequence consisting of the amino acid residues at positions 143 to 472 corresponds to a heavy chain constant region. The nucleotide sequence encoding the amino acid sequence of SEQ ID NO: 56 is shown in SEQ ID NO: 57 in the sequence listing. In the nucleotide sequence of SEQ ID NO: 57, the sequence consisting of the nucleotides at positions 1 to 57 is a signal sequence, the sequence consisting of the nucleotides at positions 58 to 426 encodes the heavy chain variable region sequence, and the sequence consisting of the nucleotides at positions 427 to 1416 encodes the heavy chain constant region sequence. The amino acid sequence of SEQ ID NO: 56 is also shown in FIG. 13.

6)-3 Humanization of 04-046 Light Chain

6)-3-1 Humanized h046-L1 Type Light Chain

A humanized h046 light chain designed by substituting threonine at amino acid position 22 with isoleucine, valine at amino acid position 23 with glutamine, leucine at amino acid position 24 with methionine, alanine at amino acid position 29 with serine, alanine at amino acid position 31 with serine, valine at amino acid position 32 with alanine, leucine at amino acid position 34 with valine, glutamine at amino acid position 36 with aspartic acid, serine at amino acid position 41 with threonine, arginine at amino acid position 58 with lysine, serine at amino acid position 59 with proline, glutamine at amino acid position 61 with lysine, glutamine at amino acid position 62 with alanine, aspartic acid at amino acid position 95 with serine, proline at amino acid position 96 with serine, valine at amino acid position 97 with leucine, glutamic acid at amino acid position 98 with glutamine, aspartic acid at amino acid position 100) with glutamic acid, isoleucine at amino acid position 102 with phenylalanine, asparagine at amino acid position 104 with threonine, alanine at amino acid position 119 with glutamine, leucine at amino acid position 123 with valine, leucine at amino acid position 125 with isoleucine, and alanine at amino acid position 128 with threonine, and inserting serine to between amino acid positions 29 and 30, in SEQ ID NO: 45 as to the variable region moiety in the human chimeric antibody 04-046Ch light chain shown in SEQ ID NO: 45, was named "humanized h046-L1 type light chain" (also referred to as "h046-L1)").

The amino acid sequence of the humanized h046-L1 type light chain is shown in SEQ ID NO: 58 in the sequence listing. In the amino acid sequence of SEQ ID NO: 58, the sequence consisting of the amino acid residues at positions 1 to 20 corresponds to a signal sequence, the sequence consisting of the amino acid residues at positions 21 to 129 corresponds to a light chain variable region, and the sequence consisting of the amino acid residues at positions 130 to 234 corresponds to a light chain constant region. The nucleotide sequence encoding the amino acid sequence of SEQ ID NO: 58 is shown in SEQ ID NO: 59 in the sequence listing. In the nucleotide sequence of SEQ ID NO: 58, the sequence consisting of the nucleotides at positions 1 to 60 is a signal sequence, the sequence consisting of the nucleotides at positions 61 to 387 encodes the light chain variable region sequence, and the sequence consisting of the nucleotides at positions 388 to 702 encodes the light chain constant region sequence. The amino acid sequence of SEQ ID NO: 58 is also shown in FIG. 14.

6)-3-2 Humanized h046-L2 Type Light Chain

A humanized h046 light chain designed by substituting threonine at amino acid position 22 with isoleucine, valine at amino acid position 23 with glutamine, leucine at amino acid position 24 with methionine, alanine at amino acid position 29 with serine, alanine at amino acid position 21 with serine, valine at amino acid position 32) with alanine, leucine at amino acid position 34 with valine, glutamine at amino acid position 36 with aspartic acid, serine at amino acid position 41 with threonine, arginine at amino acid position 58 with lysine, serine at amino acid position 59 with proline, glutamine at amino acid position 61 with lysine, aspartic acid at amino acid position 95 with serine, proline at amino acid position 96 with serine, valine at amino acid position 97 with leucine, glutamic acid at amino acid position 98 with glutamine, aspartic acid at amino acid position 100 with glutamic acid, isoleucine at amino acid position 102 with phenylalanine, asparagine at amino acid position 104 with threonine, alanine at amino acid position 119 with glutamine, leucine at amino acid position 123 with valine, leucine at amino acid position 125 with isoleucine, and alanine at amino acid position 128 with threonine, and inserting serine to between amino acid positions 29 and 30, in SEQ ID NO: 45 as to the variable region moiety in the human chimeric antibody 04-046Ch light chain shown in SEQ ID NO: 45, was named "humanized h046-L2 type light chain" (also referred to as "h046-L2)").

The amino acid sequence of the humanized h046-L2 type light chain is shown in SEQ ID NO: 60 in the sequence listing. In the amino acid sequence of SEQ ID NO: 60, the sequence consisting of the amino acid residues at positions 1 to 20 corresponds to a signal sequence, the sequence consisting of the amino acid residues at positions 21 to 129 corresponds to a light chain variable region, and the sequence consisting of the amino acid residues at positions 130 to 234 corresponds to a light chain constant region. The nucleotide sequence encoding the amino acid sequence of SEQ ID NO: 60 is shown in SEQ ID NO: 61 in the sequence listing. In the nucleotide sequence of SEQ ID NO: 61, the sequence consisting of the nucleotides at positions 1 to 60 is a signal sequence, the sequence consisting of the nucleotides at positions 61 to 387 encodes the light chain variable region sequence, and the sequence consisting of the nucleotides at positions 388 to 702 encodes the light chain constant region sequence. The amino acid sequence of SEQ ID NO: 60 is also shown in FIG. 15.

6)-3-3 Humanized h046-L6 Type Light Chain

A humanized h046 light chain designed by substituting valine at amino acid position 23 with glutamine, alanine at amino acid position 29 with serine, alanine at amino acid position 31 with serine, valine at amino acid position 32 with alanine, leucine at amino acid position 34 with valine, glutamine at amino acid position 36 with aspartic acid, serine at amino acid position 41 with threonine, arginine at amino acid position 58 with lysine, serine at amino acid position 59 with proline, glutamine at amino acid position 61 with lysine, asparagine at amino acid position 72 with aspartic acid, leucine at amino acid position 73 with arginine, aspartic acid at amino acid position 95 with serine, proline at amino acid position 96 with serine, valine at amino acid position 97 with leucine, glutamic acid at amino acid position 98 with glutamine, aspartic acid at amino acid position 100 with glutamic acid, isoleucine at amino acid position 102 with phenylalanine, alanine at amino acid position 119 with glutamine, leucine at amino acid position 123 with valine, leucine at amino acid position 125 with isoleucine, and alanine at amino acid position 128 with threonine, and inserting serine to between amino acid positions 29 and 30, in SEQ ID NO: 45 as to the variable region moiety in the human chimeric antibody 04-046Ch light chain shown in SEQ ID NO: 45, was named "humanized h046-L6 type light chain" (also referred to as "h046-L6)").

The amino acid sequence of the humanized h046-L6 type light chain is shown in SEQ ID NO: 62 in the sequence listing. In the amino acid sequence of SEQ ID NO: 62, the sequence consisting of the amino acid residues at positions 1 to 20 corresponds to a signal sequence, the sequence consisting of the amino acid residues at positions 21 to 129 corresponds to a light chain variable region, and the sequence consisting of the amino acid residues at positions 130 to 234 corresponds to a light chain constant region. The nucleotide sequence encoding the amino acid sequence of SEQ ID NO: 62 is shown in SEQ ID NO: 63 in the sequence listing. In the nucleotide sequence of SEQ ID NO: 63, the sequence consisting of the nucleotides at positions 1 to 60 is a signal sequence, the sequence consisting of the nucleotides at positions 61 to 387 encodes the light chain variable region sequence, and the sequence consisting of the nucleotides at positions 388 to 702 encodes the light chain constant region sequence. The amino acid sequence of CDRL2 (SASDRES) is shown in SEQ ID NO: 92 in the sequence listing.

The amino acid sequence of SEQ ID NO: 62 is also shown in FIG. 16.

6)-3-4 Humanized h046-L7 Type Light Chain

A humanized h046 light chain designed by substituting valine at amino acid position 23 with glutamine, alanine at amino acid position 29 with serine, alanine at amino acid position 31 with serine, valine at amino acid position 32 with alanine, leucine at amino acid position 34 with valine, glutamine at amino acid position 36 with aspartic acid, serine at amino acid position 41 with threonine, arginine at amino acid position 58 with lysine, serine at amino acid position 59 with proline, glutamine at amino acid position 61 with lysine, serine at amino acid position 71 with glycine, aspartic acid at amino acid position 95 with serine, proline at amino acid position 96 with serine, valine at amino acid position 97 with leucine, glutamic acid at amino acid position 98 with glutamine, aspartic acid at amino acid position 100 with glutamic acid, isoleucine at amino acid position 102 with phenylalanine, alanine at amino acid position 119 with glutamine, leucine at amino acid position 123 with valine, leucine at amino acid position 125 with isoleucine, and alanine at amino acid position 128 with threonine, and inserting serine to between amino acid positions 29 and 30, as to the variable region moiety in the human chimeric antibody 04-046Ch light chain shown in SEQ ID NO: 45, was named "humanized h046-L7 type light chain" (also referred to as "h046-L7)").

The amino acid sequence of the humanized h046-L7 type light chain is shown in SEQ ID NO: 64 in the sequence listing. In the amino acid sequence of SEQ ID NO: 64, the sequence consisting of the amino acid residues at positions 1 to 20 corresponds to a signal sequence, the sequence consisting of the amino acid residues at positions 21 to 129 corresponds to a light chain variable region, and the sequence consisting of the amino acid residues at positions 130 to 234 corresponds to a light chain constant region. The nucleotide sequence encoding the amino acid sequence of SEQ ID NO: 64 is shown in SEQ ID NO: 65 in the sequence listing. In the nucleotide sequence of SEQ ID NO: 65, the sequence consisting of the nucleotides at positions 1 to 60 is a signal sequence, the sequence consisting of the nucleotides at positions 61 to 387 encodes the light chain variable region sequence, and the sequence consisting of the nucleotides at positions 388 to 702 encodes the light chain constant region sequence. The amino acid sequence of CDRL2 (SAGNLES) is shown in SEQ ID NO: 93 in the sequence listing.

The amino acid sequence of SEQ ID NO: 64 is also shown in FIG. 17.

6)-4 Design of Humanized h046 by Combination of Heavy Chain and Light Chain

An antibody consisting of the humanized h046-H4e type heavy chain and the humanized h046-L1 type light chain was designed and named "humanized h046-H4e/L1" (also referred to as "h046-H4e/L1"). An antibody consisting of the humanized h046-H4e type heavy chain and the humanized h046-L2 type light chain was designed and named "humanized h046-H4e/L2" (also referred to as "h046-H4e/L2"). An antibody consisting of the humanized h046-H4e type heavy chain and the humanized h046-L6 type light chain was designed and named "humanized h046-H4e/L6" (also referred to as "h046-H4e/L6"). An antibody consisting of the humanized h046-H4e type heavy chain and the humanized h046-L7 type light chain was designed and named "humanized h046-H4e/L7" (also referred to as "h046-H4e/L7"). An antibody consisting of the humanized h046-H4b type heavy chain and the humanized h046-L1 type light chain was designed and named "humanized h046-H4b/L1" (also referred to as "h046-H4b/L1"). An antibody consisting of the humanized h046-H4b type heavy chain and the humanized h046-L2 type light chain was designed and named "humanized h046-H4b/L2" (also referred to as "h046-H4b/L2"). An antibody consisting of the humanized h046-H4b type heavy chain and the humanized h046-L6 type light chain was designed and named "humanized h046-H4b/L6" (also referred to as "h046-H4b/L6"). An antibody consisting of the humanized h046-H4b type heavy chain and the humanized h046-L7 type light chain was designed and named "humanized h046-H4b/L7" (also referred to as "h046-H4b/L7"). An antibody consisting of the humanized h046-H5b type heavy chain and the humanized h046-L1 type light chain was designed and named "humanized h046-H5b/L1" (also referred to as "h046-H5b/L1"). An antibody consisting of the humanized h046-H5b type heavy chain and the humanized h046-L2 type light chain was designed and named "humanized h046-H5b/L2" (also referred to as "h046-H5b/L2"). An antibody consisting of the humanized h046-H5b type heavy chain and the humanized h046-L6 type light chain was designed and named "humanized h046-H5b/L6" (also referred to as "h046-H5b/L6"). An antibody consisting of the humanized h046-H5b type heavy chain and the humanized h046-L7 type light chain was designed and named "humanized h046-H5b/L7" (also referred to as "h046-H5b/L7"). An antibody consisting of the humanized h046-H8 type heavy chain and the humanized h046-L1 type light chain was designed and named "humanized h046-H8/L1" (also referred to as "h046-H8/L1"). An antibody consisting of the humanized h046-H8 type heavy chain and the humanized h046-L2 type light chain was designed and named "humanized h046-H8/L2" (also referred to as "h046-H8/L2"). An antibody consisting of the humanized h046-H8 type heavy chain and the humanized h046-L6 type light chain was designed and named "humanized h046-H8/L6" (also referred to as "h046-H8/L6"). An antibody consisting of the humanized h046-H8 type heavy chain and the humanized h046-L7 type light chain was designed and named "humanized h046-H8/L7" (also referred to as "h046-H8/L7"). An antibody consisting of the humanized h046-H10 type heavy chain and the humanized h046-L1 type light chain was designed and named "humanized h046-H10/L1" (also referred to as "h046-H10/L1"). An antibody consisting of the humanized h046-H10 type heavy chain and the humanized h046-L2 type light chain was designed and named "humanized h046-H10/L2" (also referred to as "h046-H10/L2"). An antibody consisting of the humanized h046-H10 type heavy chain and the humanized h046-L6 type light chain was designed and named "humanized h046-H10/L6" (also referred to as "h046-H10/L6"). An antibody consisting of the humanized h046-H10 type heavy chain and the humanized h046-L7 type light chain was designed and named "humanized h046-H10/L7" (also referred to as "h046-H10/L7"). An antibody consisting of the human chimeric c046 heavy chain and the humanized h046-L1 type light chain was designed and named "human chimeric c046/L1" (also referred to as "h046-Hwt/L1"). An antibody consisting of the human chimeric c046 heavy chain and the humanized h046-L2 type light chain was designed and named "human chimeric c046/L2" (also referred to as "h046-Hwt/L2"). An antibody consisting of the human chimeric c046 heavy chain and the humanized h046-L6 type light chain was designed and named "human chimeric c046/L6" (also referred to as "h046-Hwt/L6"). An antibody consisting of the human chimeric c046 heavy chain and the humanized h046-L7 type light chain was designed and named "human chimeric c046/L7" (also referred to as "h046-Hwt/L7"). The antibodies thus designed can be produced in accordance with Examples 6)-5 and 6)-7, and can be evaluated in accordance with Examples 6)-6, 8), and 9).

6)-5 Expression of Humanized Anti-GPR20 Antibody—(1)

6)-5-1 Construction of Humanized h046_Heavy Chain Expression Vector

6)-5-1-1 Construction of Humanized h046-H4b Type Heavy Chain Expression Vector

The DNA fragment A shown in SEQ ID NO: 94 was synthesized (GENEART, artificial gene synthesis service). The synthesized DNA fragment was inserted into a site of the chimeric and humanized antibody IgG1 type heavy chain expression vector pCMA-G1 that had been cleaved with the restriction enzyme BlpI, by the same method as that applied in Example 5)-1-3, so as to construct plasmid A. A mutation was introduced into the plasmid A as a template using the primer set given below and KOD -Plus- Mutagenesis Kit (Toyobo Co., Ltd.), so as to construct a humanized h046-H4b type heavy chain expression vector. The constructed expression vector was named "pCMA/h046-H4b". The nucleotide sequence of the humanized h046-H4b type heavy chain is shown in SEQ ID NO: 49, and the amino acid sequence thereof is shown in SEQ ID NO: 48.

Primer Set:
5'-ATCAACCCTGGCAGCGGCCACACCAACTAC-3' (Hb-F; SEQ ID NO: 95)
5'-GAAGCCCATGTACTTCAGGCCCTGTCCAGGGG-3' (Hb-R; SEQ ID NO: 96)

6)-5-1-2 Construction of Humanized h046-H5b Type Heavy Chain Expression Vector

The DNA fragment B shown in SEQ ID NO: 97 was synthesized (GENEART, artificial gene synthesis service). The synthesized DNA fragment was inserted into a site of the chimeric and humanized antibody IgG1 type heavy chain expression vector pCMA-G1 that had been cleaved with the restriction enzyme BlpI, by the same method as that applied in Example 5)-1-3, so as to construct plasmid B. A mutation was introduced into the plasmid B as a template by the same method as that applied in 6)-5-1-1, so as to construct a humanized h046-H5b type heavy chain expression vector. The constructed expression vector was named "pCMA/h046-H5b". The nucleotide sequence of the humanized h046-H5b type heavy chain is shown in SEQ ID NO: 53, and the amino acid sequence thereof is shown in SEQ ID NO: 52.

6)-5-1-3 Construction of Humanized h046-H8 Type Heavy Chain Expression Vector

A mutation was introduced into pCMA/04-046Ch-H constructed in Example 5)-1-3 as a template using the primer set given below and KOD -Plus- Mutagenesis Kit (Toyobo Co., Ltd.), so as to construct a humanized h046-H8 type heavy chain expression vector. The constructed expression vector was named "pCMA/h046-H8". The nucleotide sequence of the humanized h046-H8 type heavy chain is shown in SEQ ID NO: 55, and the amino acid sequence thereof is shown in SEQ ID NO: 54.

Primer Set:
5'-AACATGCAGCTGTCCAGCCTGACCCCCGACGAC-3' (H08-F; SEQ ID NO: 98)
5'-GGCGGTGCTGCTGCTCTTGTCCACGGTCAG-3' (H08-R; SEQ ID NO: 99)

6)-5-1-4 Construction of Humanized h046-H10 Type Heavy Chain Expression Vector

A mutation was introduced into pCMA/h046-H8 constructed in Example 6)-5-1-3 as a template using the primer set given below and KOD -Plus- Mutagenesis Kit (Toyobo Co., Ltd.), so as to construct a humanized h046-H10 type heavy chain expression vector. The constructed expression vector was named "pCMA/h046-H10". The nucleotide sequence of the humanized h046-H10 type heavy chain is shown in SEQ ID NO: 57, and the amino acid sequence thereof is shown in SEQ ID NO: 56.

5'-GTGAGCTGCAAGGCCAGCGGCTACACCTTCACC-3' (H10-F; SEQ ID NO: 100)

5'-CTTCACGCTGCTGCCAGGCTTGGCCAGTTC-3' (H10-R; SEQ ID NO: 101)

6)-5-2 Construction of Humanized h046 Light Chain Expression Vector

6)-5-2-1 Construction of Humanized h046-L1 Type Light Chain Expression Vector

A DNA fragment corresponding to nucleotide positions 37 to 402 including a DNA sequence encoding the variable region in the humanized h046-L1 nucleotide sequence shown in SEQ ID NO: 59 was synthesized (GENEART, artificial gene synthesis service). Using the synthesized DNA fragment as a template, a DNA fragment comprising a DNA sequence encoding the humanized h046-L1 variable region was amplified with KOD -Plus- (Toyobo Co., Ltd.) and the primer set given below. Using In-Fusion HD PCR cloning kit (Clontech Laboratories, Inc.), the amplified DNA fragment was inserted into a site of the chimeric and humanized antibody light chain expression vector pCMA-LK constructed in Example 5)-1-1 that had been cleaved with the restriction enzyme BsiWI, so as to construct a humanized h046-L1 expression vector. The obtained expression vector was named "pCMA/h046-L1". The amino acid sequence of the humanized h046-L1 is shown in SEQ ID NO: 58.

Primer Set

5'-CTGTGGATCTCCGGCGCGTACGGC-3' (CM-LKF; SEQ ID NO: 90)

5'-GGAGGGGGCGGCCACCGTACG-3' (KCL-Inf-R; SEQ ID NO: 102)

6)-5-2-2 Construction of Humanized h046-L2 Type Light Chain Expression Vector

A DNA fragment comprising a DNA sequence encoding the humanized h046-L2 variable region corresponding to nucleotide positions 37 to 402 in the humanized h046-L2 nucleotide sequence shown in SEQ ID NO: 61 was synthesized (GENEART, artificial gene synthesis service). A humanized h046-L2 expression vector was constructed by the same method as that applied in Example 6)-5-2-1. The obtained expression vector was named "pCMA/h046-L2". The amino acid sequence of the humanized h046-L2 is shown in SEQ ID NO: 60.

6)-5-2-3 Construction of Humanized h046-L6 Type Light Chain Expression Vector

A DNA fragment comprising a DNA sequence encoding the humanized h046-L6 variable region corresponding to nucleotide positions 37 to 402 in the humanized h046-L6 nucleotide sequence shown in SEQ ID NO: 63 was synthesized (GENEART, artificial gene synthesis service). A humanized h046-L6 expression vector was constructed by the same method as that applied in Example 6)-5-2-1. The obtained expression vector was named "pCMA/h046-L6". The amino acid sequence of the humanized h046-L6 is shown in SEQ ID NO: 62.

6)-5-2-4 Construction of Humanized h046-L7 Type Light Chain Expression Vector

A DNA fragment comprising a DNA sequence encoding the humanized h046-L2 variable region corresponding to nucleotide positions 37 to 402 in the humanized h046-L7 nucleotide sequence shown in SEQ ID NO: 65 was synthesized (GENEART, artificial gene synthesis service). A humanized h046-L7 expression vector was constructed by the same method as that applied in Example 6)-5-2-1. The obtained expression vector was named "pCMA/h046-L7". The amino acid sequence of the humanized h046-L7 is shown in SEQ ID NO: 64.

6)-5-3 Small-Scale Production of Humanized h046 Antibody

In accordance with the manual, FreeStyle 293F cells (Invitrogen Corp.) were cultured and passaged. 1×10⁷ FreeStyle 293F cells (Invitrogen Corp.) in the logarithmic growth phase were diluted into 9.6 mL with FreeStyle 293 expression medium (Invitrogen Corp.), then seeded in 30-mL Square Storage Bottle (Nalgene), and shake-cultured at 90 rpm in an 8% CO2 incubator at 37° C. for 1 hour. 30 µg of Polyethyleneimine (Polyscience #24765) was dissolved in 200 µL of Opti-Pro SFM (Invitrogen Corp.). Meanwhile, the light chain expression vector (6 µg) and the heavy chain expression vector (4 µg) prepared using Nucleo-Bond Xtra (Takara Bio Inc.) were added to 200 µL of Opti-Pro SFM (Invitrogen Corp.). To 200 µL of the Polyethyleneimine/Opti-Pro SFM mixed solution, 200 µL of the expression vector/Opti-Pro SFM mixed solution was added, and the obtained mixture was gently stirred. After incubation for 5 minutes, the mixture was added to the FreeStyle 293F cells. The cells were shake-cultured at 90 rpm in an 8% CO2 incubator at 37° C. for 7 days. The obtained culture supernatant was filtrated through Minisart-Plus filter (Sartorius Inc.) to obtain a sample for evaluation.

Humanized h046-H4b/L7 was obtained by the combination of pCMA/h046-H4b and pCMA/h046-L7. Humanized h046-H5b/L2 was obtained by the combination of pCMA/h046-H5b and pCMA/h046-L2. Humanized h046-Hwt/L6 was obtained by the combination of pCMA/04-046Ch-H and pCMA/h046-L6. Humanized h046-H8/L1 was obtained by the combination of pCMA/h046-H8 and pCMA/h046-L1. Humanized h046-H10/L1 was obtained by the combination of pCMA/h046-H10 and pCMA/h046-L1. Humanized h046-H10/L6 was obtained by the combination of pCMA/h046-H10 and pCMA/h046-L6.

6)-6 In Vitro Evaluation of Humanized Anti-GPR20 Antibody

6)-6-1 Evaluation of Binding Activity of Humanized Anti-GPR20 Antibody

The GPR20-binding activity of the humanized anti-GPR20 antibodies produced in Example 6)-5-3 was confirmed by flow cytometry. Using Lipofectamine 2000, pcDNA3.1-hGPR20 was transiently introduced into 293T cells by the same method as that applied in Example 1)-5-1. The cells were cultured overnight under conditions of 37° C. and 5% CO2, and thereafter, a cell suspension was prepared. To the obtained cell suspension, each humanized anti-GPR20 antibody was added, and the obtained mixture was left standing at 4° C. for 1 hour. Thereafter, the cells were washed twice with PBS supplemented with 5% FBS, and then suspended by the addition of PE-labeled F(ab')2 Fragment anti-human IgG, Fcγ antibody (Jackson ImmunoResearch Inc.) that had been 320-fold diluted with PBS supplemented with 5% FBS. The cells were left standing at 4° C. for 1 hour. The cells were washed twice with PBS supplemented with 5% FBS, and then re-suspended in PBS supplemented with 5% FBS, followed by detection using a flow cytometer (BD FACSCant II; BD Biosciences). The data was analyzed using Flowjo (Tree Star, Inc.). As a result, it was confirmed that the produced humanized anti-GPR20 antibodies bound to the 293T cells transfected with pcDNA3.1-hGPR20. FIG. 24 shows the results about the humanized anti-GPR20 antibodies specifically bound to human GPR20. In the histograms of FIG. 24, the abscissa depicts the fluorescence intensity of PE indicating the amount of the antibody bound, and the ordinate depicts a cell count. The shaded histogram shows a negative control that was not reacted with an anti-GPR20 antibody, and the open histogram shows that, when each anti-GPR20 antibody was reacted, fluorescence intensity was enhanced by the binding of the antibody to GPR20 on cell surface.

6)-6-2 Evaluation of Internalization Activity of Humanized Anti-GPR20 Antibody

The internalization activity of the humanized anti-GPR20 antibodies produced in Example 6)-5-3 was evaluated using an anti-human IgG antibody reagent Hum-ZAP (Advanced Targeting Systems) conjugated with a toxin (saporin) inhibiting protein synthesis, by the same method as that applied in 1)-6. Specifically, HEK293 cells stably expressing GPR20-EGFP protein comprising human GPR20 linked at its C-terminus to EGFP were seeded at $2.5 \times 10^3$ cells/well, and then cultured overnight under conditions of 37° C. and 5% CO2. Each humanized anti-GPR20 antibody (final concentration: 0.015 to 1.27 µg/mL) and Hum-ZAP (final concentration: 1 µg/mL) were added to the culture. The cells were cultured for 4 days, and thereafter, the number of live cells was measured by the quantification of ATP using CellTiter-Glo (registered trademark) Luminescent Cell Viability Assay. As a result, the humanized anti-GPR20 antibodies, humanized h046-H4b/L7, humanized h046-H5b/L2, humanized h046-Hwt/L6, humanized h046-H8/L1, humanized h046-H10/L1 and humanized h046-H10/L6, produced in Example 6)-5-3 exhibited a cell proliferation-suppressive effect by antibody internalization.

6)-7 Large Scale Production of Humanized Anti-GPR20 Antibody—(2)

6)-7-1 Construction of Humanized h046_Heavy Chain Expression Vector

6)-7-1-1 Construction of Humanized h046-H4b Type Heavy Chain Expression Vector

A DNA fragment comprising a sequence encoding the humanized h046_H4b type heavy chain corresponding to nucleotide positions 58 to 1416 of the nucleotide sequence (2) of the humanized h046_H4b type heavy chain shown in SEQ ID NO: 103 in the sequence listing was synthesized (GENEART, artificial gene synthesis service). Using the synthesized DNA fragment, in accordance with the protocols of GS Gene Expression System (registered trademark) by Lonza, a humanized h046_H4b type heavy chain expression vector was constructed. The constructed expression vector was named "GSV-h046_H4b".

6)-7-1-2 Construction of Humanized h046-H5b Type Heavy Chain Expression Vector

A DNA fragment comprising a sequence encoding the humanized h046_H5b type heavy chain corresponding to nucleotide positions 58 to 1416 of the nucleotide sequence (2) of the humanized h046_H5b type heavy chain shown in SEQ ID NO: 104 in the sequence listing was synthesized (GENEART, artificial gene synthesis service). Using the synthesized DNA fragment, in accordance with the protocols of GS Gene Expression System (registered trademark) by Lonza, a humanized h046_H5b type heavy chain expression vector was constructed. The constructed expression vector was named "GSV-h046_H5b".

6)-7-1-3 Construction of Humanized h046-Hwt Type Heavy Chain Expression Vector

A DNA fragment comprising a sequence encoding the humanized h046_Hwt type heavy chain corresponding to nucleotide positions 58 to 1416 of the nucleotide sequence (2) of the humanized h046_Hwt type heavy chain shown in SEQ ID NO: 105 in the sequence listing was synthesized (GENEART, artificial gene synthesis service). Using the synthesized DNA fragment, in accordance with the protocols of GS Gene Expression System (registered trademark) by Lonza, a humanized h046_Hwt type heavy chain expression vector was constructed. The constructed expression vector was named "GSV-h046_Hwt".

6)-7-1-4 Construction of Humanized h046-H8 Type Heavy Chain Expression Vector

A DNA fragment comprising a sequence encoding the humanized h046_H8 type heavy chain corresponding to nucleotide positions 58 to 1416 of the nucleotide sequence (2) of the humanized h046_H8 type heavy chain shown in SEQ ID NO: 106 in the sequence listing was synthesized (GENEART, artificial gene synthesis service). Using the synthesized DNA fragment, in accordance with the protocols of GS Gene Expression System (registered trademark) by Lonza, a humanized h046_H8 type heavy chain expression vector was constructed. The constructed expression vector was named "GSV-h046_H8".

6)-7-1-5 Construction of Humanized h046-H10 Type Heavy Chain Expression Vector

A DNA fragment comprising a sequence encoding the humanized h046_H10 type heavy chain corresponding to nucleotide positions 58 to 1416 of the nucleotide sequence (2) of the humanized h046_H10 type heavy chain shown in SEQ ID NO: 107 in the sequence listing was synthesized (GENEART, artificial gene synthesis service). Using the synthesized DNA fragment, in accordance with the protocols of GS Gene Expression System (registered trademark) by Lonza, a humanized h046_H10 type heavy chain expression vector was constructed. The constructed expression vector was named "GSV-h046_H10".

6)-7-1-6 Construction of Humanized h046-H4e Type Heavy Chain Expression Vector

A DNA fragment comprising a sequence encoding the humanized h046_H4e type heavy chain corresponding to nucleotide positions 58 to 1416 of the nucleotide sequence of the humanized h046_H4e type heavy chain shown in SEQ ID NO: 51 in the sequence listing was synthesized (GENEART, artificial gene synthesis service). Using the synthesized DNA fragment, in accordance with the protocols of GS Gene Expression System (registered trademark) by Lonza, a humanized h046_H4e type heavy chain expression vector was constructed. The constructed expression vector was named "GSV-h046_H4e".

6)-7-2 Construction of Humanized h046 Light Chain Expression Vector

6)-7-2-1 Construction of Humanized h046-L1 Type Light Chain Expression Vector

A DNA fragment comprising a sequence encoding the humanized h046_L1 type light chain corresponding to nucleotide positions 61 to 702 of the nucleotide sequence (2) of the humanized h046_L1 type light chain shown in SEQ ID NO: 108 in the sequence listing was synthesized (GENEART, artificial gene synthesis service). Using the synthesized DNA fragment, in accordance with the protocols of GS Gene Expression System (registered trademark) by Lonza, a humanized h046_L1 type light chain expression vector was constructed. The constructed expression vector was named "GSV-h046_L1".

6)-7-2-2 Construction of Humanized h046-L2 Type Light Chain Expression Vector

A DNA fragment comprising a sequence encoding the humanized h046_L2 type light chain corresponding to nucleotide positions 61 to 702 of the nucleotide sequence (2) of the humanized h046_L2 type light chain shown in SEQ ID NO: 109 in the sequence listing was synthesized (GENEART, artificial gene synthesis service). Using the synthesized DNA fragment, in accordance with the protocols of GS Gene Expression System (registered trademark) by Lonza, a humanized h046_L2 type light chain expression vector was constructed. The constructed expression vector was named "GSV-h046_L2".

6)-7-2-3 Construction of Humanized h046-L6 Type Light Chain Expression Vector

A DNA fragment comprising a sequence encoding the humanized h046_L6 type light chain corresponding to nucleotide positions 61 to 702 of the nucleotide sequence (2) of the humanized h046_L6 type light chain shown in SEQ ID NO: 110 in the sequence listing was synthesized (GENEART, artificial gene synthesis service). Using the synthesized DNA fragment, in accordance with the protocols of GS Gene Expression System (registered trademark) by Lonza, a humanized h046_L6 type light chain expression vector was constructed. The constructed expression vector was named "GSV-h046_L6".

6)-7-2-4 Construction of Humanized h046-L7 Type Light Chain Expression Vector

A DNA fragment comprising a sequence encoding the humanized h046_L7 type light chain corresponding to nucleotide positions 61 to 702 of the nucleotide sequence of the humanized h046_L7 type light chain shown in SEQ ID NO: 111 in the sequence listing was synthesized (GENEART, artificial gene synthesis service). Using the synthesized DNA fragment, in accordance with the protocols of GS Gene Expression System (registered trademark) by Lonza, a humanized h046_L7 type light chain expression vector was constructed. The constructed expression vector was named "GSV-h046_L7".

6)-7-3 Construction of Humanized Anti-GPR20 Antibody Expression Vector

6)-7-3-1 Construction of Humanized h046-H4b/L7 Expression Vector

In accordance with the protocols of GS Gene Expression System (registered trademark) by Lonza, a humanized h046-H4b/L7 expression vector was constructed from the constructed expression vectors "GSV-h046_H4b" and "GSV-h046_L7". The obtained expression vector was named "DGV-h046_H4bL7-GS".

6)-7-3-2 Construction of Humanized h046-H5b/L2 Expression Vector

In accordance with the protocols of GS Gene Expression System (registered trademark) by Lonza, a humanized h046-H5b/L2 expression vector was constructed from the constructed expression vectors "GSV-h046_H5b" and "GSV-h046_L2". The obtained expression vector was named "DGV-h046_H5bL2-GS".

6)-7-3-3 Construction of Humanized h046-Hwt/L6 Expression Vector

In accordance with the protocols of GS Gene Expression System (registered trademark) by Lonza, a humanized h046-Hwt/L6 expression vector was constructed from the constructed expression vectors "GSV-h046_Hwt" and "GSV-h046_L6". The obtained expression vector was named "DGV-h046_HwtL6-GS".

6)-7-3-4 Construction of Humanized h046-H8/L1 Expression Vector

In accordance with the protocols of GS Gene Expression System (registered trademark) by Lonza, a humanized h046-H8/L1 expression vector was constructed from the constructed expression vectors "GSV-h046_H8" and "GSV-h046_L1". The obtained expression vector was named "DGV-h046_H8L1-GS".

6)-7-3-5 Construction of Humanized h046-H10/L1 Expression Vector

In accordance with the protocols of GS Gene Expression System (registered trademark) by Lonza, a humanized h046-H10/L1 expression vector was constructed from the constructed expression vectors "GSV-h046_H10" and "GSV-h046_L1". The obtained expression vector was named "DGV-h046_H10L1-GS".

6)-7-3-6 Construction of Humanized h046-H10/L6 Expression Vector

In accordance with the protocols of GS Gene Expression System (registered trademark) by Lonza, a humanized h046-H10/L6 expression vector was constructed from the constructed expression vectors "GSV-h046_H10" and "GSV-h046_L6". The obtained expression vector was named "DGV-h046_H10L6-GS".

6)-7-3-7 Construction of Humanized h046-H4e/L7 Expression Vector

In accordance with the protocols of GS Gene Expression System (registered trademark) by Lonza, a humanized h046-H4e/L7 expression vector was constructed from the constructed expression vectors "GSV-h046_H4e" and "GSV-h046_L7". The obtained expression vector was named "DGV-h046_H4eL7-GS".

6)-7-4 Preparation of Cells that Produce Humanized Anti-GPR20 Antibody

6)-7-4-1 Preparation of Cells that Produce Humanized h046-H4b/L7

CHOK1SV cells (Lonza) were transfected with the humanized h046-H4b/L7 expression vector DGV-h046_H4bL7-GS, which had been constructed in Example 6)-7-3-1 in accordance with the protocols of GS Gene Expression System (registered trademark) by Lonza, so as to construct a cell line producing the humanized h046-H4b/L7. The obtained producing cell line was named "GPR1-12".

6)-7-4-2 Preparation of Cells that Produce Humanized h046-H5b/L2

CHOK1SV cells (Lonza) were transfected with the humanized h046-H5b/L2 expression vector DGV-h046_H5bL2-GS, which had been constructed in Example 6)-7-3-2 in accordance with the protocols of GS Gene Expression System (registered trademark) by Lonza, so as to construct a cell line producing the humanized h046-H5b/L2. The obtained producing cell line was named "GPR2-15".

6)-7-4-3 Preparation of Cells that Produce Humanized h046-Hwt/L6

CHOK1SV cells (Lonza) were transfected with the humanized h046-Hwt/L6 expression vector DGV-h046_H4wtL6-GS, which had been constructed in Example 6)-7-3-3 in accordance with the protocols of GS Gene Expression System (registered trademark) by Lonza, so as to construct a cell line producing the humanized h046-Hwt/L6. The obtained producing cell line was named "GPR3-2".

6)-7-4-4 Preparation of Cells that Produce Humanized h046-H8/L1

CHOK1SV cells (Lonza) were transfected with the humanized h046-H8/L1 expression vector DGV-h046_H8L1-GS, which had been constructed in Example 6)-7-3-4 in accordance with the protocols of GS Gene Expression System (registered trademark) by Lonza, so as to construct a cell line producing the humanized h046-H8/L1. The obtained producing cell line was named "GPR4-1".

6)-7-4-5 Preparation of Cells that Produce Humanized h046-H10/L1

CHOK1SV cells (Lonza) were transfected with the humanized h046-H10/L1 expression vector DGV-h046_H10L1-GS, which had been constructed in Example 6)-7-3-5 in accordance with the protocols of GS Gene Expression System (registered trademark) by Lonza, so as to construct a cell line producing the humanized h046-H10/L1. The obtained producing cell line was named "GPR5-10".

6)-7-4-6 Preparation of Cells that Produce Humanized h046-H10/L6

CHOK1SV cells (Lonza) were transfected with the humanized h046-H10/L6 expression vector DGV-h046_H10L6-GS, which had been constructed in Example 6)-7-3-6 in accordance with the protocols of GS Gene Expression System (registered trademark) by Lonza, so as to construct a cell line producing the humanized h046-H10/L6. The obtained producing cell line was named "GPR6-7".

6)-7-4-7 Preparation of Cells that Produce Humanized h046-H4e/L7

CHOK1SV cells (Lonza) were transfected with the humanized h046-H4e/L7 expression vector DGV-h046_H4eL7-GS, which had been constructed in Example 6)-7-3-7 in accordance with the protocols of GS Gene Expression System (registered trademark) by Lonza, so as to construct a cell line producing the humanized h046-H4e/L7. The obtained producing cell line was named "GPE-23".

6)-7-5 Culture of Cells that Produce Humanized Anti-GPR20 Antibody

6)-7-5-1 Culture of Cells that Produce Humanized h046-H4b/L7

The humanized h046-H4b/L7-producing cell line "GPR1-12" prepared in Example 6)-7-4-1 was cultured using a culture apparatus Wave reactor (GE Healthcare Japan Corp.). The producing cell line "GPR1-12" was thawed in C36 (JX Energy) medium, and then cultured at 120 rpm in a 5% CO2 incubator at 37° C. The obtained culture solution was diluted with C36 medium, and then expansively cultured at 120 rpm in a 5% CO2 incubator at 37° C. The obtained culture solution was diluted with C36 medium at a cell density of $30\times10^4$ cells/mL, and then transferred into WAVE CELLBAG (GE Healthcare Biosciences Corp.), followed by culture at 37° C. in 5% CO2, at an air-supplying rate of 0.3 L/min, at a rotation rate of 18 to 24 rpm, at an angle of 6 to 8°, for 10 days. From the 3rd day after initiation of the culture, FM4Ae2 medium (self-prepared) was added every day to the culture in an amount of 6% of the initial culture volume per day. The obtained culture solution was roughly filtrated through a depth filter Millistak MCOHC054H1 (Merck Millipore), and then filtrated through a 0.22-µm filter (Sartorius Inc.) attached to Flexboy Bags. This filtrate was named "h046-H4b/L7 culture supernatant".

6)-7-5-2 Culture of Cells that Produce Humanized h046-H5b/L2

In the same manner as that applied in Example 6)-7-5-1, the humanized h046-H5b/L2-producing cell line "GPR2-15" prepared in Example 6)-7-4-2 was cultured and expanded, and thereafter, the cells were subjected to fed-batch culture using a culture apparatus Wave reactor (GE Healthcare Japan Corp.). The obtained culture was diluted with C36 medium at a cell density of $30\times10^4$ cells/mL, and then transferred into WAVE CELLBAG (GE Healthcare Bioscience), followed by culture for 11 days. The obtained culture solution was filtrated, and the obtained filtrate was named "h046-H5b/L2 culture supernatant".

6)-7-5-3 Culture of Cells that Produce Humanized h046-Hwt/L6

In the same manner as that applied in Example 6)-7-5-1, the humanized h046-Hwt/L6-producing cell line "GPR3-2" prepared in Example 6)-7-4-3 was cultured and expanded, and thereafter, the cells were subjected to fed-batch culture using a culture apparatus Wave reactor (GE Healthcare Japan Corp.). The obtained culture was diluted with C36 medium at a cell density of $30\times10^4$ cells/mL, and then transferred into WAVE CELLBAG (GE Healthcare Bioscience), followed by culture for 14 days. The obtained culture solution was filtrated, and the obtained filtrate was named "h046-Hwt/L6 culture supernatant".

6)-7-5-4 Culture of Cells that Produce Humanized h046-H8/L1

In the same manner as that applied in Example 6)-7-5-1, the humanized h046-H8/L1-producing cell line "GPR4-1" prepared in Example 6)-7-4-4 was cultured and expanded, and thereafter, the cells were subjected to fed-batch culture using a culture apparatus Wave reactor (GE Healthcare Japan Corp.). The obtained culture was diluted with C36 medium at a cell density of $30\times10^4$ cells/mL, and then transferred into WAVE CELLBAG (GE Healthcare Bioscience), followed by culture for 11 days. The obtained culture solution was filtrated, and the obtained filtrate was named "h046-H8/L1 culture supernatant".

6)-7-5-5 Culture of Cells that Produce Humanized h046-H10/L1

In the same manner as that applied in Example 6)-7-5-1, the humanized h046-H10/L1-producing cell line "GPR5-10" prepared in Example 6)-7-4-5 was cultured and expanded, and thereafter, the cells were subjected to fed-batch culture using a culture apparatus Wave reactor (GE Healthcare Japan Corp.). The obtained culture was diluted with C36 medium at a cell density of $30\times10^4$ cells/mL, and then transferred into WAVE CELLBAG (GE Healthcare Bioscience), followed by culture for 10 days. The obtained culture solution was filtrated, and the obtained filtrate was named "h046-H10/L1 culture supernatant".

6)-7-5-6 Culture of Cells that Produce Humanized h046-H10/L6

In the same manner as that applied in Example 6)-7-5-1, the humanized h046-H10/L6-producing cell line "GPR6-7" prepared in Example 6)-7-4-6 was cultured and expanded, and thereafter, the cells were subjected to fed-batch culture using a culture apparatus Wave reactor (GE Healthcare Japan Corp.). The obtained culture was diluted with C36 medium at a cell density of $30\times10^4$ cells/mL, and then transferred into WAVE CELLBAG (GE Healthcare Bioscience), followed by culture for 12 days. The obtained culture solution was filtrated, and the obtained filtrate was named "h046-H10/L6 culture supernatant".

6)-7-5-7 Culture of Cells that Produce Humanized h046-H4e/L7

In the same manner as that applied in Example 6)-7-5-1, the humanized h046-H4e/L7-producing cell line "GPE-23" prepared in Example 6)-7-4-7 was cultured and expanded, and thereafter, the cells were subjected to fed-batch culture using a culture apparatus Wave reactor (GE Healthcare Japan Corp.). The obtained culture was diluted with C36 medium at a cell density of $30\times10^4$ cells/mL, and then transferred into WAVE CELLBAG (GE Healthcare Bioscience), followed by culture for 11 days. The obtained culture solution was filtrated, and the obtained filtrate was named "h046-H4e/L7 culture supernatant".

6)-7-6 Purification of Humanized Anti-GPR20 Antibody

6)-7-6-1 Purification of Humanized h046-H4b/L7

The "h046-H4b/L7 culture supernatant" obtained in Example 6)-7-5-1 was purified by a three-step process, namely, by rProtein A affinity chromatography, anion exchange chromatography, and cation exchange chromatography. First, the culture supernatant was applied to rProtein A affinity chromatographic resin that had been equilibrated with PBS. After the entire culture solution had entered the column, the column was washed with PBS, a buffer solution containing arginine, and PBS. Subsequently, the remaining substance in the column was eluted with an acetate buffer, and an absorption peak at 280 nm was then collected. The collected solution was neutralized with a Tris buffer, and then roughly filtrated through a glass fiber filter AP20 (Merck Millipore). Thereafter, the solution was filtrated through Stericup-GV (Merck Millipore) that was a 0.22-μm filter, and the resultant filtrate was defined as an rProtein A purified pool.

Subsequently, the rProtein A purified pool was applied to an anion exchange chromatographic resin that had been equilibrated with PBS. After the entire applied solution had entered the column, PBS was supplied. A flow-through fraction and the absorption peak at 280 nm at the time of the supply of PBS were collected. The pH of the collected solution was adjusted with acetic acid. The solution was filtrated through Stericup-GV (Merck Millipore) that was a 0.22-μm filter, and the resultant filtrate was defined as an AEX purified pool.

Subsequently, the AEX purified pool was applied to a cation exchange chromatographic resin that had been equilibrated with an acetate buffer. After the entire applied solution had entered the column, the column was washed with an acetate buffer. Thereafter, elution was carried out using an acetate buffer containing a high concentration of NaCl, and the absorption peak at 280 nm was collected. The collected solution was filtrated through Stericup-GV (Merck Millipore) that was a 0.22-μm filter, and the resultant filtrate was defined as a CEX purified pool.

The CEX purified pool was concentrated to an antibody concentration of 20 mg/mL with Pellicon 3 Cassette 30 kDa (Merck Millipore), and the buffer was then replaced with a histidine buffer (25 mM histidine, 5% sorbitol, pH 6.0). Finally, the solution was filtrated through Stericup-GV (Merck Millipore) that was a 0.22-μm filter, so as to obtain a purified sample. This purified sample was named "h046_H4b/L7".

6)-7-6-2 Purification of Humanized h046-H5b/L2

The "h046-H5b/L2 culture supernatant" obtained in Example 6)-7-5-2 was purified by a three-step process, namely, by rProtein A affinity chromatography, anion exchange chromatography, and cation exchange chromatography. First, the culture supernatant was applied to rProtein A affinity chromatographic resin that had been equilibrated with PBS. After the entire culture solution had entered the column, the column was washed with PBS, a buffer solution containing arginine, and PBS. Subsequently, the remaining substance in the column was eluted with an acetate buffer, and an absorption peak at 280 nm was then collected. The collected solution was neutralized with a Tris buffer, and then roughly filtrated through a glass fiber filter AP20 (Merck Millipore). Thereafter, the solution was filtrated through Stericup-GV (Merck Millipore) that was a 0.22-μm filter, and the resultant filtrate was defined as an rProtein A purified pool.

Subsequently, the rProtein A purified pool was applied to an anion exchange chromatographic resin that had been equilibrated with PBS. After the entire applied solution had entered the column, PBS was supplied. A flow-through fraction and the absorption peak at 280 nm at the time of the supply of PBS were collected. The pH of the collected solution was adjusted with acetic acid. The solution was filtrated through Stericup-GV (Merck Millipore) that was a 0.22-μm filter, and the resultant filtrate was defined as an AEX purified pool.

Subsequently, the AEX purified pool was applied to a cation exchange chromatographic resin that had been equilibrated with an acetate buffer. After the entire applied solution had entered the column, the column was washed with an acetate buffer. Thereafter, elution was carried out using an acetate buffer containing a high concentration of NaCl, and the absorption peak at 280 nm was collected. The collected solution was filtrated through Stericup-GV (Merck Millipore) that was a 0.22-μm filter, and the resultant filtrate was defined as a CEX purified pool.

The CEX purified pool was concentrated to an antibody concentration of 40 mg/mL with Pellicon 3 Cassette 30 kDa (Merck Millipore), and the buffer was then replaced with a histidine buffer (25 mM histidine, 5% sorbitol, pH 6.0). Finally, the solution was filtrated through Stericup-GV (Merck Millipore) that was a 0.22-μm filter, so as to obtain a purified sample. This purified sample was named "h046_H5b/L2".

6)-7-6-3 Purification of Humanized h046-Hwt/L6

The "h046-Hwt/L6 culture supernatant" obtained in Example 6)-7-5-3 was purified by a three-step process, namely, by rProtein A affinity chromatography, anion exchange chromatography, and cation exchange chromatography. First, the culture supernatant was applied to rProtein A affinity chromatographic resin that had been equilibrated with PBS. After the entire culture solution had entered the column, the column was washed with PBS, a buffer solution containing arginine, and PBS. Subsequently, the remaining substance in the column was eluted with an acetate buffer, and an absorption peak at 280 nm was then collected. The collected solution was neutralized with a Tris buffer. The solution was filtrated through Millipore Express SHC (Merck Millipore) that was a 0.5/0.2-μm filter, and the resultant filtrate was defined as an rProtein A purified pool.

Subsequently, the rProtein A purified pool was applied to an anion exchange chromatographic resin that had been equilibrated with PBS. After the entire applied solution had entered the column, PBS was supplied. A flow-through fraction and the absorption peak at 280 nm at the time of the supply of PBS were collected. The pH of the collected solution was adjusted with acetic acid. The solution was filtrated through Stericup-GV (Merck Millipore) that was a 0.22-μm filter, and the resultant filtrate was defined as an AEX purified pool.

Subsequently, the AEX purified pool was applied to a cation exchange chromatographic resin that had been equilibrated with an acetate buffer. After the entire applied solution had entered the column, the column was washed with an acetate buffer. Thereafter, elution was carried out using an acetate buffer containing a high concentration of NaCl, and the absorption peak at 280 nm was collected. The collected solution was filtrated through Stericup-GV (Merck Millipore) that was a 0.22-μm filter, and the resultant filtrate was defined as a CEX purified pool.

The CEX purified pool was concentrated to an antibody concentration of 40 mg/mL with Pellicon 3 Cassette 30 kDa (Merck Millipore), and the buffer was then replaced with a histidine buffer (25 mM histidine, 5% sorbitol, pH 6.0). Finally, the solution was filtrated through Stericup-GV (Merck Millipore) that was a 0.22-μm filter, so as to obtain a purified sample. This purified sample was named "h046-Hwt/L6".

6)-7-6-4 Purification of Humanized h046-H8/L1

The "h046-H8/L1 culture supernatant" obtained in Example 6)-7-5-4 was purified by a three-step process, namely, by rProtein A affinity chromatography, anion exchange chromatography, and cation exchange chromatography. First, the culture supernatant was applied to rProtein A affinity chromatographic resin that had been equilibrated with PBS. After the entire culture solution had entered the column, the column was washed with PBS, a buffer solution containing arginine, and PBS. Subsequently, the remaining substance in the column was eluted with an acetate buffer, and an absorption peak at 280 nm was then collected. The collected solution was neutralized with a Tris buffer. The solution was filtrated through Stericup-GV (Merck Millipore) that was a 0.22-μm filter, and the resultant filtrate was defined as an rProtein A purified pool.

Subsequently, the rProtein A purified pool was applied to an anion exchange chromatographic resin that had been equilibrated with PBS. After the entire applied solution had entered the column, PBS was supplied. A flow-through fraction and the absorption peak at 280 nm at the time of the supply of PBS were collected. The pH of the collected solution was adjusted with acetic acid. The solution was filtrated through Stericup-GV (Merck Millipore) that was a 0.22-μm filter, and the resultant filtrate was defined as an AEX purified pool.

Subsequently, the AEX purified pool was applied to a cation exchange chromatographic resin that had been equilibrated with an acetate buffer. After the entire applied solution had entered the column, the column was washed with an acetate buffer. Thereafter, elution was carried out using an acetate buffer containing a high concentration of NaCl, and the absorption peak at 280 nm was collected. The collected solution was filtrated through Stericup-GV (Merck Millipore) that was a 0.22-μm filter, and the resultant filtrate was defined as a CEX purified pool.

The CEX purified pool was concentrated to an antibody concentration of 40 mg/mL with Pellicon 3 Cassette 30 kDa (Merck Millipore), and the buffer was then replaced with a histidine buffer (25 mM histidine, 5% sorbitol, pH 6.0). Finally, the solution was filtrated through Stericup-GV (Merck Millipore) that was a 0.22-μm filter, so as to obtain a purified sample. This purified sample was named "h046-H8/L1".

6)-7-6-5 Purification of Humanized h046-H10/L1

The "h046-H10/L1 culture supernatant" obtained in Example 6)-7-5-5 was purified by a three-step process, namely, by rProtein A affinity chromatography, anion exchange chromatography, and cation exchange chromatography. First, the culture supernatant was applied to rProtein A affinity chromatographic resin that had been equilibrated with PBS. After the entire culture solution had entered the column, the column was washed with PBS, a buffer solution containing arginine, and PBS. Subsequently, the remaining substance in the column was eluted with an acetate buffer, and an absorption peak at 280 nm was then collected. The collected solution was neutralized with a Tris buffer, and then roughly filtrated through a glass fiber filter AP20 (Merck Millipore). Thereafter, the solution was filtrated through Stericup-GV (Merck Millipore) that was a 0.22-μm filter, and the resultant filtrate was defined as an rProtein A purified pool.

Subsequently, the rProtein A purified pool was applied to an anion exchange chromatographic resin that had been equilibrated with PBS. After the entire applied solution had entered the column, PBS was supplied. A flow-through fraction and the absorption peak at 280 nm at the time of the supply of PBS were collected. The pH of the collected solution was adjusted with acetic acid. The solution was filtrated through Stericup-GV (Merck Millipore) that was a 0.22-μm filter, and the resultant filtrate was defined as an AEX purified pool.

Subsequently, the AEX purified pool was applied to a cation exchange chromatographic resin that had been equilibrated with an acetate buffer. After the entire applied solution had entered the column, the column was washed with an acetate buffer. Thereafter, elution was carried out using an acetate buffer containing a high concentration of NaCl, and the absorption peak at 280 nm was collected. The collected solution was filtrated through Stericup-GV (Merck Millipore) that was a 0.22-μm filter, and the resultant filtrate was defined as a CEX purified pool.

The CEX purified pool was concentrated to an antibody concentration of 40 mg/mL with Pellicon 3 Cassette 30 kDa (Merck Millipore), and the buffer was then replaced with a histidine buffer (25 mM histidine, 5% sorbitol, pH 6.0). Finally, the solution was filtrated through Stericup-GV (Merck Millipore) that was a 0.22-μm filter, so as to obtain a purified sample. This purified sample was named "h046-H10/L1".

6)-7-6-6 Purification of Humanized h046-H10/L6

The "h046-H10/L6 culture supernatant" obtained in Example 6)-7-5-6 was purified by a three-step process, namely, by rProtein A affinity chromatography, anion exchange chromatography, and cation exchange chromatography. First, the culture supernatant was applied to rProtein A affinity chromatographic resin that had been equilibrated with PBS. After the entire culture solution had entered the column, the column was washed with PBS, a buffer solution containing arginine, and PBS. Subsequently, the remaining substance in the column was eluted with an acetate buffer, and an absorption peak at 280 nm was then collected. The collected solution was neutralized with a Tris buffer. The solution was filtrated through Stericup-GV (Merck Millipore) that was a 0.22-μm filter, and the resultant filtrate was defined as an rProtein A purified pool.

Subsequently, the rProtein A purified pool was applied to an anion exchange chromatographic resin that had been equilibrated with PBS. After the entire applied solution had entered the column, PBS was supplied. A flow-through fraction and the absorption peak at 280 nm at the time of the supply of PBS were collected. The pH of the collected solution was adjusted with acetic acid. The solution was filtrated through Stericup-GV (Merck Millipore) that was a 0.22-μm filter, and the resultant filtrate was defined as an AEX purified pool.

Subsequently, the AEX purified pool was applied to a cation exchange chromatographic resin that had been equilibrated with an acetate buffer. After the entire applied solution had entered the column, the column was washed with an acetate buffer. Thereafter, elution was carried out using an acetate buffer containing a high concentration of NaCl, and the absorption peak at 280 nm was collected. The collected solution was filtrated through Stericup-GV (Merck Millipore) that was a 0.22-μm filter, and the resultant filtrate was defined as a CEX purified pool.

The CEX purified pool was concentrated to an antibody concentration of 40 mg/mL with Pellicon 3 Cassette 30 kDa (Merck Millipore), and the buffer was then replaced with a histidine buffer (25 mM histidine, 5% sorbitol, pH 6.0). Finally, the solution was filtrated through Stericup-GV (Merck Millipore) that was a 0.22-μm filter, so as to obtain a purified sample. This purified sample was named "h046-H10/L6".

6)-7-6-7 Purification of Humanized h046-H4e/L7

The "h046-H4e/L7 culture supernatant" obtained in Example 6)-7-5-7 was purified by a three-step process, namely, by rProtein A affinity chromatography, anion exchange chromatography, and cation exchange chromatography. First, the culture supernatant was applied to rProtein A affinity chromatographic resin that had been equilibrated with PBS. After the entire culture solution had entered the column, the column was washed with PBS, a buffer solution containing arginine, and PBS. Subsequently, the remaining substance in the column was eluted with an acetate buffer, and an absorption peak at 280 nm was then collected. The collected solution was neutralized with a Tris buffer. The solution was filtrated through Millipore Express SHC (Merck Millipore) that was a 0.5/0.2-μm filter, and the resultant filtrate was defined as an rProtein A purified pool.

Subsequently, the rProtein A purified pool was applied to an anion exchange chromatographic resin that had been equilibrated with PBS. After the entire applied solution had entered the column, PBS was supplied. A flow-through fraction and the absorption peak at 280 nm at the time of the supply of PBS were collected. The pH of the collected solution was adjusted with acetic acid. The solution was filtrated through Stericup-GV (Merck Millipore) that was a 0.22-μm filter, and the resultant filtrate was defined as an AEX purified pool.

Subsequently, the AEX purified pool was applied to a cation exchange chromatographic resin that had been equilibrated with an acetate buffer. After the entire applied solution had entered the column, the column was washed with an acetate buffer. Thereafter, elution was carried out using an acetate buffer containing a high concentration of NaCl, and the absorption peak at 280 nm was collected. The collected solution was filtrated through Stericup-GV (Merck Millipore) that was a 0.22-μm filter, and the resultant filtrate was defined as a CEX purified pool.

The CEX purified pool was concentrated to an antibody concentration of 40 mg/mL with Pellicon 3 Cassette 30 kDa (Merck Millipore), and the buffer was then replaced with a histidine buffer (25 mM histidine, 5% sorbitol, pH 6.0). Finally, the solution was filtrated through Stericup-GV (Merck Millipore) that was a 0.22-μm filter, so as to obtain a purified sample. This purified sample was named "h046-H4e/L7".

Example 7: Production of Anti-GPR20 Antibody-Drug Conjugate

7)-1 Production of Antibody-Drug Conjugate—(1)

[Formula 14]

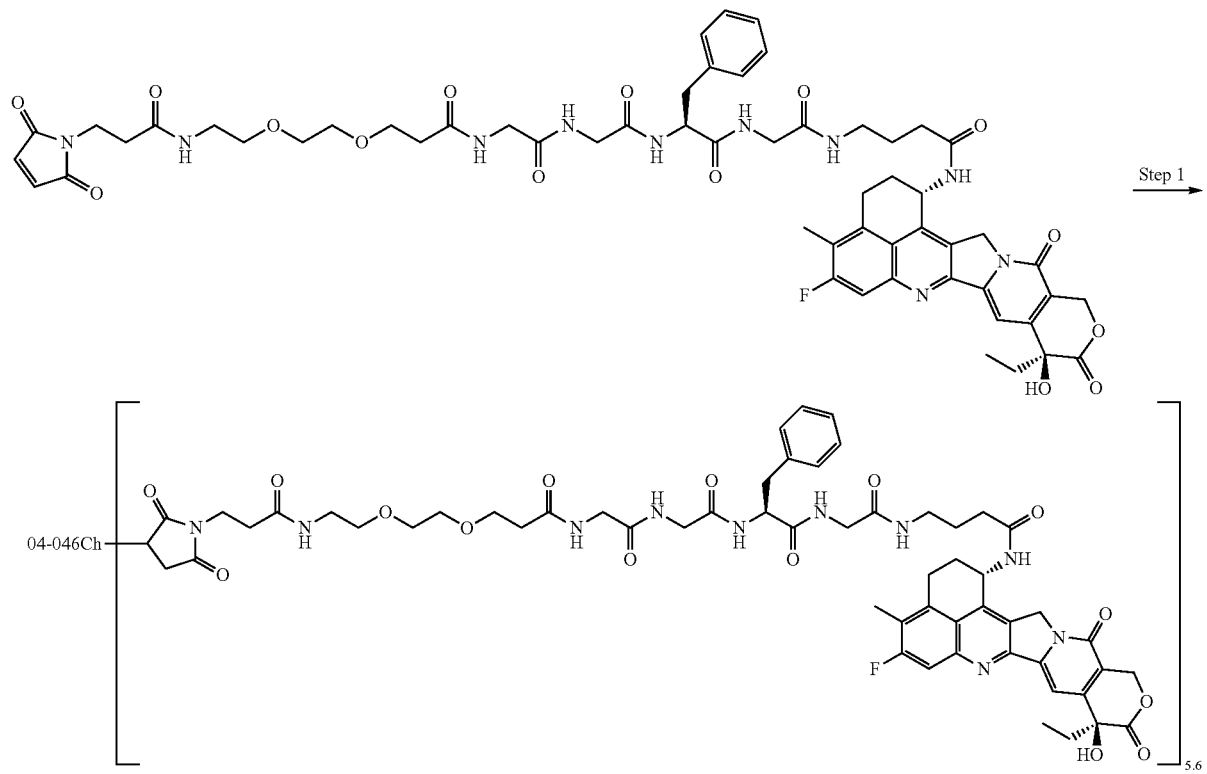

Step 1: Antibody-Drug Conjugate (1)

Reduction of antibody: 04-046Ch produced in Example 5)-2 was adjusted to 10 mg/mL with PBS6.0/EDTA by using common procedures B (using 1.47 mLmg$^{-1}$cm$^{-1}$ as 280 nm absorption coefficient) and C described in production method 1. To this solution (3.40 mL), an aqueous solution of 9.4 mM TCEP (Tokyo Chemical Industry Co., Ltd.) (0.104 mL; 5.0 equivalents per antibody molecule) and a 1 M aqueous dipotassium hydrogen phosphate solution (Nacalai Tesque, Inc.; 0.170 mL) were added. After confirming that the solution had a pH within 7.4±0.1, the interchain disulfide bond in the antibody was reduced by incubating the solution at 37° C. for 1 hour.

Conjugation between antibody and drug linker: The above-described solution was incubated at 15° C. for 10 minutes. Subsequently, a 10 mM solution of N-{3-[2-(2-{[3-(2,5-dioxo-2,5-dihydro-1H-pyrrol-1-yl)propanoyl]amino}ethoxy)ethoxy]propanoyl}glycylglycyl-L-phenyl-alanyl-N-(4-{[(1S,9S)-9-ethyl-5-fluoro-9-hydroxy-4-methyl-10,13-dioxo-2,3,9,10,13,15-hexahydro-1H,12H- benzo[de]pyrano[3',4':6,7]indolizino[1,2-b]quinolin-1-yl]amino}-4-oxobutyl)glycinamide in dimethyl sulfoxide (0.189 mL; 8.6 equivalents per antibody molecule) was added thereto, and the obtained mixture was incubated at 15° C. for 1 hour to conjugate the drug linker to the antibody. Subsequently, an aqueous solution of 100 mM NAC (Sigma-Aldrich Co. LLC) (0.0284 mL; 12.9 equivalents per antibody molecule) was added thereto, and the obtained mixture was further stirred at room temperature for 20 minutes to terminate the reaction of the drug linker.

Purification: The above-described solution was purified by common procedure D described in production method 1 to obtain 14.0 mL of a solution containing the antibody-drug conjugate "046Ch-ADC2".

Characterization: Using common procedure E (using $\varepsilon_{D,280}$=4964 and $\varepsilon_{D,370}$=18982) described in production method 1, the following characteristic values were obtained.

Antibody concentration: 2.26 mg/mL, antibody yield: 31.6 mg (93%), and average number of conjugated drug molecules (n) per antibody molecule: 5.6.

7)-2 Production of Antibody-Drug Conjugate (2)

9.4 mM TCEP (Tokyo Chemical Industry Co., Ltd.) (0.104 mL; 5.0 equivalents per antibody molecule) and a 1 M aqueous dipotassium hydrogen phosphate solution (Nacalai Tesque, Inc.; 0.0509 mL) were added. After confirming that the solution had a pH within 7.0±0.1, the interchain disulfide bond in the antibody was reduced by incubating the solution at 37° C. for 1 hour.

Conjugation between antibody and drug linker: The above-described solution was incubated at 15° C. for 10 minutes. Subsequently, a 9.3 M solution of N-[6-(2,5-dioxo-2,5-dihydro-1H-pyrrol-1-yl)hexanoyl]glycylglycyl-L-phenylalanyl-N-[(2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-oxoethoxy)methyl]glycinamide in dimethyl sulfoxide (0.176 mL; 8.6 equivalents per antibody molecule) was added thereto, and the obtained mixture was incubated at 15° C. for 1 hour to conjugate the drug linker to the antibody. Subsequently, an aqueous solution of 100 mM NAC (Sigma-Aldrich Co. LLC) (0.0284 mL; 12.9 equivalents per antibody molecule) was added thereto, and the

[Formula 15]

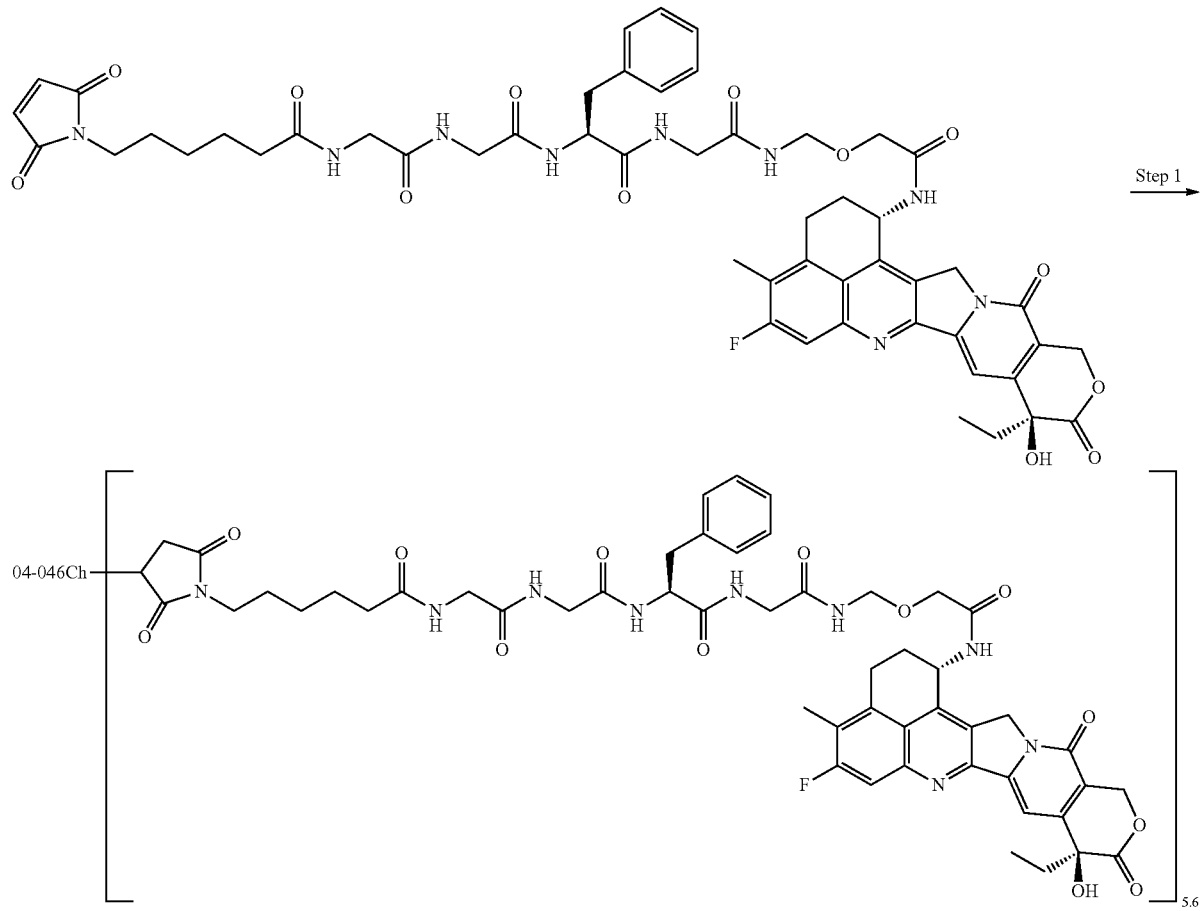

Step 1: Antibody-Drug Conjugate (2)

Reduction of antibody: 04-046Ch produced in Example 5)-2 was adjusted to 10 mg/mL with PBS6.0/EDTA by using common procedures B (using 1.47 mLmg$^{-1}$cm$^{-1}$ as 280 nm absorption coefficient) and C described in production method 1. To this solution (3.40 mL), an aqueous solution of obtained mixture was further stirred at room temperature for 20 minutes to terminate the reaction of the drug linker.

Purification: The above-described solution was purified by common procedure D described in production method 1 to obtain 14.0 mL of a solution containing the antibody-drug conjugate "046Ch-ADC1".

Characterization: Using common procedure E (using $\varepsilon_{D,280}$=5178 and $\varepsilon_{D,370}$=20217) described in production method 1, the following characteristic values were obtained.

Antibody concentration: 2.23 mg/mL, antibody yield: 31.2 mg (92%), and average number of conjugated drug molecules (n) per antibody molecule: 5.6.

7)-3 Production of Antibody-Drug Conjugate (3)

[Formula 16]

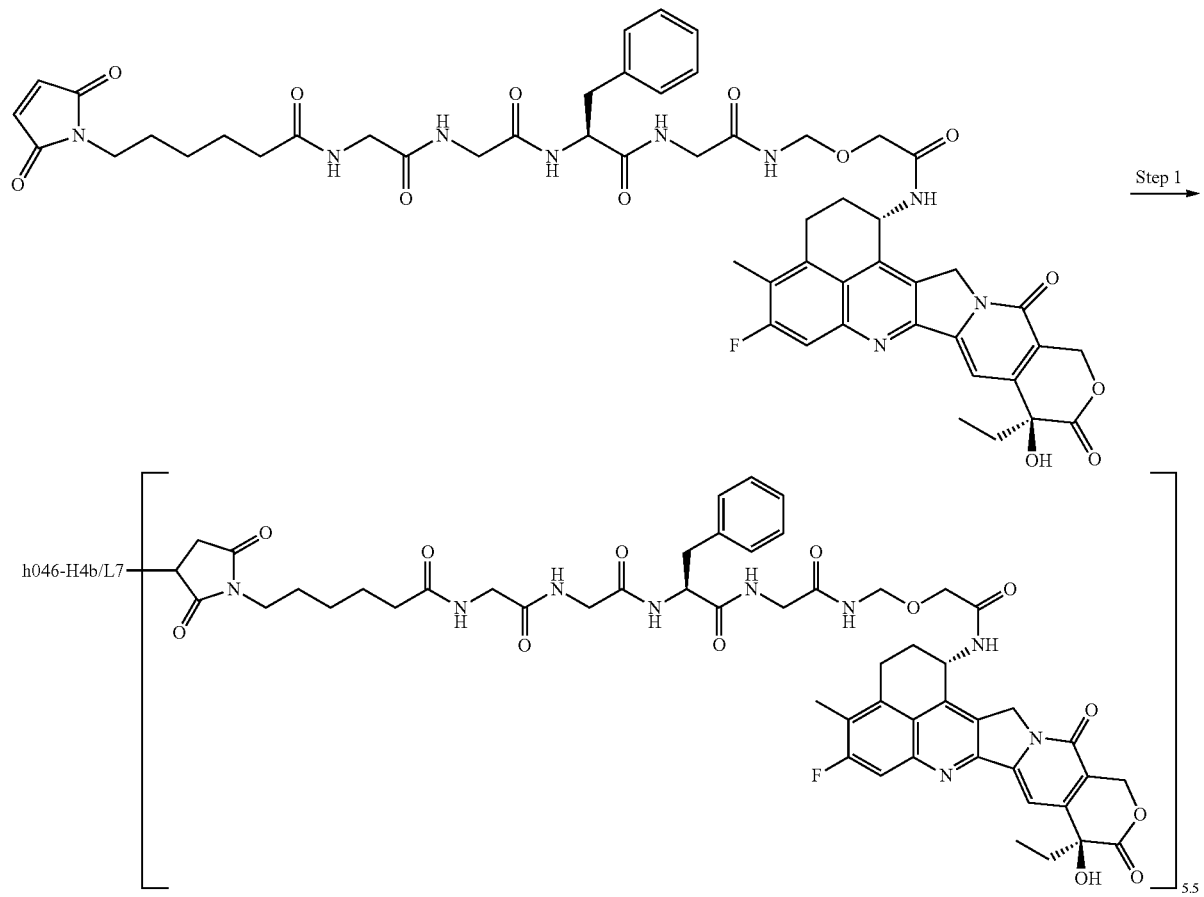

Step 1: Antibody-Drug Conjugate (3)

Reduction of antibody: h046-H4b/L7 produced in Example 6)-7-6-1 was adjusted to 10 mg/mL with PBS6.0/EDTA by using common procedures B (using 1.31 mLmg$^{-1}$cm$^{-1}$ as 280 nm absorption coefficient) and C described in production method 1. To this solution (6.25 mL), an aqueous solution of 10 mM TCEP (Tokyo Chemical Industry Co., Ltd.) (0.237 mL; 5.5 equivalents per antibody molecule) and a 1 M aqueous dipotassium hydrogen phosphate solution (Nacalai Tesque, Inc.; 0.0940 mL) were added. After confirming that the solution had a pH within 7.0±0.1, the interchain disulfide bond in the antibody was reduced by incubating the solution at 37° C. for 1 hour.

Conjugation between antibody and drug linker: The above-described solution was incubated at 15° C. for 10 minutes. Subsequently, a 10 mM solution of N-[6-(2,5-dioxo-2,5-dihydro-1H-pyrrol-1-yl)hexanoyl]glycylglycyl-L-phenylalanyl-N-[(2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-oxoethoxy)methyl]glycinamide in dimethyl sulfoxide (0.388 mL; 9.0 equivalents per antibody molecule) was added thereto, and the obtained mixture was incubated at 15° C. for 1 hour to conjugate the drug linker to the antibody. Subsequently, an aqueous solution of 100 mM NAC (Sigma-Aldrich Co. LLC) (0.0390 mL; 9.0 equivalents per antibody molecule) was added thereto, and the obtained mixture was further stirred at room temperature for 20 minutes to terminate the reaction of the drug linker.

Purification: The above-described solution was purified by common procedure D described in production method 1 to obtain 30.0 mL of a solution containing the antibody-drug conjugate "h046-H4b/L7-ADC1".

Characterization: Using common procedures E and F ((using $\varepsilon_{D,280}$=5178 and $\varepsilon_{D,370}$=20217) described in production method 1, the following characteristic values were obtained.

Antibody concentration: 2.03 mg/mL, antibody yield: 61.0 mg (97%), average number of conjugated drug molecules (n) per antibody molecule measured by common procedure E: 5.5, and average number of conjugated drug molecules (n) per antibody molecule measured by common procedure F: 7.8.

7)-4 Production of Antibody-Drug Conjugate (4)

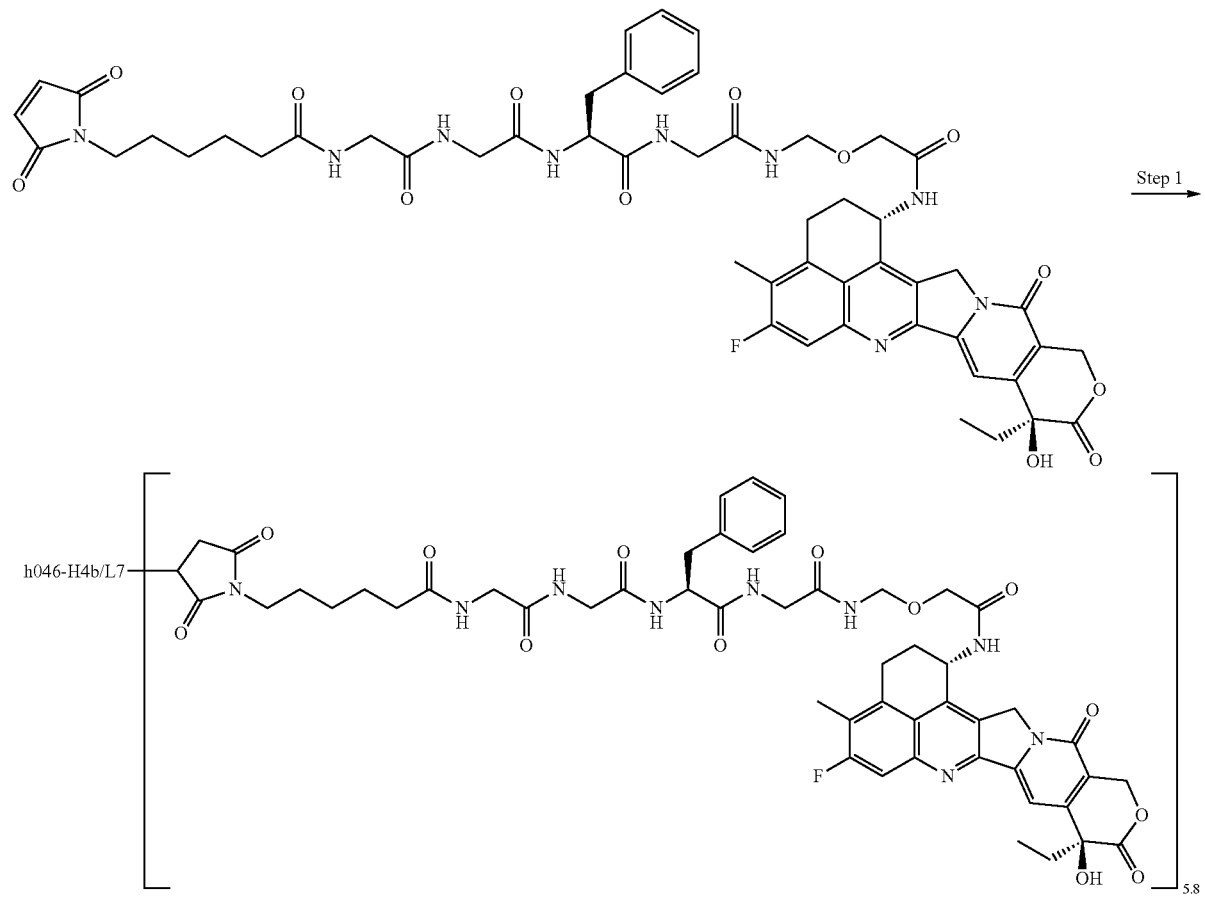

Step 1: Antibody-Drug Conjugate (4)

Reduction of antibody: h046-H4b/L7 produced in Example 6)-7-6-1 was adjusted to 10 mg/mL with PBS6.0/EDTA by using common procedures B (using 1.31 mLmg$^{-1}$cm$^{-1}$ as 280 nm absorption coefficient) and C described in production method 1. This solution (300 mL) was placed in a 1000-mL polycarbonate Erlenmeyer flask, and then charged with a 1 M aqueous dipotassium hydrogen phosphate solution (4.80 mL) and thereafter with a 10 mM aqueous TCEP solution (11.3 mL; 5.5 equivalents per antibody molecule) at room temperature with stirring using a magnetic stirrer. After confirming that the solution had a pH within 7.0±0.1, the stirring was terminated, and the interchain disulfide bond in the antibody was reduced by incubating the solution at 37° C. for 2 hours.

Conjugation between antibody and drug linker: The above-described solution was cooled to 15° C. Thereafter, a DMSO solution containing 10 mM N-[6-(2,5-dioxo-2,5-dihydro-1H-pyrrol-1-yl)hexanoyl]glycylglycyl-L-phenylalanyl-N-[(2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-oxoethoxy)methyl]glycinamide (18.5 mL; 9.0 equivalents per antibody molecule) was gradually added dropwise thereto with stirring. The obtained mixture was stirred at 15° C. for 30 minutes to conjugate the drug linker to the antibody. Subsequently, a 100 mM aqueous NAC solution (1.85 mL; 9.0 equivalents per antibody molecule) was added thereto with stirring, and the obtained mixture was further stirred at room temperature for 20 minutes to terminate the reaction of unreacted drug linker.

Purification: The obtained solution was purified by ultrafiltration using an ultrafiltration apparatus constituted by an ultrafiltration membrane (Merck Japan, Ltd., Pellicon XL Cassette, Ultracell 30 KDa), a tube pump (Cole-Parmer International, USA, MasterFlex pump model 77521-40, pump head model 7518-00), and a tube (Cole-Parmer International, USA, MasterFlex tube L/516). Specifically, while ABS was added dropwise (a total of 3.00 L) as a buffer solution for purification to the reaction solution, ultrafiltration purification was carried out, so as to replace the buffer with ABS and further concentrate the solution while removing non-conjugated drug linker and other low-molecular-weight reagents. The obtained purified solution was subjected to microfiltration (0.22 µm, PVDF membrane, twice) to obtain 83.0 mL of a solution containing the antibody-drug conjugate "h046-H4b/L7-ADC1".

Characterization: Using common procedures E and F (using $\varepsilon_{D,280}$=5178 and $\varepsilon_{D,370}$=20217), the following characteristic values were obtained.

Antibody concentration: 23.1 mg/mL, antibody yield: 2.94 g (98%), average number of conjugated drug molecules (n) per antibody molecule measured by common procedure E: 5.8, and average number of conjugated drug molecules (n) per antibody molecule measured by common procedure F: 7.4.

7)-5 Production of Antibody-Drug Conjugate (5)

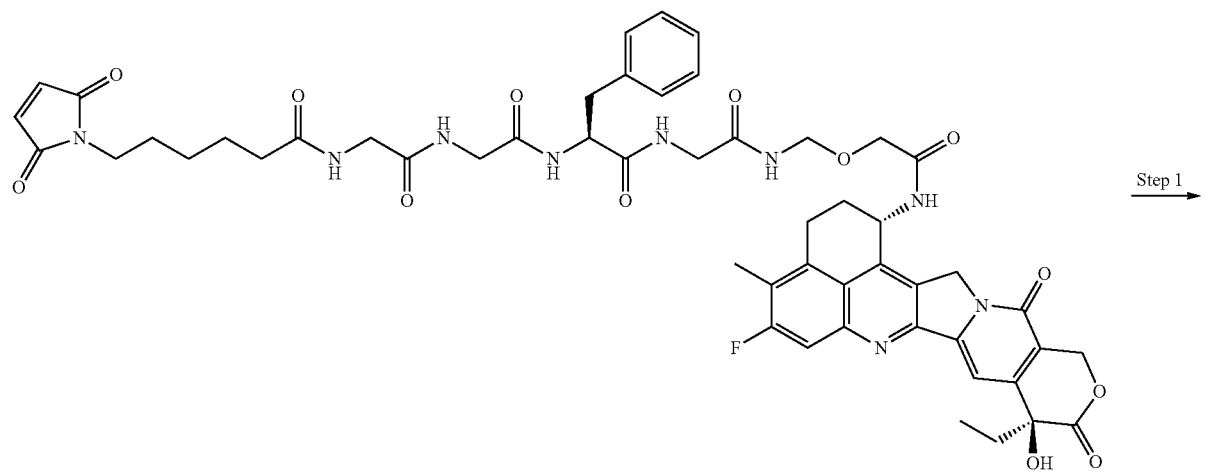

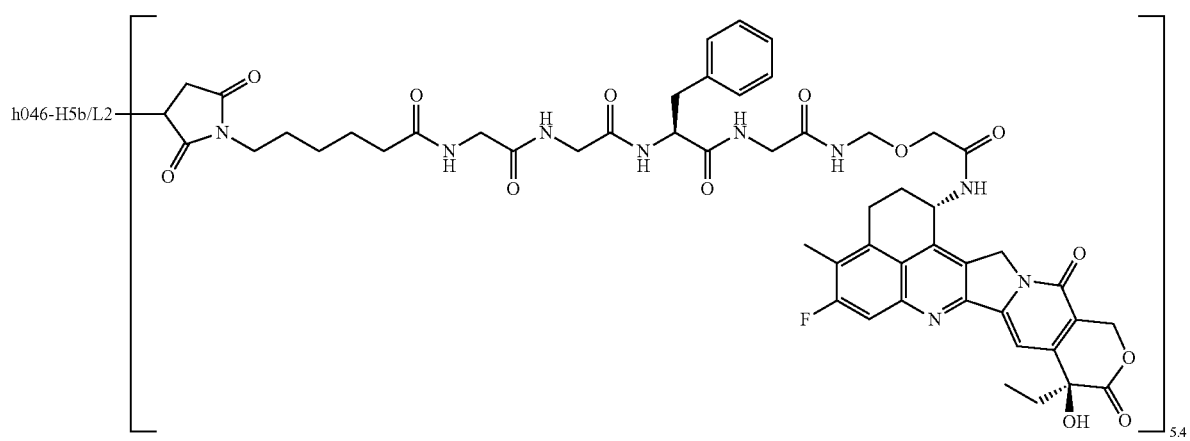

Step 1: Antibody-Drug Conjugate (5)

Using h046-H5b/L2 (using 1.31 mLmg$^{-1}$cm$^{-1}$ as 280 nm absorption coefficient) produced in Example 6)-7-6-2, the antibody-drug conjugate "h046-H5b/L2-ADC1" was obtained by the same method as that applied in step 1 of Example 7-3.

Antibody concentration: 2.04 mg/mL, antibody yield: 61.3 mg (98%), average number of conjugated drug molecules (n) per antibody molecule measured by common procedure E: 5.4, and average number of conjugated drug molecules (n) per antibody molecule measured by common procedure F: 7.9.

7)-6 Production of Antibody-Drug Conjugate (6)

[Formula 19]

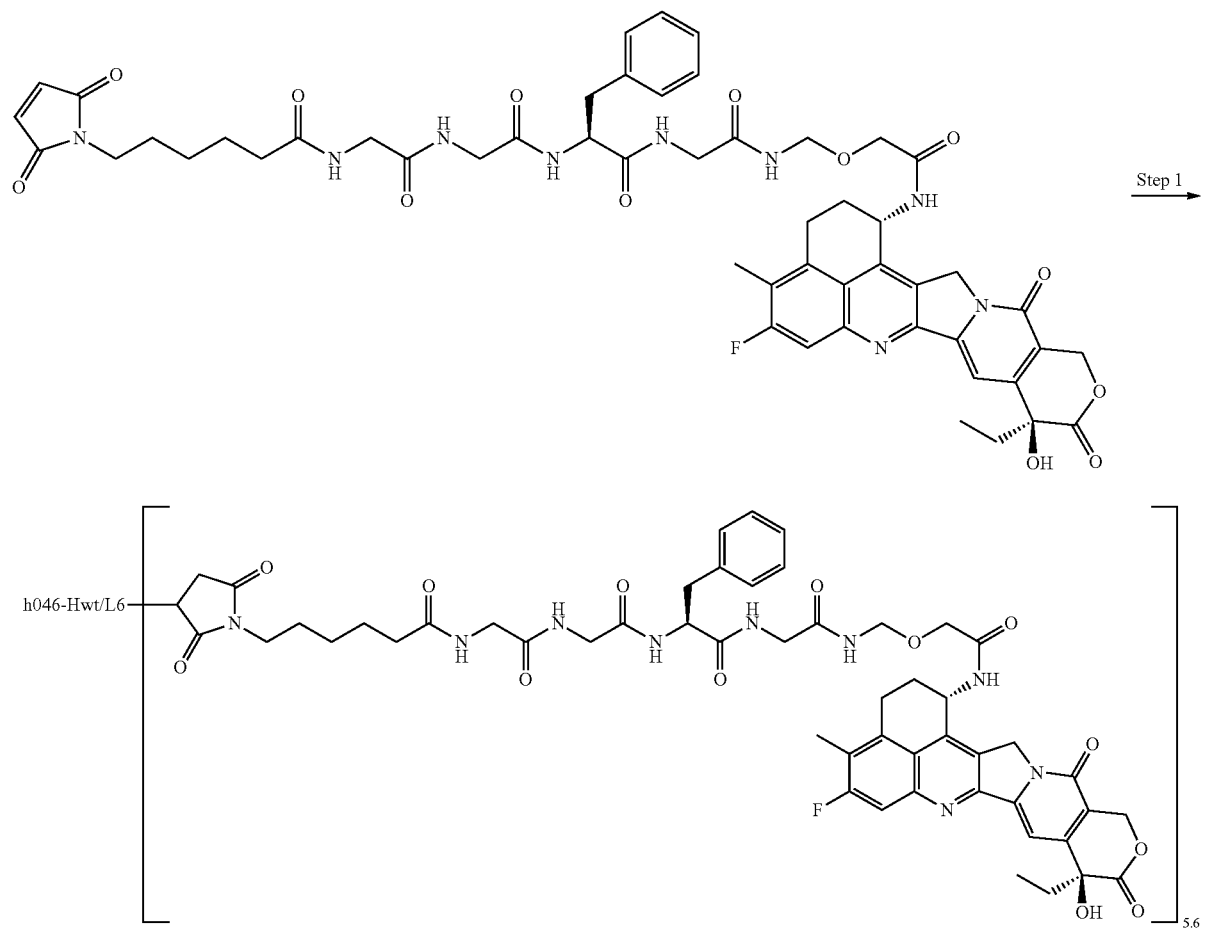

Step 1: Antibody-Drug Conjugate (6)

Using h046-Hwt/L6 (using 1.31 mLmg$^{-1}$cm$^{-1}$ as 280 nm absorption coefficient) produced in Example 6)-7-6-3, the antibody-drug conjugate "h046-Hwt/L6-ADC1" was obtained by the same method as that applied in step 1 of Example 7-3.

Antibody concentration: 2.03 mg/mL, antibody yield: 60.9 mg (95%), average number of conjugated drug molecules (n) per antibody molecule measured by common procedure E: 5.6, and average number of conjugated drug molecules (n) per antibody molecule measured by common procedure F: 7.8.

7)-7 Production of Antibody-Drug Conjugate (7)

[Formula 20]

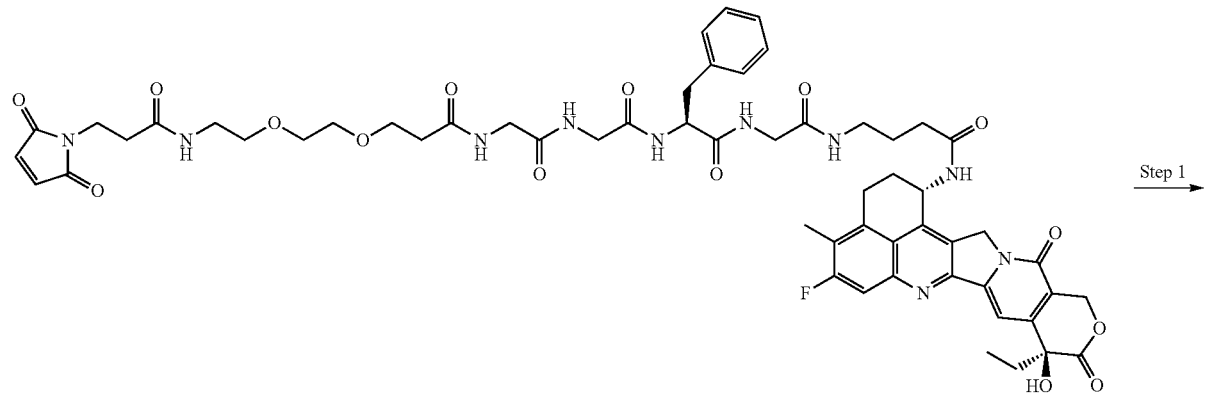

Step 1

-continued

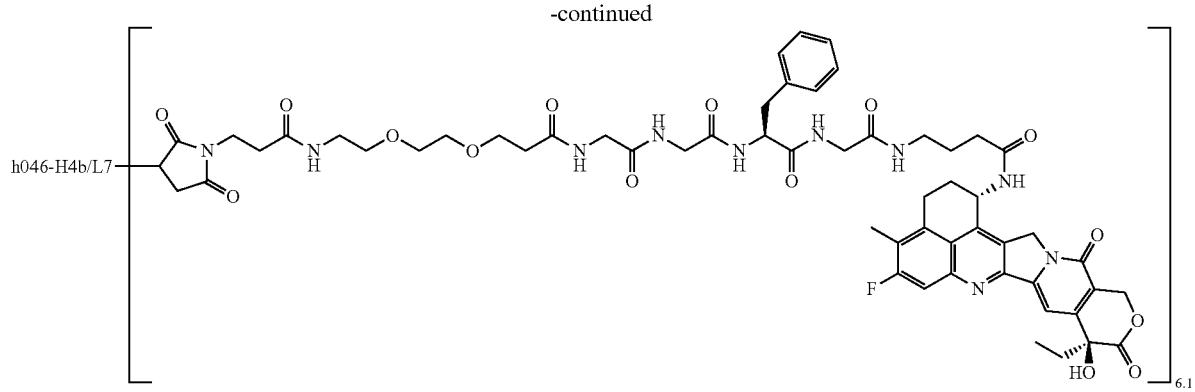

Step 1: Antibody-Drug Conjugate (7)

Reduction of antibody: h046-H4b/L7 produced in Example 6)-7-6-1 was adjusted to 10 mg/mL with PBS6.0/EDTA by using common procedures B (using 1.31 mLmg$^{-1}$cm$^{-1}$ as 280 nm absorption coefficient) and C described in production method 1. To this solution (5.00 mL), an aqueous solution of 10 mM TCEP (Tokyo Chemical Industry Co., Ltd.) (0.193 mL; 5.5 equivalents per antibody molecule) and a 1 M aqueous dipotassium hydrogen phosphate solution (Nacalai Tesque, Inc.; 0.0752 mL) were added. After confirming that the solution had a pH within 7.0±0.1, the interchain disulfide bond in the antibody was reduced by incubating the solution at 37° C. for 1 hour.

Conjugation between antibody and drug linker: The above-described solution was incubated at 15° C. for 10 minutes. Subsequently, a 10 mM solution of N-{3-[2-(2-{[3-(2,5-dioxo-2,5-dihydro-1H-pyrrol-1-yl)propanoyl]amino}ethoxy)ethoxy]propanoyl}glycylglycyl-L-phenylalanyl-N-(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl)glycinamide in dimethyl sulfoxide (0.315 mL; 9.0 equivalents per antibody molecule) was added thereto, and the obtained mixture was incubated at 15° C. for 1 hour to conjugate the drug linker to the antibody. Subsequently, an aqueous solution of 100 mM NAC (Sigma-Aldrich Co. LLC) (0.0316 mL; 9.0 equivalents per antibody molecule) was added thereto, and the obtained mixture was further stirred at room temperature for 20 minutes to terminate the reaction of the drug linker.

Purification: The above-described solution was purified by common procedure D described in production method 1 to obtain 24.0 mL of a solution containing the antibody-drug conjugate "h046-H4b/L7-ADC2".

Characterization: Using common procedures E and F (using $\varepsilon_{D,280}$=4964 and $\varepsilon_{D,370}$=18982) described in production method 1, the following characteristic values were obtained.

Antibody concentration: 2.07 mg/mL, antibody yield: 49.6 mg (99%), average number of conjugated drug molecules (n) per antibody molecule measured by common procedure E: 6.1, and average number of conjugated drug molecules (n) per antibody molecule measured by common procedure F: 7.6.

7)-8 Production of Antibody-Drug Conjugate (8)

[Formula 21]

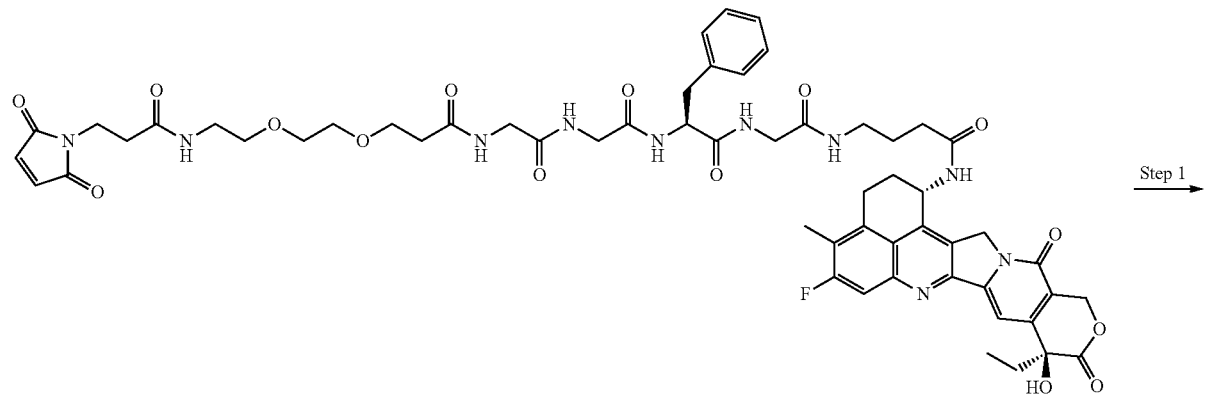

Step 1

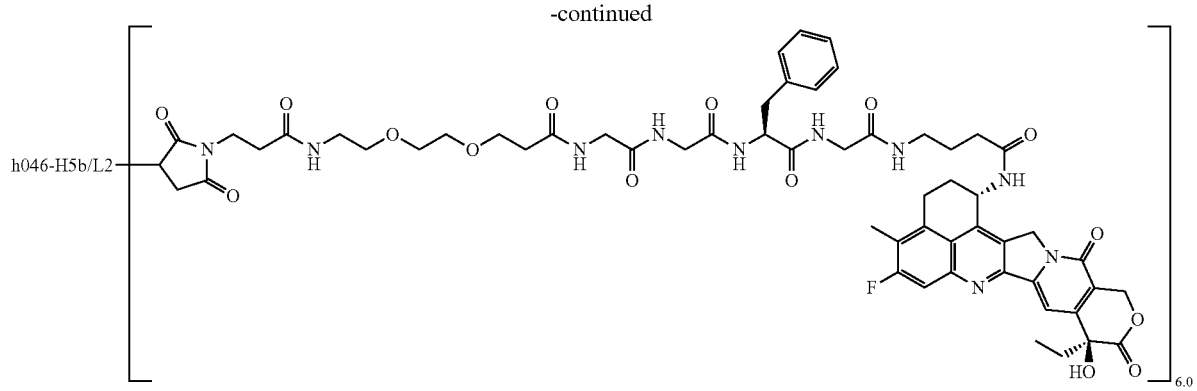

Step 1: Antibody-Drug Conjugate (8)

Reduction of antibody: h046-H5b/L2 produced in Example 6)-7-6-2 was adjusted to 10 mg/mL with PBS6.0/EDTA by using common procedures B (using 1.31 mLmg$^{-1}$cm$^{-1}$ as 280 nm absorption coefficient) and C described in production method 1. To this solution (6.25 mL), an aqueous solution of 10 mM TCEP (Tokyo Chemical Industry Co., Ltd.) (0.237 mL; 5.5 equivalents per antibody molecule) and a 1 M aqueous dipotassium hydrogen phosphate solution (Nacalai Tesque, Inc.; 0.0940 mL) were added. After confirming that the solution had a pH within 7.0±0.1, the interchain disulfide bond in the antibody was reduced by incubating the solution at 37° C. for 1 hour.

Conjugation between antibody and drug linker: The above-described solution was incubated at 15° C. for 10 minutes. Subsequently, a 10 mM solution of N-{3-[2-(2-{[3-(2,5-dioxo-2,5-dihydro-1H-pyrrol-1-yl)propanoyl]amino}ethoxy)ethoxy]propanoyl}glycylglycyl-L-phenylalanyl-N-(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl)glycinamide in dimethyl sulfoxide (0.388 mL; 9.0 equivalents per antibody molecule) was added thereto, and the obtained mixture was incubated at 15° C. for 1 hour to conjugate the drug linker to the antibody. Subsequently, an aqueous solution of 100 mM NAC (Sigma-Aldrich Co. LLC) (0.0390 mL; 9.0 equivalents per antibody molecule) was added thereto, and the obtained mixture was further stirred at room temperature for 20 minutes to terminate the reaction of the drug linker.

Purification: The above-described solution was purified by common procedure D described in production method 1 to obtain 30.0 mL of a solution containing the antibody-drug conjugate "h046-H5b/L2-ADC2".

Characterization: Using common procedures E and F (using $\varepsilon_{D,280}$=4964 and $\varepsilon_{D,370}$=18982) described in production method 1, the following characteristic values were obtained.

Antibody concentration: 2.07 mg/mL, antibody yield: 62.2 mg (99%), average number of conjugated drug molecules (n) per antibody molecule measured by common procedure E: 6.0, and average number of conjugated drug molecules (n) per antibody molecule measured by common procedure F: 7.7.

7)-9 Production of Antibody-Drug Conjugate (9)

[Formula 22]
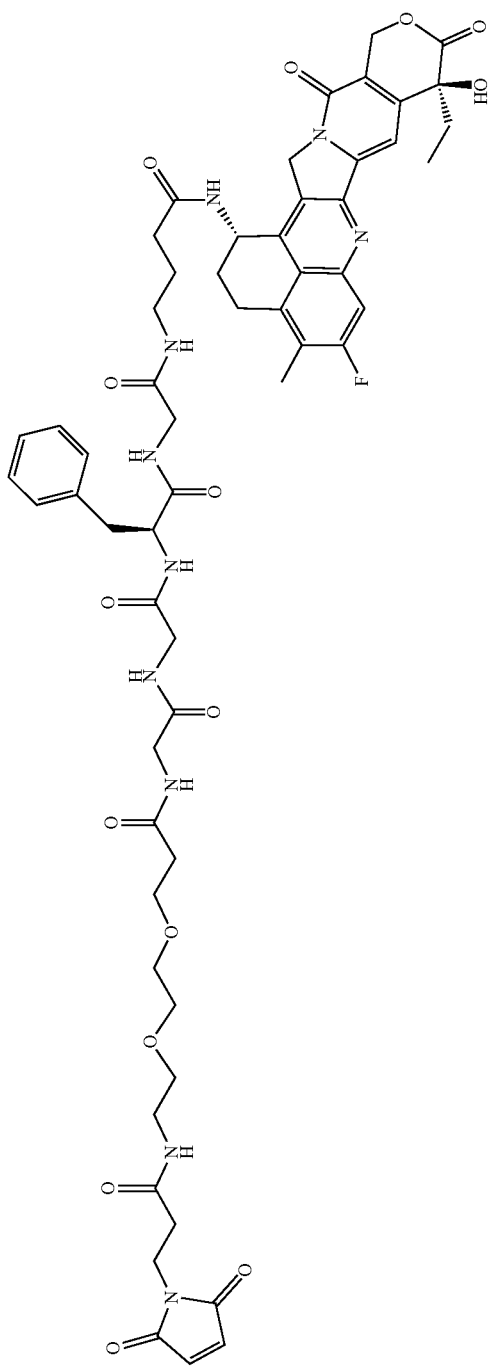 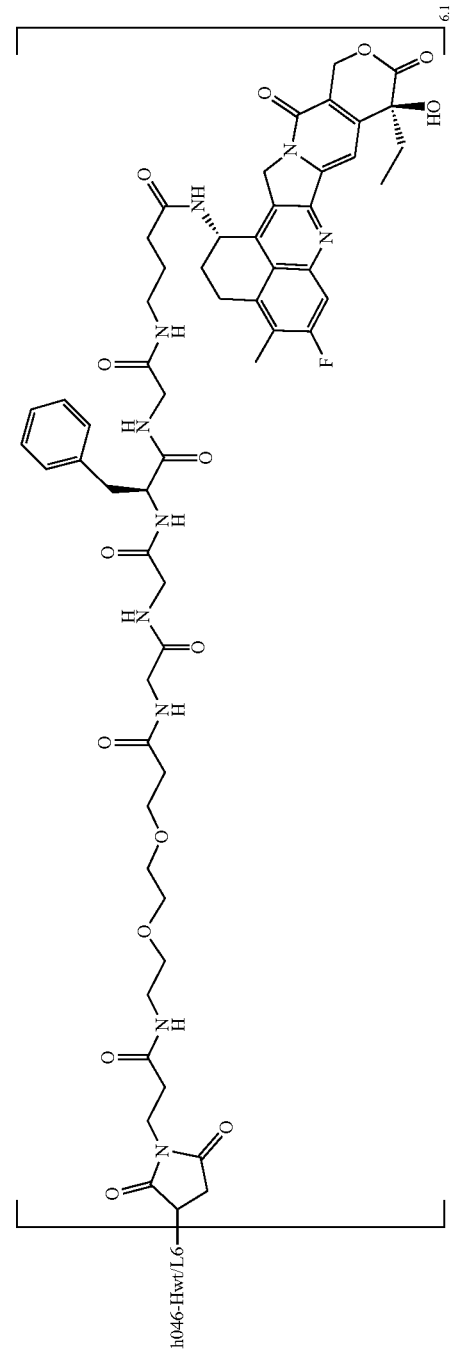

Step 1: Antibody-Drug Conjugate (9)

Using h046-Hwt/L6 (using 1.31 mLmg$^{-1}$cm$^{-1}$ as 280 nm absorption coefficient) produced in Example 6)-7-6-3, the antibody-drug conjugate "h046-Hwt/L6-ADC2" was obtained by the same method as that applied in step 1 of Example 7)-8.

Antibody concentration: 2.10 mg/mL, antibody yield: 62.9 mg (99%), average number of conjugated drug molecules (n) per antibody molecule measured by common procedure E: 6.1, and average number of conjugated drug molecules (n) per antibody molecule measured by common procedure F: 7.4.

7)-10 Production of Antibody-Drug Conjugate (10)

Step 1: Antibody-Drug Conjugate (10)

Using h046-H8/L1 (using 1.31 mLmg$^{-1}$cm$^{-1}$ as 280 nm absorption coefficient) produced in Example 6)-7-6-4, the antibody-drug conjugate "h046-H8/L1-ADC1" was obtained by the same method as that applied in step 1 of Example 7)-3.

Antibody concentration: 1.75 mg/mL, antibody yield: 52.6 mg (86%), average number of conjugated drug molecules (n) per antibody molecule measured by common procedure E: 5.6, and average number of conjugated drug molecules (n) per antibody molecule measured by common procedure F: 7.9.

[Formula 23]

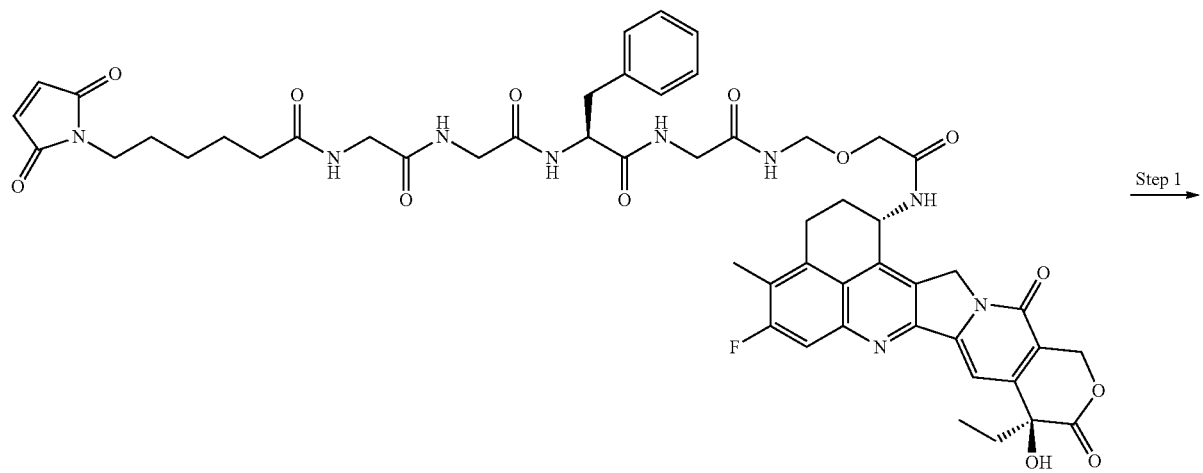

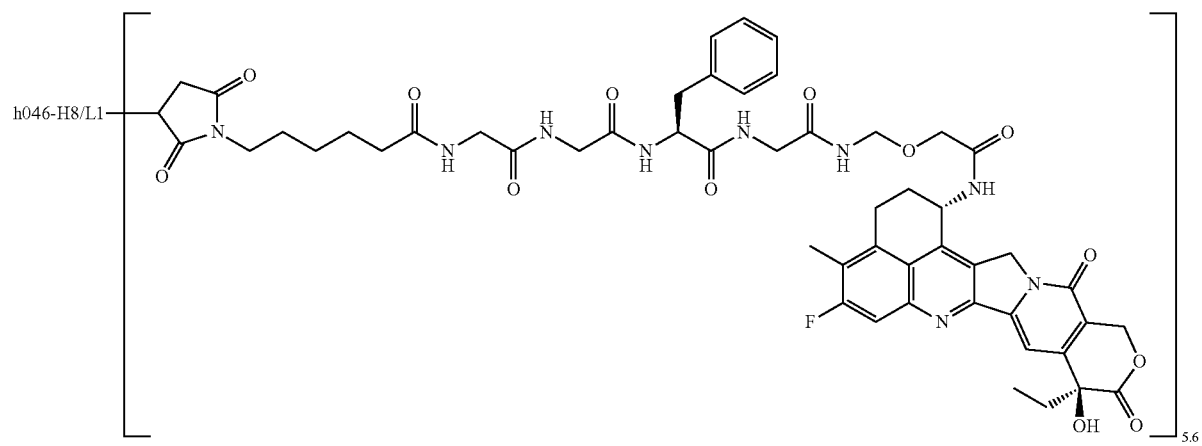

7)-11 Production of Antibody-Drug Conjugate (11)

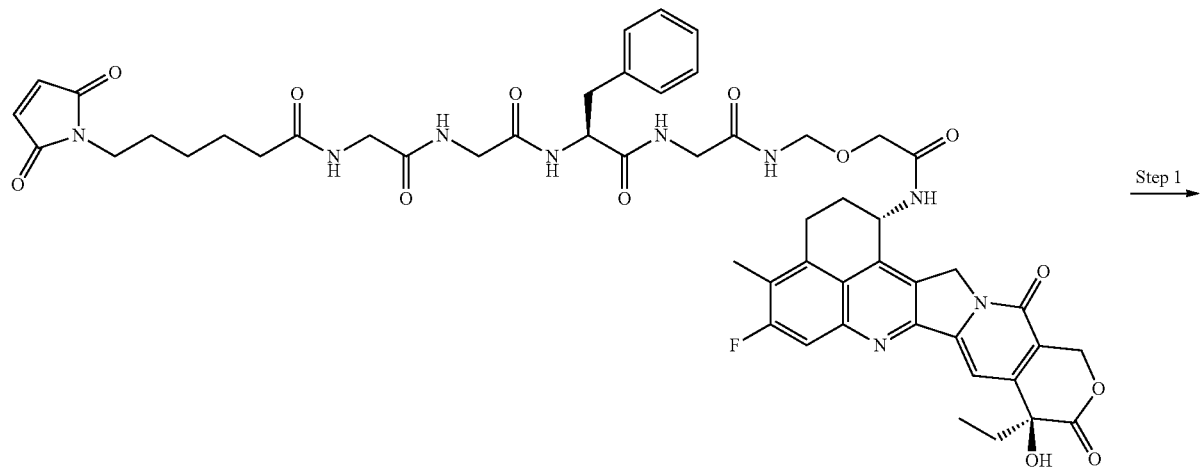

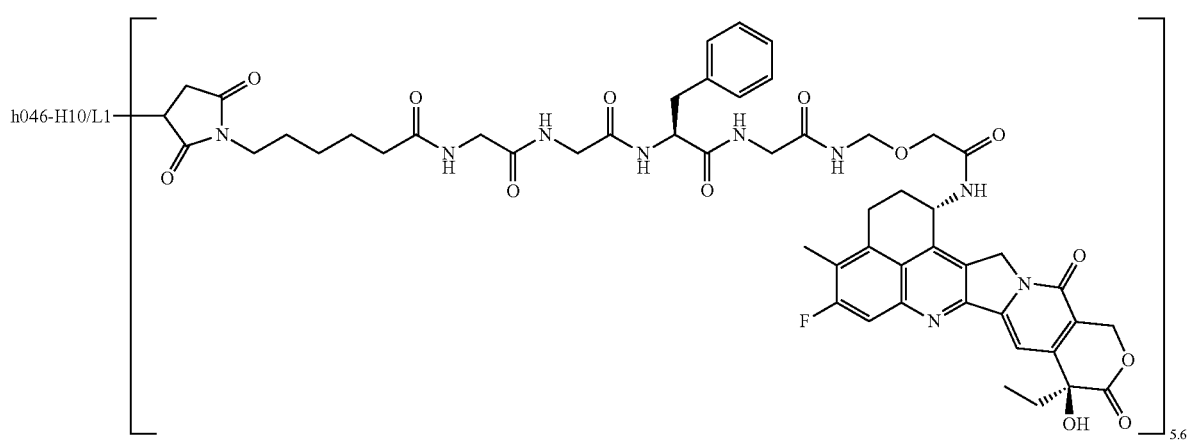

Step 1: Antibody-Drug Conjugate (11)

Using h046-H10/L1 (using 1.31 mLmg$^{-1}$cm$^{-1}$ as 280 nm absorption coefficient) produced in Example 6)-7-6-5, the antibody-drug conjugate "h046-H10/L1-ADC1" was obtained by the same method as that applied in step 1 of Example 7)-3.

Antibody concentration: 1.85 mg/mL, antibody yield: 55.6 mg (90%), average number of conjugated drug molecules (n) per antibody molecule measured by common procedure E: 5.6, and average number of conjugated drug molecules (n) per antibody molecule measured by common procedure F: 7.9.

7)-12 Production of Antibody-Drug Conjugate (12)

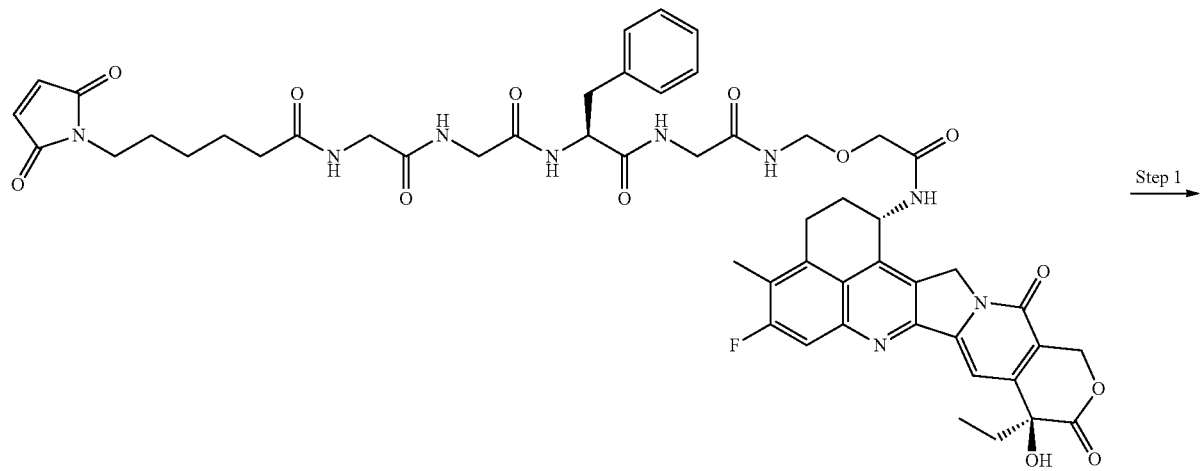

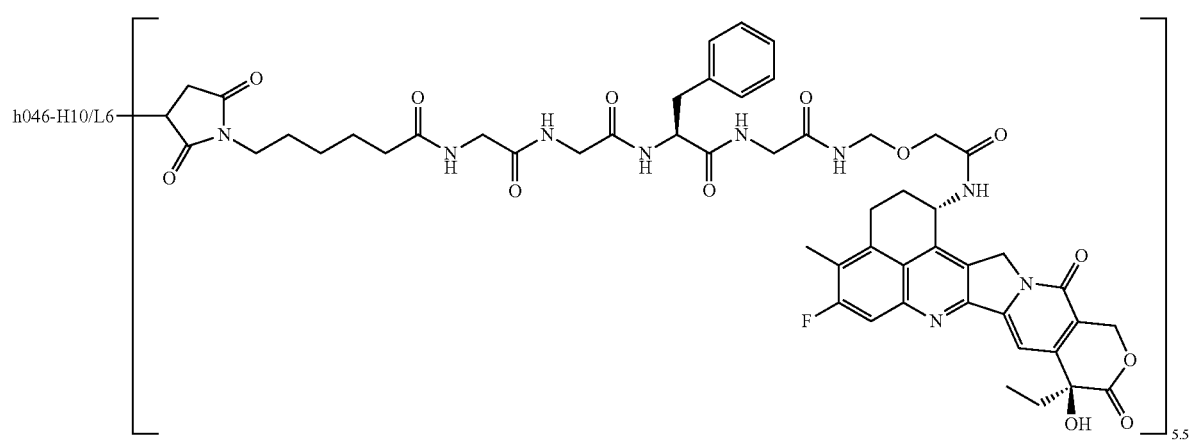

Step 1: Antibody-Drug Conjugate (12)

Using h046-H10/L6 (using 1.31 mLmg⁻¹cm⁻¹ as 280 nm absorption coefficient) produced in Example 6)-7-6-6, the antibody-drug conjugate "h046-H10/L6-ADC1" was obtained by the same method as that applied in step 1 of Example 7)-3.

Antibody concentration: 1.83 mg/mL, antibody yield: 55.0 mg (87%), average number of conjugated drug molecules (n) per antibody molecule measured by common procedure E: 5.5, and average number of conjugated drug molecules (n) per antibody molecule measured by common procedure F: 8.0.

7)-13 Production of Antibody-Drug Conjugate (13)

[Formula 26]

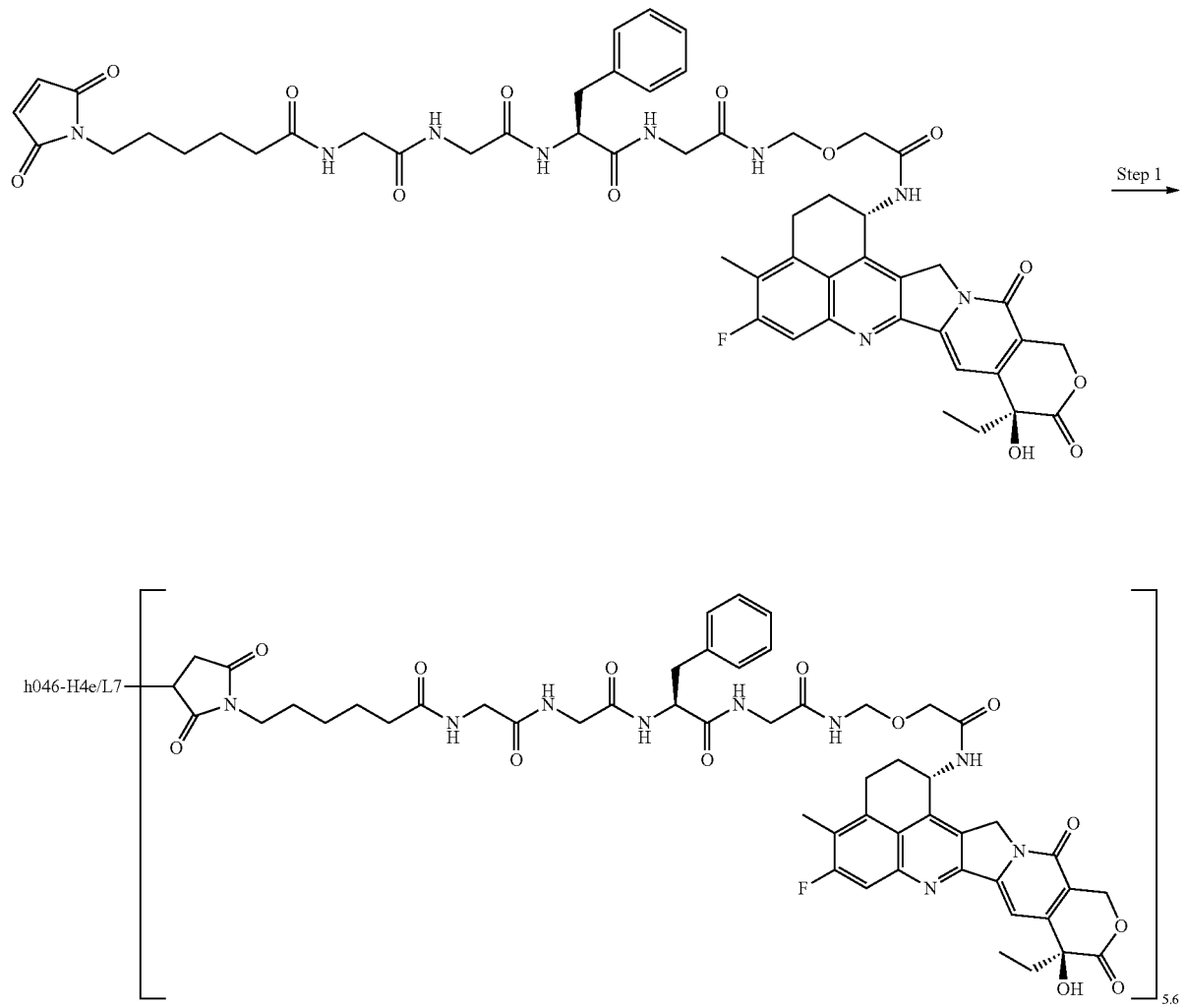

Step 1: Antibody-Drug Conjugate (13)

Reduction of antibody: h046-H4e/L7 produced in Example 6)-7-6-7 was adjusted to 10 mg/mL with PBS6.0/EDTA by using common procedures B (using 1.31 mLmg$^{-1}$cm$^{-1}$ as 280 nm absorption coefficient) and C described in production method 1. To this solution (11.0 mL), an aqueous solution of 10 mM TCEP (Tokyo Chemical Industry Co., Ltd.) (0.412 mL; 5.5 equivalents per antibody molecule) and a 1 M aqueous dipotassium hydrogen phosphate solution (Nacalai Tesque, Inc.; 0.165 mL) were added. After confirming that the solution had a pH within 7.0±0.1, the interchain disulfide bond in the antibody was reduced by incubating the solution at 37° C. for 1 hour.

Conjugation between antibody and drug linker: The above-described solution was incubated at 15° C. for 10 minutes. Subsequently, a 10 mM solution of N-[6-(2,5-dioxo-2,5-dihydro-1H-pyrrol-1-yl)hexanoyl]glycylglycyl-L-phenylalanyl-N-[(2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-oxoethoxy)methyl]glycinamide in dimethyl sulfoxide (0.674 mL; 9.0 equivalents per antibody molecule) was added thereto, and the obtained mixture was incubated at 15° C. for 1 hour to conjugate the drug linker to the antibody. Subsequently, an aqueous solution of 100 mM NAC (Sigma-Aldrich Co. LLC) (0.0674 mL; 9.0 equivalents per antibody molecule) was added thereto, and the obtained mixture was further stirred at room temperature for 20 minutes to terminate the reaction of the drug linker.

Purification: The above-described solution was purified by common procedure D described in production method 1 to obtain 34.5 mL of a solution containing the antibody-drug conjugate "h046-H4e/L7-ADC1".

Characterization: Using common procedures E and F (using $\varepsilon_{D,280}$=5178 and $\varepsilon_{D,370}$=20217) described in production method 1, the following characteristic values were obtained.

Antibody concentration: 3.01 mg/mL, antibody yield: 104 mg (95%), average number of conjugated drug molecules (n) per antibody molecule measured by common procedure E: 5.6, and average number of conjugated drug molecules (n) per antibody molecule measured by common procedure F: 7.7.

7)-14 Production of Antibody-Drug Conjugate (14)

[Formula 27]

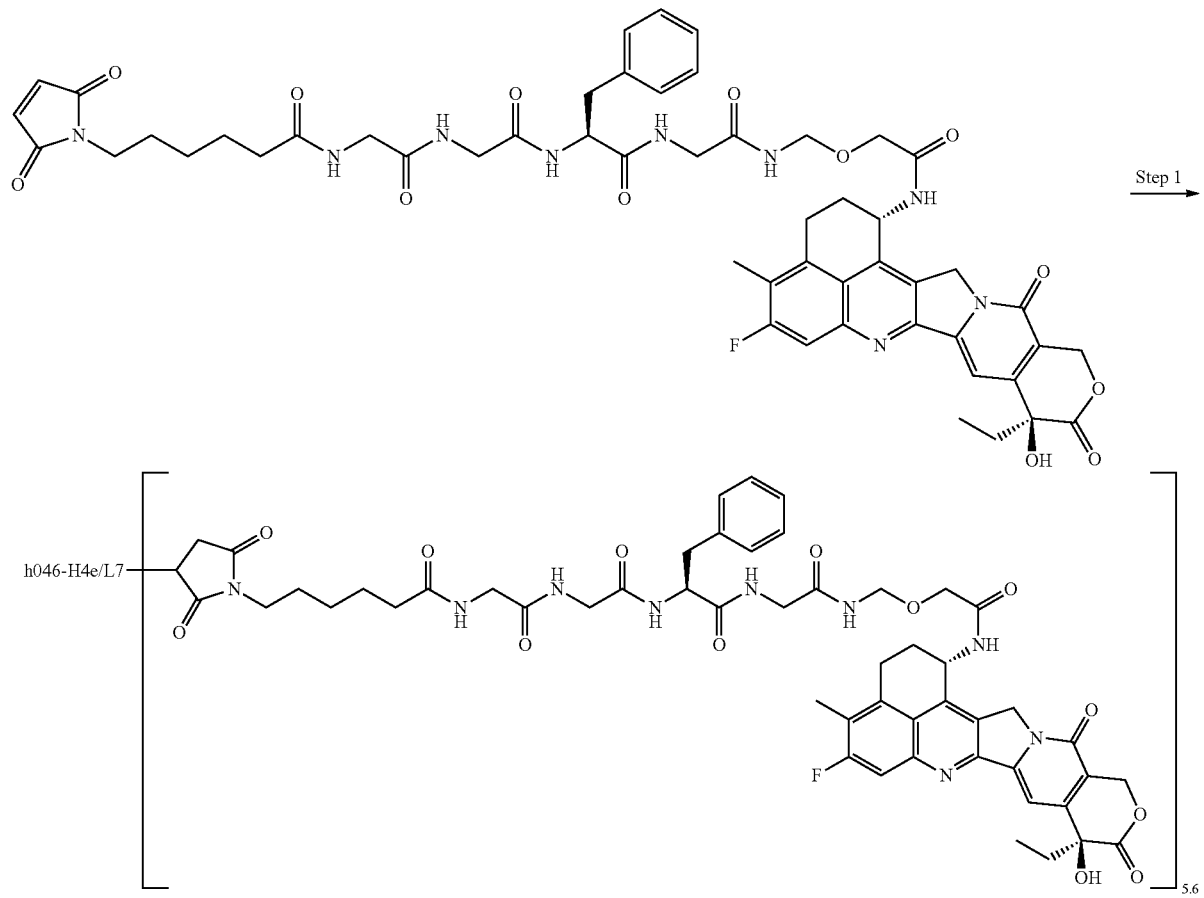

Step 1: Antibody-Drug Conjugate (14)

Using h046-H4e/L7 (using 1.31 mLmg$^{-1}$cm$^{-1}$ as 280 nm absorption coefficient) produced in Example 6)-7-6-7, the antibody-drug conjugate "h046-H4e/L7-ADC1" was obtained by the same method as that applied in step 1 of Example 7-13.

Antibody concentration: 3.14 mg/mL, antibody yield: 108 mg (99%), average number of conjugated drug molecules (n) per antibody molecule measured by common procedure E: 5.6, and average number of conjugated drug molecules (n) per antibody molecule measured by common procedure F: 7.6.

Example 8: Evaluation of In Vitro Activity of Antibody-Drug Conjugates

8)-1-1 Evaluation of Binding Activity of Humanized Anti-GPR20 Antibody and Antibody-Drug Conjugate The GPR20-binding activity of the humanized anti-GPR20 antibodies produced in Example 6)-7-6 and the antibody-drug conjugates produced in Example 7 was evaluated by flow cytometry. As a result of analyzing, using a flow cytometer (BD FACSCant II; BD Biosciences), their binding to 293T cells transiently transfected with pcDNA3.1-hGPR20 by the same method as that applied in Example 6)-6-1, antibody concentration-dependent binding activity was confirmed. Representative reaction examples thereof are shown in FIG. 25. In FIG. 25, the abscissa depicts an antibody concentration (nM), and the ordinate depicts the amount of the antibody bound based on MFI (mean fluorescence intensity). As shown in FIG. 25, the amounts of the humanized anti-GPR20 antibodies h046-H4b/L7 and h046-H4e/L7, and the antibody-drug conjugates (4) and (13) bound to the 293T cells transfected with pcDNA3.1-hGPR20 were increased in a concentration-dependent manner.

8)-2 Generation of a Stably-Expressing Cell Line, GIST-T1/GPR20

A stable cell line, GIST-T1/GPR20 was produced by infecting GIST-T1 cells (available from Cosmo Bio Co., Ltd.) with recombinant retrovirus for human GPR20 expression.

8)-2-1 Preparation of Human GPR20 Expression Retrovirus Vector

A human GPR20 expression retrovirus vector was prepared using In-Fusion HD Cloning Kit (Clontech Laboratories, Inc.). Specifically, using the human GPR20 expression vector pcDNA3.1-hGPR20 produced in Example 1 as a template, PCR reaction was carried out with the primer set given below. In this reaction, KOD FX DNA polymerase (Toyobo Co., Ltd.) was used, and the reaction was carried out at 30 cycles each involving 98° C. for 10 seconds, 58° C. for 30 seconds, and 68° C. for 2 minutes. Thereafter, the obtained PCR product comprising a GPR20 cDNA fragment was subjected to agarose gel electrophoresis, and DNA having the size of interest was extracted using QlAquick Gel Extraction Kit (Qiagen N.V.). Using In-Fusion HD Enzyme premix, this DNA fragment was mixed with retrovirus vector pLPCX (Clontech Laboratories, Inc.) that had been digested with the restriction enzymes EcoRI and NotI. After ligation reaction, *Escherichia coli* TOP10 (Invitrogen Corp.) was transformed with the ligation product to construct human GPR20 expression retrovirus vector pLPCX-GPR20. The primer set used in PCR was as follows.

PCR primer set (for In-Fusion cloning of pLPCX and GPR20 cDNA fragment)

5'-CTCAAGCTTCGAATTCAC-CATGCCCTCTGTGTCTCCA-3' (LPCX-1; SEQ ID NO: 112)

5'-TTGGCCGAGGCGGCCTCCTAAGCCTCGGGCC-CATTAG-3' (LPCX-1; SEQ ID NO: 113)

8)-2-2 Establishment of Stably Expressing Cell Line GIST-T1/GPR20

Using Lipofectamine 2000 (Invitrogen Corp.), pLPCX-GPR20 was transiently introduced into retrovirus packaging cells 293-10A1. 72 hours later, a culture supernatant containing recombinant retrovirus was collected, and then added to the GIST-T1 cell culture system, so that the cells were infected with the virus. 3 days after the infection, the GIST-T1 cells were seeded at 1 cell/well over a 96-well plate, and then cultured under conditions of 37° C. and 5% CO2 for a long period in a medium to which 0.3 to 1 µg/mL puromycin had been added, so as to establish cell line GIST-T1/GPR20 stably expressing GPR20.

8)-3 Evaluation of In Vitro Cell Proliferation-Suppressive Activity of ADC Against GIST-T1/GPR20 Cells The GIST-T1/GPR20 cells were seeded over a 96-well plate at $2.5 \times 10^3$ cells/100 µL/well in DMEM medium supplemented with 10% FBS, and the cells were then cultured overnight under conditions of 37° C. and 5% CO2. Each antibody-drug conjugate produced in Example 7 was added to the cells such that the final concentrations were from 0.032 to 100 nM. After culture for 7 to 11 days, the number of live cells was measured by the quantification of ATP using CellTiter-Glo (registered trademark) Luminescent Cell Viability Assay. FIG. 26 shows concentration-dependent cell proliferation-suppressive activity when the antibody-drug conjugate (1) produced from the human chimeric antibody was added to the cells, and FIG. 27 shows concentration-dependent cell proliferation-suppressive activity when each of the antibody-drug conjugates (7), (8) and (9) produced from the humanized antibodies was added to the cells. hIgG-ADC2 in this experiment was an antibody-drug conjugate produced from human IgG recognizing an antigen unrelated to GPR20, and was used as a negative control.

Example 9: In Vivo Antitumor Effect of Antibody-Drug Conjugate

The antitumor effects of the antibody-drug conjugates were evaluated using animal models derived from immunodeficient mice by the transplantation of human gastrointestinal stromal tumor-derived cells. Five- to 6-week-old female BALB/c nude mice (CAnN.Cg-Foxnlnu/CrlCrlj, Charles River Laboratories Japan Inc.) were acclimatized for 4 to 7 days under SPF conditions before use in the experiment. The mice were fed with a sterilized solid diet (FR-2, Funabashi Farms Co., Ltd) and given sterilized tap water (which had been prepared by adding a 5 to 15 ppm sodium hypochlorite solution to tap water). The longest diameter and the shortest diameter of the transplanted tumor were measured once or twice a week using electronic digital calipers (CD-15CX, Mitutoyo Corp.), and the volume of the tumor was then calculated according to the following equation.

$$\text{Tumor volume (mm}^3) = \frac{1}{2} \times \text{Longest diameter (mm)} \times [\text{Shortest diameter (mm)}]^2$$

Each antibody-drug conjugate was diluted with ABS buffer (10 mM acetate buffer, 5% sorbitol, pH 5.5) (Nacalai Tesque, Inc.), and the dilution was intravenously administered at a volume of 10 mL/kg to the tail of each mouse. ABS buffer was administered in the same manner as above to a control group (vehicle group). Five or six mice per group were used in the experiment.

9)-1 Antitumor Effect—(1)

The GIST-T1/GPR20 cells prepared in 8)-1-2 were suspended in Matrigel (Corning Inc.), and the cell suspension was subcutaneously transplanted at a dose of $5 \times 10^6$ cells to the right flank region of each female nude mouse (Day 0). On Day 14, the mice were randomly grouped. On Day 14, the antibody-drug conjugate (1) or (2) was intravenously administered at a dose of 10 mg/kg to the tail of each mouse. As a negative control, an antibody-drug conjugate produced using human IgG was administered at a dose of 10 mg/kg in the same manner as above. The administration of the antibody-drug conjugate (1) or (2) remarkably decreased tumor volume, and both the antibody-drug conjugates were effective for tumor regression (FIG. 28). It is to be noted that, in the drawing, the abscissa depicts the number of days, and the ordinate depicts tumor volume. hIgG-ADC1 and hIgG-ADC2 were antibody-drug conjugates produced from human IgG recognizing an antigen unrelated to GPR20, and were used as negative controls.

9)-2 Antitumor Effect—(2)

$2 \times 10^7$ cells of human gastrointestinal stromal tumor cell line GIST430 (obtained from Brigham Women's Hospital) were subcutaneously transplanted to the right flank region of each female nude mouse (Day 0). On Day 29, the mice were randomly grouped. On Days 29, 36, and 43, the antibody-drug conjugate (1) or (2) was intravenously administered at a dose of 10 mg/kg to the tail of each mouse. The administration of the antibody-drug conjugate (1) or (2) remarkably decreased tumor volume compared with that in the control group, and both the antibody-drug conjugates exerted a tumor growth-suppressive effect (FIG. 29).

9)-3 Antitumor Effect—(3)

In the same manner as that applied in Example 9)-1, the GIST-T1/GPR20 cells were subcutaneously transplanted to female nude mice (Day 0). On Day 24, the mice were randomly grouped. On Day 24, the antibody-drug conjugate (6) or (9) was intravenously administered at a dose of 10 mg/kg to the tail of each mouse. The administration of the antibody-drug conjugate (6) or (9) remarkably decreased tumor volume, and both the antibody-drug conjugates were effective for tumor regression (FIG. 30).

9)-4 Antitumor Effect—(4)

In the same manner as that applied in Example 9)-1, the GIST-T1/GPR20 cells were subcutaneously transplanted to female nude mice (Day 0). On Day 17, the mice were randomly grouped. On Day 17, the antibody-drug conjugate (3), (5), (6), (10), (11), or (12) was intravenously administered at a dose of 1 mg/kg to the tail of each mouse. The administration of the antibody-drug conjugate (3), (5), (6), (10), (11), or (12) remarkably decreased tumor volume, and all the antibody-drug conjugates exerted a tumor growth-suppressive effect (FIG. 31).

9)-5 Antitumor Effect—(5)

In the same manner as that applied in Example 9)-1, the GIST-T1/GPR20 cells were subcutaneously transplanted to female nude mice (Day 0). On Day 17, the mice were randomly grouped. On Day 17, the antibody-drug conjugate (13) was intravenously administered at a dose of 0.3, 1, or 3 mg/kg to the tail of each mouse. The administration of the antibody-drug conjugate (13) decreased tumor volume in a dose-dependent manner, and the antibody-drug conjugate was effective for tumor regression at a dose of 1 mg/kg or more (FIG. 32).

9)-6 Antitumor Effect—(6)

GIST020 (obtained from National Institutes of Biomedical Innovation, Health and Nutrition), which had been passaged and maintained by subcutaneously transplanting a tumor block excised from a patient with gastrointestinal stromal tumor in the small intestine to immunodeficient mice, was subcutaneously transplanted to the right flank regions of female nude mice (Day 0). On Day 55, the mice were randomly grouped. On Days 55 and 75, the antibody-drug conjugate (4) or (13) was intravenously administered at a dose of 10 mg/kg to the tail of each mouse. The administration of the antibody-drug conjugate (4) or (13) remarkably decreased tumor volume compared with that in the control group, and both the antibody-drug conjugates exerted a tumor growth-suppressive effect (FIG. 33).

9)-7 Antitumor Effect—(7)

GIST1 (obtained from University of Toyama), which had been passaged and maintained by subcutaneously transplanting a tumor block excised from a patient with gastrointestinal stromal tumor in the esophagus to immunodeficient mice, was subcutaneously transplanted to the right flank regions of female nude mice (Day 0). On Day 38, the mice were randomly grouped. On Days 38 and 59, the antibody-drug conjugate (13) was intravenously administered at a dose of 3 or 10 mg/kg to the tail of each mouse. The administration of the antibody-drug conjugate (13) remarkably decreased tumor volume compared with that in the control group, and the antibody-drug conjugate exerted a tumor growth-suppressive effect (FIG. 34).

9)-8 Antitumor Effect—(8)

$1 \times 10^7$ cells of stomach cancer cell line NCI-N87 strongly expressing a HER2 molecule but expressing no GPR20 were subcutaneously transplanted to the right flank regions of female nude mice (Day 0). On Day 6, the mice were randomly grouped. On Day 6, the antibody-drug conjugate (14) was intravenously administered at a dose of 3 or 10 mg/kg to the tail of each mouse. However, the antibody-drug conjugate (14) exhibited no significant tumor growth-suppressive effect. On the other hand, the administration of a drug conjugate produced from an anti-HER2 antibody remarkably decreased tumor volume compared with that in the control group, and the antibody-drug conjugate exerted a tumor growth-suppressive effect (FIG. 35).

9)-9 Antitumor Effect—(9)

GIST074 (obtained from National Institutes of Biomedical Innovation, Health and Nutrition), which had been passaged and maintained by subcutaneously transplanting a tumor block derived from a patient with gastrointestinal stromal tumor in the stomach unresponsive to regorafenib treatment to immunodeficient mice, was subcutaneously transplanted to the right flank regions of female nude mice (Day 0). On Day 29, the mice were randomly grouped. On Days 29 and 50, the antibody-drug conjugate (14) was intravenously administered at a dose of 10 mg/kg to the tail of each mouse. The administration of the antibody-drug conjugate (14) completely suppressed tumor growth (FIG. 36). On the other hand, when imatinib, sunitinib, and regorafenib were orally administered once a day at doses of 90, 30, and 4 mg/kg, respectively, on the days indicated by the triangle marks in FIG. 36, tumor growth was not completely suppressed. As is evident from these results, the antibody-drug conjugate (14) exerted an antitumor effect even on gastrointestinal stromal tumor that exhibited resistance to the 3 tyrosine kinase inhibitors serving as standard therapeutic drugs.

9)-10 Antitumor Effect—(10)

The effect of combined use with sunitinib was evaluated in models with human gastrointestinal stromal tumor cell line GIST430/654 (obtained from Brigham Women's Hospital) having imatinib resistance mutation V654A in KIT gene. $2 \times 10^7$ cells of GIST430/654 were subcutaneously transplanted to the right flank region of each female nude mouse (Day 0). On Day 21, the mice were randomly grouped. As shown in FIG. 37, on Day 21, the antibody-drug conjugate (3) was intravenously administered at a single dose of 10 mg/kg to the tail of each mouse. Imatinib and sunitinib were orally administered once a day at doses of 150 and 40 mg/kg, respectively, on the days indicated by the triangle marks. In the GIST430/654 models, imatinib did not suppress tumor growth, whereas the suppression of tumor growth was observed in the group to which the antibody-drug conjugate (3) or sunitinib had been administered. In the combined use group of the antibody-drug conjugate (3) and sunitinib, stronger medicinal effects than those brought about by single agents were observed, and tumor regression was found.

INDUSTRIAL APPLICABILITY

The present invention provides an anti-GPR20 antibody having internalization activity and an antibody-drug conjugate comprising the antibody. The antibody-drug conjugate can be used as a therapeutic drug for gastrointestinal stromal tumor, and the like.

SEQUENCE LISTING FREE TEXT

SEQ ID NO: 44: Amino acid sequence of 04-046Ch heavy chain
SEQ ID NO: 45: Amino acid sequence of 04-046Ch light chain
SEQ ID NO: 46: Nucleotide sequence of 04-046Ch antibody heavy chain
SEQ ID NO: 47: Nucleotide sequence of 04-046Ch light chain
SEQ ID NO: 48: Amino acid sequence of h046-H4b
SEQ ID NO: 49: Nucleotide sequence (1) of h046-H4b
SEQ ID NO: 50: Amino acid sequence of h046-H4e
SEQ ID NO: 51: Nucleotide sequence of h046-H4e
SEQ ID NO: 52: Amino acid sequence of h046-H5b
SEQ ID NO: 53: Nucleotide sequence (1) of h046-H5b
SEQ ID NO: 54: Amino acid sequence of h046-H8
SEQ ID NO: 55: Nucleotide sequence (1) of h046-H8
SEQ ID NO: 56: Amino acid sequence of h046-H10
SEQ ID NO: 57: Nucleotide sequence (1) of h046-H10
SEQ ID NO: 58: Amino acid sequence of h046-L1
SEQ ID NO: 59: Nucleotide sequence (1) of h046-L1
SEQ ID NO: 60: Amino acid sequence of h046-L2
SEQ ID NO: 61: Nucleotide sequence (1) of h046-L2
SEQ ID NO: 62: Amino acid sequence of h046-L6

SEQ ID NO: 63: Nucleotide sequence (1) of h046-L6
SEQ ID NO: 64: Amino acid sequence of h046-L7
SEQ ID NO: 65: Nucleotide sequence (1) of h046-L7
SEQ ID NO: 66: PCR primer Nhe-polyC-S
SEQ ID NO: 67: PCR primer rIgγ-AS1
SEQ ID NO: 68: PCR primer rIgγ-AS2
SEQ ID NO: 69: PCR primer rIgκ-AS
SEQ ID NO: 70: PCR primer rIgγ-seq
SEQ ID NO: 71: PCR primer rIgκ-seq
SEQ ID NO: 72: PCR primer NFLAG-1
SEQ ID NO: 73: PCR primer NFLAG-2
SEQ ID NO: 74: PCR primer mEC2-1
SEQ ID NO: 75: PCR primer mEC2-2
SEQ ID NO: 76: PCR primer mEC3-1
SEQ ID NO: 77: PCR primer mEC3-2
SEQ ID NO: 78: PCR primer mEC4-1
SEQ ID NO: 79: PCR primer mEC4-2
SEQ ID NO: 80: PCR primer mEC1-1
SEQ ID NO: 81: PCR primer mEC1-2
SEQ ID NO: 82: PCR primer mEC1-3
SEQ ID NO: 83: PCR primer mEC1-4
SEQ ID NO: 85: PCR primer 3.3-F1
SEQ ID NO: 86: PCR primer 3.3-R1
SEQ ID NO: 88: PCR primer EG-Inf-F
SEQ ID NO: 89: PCR primer EG1-Inf-R
SEQ ID NO: 90: PCR primer CM-LKF
SEQ ID NO: 91: PCR primer 046L-R
SEQ ID NO: 92: Amino acid sequence of h046-L6 CDRL2
SEQ ID NO: 93: Amino acid sequence of h046-L7 CDRL2
SEQ ID NO: 94: DNA fragment A
SEQ ID NO: 95: PCR primer Hb-F
SEQ ID NO: 96: PCR primer Hb-R
SEQ ID NO: 97: DNA fragment B
SEQ ID NO: 98: H08-F
SEQ ID NO: 99: H08-R
SEQ ID NO: 100: H10-F
SEQ ID NO: 101: H10-R
SEQ ID NO: 102: PCR primer KCL-Inf-R
SEQ ID NO: 103: Nucleotide sequence (2) of h046-H4b
SEQ ID NO: 104: Nucleotide sequence (2) of h046-H5b
SEQ ID NO: 105: Nucleotide sequence (2) of h046-Hwt
SEQ ID NO: 106: Nucleotide sequence (2) of h046-H8
SEQ ID NO: 107: Nucleotide sequence (2) of h046-H10
SEQ ID NO: 108: Nucleotide sequence (2) of h046-L1
SEQ ID NO: 109: Nucleotide sequence (2) of h046-L2
SEQ ID NO: 110: Nucleotide sequence (2) of h046-L6
SEQ ID NO: 111: Nucleotide sequence (2) of h046-L7
SEQ ID NO: 112: PCR primer LPCX-1
SEQ ID NO: 113: PCR primer LPCX-2

The invention claimed is:

1. An anti-G protein-coupled receptor 20 (GPR20) antibody or a GPR20-binding fragment thereof, comprising a light chain complementarity determining region 1 (CDRL1), a CDRL2, and a CDRL3, and a heavy chain complementarity determining region 1 (CDRH1), CDRH2, and CDRH3, wherein:
   (a) the CDRL1 comprises SEQ ID NO: 9;
   (b) the CDRL2 comprises SEQ ID NO: 10, SEQ ID NO: 92, or SEQ ID NO: 93;
   (c) the CDRL3 comprises SEQ ID NO: 11;
   (d) the CDRH1 comprises SEQ ID NO: 4;
   (e) the CDRH2 comprises SEQ ID NO: 5; and
   (f) the CDRH3 comprises SEQ ID NO: 6.

2. The anti-GPR20 antibody or GPR20-binding fragment thereof according to claim 1, wherein the CDRL2 comprises SEQ ID NO: 10.

3. The anti-GPR20 antibody or GPR20-binding fragment thereof according to claim 1, wherein the CDRL2 comprises SEQ ID NO: 92.

4. The anti-GPR20 antibody or GPR20-binding fragment thereof according to claim 1, wherein the CDRL2 comprises SEQ ID NO: 93.

5. The anti-GPR20 antibody or GPR20-binding fragment thereof according to claim 1, wherein the antibody or fragment comprises a heavy chain variable region comprising SEQ ID NO: 3, or amino acid residues 20-142 of SEQ ID NO: 50 and a light chain variable region comprising SEQ ID NO: 8, amino acid residues 21-129 of SEQ ID NO: 62, or amino acid residues 21-129 of SEQ ID NO: 64.

6. The anti-GPR20 antibody or GPR20-binding fragment thereof according to claim 1, wherein the antibody or fragment is humanized or comprises a human constant region.

7. The anti-GPR20 antibody or GPR20-binding fragment thereof according to claim 1, wherein the antibody comprises a heavy chain comprising amino acid residues 20-471 or amino acid residues 20-472 of SEQ ID NO: 50 and a light chain comprising amino acid residues 21-234 of SEQ ID NO: 64.

8. The anti-GPR20 antibody or GPR20-binding fragment thereof according to claim 1, wherein the fragment is selected from the group consisting of Fab, F (ab) 2, Fab' and Fv.

9. The anti-GPR20 antibody or GPR20-binding fragment thereof according to claim 1, wherein the antibody comprises one or more modifications selected from the group consisting of: glycosylation to an N-bond, glycosylation to an O-bond, processing to an N-terminal, processing to a C-terminal, deamidation, isomerization of aspartic acid, oxidation of methionine, addition of a methionine residue to an N-terminal, amidation of a proline residue, and a heavy chain having one or two amino acids deleted at the carboxyl terminal.

10. The anti-GPR20 antibody or GPR20-binding fragment thereof according to claim 1, wherein the antibody comprises a heavy chain in which one or two amino acids are deleted from the carboxy terminus of the heavy chain.

11. The anti-GPR20 antibody or GPR20-binding fragment thereof according to claim 1, wherein the carboxy terminus of the heavy chain is amidated.

12. The anti-GPR20 antibody or GPR20-binding fragment thereof according to claim 1, wherein the antibody comprises a sugar chain modification modulated to enhance antibody-dependent cytotoxic activity.

13. An antibody-drug conjugate (ADC), comprising the anti-GPR20 antibody or GPR20-binding fragment thereof according to claim 1 and a drug-linker structure comprising an antitumor compound connected to the antibody by a linker.

14. The ADC according to claim 13, wherein the antitumor compound has the following formula:

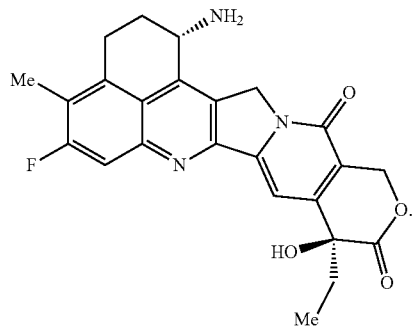 [SMILES: CC[C@@]1(O)C(=O)OCc2c1cc1n(c2=O)Cc2c-1nc1cc(F)c(C)c3c1c2[C@@H](N)CC3]

15. The ADC according to claim 13, wherein the linker is selected from the group consisting of:
-(Succinimid-3-yl-N)—CH$_2$CH$_2$—C(=O)-GGFG-NH—CH$_2$CH$_2$CH$_2$—C(=O)—;
-(Succinimid-3-yl-N)—CH$_2$CH$_2$CH$_2$CH$_2$CH$_2$—C(=O)-GGFG-NH—CH$_2$CH$_2$CH$_2$—C(=O)—;
-(Succinimid-3-yl-N)—CH$_2$CH$_2$CH$_2$CH$_2$CH$_2$—C(=O)-GGFG-NH—CH$_2$—O—CH$_2$—C(=O)—;
-(Succinimid-3-yl-N)—CH$_2$CH$_2$CH$_2$CH$_2$CH$_2$—C(=O)-GGFG-NH—CH$_2$CH$_2$—O—CH$_2$—C(=O)—;
-(Succinimid-3-yl-N)—CH$_2$CH$_2$—C(=O)—NH—CH$_2$CH$_2$O—CH$_2$CH$_2$O—CH$_2$CH$_2$—C(=O)-GGFG-NH—CH$_2$CH$_2$CH$_2$—C(=O)—; and
-(Succinimid-3-yl-N)—CH$_2$CH$_2$—C(=O)—NH—CH$_2$CH$_2$O—CH$_2$CH$_2$O—CH$_2$CH$_2$O—CH$_2$CH$_2$O—CH$_2$CH$_2$—C(=O)-GGFG-NH—CH$_2$CH$_2$CH$_2$—C(=O)—;

wherein -(Succinimid-3-yl-N)— is the following formula:

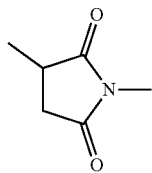

and wherein the antibody is bound to the linker at position 3 of -(Succinimid-3-yl-N), the nitrogen at position 1 of -(Succinimid-3-yl-N) is bound to the first methyl group of the linker, and the antitumor compound is bound to the carbonyl group of the —C(=O)—-moiety.

16. The ADC according to claim 13, wherein the drug-linker structure has the following structure and AB denotes the antibody:

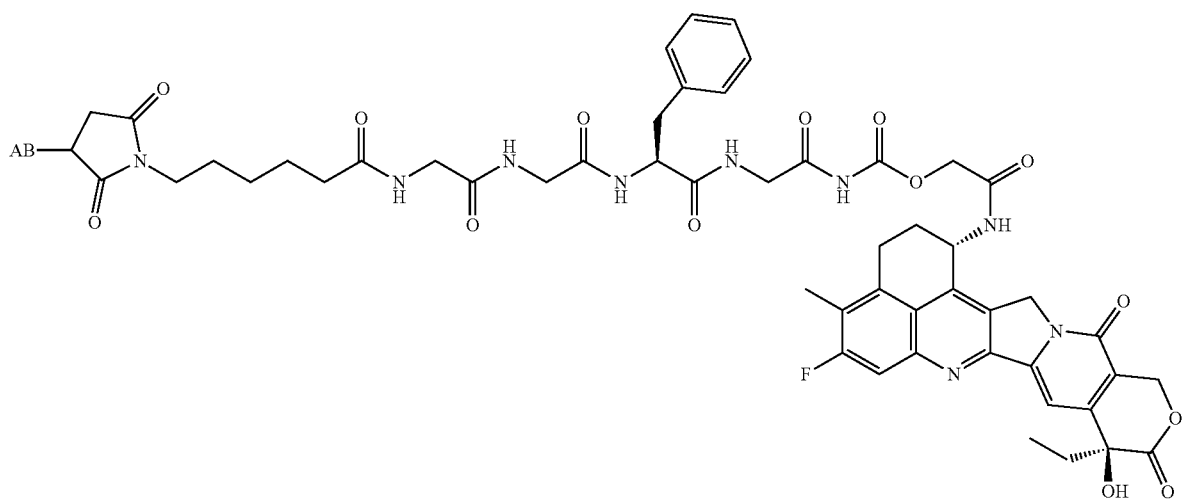

17. The ADC according to claim 13, wherein the drug-linker structure has the following structure; wherein AB denotes the antibody n indicates the average number of bound drug-linker structures per antibody that are bound to the antibody:

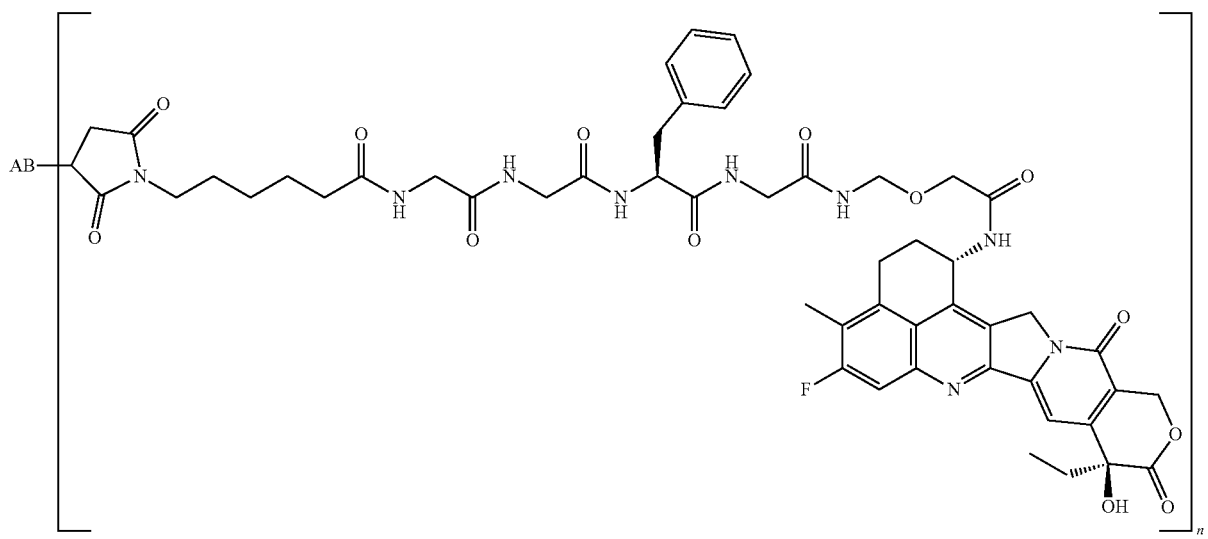

and wherein an average of 1 to 10 drug-linker structures are connected to the antibody.

18. The ADC according to claim 13, wherein an average of 7 to 8 drug-linker structures are connected to the antibody.

19. A polynucleotide encoding an anti-GPR20 antibody or GPR20-binding fragment thereof according to claim 1.

20. A method of producing an anti-GPR20 antibody or a GPR20-binding fragment thereof, comprising culturing a host cell comprising an expression vector comprising the polynucleotide according to claim 19, and collecting an anti-GPR20 antibody or a GPR20-binding fragment thereof from the culture.

21. An anti-G protein-coupled receptor 20 (GPR20) antibody comprising a heavy chain variable region comprising amino acid residues 20-142 of SEQ ID NO: 48, amino acid residues 20-142 of SEQ ID NO: 50, amino acid residues 20-142 of SEQ ID NO: 52, amino acid residues 20-142 of SEQ ID NO: 54, amino acid residues 20-142 of SEQ ID NO: 56, or amino acid residues 20-142 of SEQ ID NO: 44; and a light chain variable region comprising amino acid residues 21-129 of SEQ ID NO: 58, amino acid residues 21-129 of SEQ ID NO: 60, amino acid residues 21-129 of SEQ ID NO: 62, amino acid residues 21-129 of SEQ ID NO: 64, or amino acid residues 21-128 of SEQ ID NO: 45.

22. The anti-GPR20 antibody according to claim 21, wherein the antibody comprises a heavy chain comprising amino acid residues 20-472 of SEQ ID NO: 48, amino acid residues 20-472 of SEQ ID NO: 50, amino acid residues 20-472 of SEQ ID NO: 52, amino acid residues 20-472 of SEQ ID NO: 54, amino acid residues 20-472 of SEQ ID NO: 56, or amino acid residues 20-472 of SEQ ID NO: 44; and the light chain region comprising amino acid residues 21-234 of SEQ ID NO: 58, amino acid residues 21-234 of SEQ ID NO: 60, amino acid residues 21-234 of SEQ ID NO: 62, amino acid residues 21-234 of SEQ ID NO: 64, or amino acid residues 21-233 of SEQ ID NO: 45.

23. An antibody-drug conjugate (ADC), comprising the anti-GPR20 antibody according to claim 21 and a drug-linker structure comprising an antitumor compound connected to the antibody by a linker; wherein the antitumor compound has the following formula:

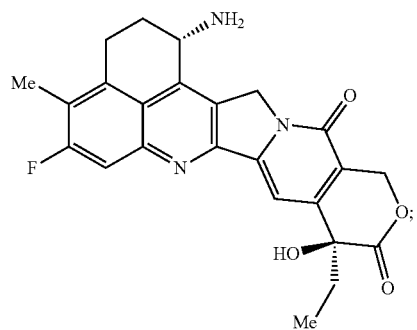 [SMILES: CC[C@@]1(O)C(=O)OCc2c1cc1n(c2=O)Cc2c-1nc1cc(F)c(C)c3c1c2[C@@H](N)CC3]

and wherein the linker is selected from the group consisting of:

-(Succinimid-3-yl-N)—CH$_2$CH$_2$—C(=O)-GGFG-NH—CH$_2$CH$_2$CH$_2$—C(=O)—;

-(Succinimid-3-yl-N)—CH$_2$CH$_2$CH$_2$CH$_2$CH$_2$—C(=O)-GGFG-NH—CH$_2$CH$_2$CH$_2$—C(=O)—;

-(Succinimid-3-yl-N)—CH$_2$CH$_2$CH$_2$CH$_2$CH$_2$—C(=O)-GGFG-NH—CH$_2$—O—CH$_2$—C(=O)—;

-(Succinimid-3-yl-N)—CH$_2$CH$_2$CH$_2$CH$_2$CH$_2$—C(=O)-GGFG-NH—CH$_2$CH$_2$—O—CH$_2$—C(=O)—;

-(Succinimid-3-yl-N)—CH$_2$CH$_2$—C(=O)—NH—CH$_2$CH$_2$O—CH$_2$CH$_2$O—CH$_2$CH$_2$—C(=O)-GGFG-NH—CH$_2$CH$_2$CH$_2$—C(=O)—; and -(Succinimid-3-yl-N)—CH$_2$CH$_2$—C(=O)—NH—CH$_2$CH$_2$O—CH$_2$CH$_2$O—CH$_2$CH$_2$O—CH$_2$CH$_2$O—CH$_2$CH$_2$—C(=O)-GGFG-NH—CH$_2$CH$_2$CH$_2$—C(=O)—;

wherein -(Succinimid-3-yl-N)— is the following formula:

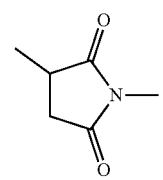

and wherein the antibody is bound to the linker at position 3 of -(Succinimid-3-yl-N), the nitrogen at position 1 of -(Succinimid-3-yl-N) is bound to the first methyl group of the linker, and the antitumor compound is bound to the carbonyl group of the —C(=O)—-moiety.

24. The ADC according to claim 23, wherein the drug-linker structure has the following structure; wherein AB denotes the antibody n indicates the average number of bound drug-linker structures per antibody that are bound to the antibody:

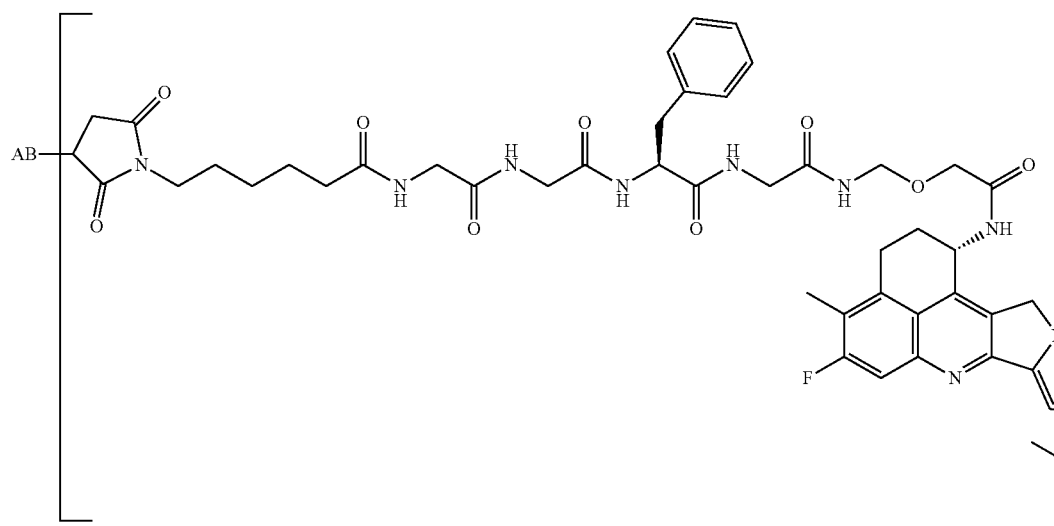

and wherein an average of 1 to 10 drug-linker structures are connected to the antibody.

25. The ADC according to claim 23, wherein an average of 7 to 8 drug-linker structures are connected to the antibody.

26. The ADC of claim 23, wherein the anti-GPR20 antibody comprises a heavy chain in which one or two amino acids are deleted from the carboxy terminus of the heavy chain, and wherein the carboxy terminus of the heavy chain is amidated.

27. An antibody-drug conjugate (ADC), comprising an anti-GPR20 antibody and a drug-linker structure comprising an antitumor compound connected to the antibody by a linker; wherein the antibody comprises a CDRL1 comprising SEQ ID NO: 9; a CDRL2 comprising SEQ ID NO: 10, SEQ ID NO: 92, or SEQ ID NO: 93; a CDRL3 comprising SEQ ID NO: 11; a CDRH1 comprising SEQ ID NO: 4; a CDRH2 comprising SEQ ID NO: 5; and a CDRH3 comprising SEQ ID NO: 6;

wherein the antitumor compound has the following formula:

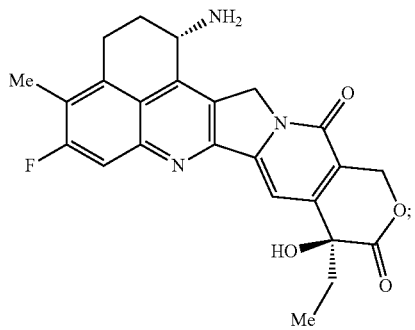 [SMILES: CC[C@@]1(O)C(=O)OCc2c1cc1n(c2=O)Cc2c-1nc1cc(F)c(C)c3c1c2[C@@H](N)CC3]

and wherein the linker consisting of:

-(Succinimid-3-yl-N)—CH$_2$CH$_2$CH$_2$CH$_2$CH$_2$—C(=O)-GGFG-NH—CH$_2$—O—CH$_2$—C(=O)—;

wherein -(Succinimid-3-yl-N)— is the following formula:

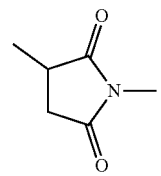

and wherein the antibody is bound to the linker at position 3 of -(Succinimid-3-yl-N), the nitrogen at position 1 of -(Succinimid-3-yl-N) is bound to the first methyl group of the linker, and the antitumor compound is bound to the carbonyl group of the —C(=O)—-moiety.

28. The ADC according to claim 27, wherein the anti-GPR20 antibody comprises a heavy chain comprising amino acid residues 20-471 or amino acid residues 20-472 of SEQ ID NO: 50 and a light chain comprising amino acid residues 21-234 of SEQ ID NO: 64.

29. The ADC according to claim 27, wherein an average of 7 to 8 drug-linker structures are connected to the antibody.

30. A method of treating a tumor comprising administering to an individual an ADC according to claim 27.

* * * * *